(12) United States Patent
Albert et al.

(10) Patent No.: US 12,156,966 B2
(45) Date of Patent: Dec. 3, 2024

(54) METHODS AND SYSTEMS FOR DELIVERING FORMULATIONS TO USERS USING MODULAR DEVICE HAVING REMOVABLE CARTRIDGE

(71) Applicant: MICRONEB TECH HOLDINGS, INC., St Petersburg, FL (US)

(72) Inventors: Pradeep Albert, Sarasota, FL (US); Christine Nichols, Largo, FL (US); David J. Condron, Seminole, FL (US); Brian Artze, Gulfport, FL (US); Fadi Saba, St Petersburg, FL (US); Jesse Klein, Clearwater, FL (US); Vijay Vad, New York, NY (US); Shawn Best, Tampa, FL (US)

( * ) Notice: Subject to any disclaimer, the term of this patent is extended or adjusted under 35 U.S.C. 154(b) by 0 days.

(21) Appl. No.: 18/654,471

(22) Filed: May 3, 2024

(65) Prior Publication Data
US 2024/0277949 A1 Aug. 22, 2024

Related U.S. Application Data

(63) Continuation-in-part of application No. 18/529,978, filed on Dec. 5, 2023, and a continuation-in-part of
(Continued)

(51) Int. Cl.
*A61M 15/00* (2006.01)
*A61M 11/00* (2006.01)

(52) U.S. Cl.
CPC ...... *A61M 15/0085* (2013.01); *A61M 11/005* (2013.01); *A61M 15/0025* (2014.02);
(Continued)

(58) Field of Classification Search
CPC ............ A61M 11/005; A61M 15/0085; A61M 15/0028
See application file for complete search history.

(56) References Cited

U.S. PATENT DOCUMENTS

| 5,791,134 A | 8/1998 | Schneider et al. |
| 7,219,668 B2 | 5/2007 | Flynn |

(Continued)

FOREIGN PATENT DOCUMENTS

| CN | 215608554 U | 1/2022 | |
| CN | 106422005 B | * 6/2023 | .......... A61M 11/005 |

(Continued)

*Primary Examiner* — Kathryn E Ditmer
(74) *Attorney, Agent, or Firm* — Derek Fahey, Esq.; The IP Plus Firm, PLLC

(57) ABSTRACT

Methods and systems for delivering formulations to users using modular device having atomizer and wick assembly are disclosed. A formulation delivery system that includes a mouthpiece with a first attaching structure at one end and a removable cartridge with a second attaching structure that connects to the mouthpiece. The removable cartridge houses an atomizer at its first end and features a wick assembly with a removable cap and a wick made from an absorbent material. The wick, which transports fluid to the atomizer, is connected at one end to the removable cap and at the other end abuts the atomizer. The system also includes a channel within the removable cartridge; this channel extends to the cartridge's first end and houses the wick, while the removable cap is located outside the channel. Additionally, the system incorporates electronics that maintain a removable electrical connection with the cartridge.

9 Claims, 71 Drawing Sheets

Related U.S. Application Data application No. 18/373,142, filed on Sep. 26, 2023, now Pat. No. 11,944,742, which is a continuation-in-part of application No. 18/449,838, filed on Aug. 15, 2023, now Pat. No. 11,925,748, which is a continuation-in-part of application No. 18/224,502, filed on Jul. 20, 2023, now Pat. No. 11,844,900, which is a continuation-in-part of application No. 18/207,242, filed on Jun. 8, 2023, now Pat. No. 11,850,356.

(60) Provisional application No. 63/437,568, filed on Jan. 6, 2023.

(52) U.S. Cl.
CPC .... *A61M 15/0028* (2013.01); *A61M 15/0086* (2013.01); *A61M 2205/3569* (2013.01)

(56) References Cited

U.S. PATENT DOCUMENTS

| | | | |
|---|---|---|---|
| 8,201,752 B2* | 6/2012 | Brodbeck | A61L 9/015 239/45 |
| 9,746,194 B2* | 8/2017 | Brodbeck | A61M 16/109 |
| 10,015,990 B2* | 7/2018 | Mironov | H05B 3/146 |
| 2009/0220222 A1* | 9/2009 | Rabin | A61M 16/109 392/394 |
| 2010/0222752 A1* | 9/2010 | Collins, Jr. | B05B 17/0623 604/296 |
| 2013/0061849 A1 | 3/2013 | Lemper | |
| 2016/0271357 A1 | 9/2016 | Islava et al. | |
| 2016/0339198 A1 | 11/2016 | Fraser et al. | |
| 2019/0143053 A1 | 5/2019 | Chen et al. | |
| 2021/0068455 A1* | 3/2021 | Jones | A61M 15/06 |
| 2021/0244099 A1* | 8/2021 | Force | A24F 40/40 |
| 2022/0074586 A1* | 3/2022 | Barfod | A61L 9/037 |
| 2022/0134026 A1* | 5/2022 | Niebuhr | A24F 40/10 128/200.14 |

FOREIGN PATENT DOCUMENTS

| | | | |
|---|---|---|---|
| GB | 2442267 A | | 4/2008 |
| KR | 102279507 B1 | * | 7/2021 |
| WO | 2010100557 A1 | | 9/2010 |
| WO | 2017192767 A1 | | 11/2019 |

\* cited by examiner

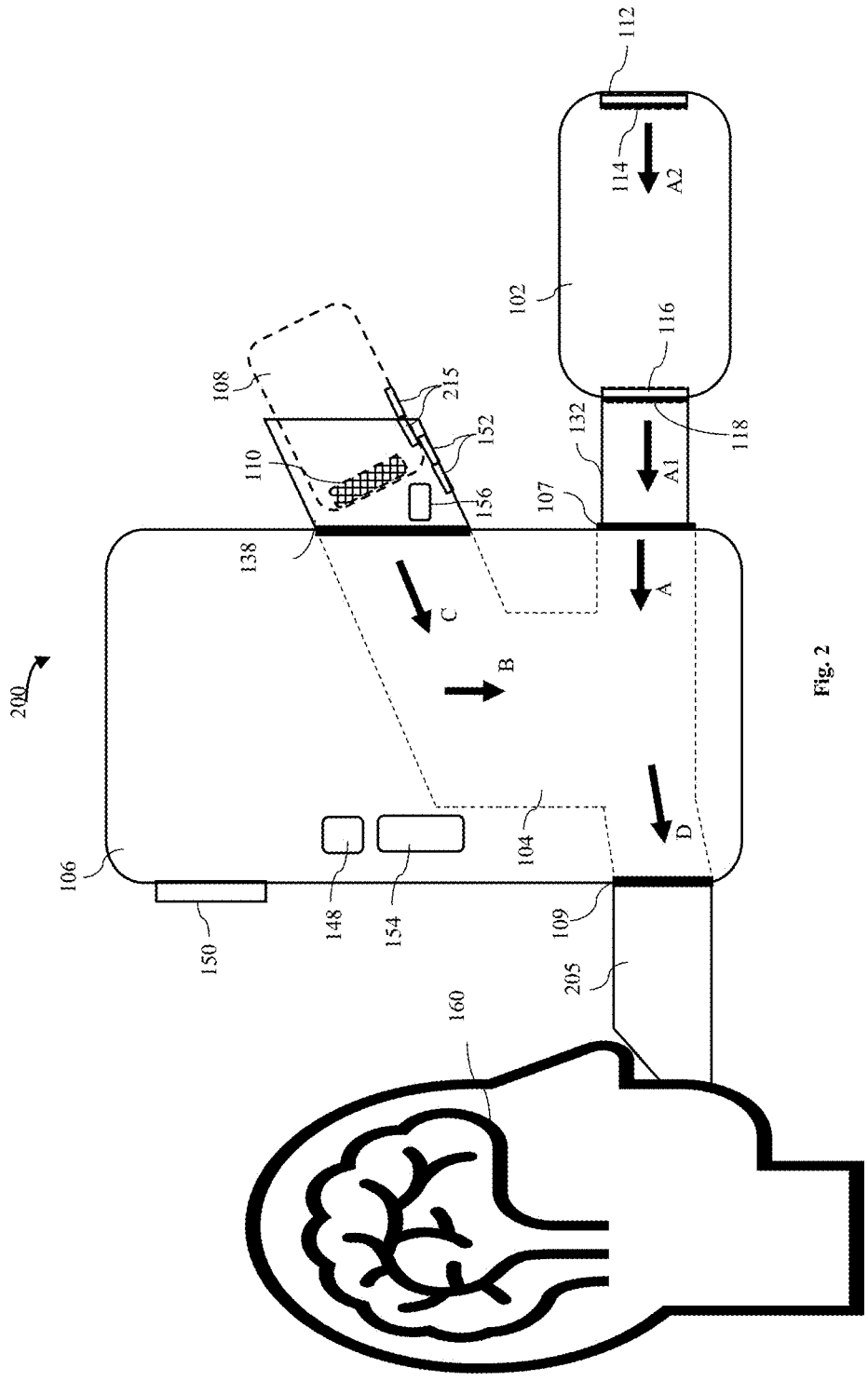

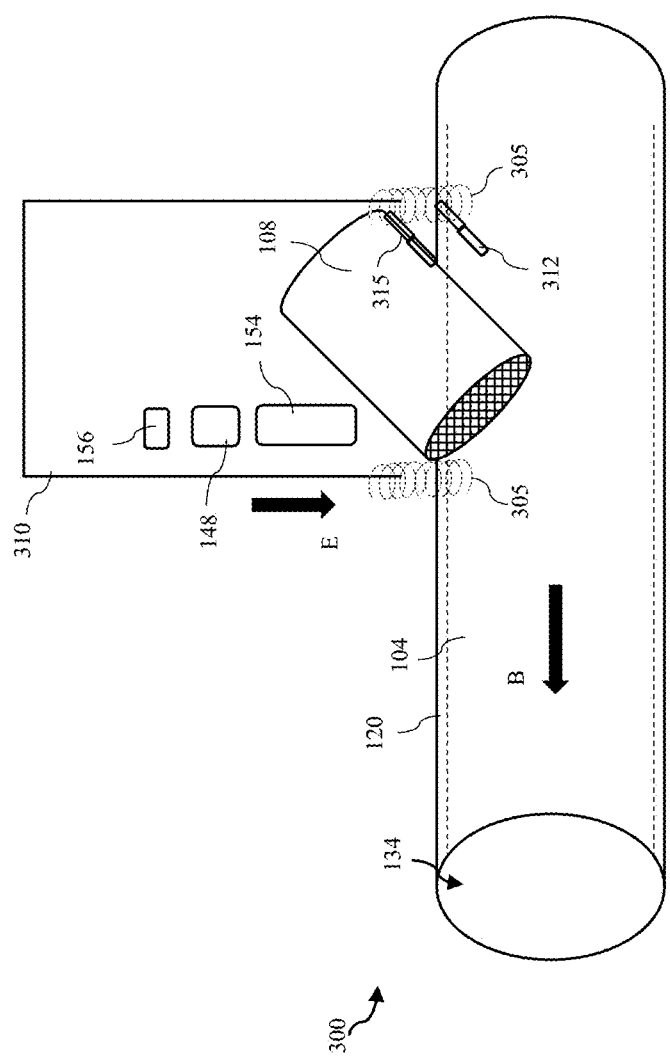

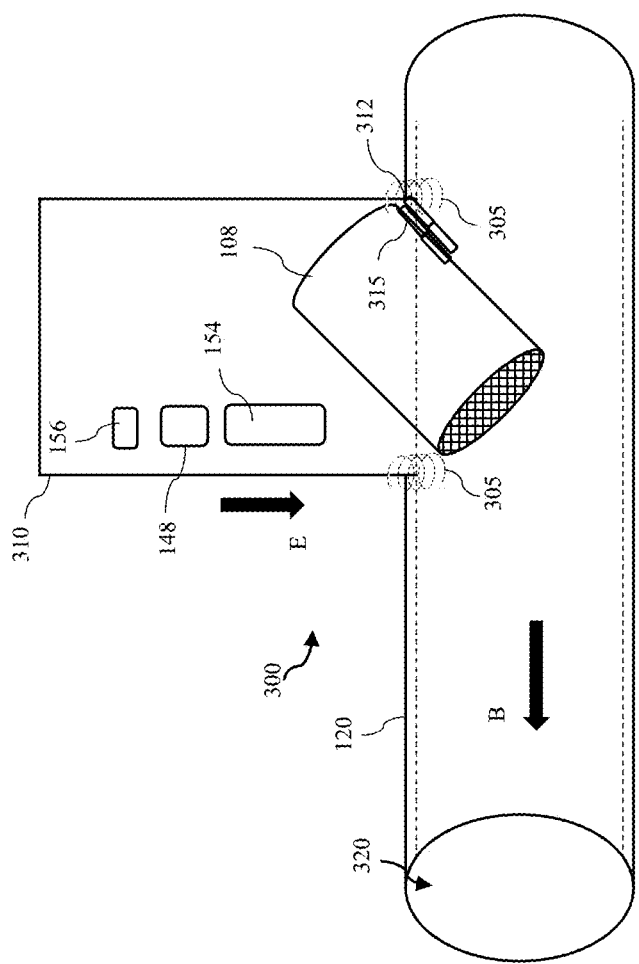

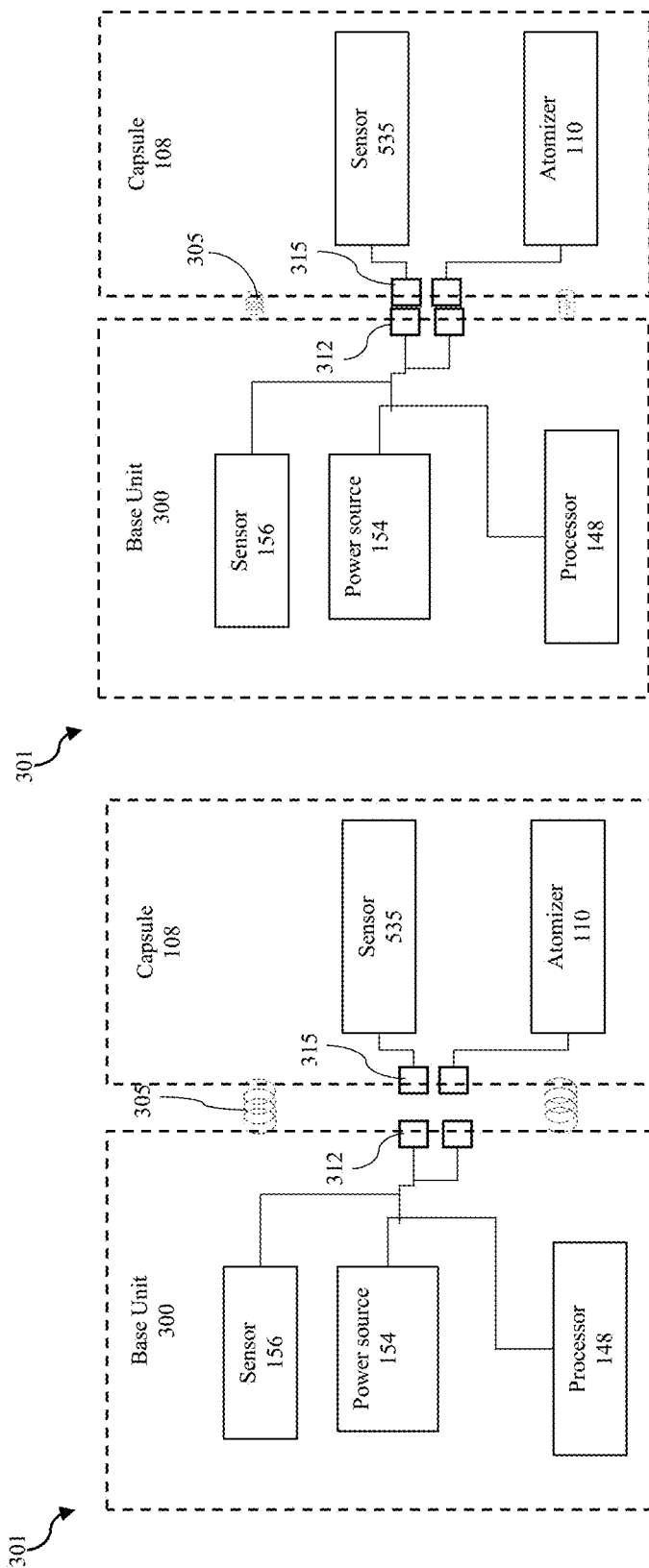

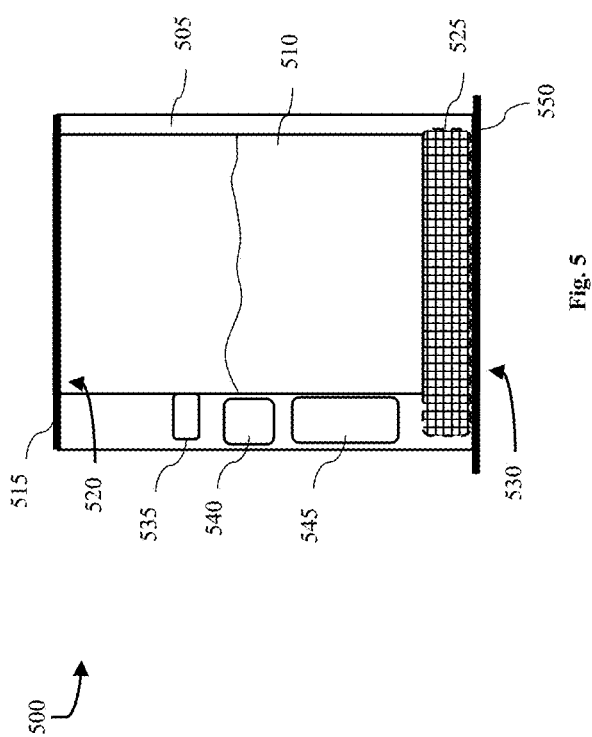

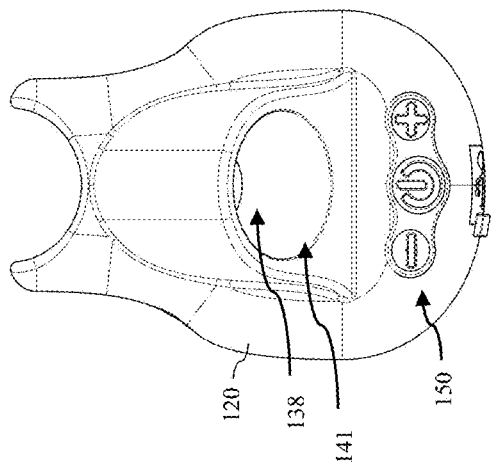
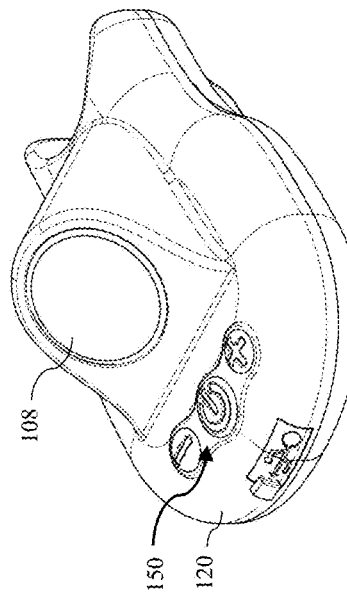
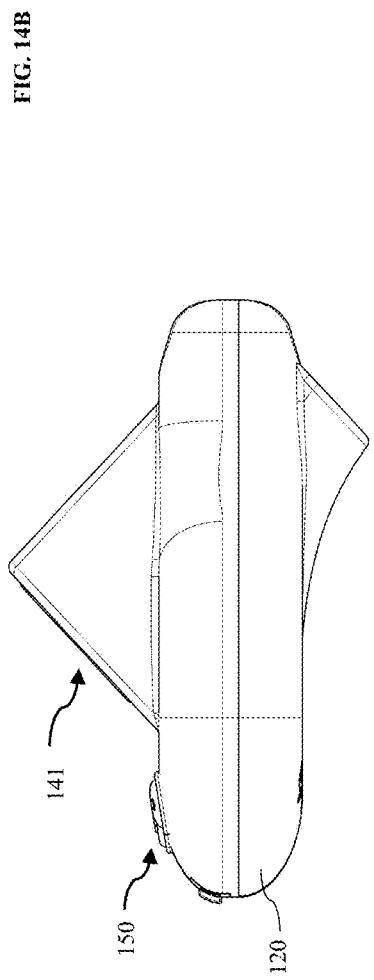
FIG. 14A
FIG. 14B
FIG. 14C

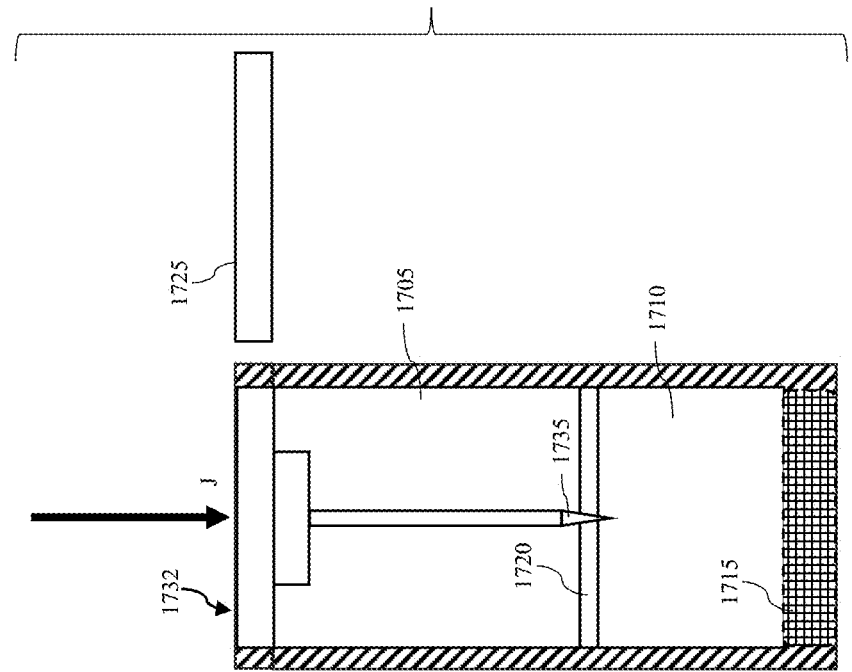
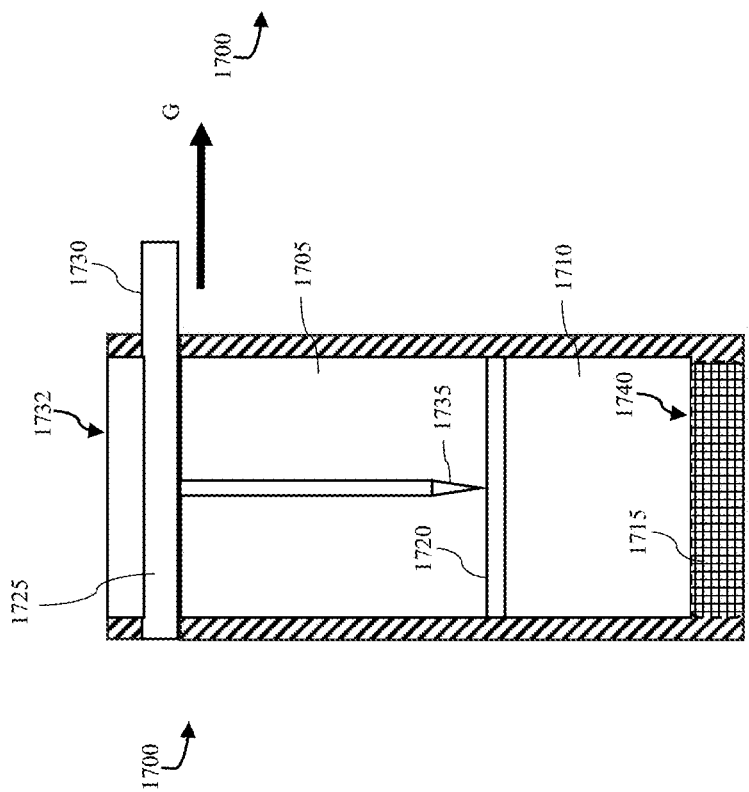
FIG. 17A
FIG. 17B

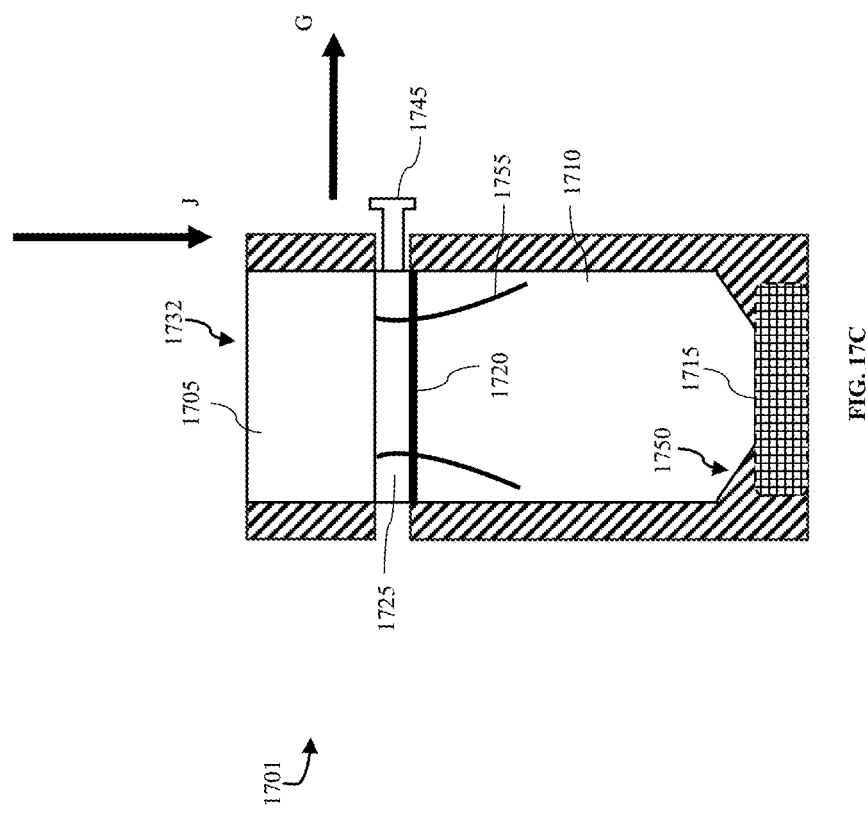

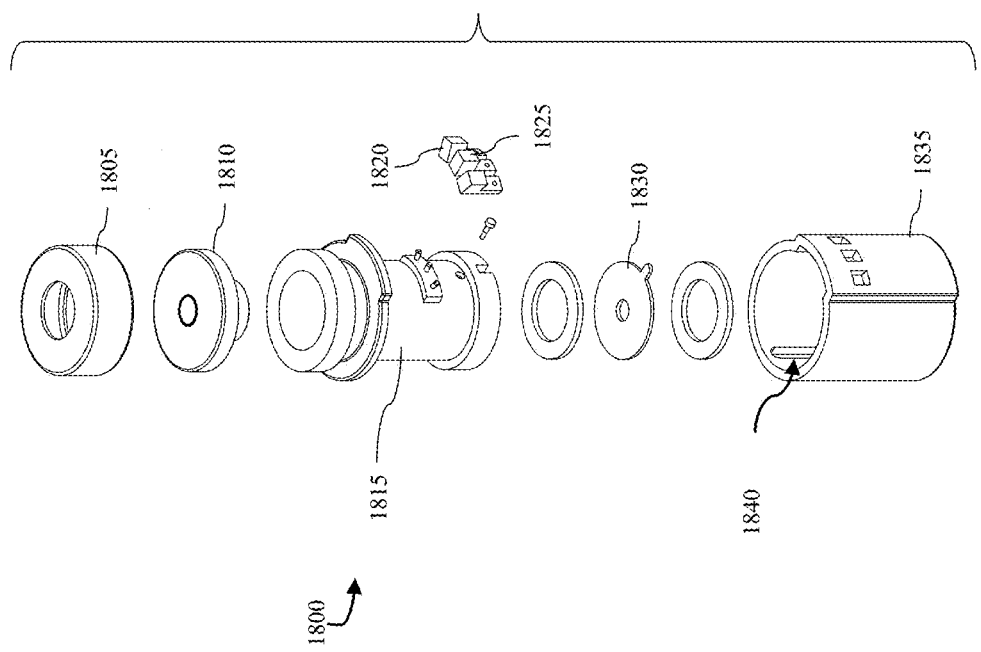

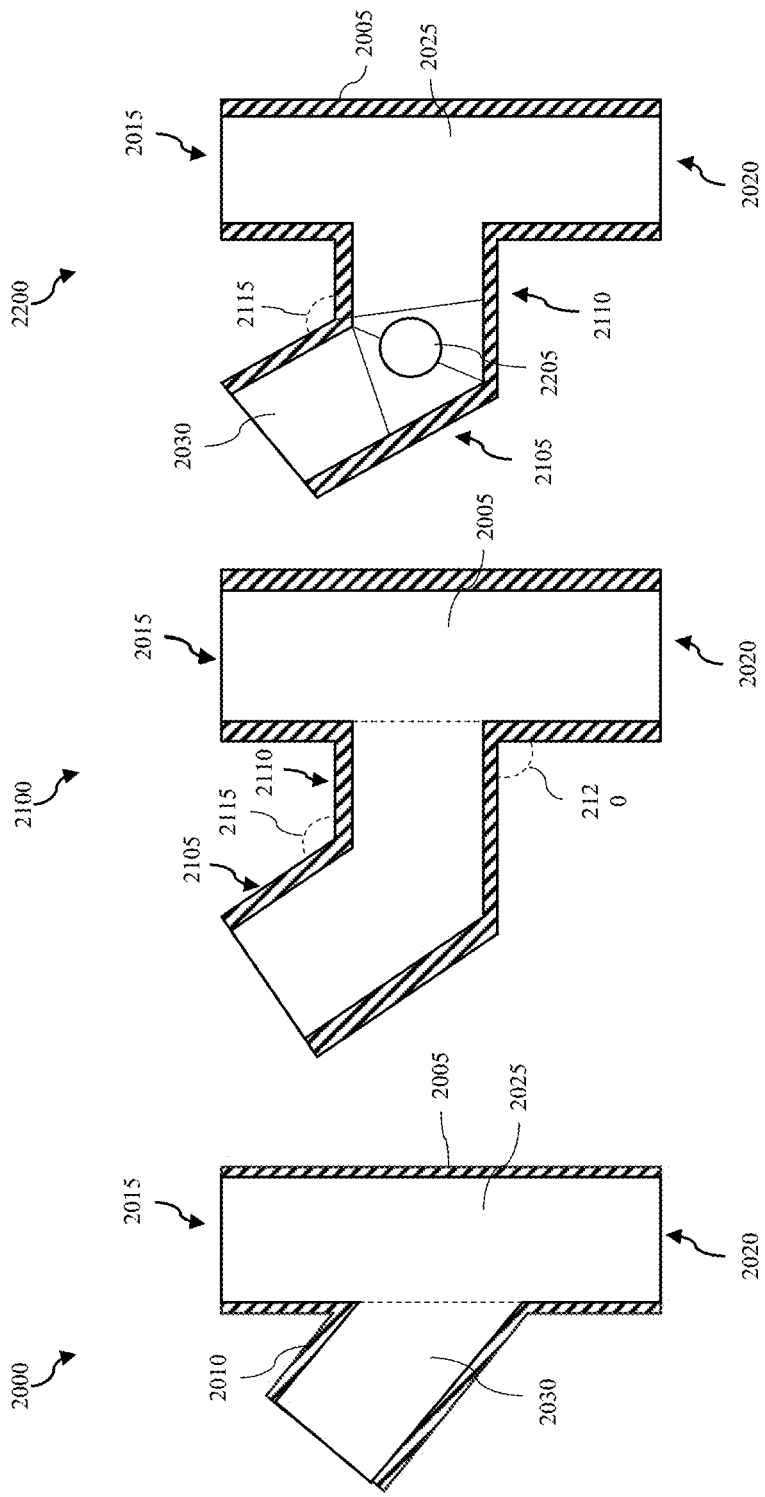

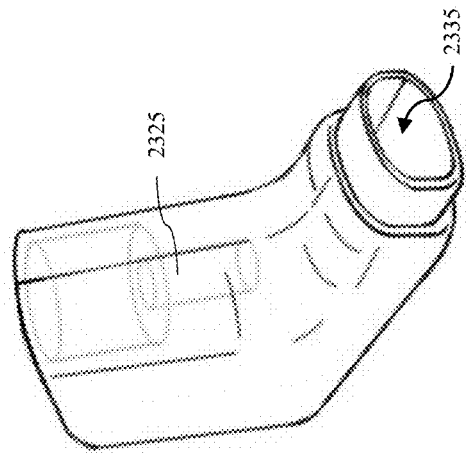
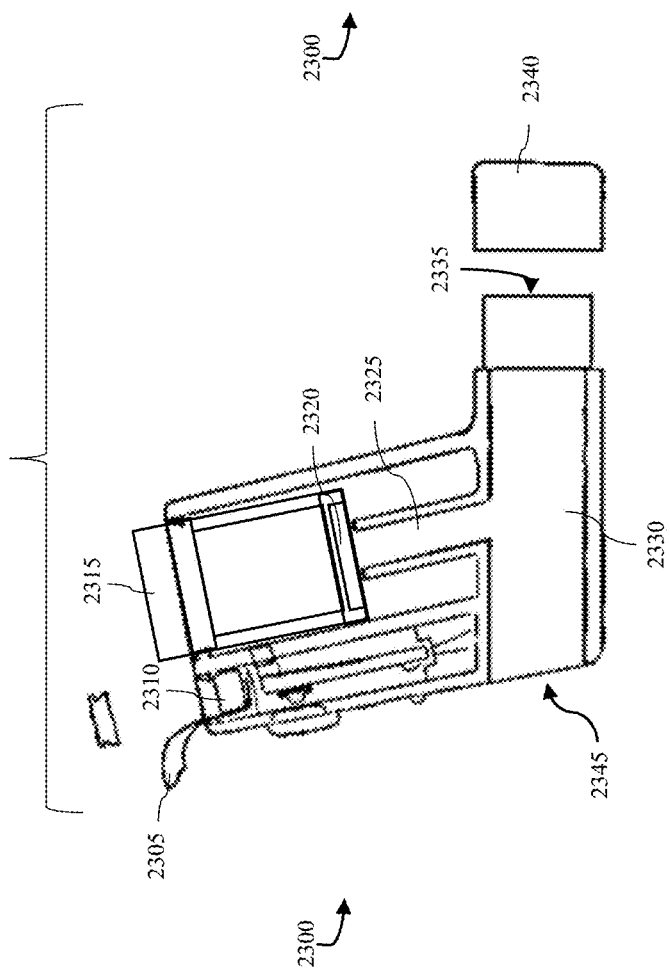
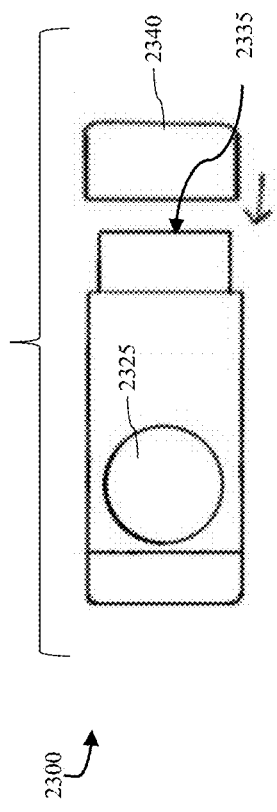

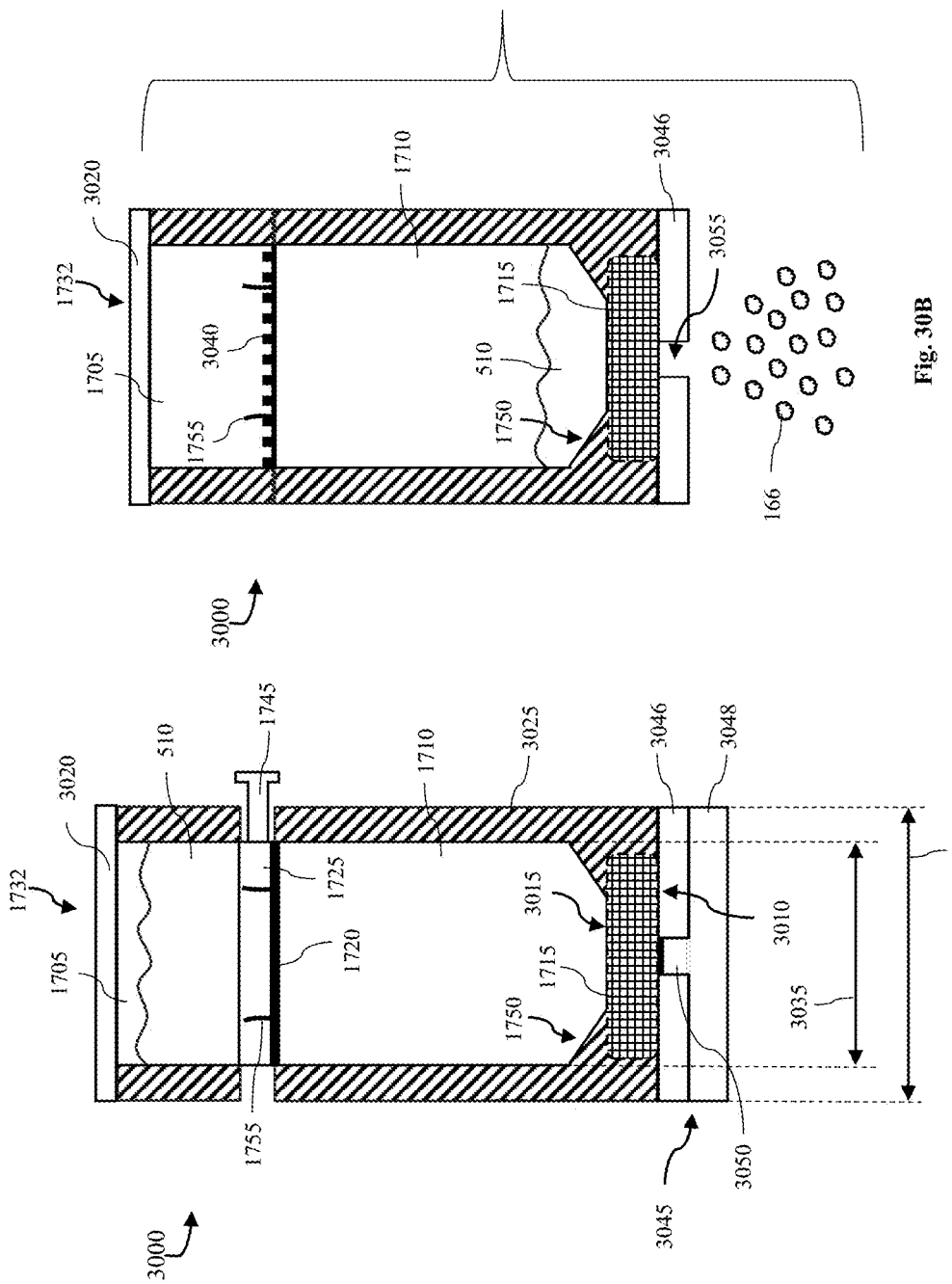

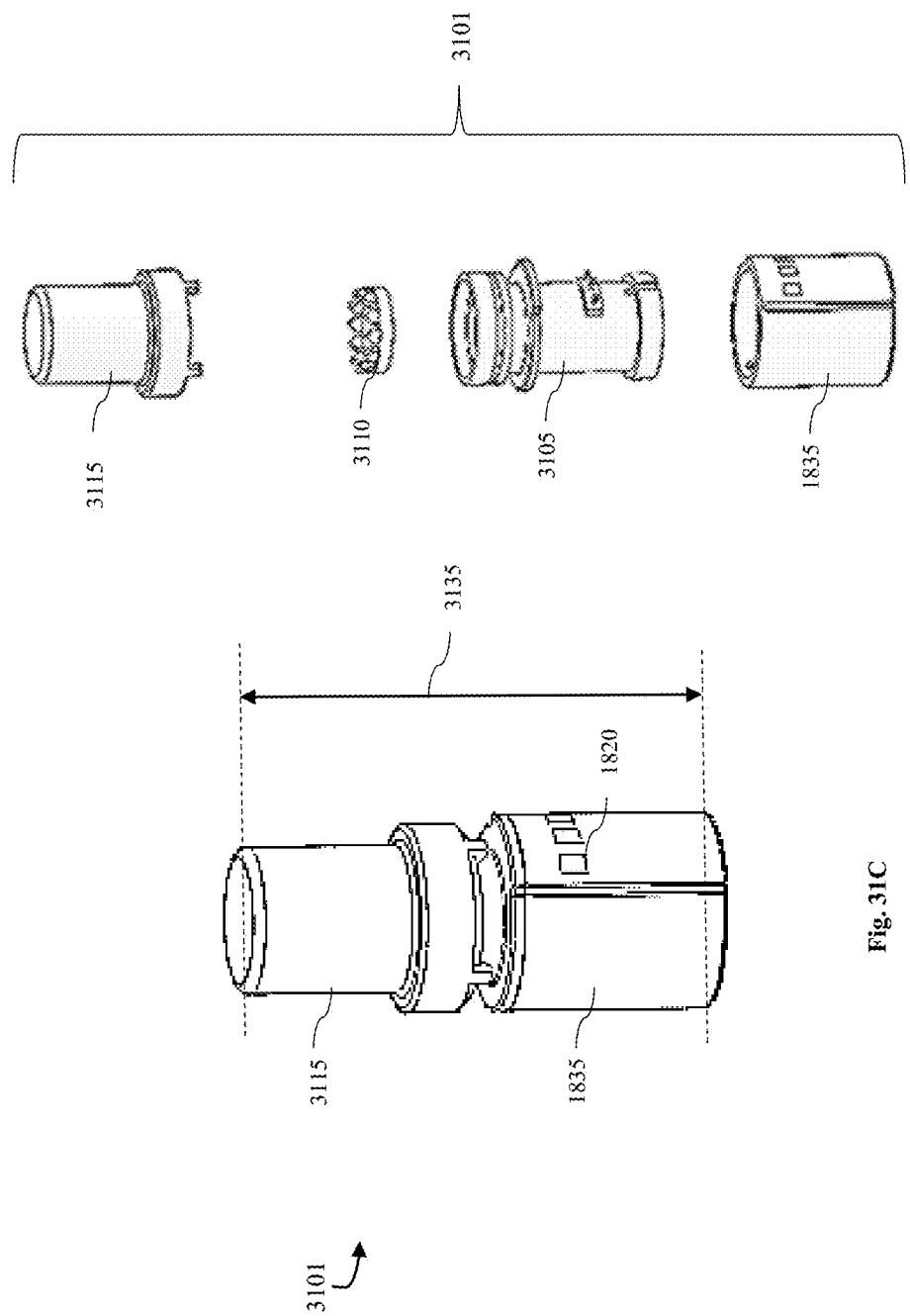

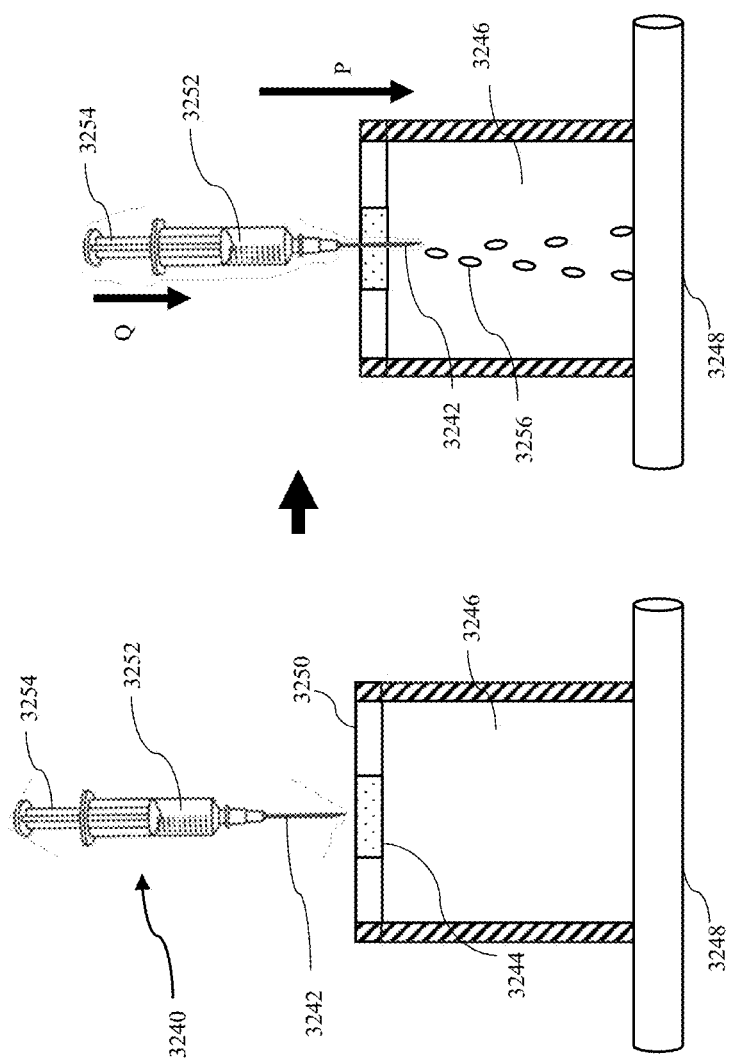

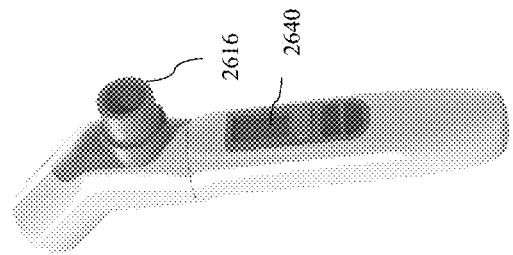
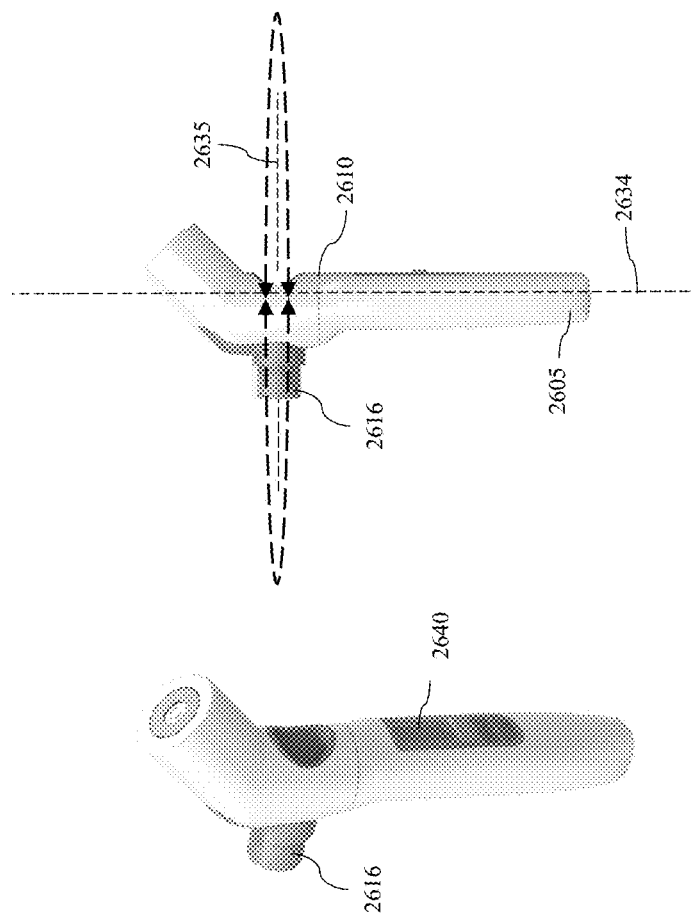
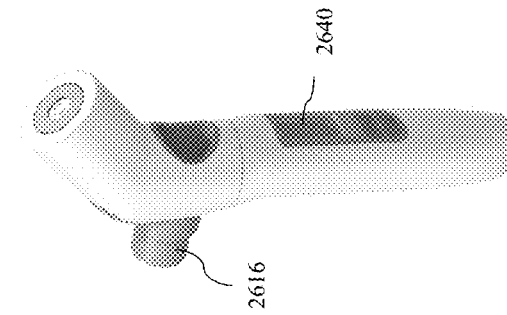
Fig. 36C
Fig. 36B
Fig. 36A

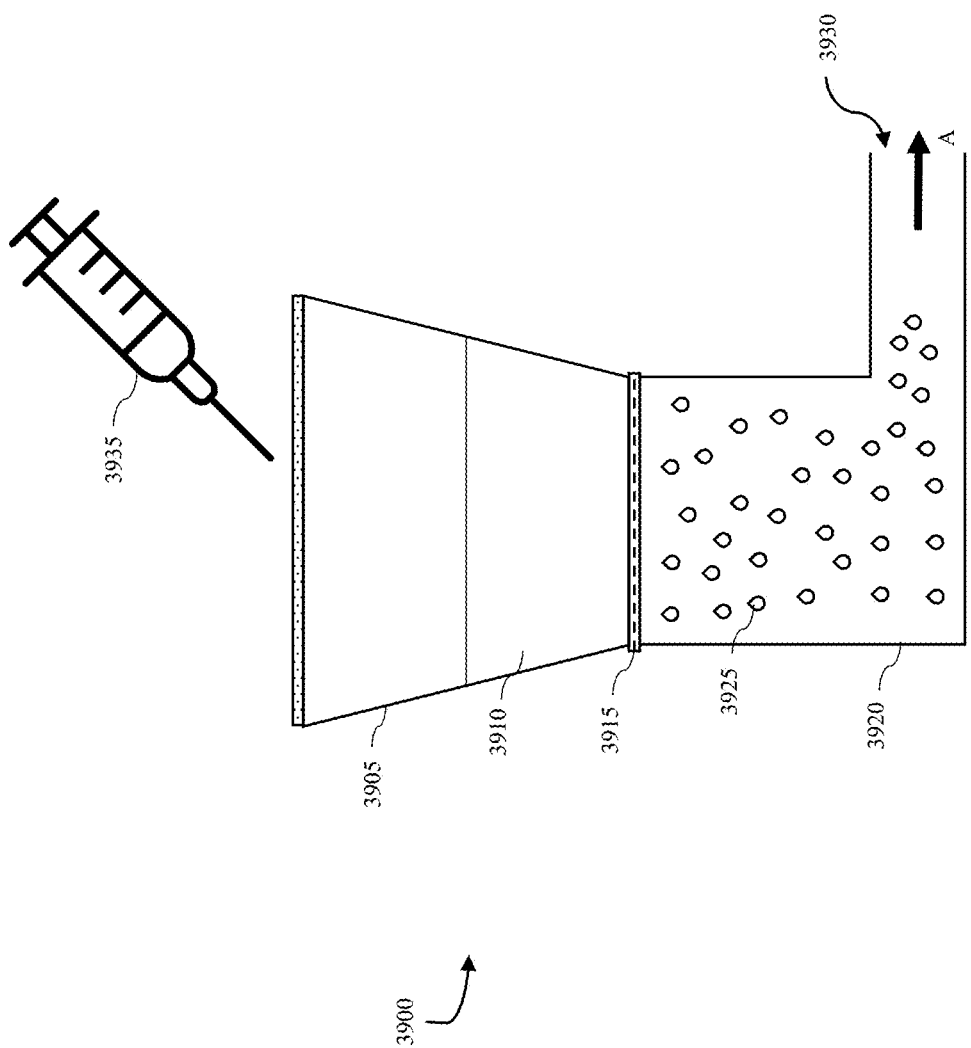

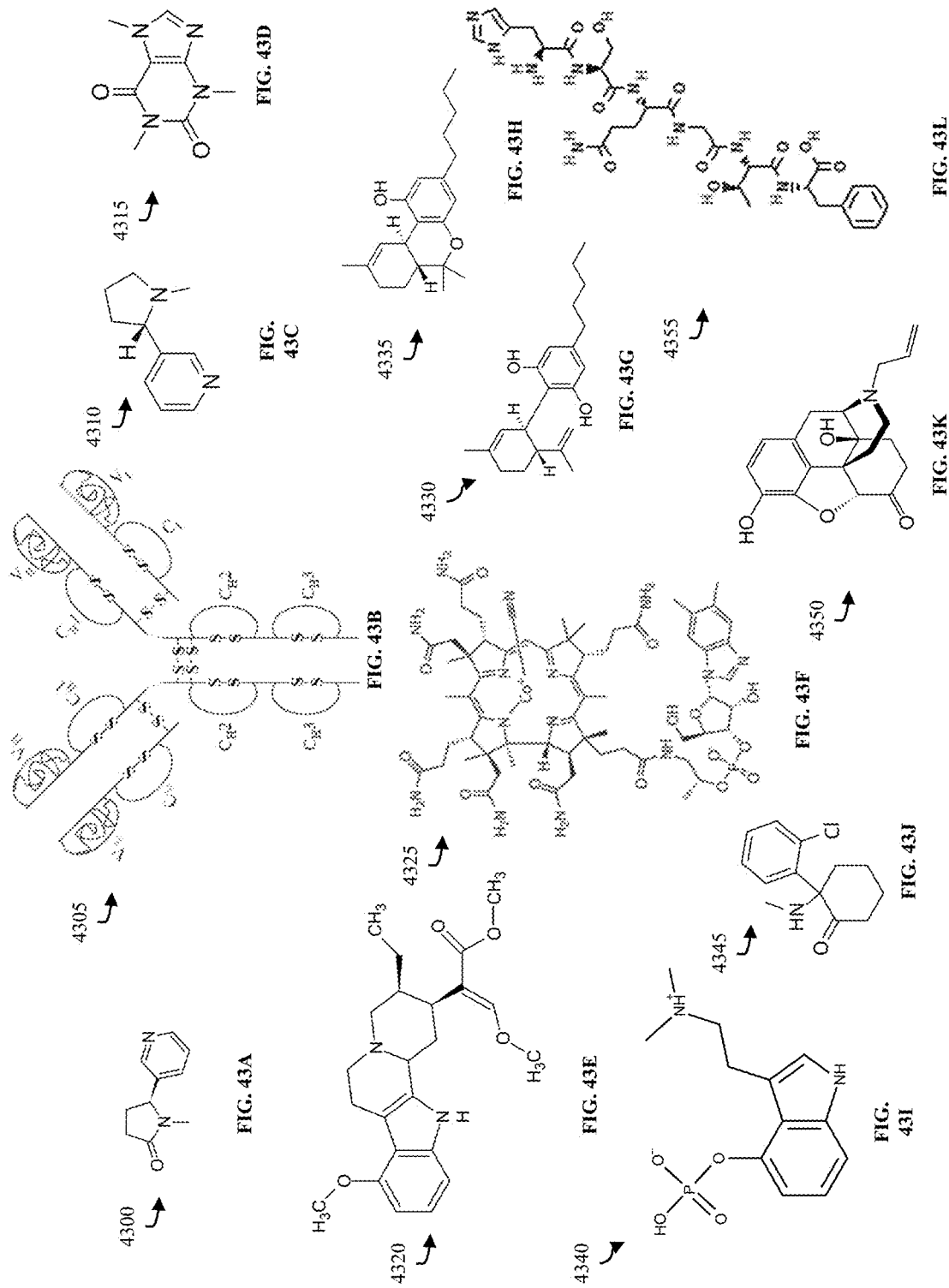

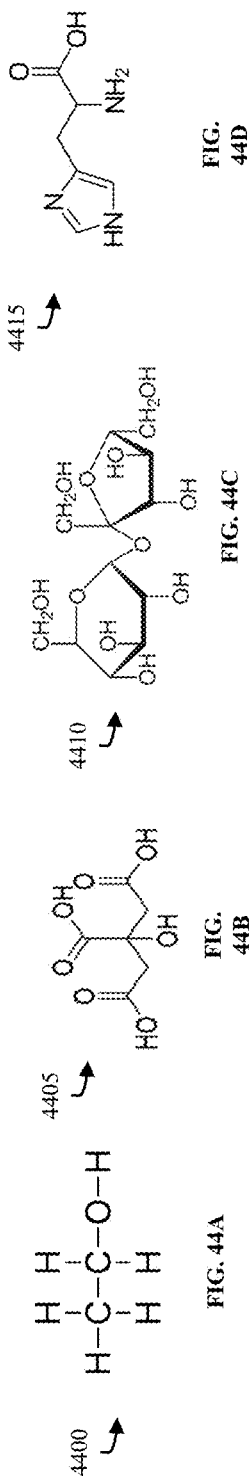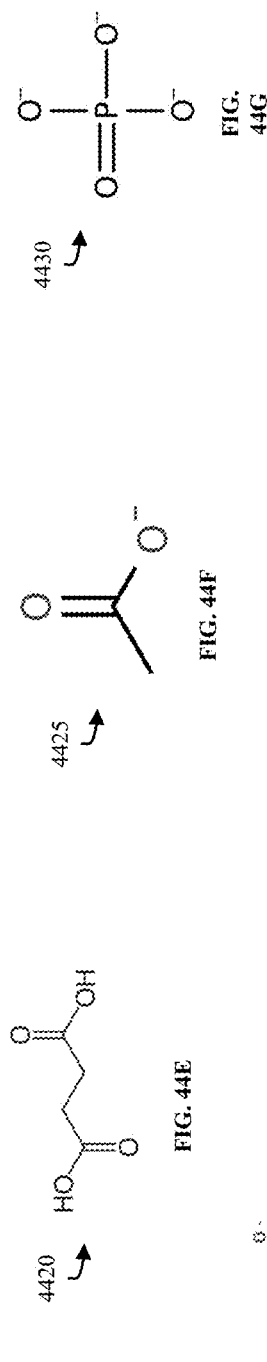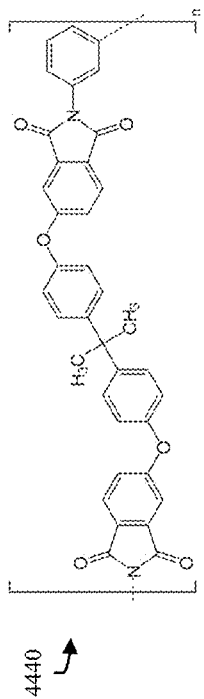
FIG. 44A, FIG. 44B, FIG. 44C, FIG. 44D, FIG. 44E, FIG. 44F, FIG. 44G, FIG. 44H, FIG. 44I

4450

4455

4445

METHODS AND SYSTEMS FOR DELIVERING FORMULATIONS TO USERS USING MODULAR DEVICE HAVING REMOVABLE CARTRIDGE

REFERENCE TO RELATED APPLICATIONS

This application is a continuation in part application of U.S. Non-Provisional application Ser. No. 18/529,978 titled "Apparatus, Methods, and Systems for Providing Pharmaceutical Compositions and Administering Medications to Patients" and filed Dec. 5, 2023, which claims the benefit of U.S. Provisional Application Ser. No. 63/437,568 titled "Compositions, Methods, and Systems for Providing a Nebulized Solution" and filed Jan. 6, 2023.

The U.S. Non-Provisional application Ser. No. 18/529,978 is also a continuation in part application of U.S. Non-Provisional application Ser. No. 18/373,142 titled "Apparatus, Methods, and Systems for Administering a Medication to an Animal" and filed Sep. 16, 2023, which is a continuation in part application of U.S. Non-Provisional application Ser. No. 18/449,838 titled "Apparatus, Methods, and Systems for Administering a Medication to a Patient" and filed Aug. 15, 2023, which is a continuation in part application of U.S. Non-Provisional application Ser. No. 18/224,502 titled "Apparatus, Methods, and Systems for Administering a Medication to a Patient" and filed Jul. 20, 2023, which is a continuation in part application of U.S. Non-Provisional application Ser. No. 18/207,242 titled "Apparatus, Methods, and Systems for Administering a Medication to a Patient" and filed Jun. 8, 2023, the subject matter of each of which is incorporated herein by reference.

CROSS-REFERENCES

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

TECHNICAL FIELD

The present disclosure relates to the field of mesh nebulizers, and more specifically to the field of mesh nebulizers for administering medications.

BACKGROUND OF THE INVENTION

A mesh nebulizer, also known as a vibrating mesh nebulizer, is a type of device used to deliver medication in a fine mist or aerosol form, which makes it easier for patients to inhale the medication directly into their lungs. This is particularly useful for the treatment of respiratory diseases like asthma, COPD (chronic obstructive pulmonary disease), or cystic fibrosis. The "mesh" in the name refers to a key component of the nebulizer: a small plate with multiple tiny holes, or a "mesh". This mesh vibrates at high frequencies, causing the liquid medication to be pushed through the tiny holes in the mesh, creating a fine mist or aerosol that can be inhaled. Mesh nebulizers are generally more efficient and portable than traditional jet nebulizers. They tend to be quiet, lightweight, and capable of nebulizing a wide range of medications. However, they can be more expensive, and the mesh plate can become blocked over time, requiring replacement. Proper cleaning and maintenance are important to keep the device functioning properly.

Inhalers are another form of medical devices that are used to deliver medication directly into the lungs. They are commonly used to treat conditions like asthma and chronic obstructive pulmonary disease (COPD). There are two main types of inhalers: metered-dose inhalers (MDIs) and dry powder inhalers (DPIs). MDIs use a chemical propellant to push the medication out of the inhaler. The user pushes down on the top of the inhaler and inhales at the same time to ensure the medication reaches the lungs. MDIs also can be used with a spacer, a tube-like device which provides a space for the medication to mix with air before reaching the lungs. This makes it easier for the medication to be inhaled and is especially helpful for children or people who have difficulty coordinating their breath with the release of the medication. DPIs do not use a chemical propellant. Instead, the medication is in a powder form, which the user inhales. Because they require a strong, quick inhalation to get the medication into the lungs, DPIs can be harder for some people to use than MDIs. Inhalers can deliver a variety of medications. However, the effectiveness of inhalers depends significantly on correct usage. Mistakes in technique can result in less medication reaching the lungs. These mistakes could include breathing too quickly or not deeply enough, not shaking the inhaler before use, or not using a spacer if needed. Some inhalers, especially newer or brand-name inhalers, can be quite expensive, potentially posing a financial burden.

Despite the various advancements in the field of medication delivery via capsules, there exist several challenges that continue to impact both patient compliance and the overall effectiveness of the treatment. One major challenge is the management of precise dosage control. In many instances, the ability to ensure a patient receives the exact dose of medication prescribed is crucial for the treatment's efficacy. However, it is a common problem that current capsule systems might not always deliver the accurate dose due to the limitations in the mechanism of action or variability in user technique. Further, many capsule systems for medication delivery require intricate instructions for use, which can lead to user errors. This is particularly relevant in instances where capsules need to be loaded into a device, such as an inhaler, where improper loading could result in suboptimal medication delivery. User-friendliness and ease of use are paramount in designing such systems, and any complexity can lead to misuse or non-compliance.

The potential for contamination is another issue that is often encountered in these systems. This can occur during the loading of the capsule into the delivery device or during the process of administering the medication itself. Both scenarios can compromise the sterility of the medication, leading to potential health risks. Another concern with these systems is the difficulty of integrating modern technologies such as sensors and connectivity features. The inclusion of these technologies could enhance the performance and functionality of the capsule systems by enabling real-time monitoring, improving dosage control, or allowing for personalized treatments. However, the integration of such features in a compact and user-friendly form remains a significant challenge. Regarding the specific use of medicine vials, while their adoption has provided a convenient way to store and administer liquid medication, issues arise in terms of potential wastage and the need for preservatives. Many vials are single-use to maintain sterility, but this can lead to medication wastage if the full vial content is not used. Additionally, the need for preservatives in multi-dose vials to prevent microbial contamination can lead to potential allergic reactions or side effects.

A common challenge observed in prior art pertaining to medication delivery via capsules revolves around the lack of interchangeability. A significant number of the pre-existing capsule systems are designed for a specific medication or a particular type of medication. This can be due to the unique physical or chemical properties of the medication, such as particle size in case of inhaled medication, or stability considerations for certain biologics. The lack of a standardized, universal system restricts the ability to switch between different medications using the same delivery device, limiting the versatility of the treatment options. Moreover, the ease of transportation is another aspect that remains wanting in many prior art capsule systems. Certain systems, particularly those requiring intricate loading or handling procedures, can prove cumbersome to transport, and potentially fragile. This is a critical consideration for patients who need to carry their medication for use throughout the day, or during travel. Ideally, medication delivery systems should be robust, compact, and portable, making them convenient for users to carry and use as required. Non-invasive administration of medication is an essential aspect of patient compliance and comfort. In the prior art, many delivery systems, particularly for certain conditions, might require invasive procedures such as injections, which can cause discomfort or distress to patients. These methods also raise potential issues of sterility and can increase the risk of infection. Therefore, there is a persistent need for delivery systems that can efficiently administer medication in a non-invasive manner, such as inhalation or oral administration, without compromising on the medication's efficacy.

Referring to compositions, methods, and systems for treating opioid dependency and opioid overdose, opioid dependency is a chronic condition characterized by a physical and psychological reliance on opioids. This dependency often arises from prolonged opioid use, whether for medical or non-medical reasons. The treatment of opioid dependency is complex, involving a gradual weaning process to mitigate withdrawal symptoms and reduce reliance on the drug. Effective management of opioid dependency requires a carefully calibrated approach to medication, often necessitating tailored dosages and controlled administration to support gradual reduction in opioid use.

In contrast, opioid overdose presents an acute emergency scenario. Overdosing on opioids can lead to critical symptoms such as respiratory depression, unconsciousness, and, in severe cases, death. Rapid intervention is crucial in these situations. Medications such as naloxone have been developed to counteract the life-threatening effects of an opioid overdose. The swift administration of such medications can reverse the overdose symptoms, making speed and efficiency in drug delivery systems critical for successful emergency response.

Both these aspects—the chronic management of opioid dependency and the acute response to opioid overdose—highlight the need for versatile and effective pharmaceutical solutions. These solutions must be adaptable to different scenarios, ranging from controlled, gradual dosage for dependency treatment to rapid, emergency administration for overdoses. The development of such treatments and delivery systems is central to addressing the complexities and urgent needs posed by the opioid crisis.

Naloxone is a critical drug in the fight against opioid overdose. As an opioid antagonist, it rapidly reverses the effects of opioid overdose, including respiratory depression, sedation, and hypotension, by displacing opioids from receptor sites in the brain. Its life-saving capabilities have been recognized globally, with its use in emergency settings being pivotal for immediate response to opioid overdoses. For broader accessibility, especially in non-medical environments, naloxone is also formulated for intramuscular or subcutaneous injection, frequently deployed using auto-injectors. Furthermore, nasal spray formulations of naloxone have gained prominence due to their needle-free, user-friendly nature, significantly enhancing public health responses to opioid overdoses.

A pressing issue in contemporary public health is the increasing incidence of xylazine, traditionally a veterinary sedative, being ingested by humans, often unknowingly, through its incorporation into street drugs. xylazine, not approved for human use, poses significant health risks when consumed by humans, leading to profound sedation, respiratory depression, and other severe side effects. The contamination of street drugs with xylazine has become a dangerous trend, contributing to a rise in drug-related emergencies and complications. This emerging problem highlights an urgent need for effective measures to counteract the effects of xylazine in humans. While Naloxone, commonly used to reverse opioid overdose, is ineffective against xylazine, the potential role of yohimbine, an alpha-2 adrenergic receptor antagonist, comes into focus. Given yohimbine's efficacy in reversing xylazine's effects in veterinary contexts, there is a growing interest in exploring its applicability for similar use in humans. The development of a safe and effective antidote or treatment protocol involving Yohimbine could be pivotal in addressing the complications arising from xylazine ingestion in humans. This situation underscores the need for rapid response from the medical community and drug regulatory authorities to mitigate this emerging public health concern. Tolazoline, a vasodilator and an alpha-adrenergic antagonist, is known for reversing the effects of sedatives and for its use in various medical applications. Its potential contribution to opioid overdose treatment is intriguing, given its pharmacological profile, which could complement the actions of other agents in managing the effects of opioid toxicity. Tolazoline is typically administered intravenously, especially in hospital environments for diagnosing vascular disorders and treating skin ulcers. In neonatal care, particularly in veterinary medicine, tolazoline is used intravenously to reverse sedative effects in neonates.

Albuterol, primarily known for treating bronchospasm in conditions like asthma and chronic obstructive pulmonary disease, works by relaxing the muscles in the airways and increasing airflow to the lungs. Albuterol is most effectively delivered through inhalation using metered-dose inhalers or nebulizers. This method ensures direct lung delivery, providing swift symptom relief. Additionally, albuterol is available in oral forms, including tablets and liquid preparations, though these are less common compared to inhalation routes. In severe cases, intravenous administration of albuterol may be warranted, albeit in a strictly monitored hospital setting.

Each of these active ingredients has a unique profile and mechanism of action, making them valuable in addressing various aspects of opioid overdose and dependency. However, the inherent limitations in prior art related to interchangeability, transportability, and non-invasive administration pose significant barriers to optimal patient care. The need for more adaptable, easily transportable, and less invasive delivery systems persists, driving the continuous pursuit for innovation in this field. As a result, there exists a need for improvements over the prior art and more particularly for improved, user-friendly, and reliable capsule systems and pharmaceutical compositions that can provide accurate dosing, maintain sterility, and integrate modern technologies for enhanced monitoring and control.

BRIEF SUMMARY OF THE INVENTION

Methods and systems for delivering formulations to users using modular device having removable cartridge are disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a formulation delivery system that includes a mouthpiece with a first attaching structure at one end and a removable cartridge with a second attaching structure that connects to the mouthpiece. The removable cartridge houses an atomizer at its first end and features a wick assembly with a removable cap and a wick made from an absorbent material. The wick, which transports fluid to the atomizer, is connected at one end to the removable cap and at the other end abuts the atomizer. The system also includes a channel within the removable cartridge; this channel extends to the cartridge's first end and houses the wick, while the removable cap is located outside the channel. Additionally, the system incorporates electronics that maintain a removable electrical connection with the cartridge.

In one embodiment, a method of administering at least one medication to a patient into the patient's mouth is disclosed. The method includes dispensing, using an atomizer, the at least one medication from a capsule in fluid communication with a tubular chamber, into the tubular chamber; and causing, air within a resilient air bladder in fluid communication with the tubular chamber to be conveyed from the resilient air bladder and into the tubular chamber such that the air conveyed from the resilient air bladder and the at least one medication dispensed from the capsule is administered to the patient. The method also includes, prior to dispensing the at least one medication from the capsule, disposing device on the patient's face and or a mouthpiece defining a tubular shaped body to be inserted into the patient's mouth. The device includes a mask defining a mask chamber within the mask that is surrounded by a rim on the periphery of the mask. The mask is to be positioned over the patient's mouth and nose, and by applying force with a hand of a rescuer to the mask to obtain a substantially air-tight seal against the patient's face. While applying the force with the hand of the rescuer to the mask, engaging with a second hand of the rescuer, a user interface on the device to cause the atomizer to atomize and to dispense the at least one medication from the capsule. While applying the force to the mask with the hand of the rescuer, and either during or after engaging with the user interface to cause the dispensing of the at least one medication from the capsule, the method further includes applying a second force with the second hand of the rescuer, to the resilient air bladder so that the air within the resilient air bladder is conveyed from the resilient air bladder and into the tubular chamber such that the air conveyed from the resilient air bladder and the at least one medication dispensed from the capsule is administered to the patient. One inventive aspect of this device is that only a single rescuer may be needed to easily administer medication to a patient.

Prior to dispensing the at least one medication from the capsule, the method further includes receiving, with a processor, a signal to start the atomizer to atomize the at least one medication, determining, using the processor based on the signal, a maximum volume of the at least one medication to atomize and/or a maximum amount of time to atomize the at least one medication. Next, the process sends, to the atomizer, a signal to cause the atomizer to atomize the maximum volume of the at least one medication and/or the at least one medication for the maximum amount of time. After the maximum volume or time has been attained, the process the receives, a third signal from a sensor that monitors an atomized volume of the at least one medication within the capsule or a first amount of time the atomizer atomizes the at least one medication. The signal is received from at least one of a remote computing device and the capsule. The method includes, after the processor determines that the atomized volume is at least as much as the maximum volume based on the third signal received and/or the first amount of time is at least as much as the maximum amount of time, then stopping the atomizer from continuing to atomize the at least one medication within the capsule. The processor is configured to send a fourth signal to stop the atomizer from continuing to atomize the at least one medication within the capsule after the processor determines that the atomized volume is at least as much as the maximum volume based on the third signal received.

In another embodiment, a system for administering at least one medication to a patient is disclosed. The system includes a resilient air bladder in fluid communication with a tubular chamber of a base unit, a capsule in fluid communication with the tubular chamber configured for carrying the at least one medication, and an atomizer disposed at least proximate to the capsule and in fluid communication with the tubular chamber. The atomizer is configured to atomize the at least one medication that is disposed within the capsule. The system further includes an air inlet and a first one-way valve in fluid communication with the resilient air bladder configured to allow fresh air to enter the resilient air bladder. The system includes an air outlet and a second one-way value in fluid communication the resilient air bladder and the tubular chamber. Fresh air is drawn into the resilient air bladder when it inflates.

Fresh air is forced through the second one-way valve and to the tubular chamber when the resilient air bladder deflates. Fresh air and the at least one medication atomized by the atomizer to mix together within the tubular chamber. The system further includes a mask defining a mask chamber within the mask. The mask is positioned over the patient's mouth and nose, a rim extending about a periphery of the mask to form a seal with the patient's face. In another embodiment, the system may include a mouthpiece defining a tubular shaped body. The capsule includes a capsule chamber for housing the at least one medication, a rubber section covering an open side of the capsule, the atomizer proximate to a second side of the capsule, and a sensor for detecting an amount of the at least one medication in the capsule.

In one embodiment, the mask attachment for the described capsule system is a specially designed piece that can be retrofit, sized, and shaped to substantially cover an animal's nose and/or mouth. Serving as the interface between the device and the animal, it facilitates the delivery of atomized medication. This mask attachment works in conjunction with the capsule system to direct the atomized medication to the desired area of the animal's respiratory system. By being adjustable in size and shape, it ensures that the mask can effectively conform to various animal anatomies, creating a seal that optimizes medication delivery. The mask attachment may be made of medical-grade silicone, rubber, or other flexible and non-reactive materials, allowing for easy cleaning, sterilization, and customization to different sizes and shapes. The customizability and retrofitting ability of the mask attachment represent a significant advancement over previous designs, overcoming prior limitations by providing more effective, comfortable, and controlled administration of atomized medication, thus offering more versatile and humane treatment options for animals in a medical setting.

The system further includes a housing and a first channel spanning from a first side of the housing to a second side of the housing. The system further includes a first longitudinal axis of the first channel, a first end portion of the first channel configured to receive a portion of a conduit that is in fluid communication with the air outlet of the resilient air bladder, and a second end portion of the first channel configured to receive a portion of either the mouthpiece or the mask. The system further includes a second channel disposed on the housing configured to receive a portion of the capsule and a second longitudinal axis defined by the second channel. The second longitudinal axis defines at most a 90-degree angle relative to the first longitudinal axis of the first channel. However, other angles, such as a 45-degree angle may be used and is within the spirit and scope of the present invention.

The system further includes a processor housed by the housing. The housing houses the user interface housed by the housing. The user interface is configured to be acted on by a rescuer to start the atomizer to atomize the at least one medication. The user interface may include control for being manipulated by the hands of a user, a graphical display, an audio sensor for receiving audio signals from the user to control the device. The processor is configured for receiving a signal to start the atomizer to atomize the at least one medication, sending a second signal to the atomizer to cause the atomizer to atomize the at least one medication within the capsule and convey the atomized at least one medication into the second channel, receiving a third signal from the sensor when the sensor detects that the at least one medication within the capsule is less than a minimum threshold, and sending a fourth signal to turn off the atomizer after the third signal is received.

In another embodiment, a method for administering at least one medication to a patient when the patient is unconscious and when the patient is consciousness is disclosed. The method includes inserting a capsule containing the at least one medication into a device in fluid communication with a tubular chamber, wherein the at least one medication is a liquid formulation. The method further includes activating an atomizer to atomize the at least one medication to generate at least one atomized medication comprising a plurality of particles, wherein each particle of said plurality of particles is at most four microns in diameter. The method further includes dispensing the at least one atomized medication from the capsule in fluid communication with the tubular chamber, into the tubular chamber and administering the at least one atomized medication to the patient using the device. If the patient is unconsciousness, then administering the at least one atomized medication comprises at least partially deflating a resilient air bladder in fluid communication with the tubular chamber causing air within the resilient air bladder to be conveyed from the resilient air bladder into the tubular chamber. Prior to administering the at least one atomized medication to the patient using the device, the method includes applying a force to a mask, positioned over the patient's nose and the patient's mouth and in fluid communication with the tubular chamber. The resilient air bladder is removable.

The method further includes removing the resilient air bladder from a receiving section and attaching a cap to cover an opening of the receiving section. If the patient is consciousness, then the method includes administering the at least one atomized medication to the patient using the device comprises conveying the at least one atomized medication from the tubular chamber though at least one of a mouthpiece that is in fluid communication with the tubular chamber and a mask, positioned over the patient's nose and the patient's mouth and in fluid communication with the tubular chamber. The capsule includes a first chamber comprising the liquid formulation, a second chamber below and separate from the first chamber, and the atomizer disposed at least proximate to a portion of the second chamber that is distal to the first chamber. The method further includes causing the liquid formulation to move from the first chamber to the second chamber. Prior to causing the liquid formulation to move from the first chamber to the second chamber, the method further includes removing a stop on the capsule that inhibits the first chamber from translating relative to the second chamber. After removing the stop of the capsule, the method includes applying a second force to the first chamber causing the first chamber to translate relative to the second chamber rupturing a membrane disposed between the first chamber and the second chamber thus providing fluid communication between the first chamber and the second chamber. Prior to activating the atomizer, the method includes providing power to the atomizer by removing an insulator that prevents electrical communication between the atomizer and a power source. The method further includes conveying the at least one atomized medication through a second tubular chamber that is disposed between the patient's face and the tubular chamber thereby causing the at least one atomized medication to form a substantially stable and uniform aerosol. The at least one medication comprises a narcotic antagonist.

If the patient is in an intubated state, the method further includes removing the resilient air bladder from a receiving section of the device, attaching a conduit in fluid communication with a ventilator air outlet to the receiving section. and attaching an endotracheal tube to the device so that endotracheal tube is in fluid communication with the tubular chamber and the conduit. The receiving section is a first end portion of a first channel of the device configured to receive a portion of a conduit that is in fluid communication with an air outlet of the resilient air bladder. The tubular chamber is a removable modular tubular extension including a first extension tubular chamber and a second extension tubular chamber. The first extension tubular chamber includes a first extension receiving section and a second extension chamber receiving section and defines the first channel. The second extension tubular chamber is substantially in fluid communication with the first extension tubular chamber. The method further includes inserting the second extension tubular chamber into a device receiving section such that the second extension tubular chamber is in fluid communication with the second channel of the device and such that the second extension tubular chamber defines at least a portion of the second channel. The tubular chamber of the device comprises a first channel having a first end portion, a second end portion, and a first longitudinal axis.

The second extension tubular chamber includes a first portion substantially perpendicular to the first extension tubular chamber and a second portion disposed at a first angle relative to a longitudinal axis of the first portion and which corresponds to the first longitudinal axis of the first channel. An angle between the first extension tubular chamber and the second extension tubular chamber is adjustable. The method further includes adjusting the angle between the first extension tubular chamber and the second extension tubular chamber to a predetermined angle and locking the angle between the first extension tubular chamber and the second extension tubular chamber at the predetermined angle. The method includes linking the capsule to the device such that the capsule further includes a transponder. The method includes administering the at least one atomized medication to the patient using the device further includes the at least one atomized medication breaking the patient's blood brain barrier.

In another embodiment, a capsule system for use with a medical device for administering at least one atomized medication to a patient is disclosed. The capsule system comprises at least one chamber, at least one medication disposed within the at least one chamber, and an atomizer at a lower end portion of the capsule system. The capsule system further includes at least one electrical contact and at least one sensor. The at least one sensor is a fluid sensor. The at least one electrical contact is in electrical communication with a power source.

The capsule system also comprises a housing that substantially encloses the at least one chamber, the housing comprising an asymmetrical transverse cross-sectional shape. The atomizer is disposed proximate to a bottom portion of the at least one chamber. The at least one chamber comprises at least one tapered wall section to direct the at least one medication toward the atomizer. The capsule system further includes a stopper in fluid communication with the at least one chamber.

The capsule system further comprises an electrical conductor connecting the capsule to the medical device such that the capsule comprises a port. The medical device comprises at least one of a display, a processor, and a power source. The capsule comprises a capsule width and the at least one chamber comprises a chamber width such that the chamber width substantially spans the capsule width. The at least one chamber is in fluid communication with an external container via an elongated tube, the external container having the at least one medication.

The capsule comprises a plug disposed at the lower end portion of the capsule system. The at least one chamber comprises a first chamber disposed above a second chamber; wherein the first chamber comprises the at least one medication and the second chamber comprises the atomizer. A membrane preventing fluid communication is disposed between the first chamber from the second chamber. A stop is disposed between the first chamber and the second chamber inhibiting the first chamber from translating relative to the second chamber. At least one rupturing element is in attachment with the first chamber configured to engage the membrane when a first force is applied to translate the first chamber relative to the second chamber.

In another embodiment, a method for veterinary administration of at least one medication to an animal is disclosed. The method includes inserting a capsule containing the at least one medication into a device in fluid communication with a tubular chamber, wherein the at least one medication is a liquid formulation and activating an atomizer to atomize the at least one medication to generate at least one atomized medication. Prior to administering the at least one atomized medication to the animal using the device, the method further includes applying a force to a mask, positioned over an animal's muzzle and in fluid communication with the tubular chamber. The method also includes administering the at least one atomized medication to the animal using the device.

In one, embodiment the animal may a horse or other large animal. The at least one medication may be an aqueous suspension or a solution comprising at least one of cells, cellular byproducts, and cell-derived products. The cells, the cellular byproducts, and cell-derived products are stem cells. The at least one medication comprises at least one of peptides, proteins, growth factors, cytokines, exosomes, and extracellular vesicles derived from human mesenchymal stem cells suspended and/or dissolved in an aqueous medium. The at least one medication comprises no preservatives. The capsule comprises a first chamber comprising the liquid formulation and a second chamber below and separate from the first chamber. The atomizer is disposed at least proximate to a portion of the second chamber that is distal to the first chamber.

Administering the at least one atomized medication comprises at least partially deflating a resilient air bladder in fluid communication with the tubular chamber causing air within the resilient air bladder to be conveyed from the resilient air bladder into the tubular chamber. The method further comprises causing the liquid formulation to move from the first chamber to the second chamber. Prior to causing the liquid formulation to move from the first chamber to the second chamber, the method further comprises removing a stop on the capsule that inhibits the first chamber from translating relative to the second chamber. After removing the stop of the capsule, applying a second force to the first chamber causing the first chamber to translate relative to the second chamber rupturing a membrane disposed between the first chamber and the second chamber thus providing fluid communication between the first chamber and the second chamber. Prior to activating the atomizer, the method comprises providing power to the atomizer by removing an insulator that prevents electrical communication between the atomizer and a power source. The method further comprises conveying the at least one atomized medication through a second tubular chamber that is disposed between the animal's muzzle and the tubular chamber thereby causing the at least one atomized medication to form a substantially stable and uniform aerosol.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 2 is a diagram of a side view of a system for administering medication to a patient, according to a second embodiment;

FIG. 3A is a diagram of a side view of a system for administering medication to a patient, according to a third embodiment, wherein a biasing element is in an extended state;

FIG. 3B is a diagram of a side view of a system for administering medication to a patient, according to the third embodiment, wherein a biasing element is in a compressed state;

FIG. 3C is a diagram illustrating the main electrical components of the system for administering medication to a patient, wherein biasing elements are in an extended state, according to the third embodiment;

FIG. 3D is a diagram illustrating the main electrical components of the system for administering medication to a patient, wherein biasing elements are in a compressed state, according to the third embodiment;

FIG. 5 is a diagram of a front view of a capsule, according to a first example embodiment;

FIG. 14A is a perspective view of an attachment for administering medication to a patient, according to the first embodiment;

FIG. 14B is a top view of an attachment for administering medication to a patient, according to the first embodiment;

FIG. 14C is a side view of an attachment for administering medication to a patient, according to the first embodiment;

FIG. 17A is a cross-sectional side view of the capsule including a stop, according to a fourth example embodiment;

FIG. 17B is a cross-section of a side view of the capsule, wherein the stop is removed, according to a fourth example embodiment;

FIG. 17C is a cross-section of a side view of the capsule, according to a fifth example embodiment;

FIG. 18D is an exploded perspective view of the capsule, according to the third example embodiment;

FIG. 20 is a cross-section of a modular tubular extension, according to a first example embodiment.

FIG. 21 is a cross-section of a modular tubular extension, according to a second example embodiment.

FIG. 22 is a cross-section of a modular tubular extension, according to a third example embodiment.

FIG. 23 illustrates the device for administering at least one medication to a patient in an unconscious state to a conscious state, according to an inhaler embodiment.

FIG. 24 illustrates the device for administering at least one medication to a patient in an unconscious state to a conscious state, according to the inhaler embodiment.

FIG. 25 illustrates the device for administering at least one medication to a patient in an unconscious state to a conscious state, according to the inhaler embodiment.

FIG. 30A is a cross-section of a side view of a capsule system for use with a medical device for administering at least one atomized medication to a patient, according to an example embodiment;

FIG. 30B is a cross-section of a side view of the capsule system, according to an example embodiment;

FIG. 31C is a side perspective view of a capsule system including the removable container, according to an example embodiment;

FIG. 31D is an exploded perspective view of the capsule system including the removable container, according to an example embodiment;

FIGS. 32C and 32D illustrate operation of a removable cartridge of a device for administering at least one formulation to a user, according to another example embodiment.

FIG. 36A is a perspective side view of the wand embodiment of the medical device, according to an example embodiment;

FIG. 36B is a side view of the wand embodiment of the medical device, according to an example embodiment;

FIG. 36C is a perspective side view of the wand embodiment of the medical device, according to an example embodiment.

Figure 38A:
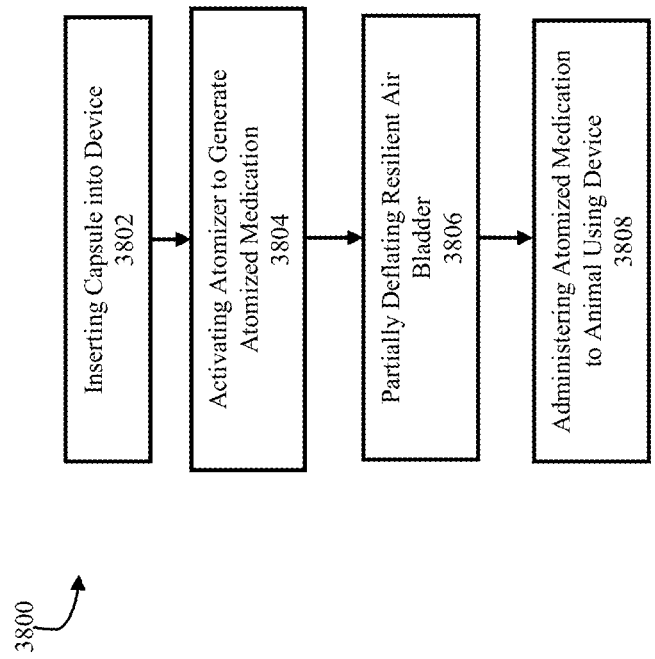
FIG. 38A is a flowchart diagram illustrating steps for a method for veterinary administration of at least one medication to an animal, according to an example embodiment.
Figure 38B:
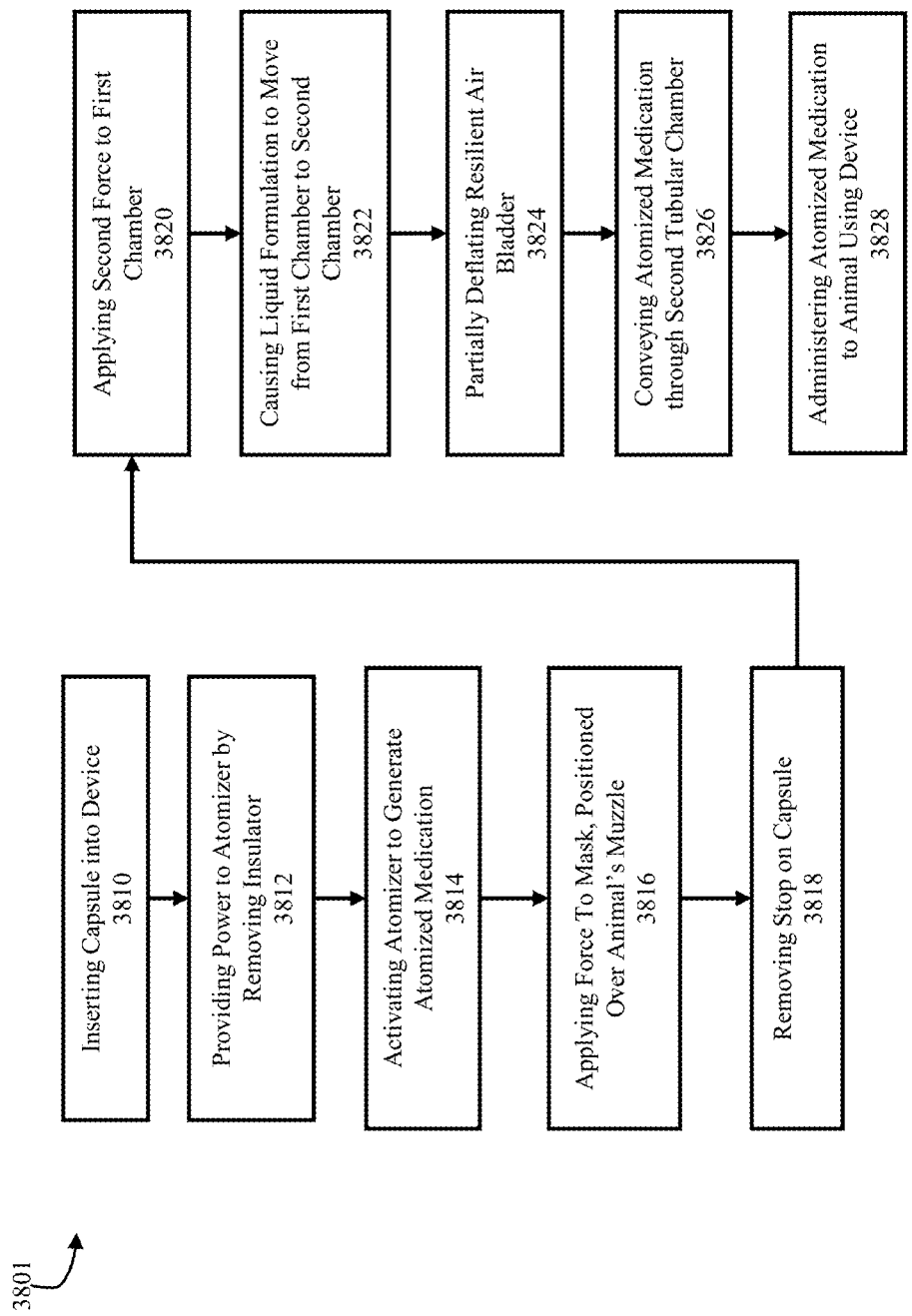

FIG. 38B a flowchart diagram illustrating steps for a method for veterinary administration of at least one medication to an animal, according to an example embodiment.

Figure 40:
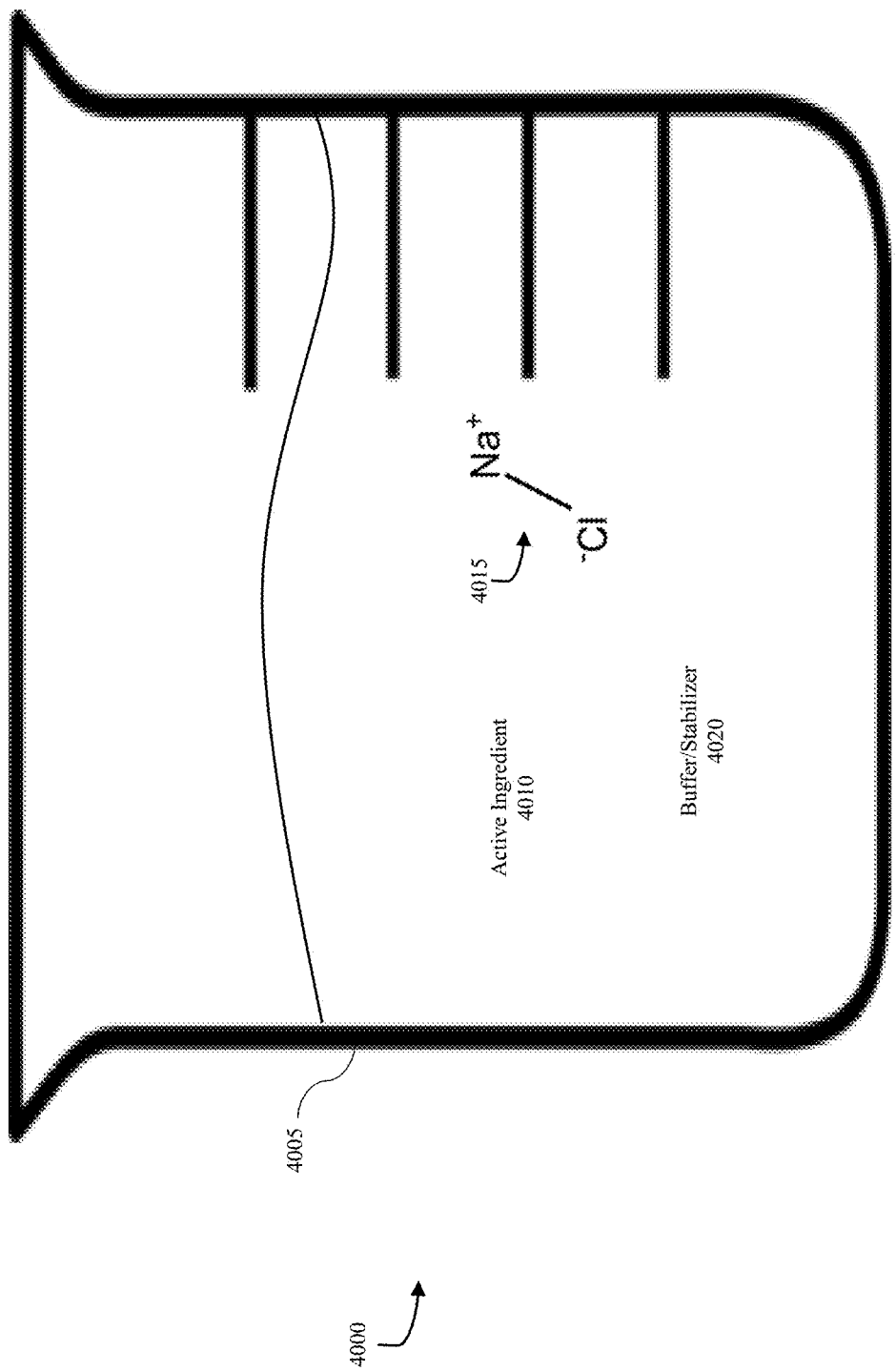
Figure 41:
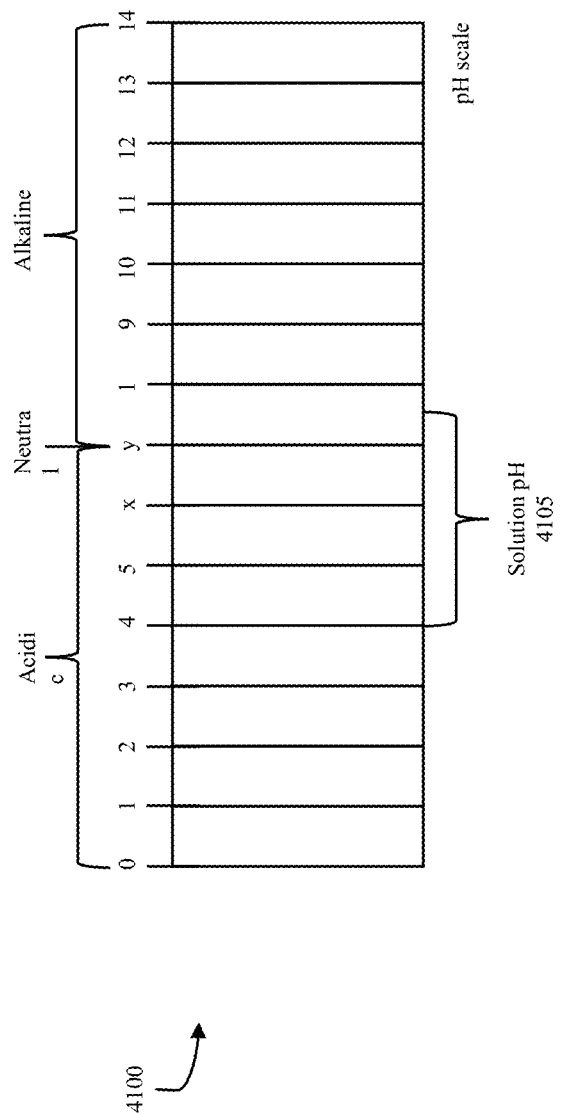
Figure 42:
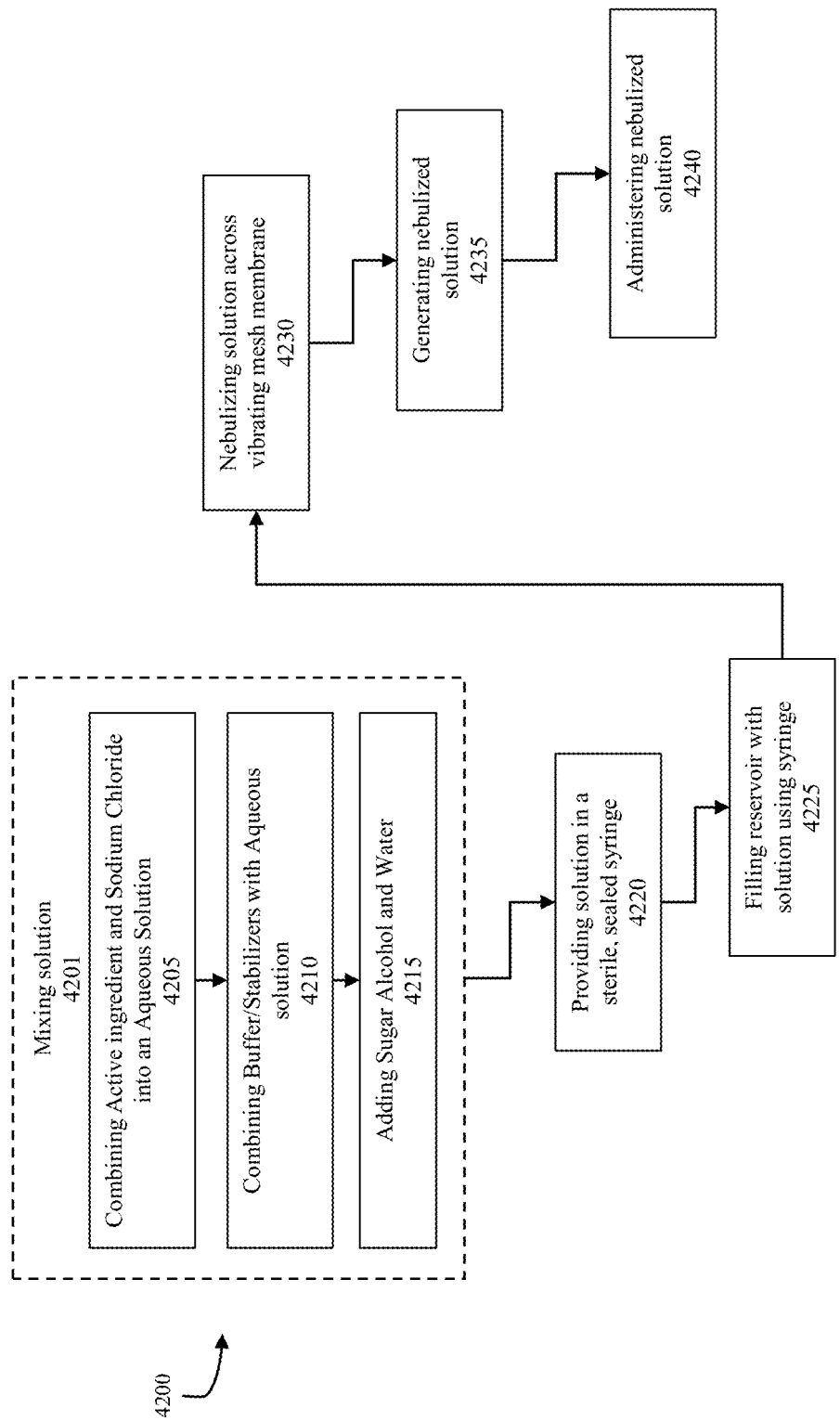
Figure 44K:
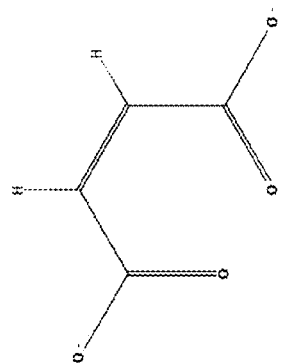
Figure 44L:
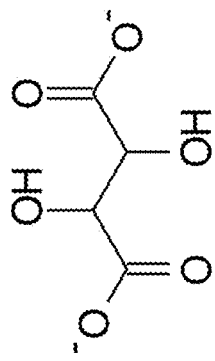
Figure 44J:
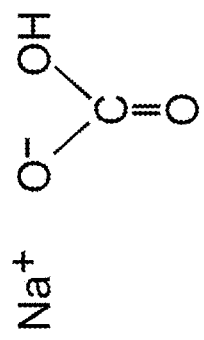
Figure 45:
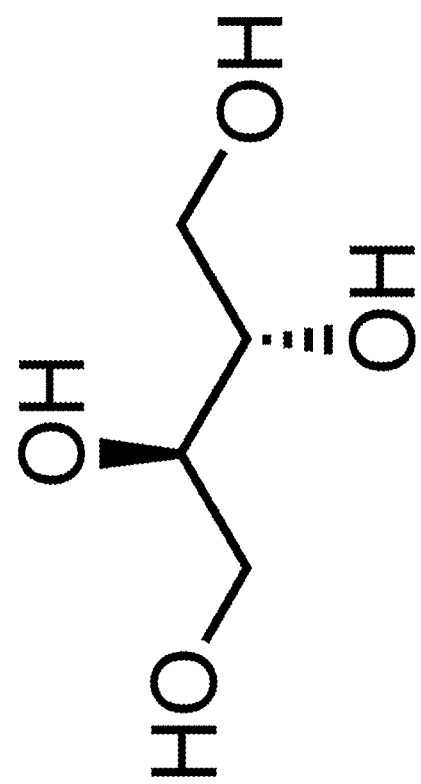
Figure 46:
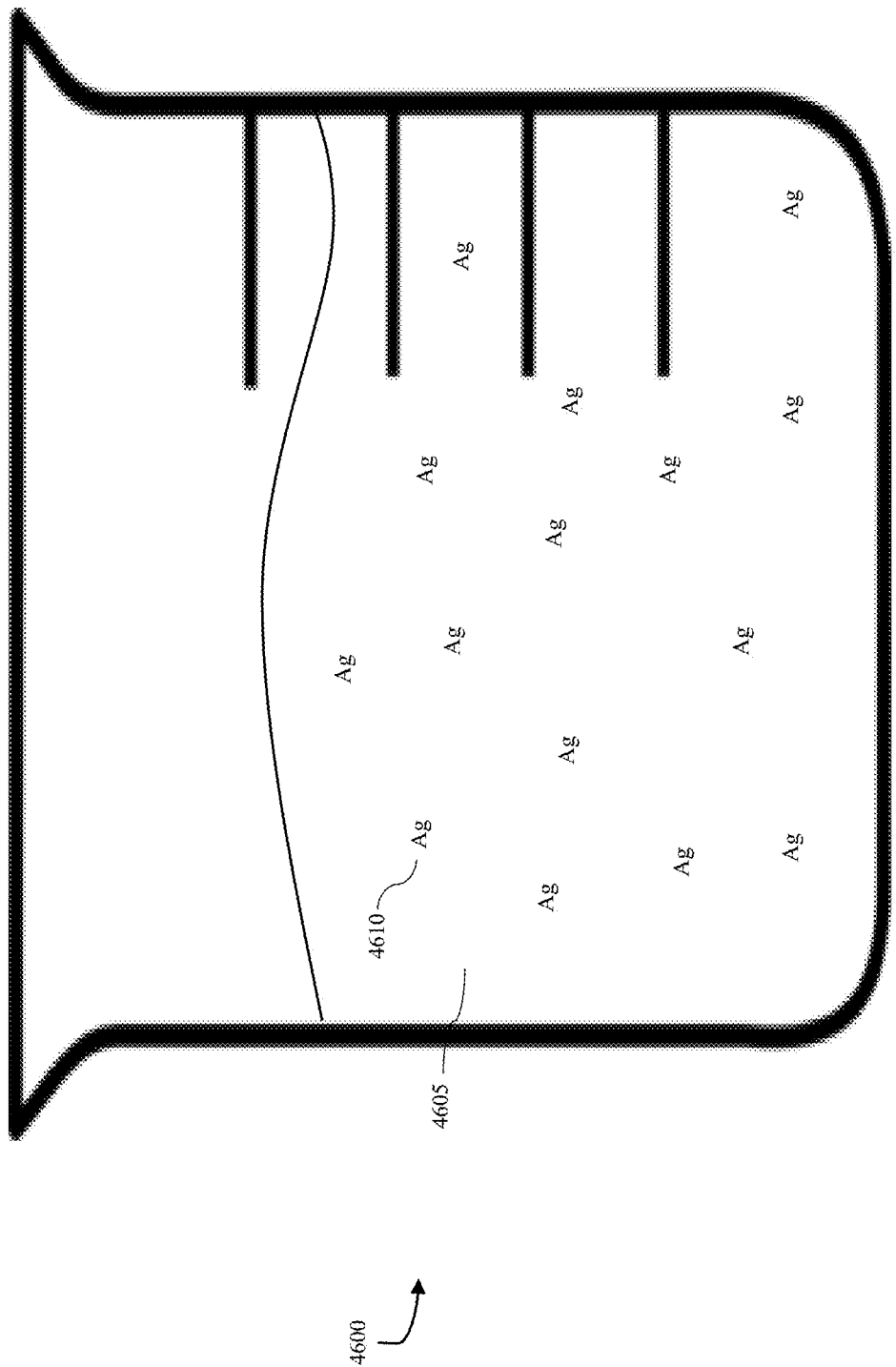

FIG. 39 is a side view of an active vibrating instrument, according to an example embodiment;

FIG. 40 is a side view of a beaker containing a solution for use with the active vibrating instrument, according to an example embodiment;

FIG. 41 is a block diagram of a pH scale, according to an example embodiment;

FIG. 42 is a flow diagram of a method of administering the solution for use with the active vibrating instrument, according to an example embodiment;

FIG. 43A is a perspective view of the molecular structure of cotinine, according to an example embodiment;

FIG. 43B is a perspective view of the molecular structure of adalimumab, according to an example embodiment;

FIG. 43C is a perspective view of the molecular structure of nicotine, according to an example embodiment;

FIG. 43D is a perspective view of the molecular structure of caffeine, according to an example embodiment;

FIG. 43E is a perspective view of the molecular structure of kratom, according to an example embodiment;

FIG. 43F is a perspective view of the molecular structure of vitamin B12, according to an example embodiment;

FIG. 43G is a perspective view of the molecular structure of cannabidiol, according to an example embodiment;

FIG. 43H is a perspective view of the molecular structure of tetrahydrocannabinol, according to an example embodiment;

FIG. 43I is a perspective view of the molecular structure of psilocybin, according to an example embodiment;

FIG. 43J is a perspective view of the molecular structure of ketamine, according to an example embodiment;

FIG. 43K is a perspective view of the molecular structure of naloxone (Narcan®), according to an example embodiment;

FIG. 43L is a perspective view of the molecular structure of glucagon, according to an example embodiment;

FIG. 44A is a perspective view of the molecular structure of ethyl alcohol, according to an example embodiment;

FIG. 44B is a perspective view of the molecular structure of citric acid, according to an example embodiment;

FIG. 44C is a perspective view of the molecular structure of sucrose, according to an example embodiment;

FIG. 44D is a perspective view of the molecular structure of histidine, according to an example embodiment;

FIG. 44E is a perspective view of the molecular structure of succinate, according to an example embodiment;

FIG. 44F is a perspective view of the molecular structure of acetate, according to an example embodiment;

FIG. 44G is a perspective view of the molecular structure of phosphate, according to an example embodiment;

FIG. 44H is a perspective view of the molecular structure of citrate, according to an example embodiment;

FIG. 44I is a perspective view of the molecular structure of polyetherimide, according to an example embodiment;

FIG. 44J is a perspective view of the molecular structure of sodium bicarbonate, according to an example embodiment;

FIG. 44K is a perspective view of the molecular structure of maleate, according to an example embodiment;

FIG. 44L is a perspective view of the molecular structure of tartrate, according to an example embodiment;

FIG. 45 is a perspective view of the molecular structure of a sugar alcohol, according to an example embodiment; and FIG. 46 is a side view of colloidal silver in a beaker, according to an example embodiment.

Figure 48:
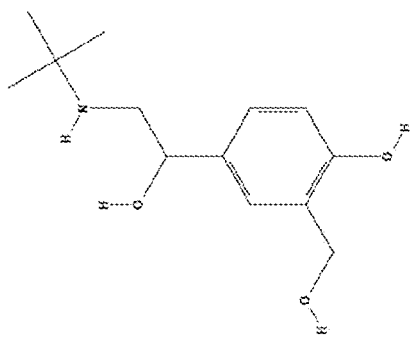
Figure 50:
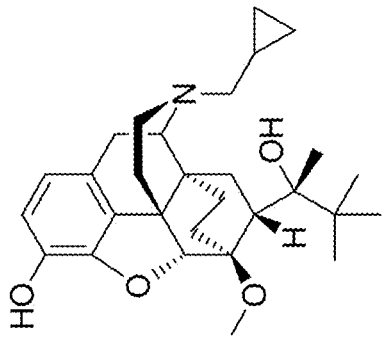
Figure 47:
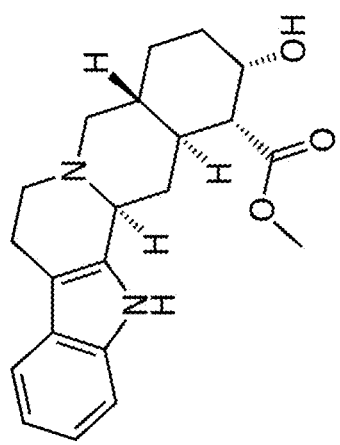
Figure 49:
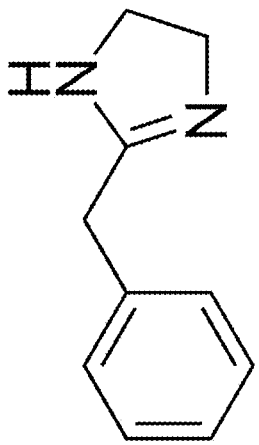

FIG. 47 is a perspective view of the molecular structure of yohimbine, according to an example embodiment;

FIG. 48 is a perspective view of the molecular structure of albuterol, according to an example embodiment;

FIG. 49 is a perspective view of the molecular structure of tolazoline, according to an example embodiment;

FIG. 50 is a perspective view of the molecular structure of buprenorphine, according to an example embodiment;

Like reference numerals refer to like parts throughout the various views of the drawings. FIGS. 11A through 16B, FIGS. 18A through 18D, FIGS. 31A through 31B, and FIGS. 34A through 36C are drawn to scale.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims. In the accompanying figures, dashed lines are employed to denote the presence of components or structures that are contained within another device, which is illustrated using straight bold lines. This graphical representation provides the overall device architecture and its functional interrelationships with other components.

The disclosed embodiments improve upon the problems with the prior art by providing an apparatus, system, and method that allows for controlled and measured doses of medication that need to be administered to a patient via inhalation, such as in the treatment of respiratory conditions or overdoses. The method allows for precise administration of the medication because it ensures the system administers the medication in the capsule depending on the needs of certain medical situations. The system includes modular components such that the apparatus can be utilized in different scenarios. For example, depending on the type of modular cardiopulmonary device, the system may be used on a patient that is laying down, positioned upright, conscious, or unconscious. The system may allow a patient to treat themselves or may require an authorized user to treat the patient using the system. The system is configured to only require one rescuer having two hands to operate the system.

Additionally, the system is more convenient than the prior art because the attachment for the modular cardiopulmonary device includes integrated medication monitoring and an adjustably automated dispensing of medication. The attachment also allows for more adaptability and portability because it has modular fittings that can allow for attachment with commonly used cardiopulmonary devices, such as resuscitation bags and breathing masks.

The system also improves over the prior art because the medication is held in capsules that includes an atomizer that abuts the medication. Gravity forces the medication to be pressed against the medication to allow for efficient atomization. The capsule is compatible with the attachment because both include electrical contacts that, when paired up, provide electrical communication between the capsule and the attachment.

The disclosed system and methods described herein represents a significant improvement over prior art by incorporating a sophisticated capsule system for administering atomized medication. Specifically, the system comprises at least one chamber housing the medication, an atomizer to convert the medication into a fine mist, and various additional components such as sensors and electrical contacts. This design allows for a more controlled and precise delivery of medication, enabling targeted treatment with reduced risk of overdose or underdose.

The disclosed embodiments improve upon the problems with the prior art by providing a device for delivering medication to a patient having a wick. The wick in the device offers distinct advantages by facilitating the efficient transfer of medication from the reservoir to the atomizer. The wick efficiently adsorbs the liquid formulation and consistently delivers it to the atomizer, ensuring a fine, uniform mist is produced for inhalation. This mechanism enhances the precision of dose delivery and improves the overall effectiveness of the inhalation therapy, minimizing waste and maximizing the therapeutic effect.

In the general practice of medicine for humans, the disclosed invention offers significant improvements over prior art, particularly addressing concerns around modularity, interchangeability, and speed in administration. Modularity enables customization of medical devices to suit individual patient needs and particular medical conditions, allowing for a more targeted and efficient approach. With the invention's design, various components can be added or removed with ease, thereby adapting the device to different scenarios and patient requirements. The interchangeability feature ensures that parts can be substituted without compromising the integrity or functionality of the device, thus increasing its utility and flexibility. This adaptability not only reduces costs by allowing components to be reused across different applications but also facilitates quick adjustments in emergency situations. Finally, the invention's design emphasizes rapid administration of medication, significantly reducing the time required to prepare and deliver treatments. This is particularly crucial in critical care situations, where every second can make a difference in patient outcomes. By addressing these key areas, the invention enhances the efficiency, adaptability, and responsiveness of medical treatment, setting a new standard in patient care.

The modularity of the device with replaceable parts as disclosed in the embodiments offers significant advantages, particularly in terms of customization, cost-efficiency, and ease of maintenance. In the disclosed embodiments featuring an interchangeable cartridge system with a wick, users can tailor the device to meet specific medical needs by selecting different cartridge configurations to be used with various attachments, such as a mouthpiece, a base unit with a resilient bladder, or a mask. The base unit defines a mixing chamber and a plurality of openings. This flexibility allows for targeted treatment delivery and adaptation to diverse patient requirements or treatment scenarios. Moreover, the ability to replace individual components, such as the cartridge or wick, rather than the entire device, significantly reduces waste and maintenance costs. This is especially beneficial in medical settings where sterile, functional equipment is paramount, as it ensures devices can be kept in optimal working condition without the need for complete replacements. Consequently, modularity enhances both the functional lifespan of the device and its overall efficiency in clinical applications. The use of attachment parts on interchangeable components in the disclosed embodiments enhances the user experience by simplifying the attachment and detachment of the components. This design feature allows for quick and easy interchangeability of parts, which is particularly beneficial in environments where time and efficiency are critical, such as in medical or clinical settings. By facilitating seamless connections between components, such as the mouthpiece, cartridge, and other modular parts, users can effortlessly assemble or modify the device according to specific needs without requiring specialized tools or technical skills. This not only reduces downtime when replacing or upgrading parts but also minimizes potential errors or issues related to improper assembly. Moreover, the ease of changing components encourages regular maintenance and cleaning, thereby improving the overall hygiene and performance of the device. In essence, these attachment features promote a more flexible, reliable, and user-friendly operation, significantly enhancing the practical utility of the device.

The disclosed embodiments also improve over the prior art by providing a covering member for the atomizer and, in some cases, a sealing member to separate the liquid formulation from the wick and atomizer. The covering member for the atomizer and the sealing member provide distinct advantages in terms of safety and efficiency. The covering member serves as a protective barrier, safeguarding the atomizer from direct exposure to external contaminants that could compromise the purity and effectiveness of the formulation being delivered. Additionally, the inclusion of a sealing member further enhances the device's functionality by preventing unwanted leakage or diffusion of the liquid formulation, ensuring that the delivery is precise and controlled. This separation not only maintains the integrity of the formulation but also prolongs the lifespan of both the wick and atomizer by minimizing potential clogging or corrosion caused by prolonged contact with harsh or viscous liquids. As a result, these features contribute significantly to maintaining the reliability, safety, and effectiveness of the delivery system in clinical or therapeutic settings.

Regarding the specific pharmaceutical compositions and capsule delivery systems disclosed herein, they represent a significant leap over prior art, especially in terms of aerosol drug delivery for treating opioid dependency and overdose. The pharmaceutical compositions are uniquely formulated for optimal stability and efficacy. Traditional aerosolized medications often struggle with maintaining the stability of certain active ingredients sensitive to light and air. The disclosed embodiments overcome these challenges by hermetically sealing the capsules, thereby protecting the ingredients from degradation and ensuring their potency and effectiveness until administration.

A key advancement is the precise control over medication dosage. The capsule system is engineered to deliver exact drug amounts, accommodating patient-specific needs. This feature is crucial for opioid dependency treatment that requires gradual dose adjustments and for the immediate response necessary in opioid overdose situations. The capsule system design places a premium on patient safety and convenience. Unlike traditional aerosol delivery methods that may involve complex preparation and pose risks of dosage errors, this system simplifies the process. It potentially includes pre-filled, single-use capsules and automated delivery systems, requiring minimal user intervention and significantly reducing the likelihood of errors. The system offers versatility in administration routes, a substantial improvement over traditional aerosol systems limited in application. This versatility ensures the treatment can be effectively administered via different routes, including intramuscular, intravenous, and atomized aerosol, depending on the patient's condition and clinical requirements. Another enhancement is the integration of the capsule system with modern technology. Innovations such as patient weight input for dose calculation and electronic monitoring of dosage delivery augment the system's effectiveness and ease of use, representing a significant advancement from traditional aerosol systems that may lack these capabilities.

Regarding the improvements in pharmaceutical compositions as disclosed herein over the prior art, the compositions presented herein mark a significant advancement over existing formulations, particularly in the context of treating opioid dependency and overdose. These compositions are expertly designed for enhanced stability, encapsulating active ingredients like yohimbine in hermetically sealed capsules to protect them from environmental factors like light and air. This ensures that their efficacy and potency are preserved until the moment of administration. A notable feature of these compositions is the precision in dosage control, allowing for individualized dosing critical in both the gradual management of opioid dependency and the urgent response needed in cases of overdose. While this precision is particularly relevant for compounds like naloxone used in opioid overdose, it is important to note that the use of yohimbine, primarily recognized for its efficacy in counteracting the effects of substances like xylazine in veterinary applications, requires careful consideration and adjustment when discussed in the context of human treatments. The dosing precision and adaptability of these compositions are not only aligned with the latest demands and standards in opioid treatment protocols but are also increasingly pertinent in addressing the emerging challenges posed by xylazine misuse in humans. This underscores the need for versatile pharmaceutical solutions capable of addressing a broad spectrum of medical emergencies, including those related to both opioid and xylazine exposure. The flexibility in their formulation is another key improvement, providing the capability to incorporate a variety of active ingredients or their combinations, thereby broadening the treatment spectrum beyond the limitations of traditional pharmaceutical formulations. Moreover, these compositions are formulated with an emphasis on patient safety, avoiding additives like certain buffers that could lead to adverse reactions. Their compatibility with advanced drug delivery systems, such as vibrating mesh nebulizers, further enhances their applicability, ensuring efficient and effective administration. Collectively, these attributes represent a considerable step forward in pharmaceutical compositions, aligning with the latest demands and standards in opioid treatment protocols and xylazine treatment protocols.

Yohimbine, a compound of significant therapeutic interest, presents unique challenges when dissolved in aqueous solutions, primarily due to its instability that can lead to degradation, impacting both its efficacy and safety. This instability is attributed to factors like oxidation, hydrolysis, and exposure to light, heat, and certain pH conditions. To circumvent these issues, yohimbine is typically maintained in a solid, preferably powdered form, until required for use.

The powdered form of yohimbine offers substantial stability advantages. It mitigates the risk of degradation reactions more common in liquid formulations and enables a controlled release of the active ingredient upon reconstitution, crucial for maintaining its therapeutic efficacy. This approach is vital in pharmaceutical applications where the stability of the active ingredient is paramount.

The pharmaceutical compositions disclosed herein significantly improve upon these challenges. They are designed with a keen understanding of yohimbine's stability concerns, often incorporating encapsulation techniques or the combination of yohimbine with stabilizing agents. These strategies effectively prevent degradation until the compound is dissolved or suspended in a liquid medium immediately prior to administration. By doing so, these innovative formulations ensure that yohimbine remains stable during storage and is only activated at the intended time of use. This maintains the compound's therapeutic efficacy and safety, representing a substantial improvement over traditional methods of handling yohimbine in pharmaceutical applications.

Further, the disclosed embodiments improve over the prior art by providing a design of this device, having the circuit board affixed to the bottom of the mouthpiece in some embodiments. In such design, a removable cartridge and battery are inserted from the top, that offers a compact and space-efficient configuration. By compartmentalizing the electronic components and power source at opposite ends, the design optimizes internal space, allowing for a slimmer profile which enhances portability and ease of handling. This spatial arrangement also segregates sensitive electronic circuits from the vaporization area, which can minimize heat exposure and potential liquid damage to the electronics, thereby enhancing the device's durability and reliability. Moreover, the distinct separation facilitates easier assembly and maintenance, as components can be accessed and replaced independently, streamlining both manufacturing and user experience. The disclosed embodiments provide multiple modes of operation for conveying the formulation to the wick, thereby offering versatility in its use and configuration. By allowing for variable control of the formulation's flow, users can personalize their experience based on preferences or specific needs.

Referring now to the Figures, FIG. 1A is a side view of a system 100 for administering at least one medication to a patient, according to a first embodiment. FIG. 1B is a side view of a base unit or an attachment 106 for administering medication to a patient, according to the first embodiment. Additionally, FIGS. 13 through 15B also depict views showing additional example embodiments. FIG. 13 is a side view of the system 1300, according to the first embodiment. FIGS. 14A through 14C are various views of the housing 120 of the system 1400, according to the first embodiment. FIG. 15A is a perspective view of the attachment 1500, according to the first embodiment. FIG. 15B is an exploded perspective view of the attachment 1500, according to the first embodiment. The medication is in fluid form. FIG. 15B also includes mating threads 121 on the capsule 108 and the walls of the base unit so that the capsule may be rotated so that it moves into the base unit such that the capsule engages with an actuator that causes the atomizer to be powered thus atomizing the medication. In other embodiments, the threads 121 may be used to simply secure the capsule within the base unit. The system includes a resilient air bladder 102 in fluid communication with a tubular chamber 104 of a base unit. The tubular chamber is a hollow enclosed space within the base unit. The resilient air bladder supplies the system with fresh air. Other types of cardiopulmonary devices configured to supply air into the system may be used and are within the spirit and scope of the present invention. The resilient air bladder is a resuscitation bag, which is commonly used by medical professionals.

The base unit is the attachment 106 that including receiving sections 107 and 109 that provides modular fittings such that commonly used medical components, such as medical face masks or medical mouthpieces, and modular cardiopulmonary devices may be attached. The base unit may also be described herein as a device or medical device. Each of the receiving sections includes an opening into the first channel. The first channel may have a cross-sectional shape defining a circle, but other shapes may be used and are within the spirit and scope of the present invention and as such the openings of the receiving sections 107 and 109 may also be a circular shaped opening. The attachment is configured for connecting to a modular cardiopulmonary device. The modular cardiopulmonary device is defined by the resilient air bladder and at least a mask 142 or mouthpiece (205 in FIG. 2). Modular fittings refer to pre-manufactured parts or components that can be assembled, interchanged, or replaced with relative ease. They are designed to be used in different configurations to meet various requirements. The key advantage of modular fittings is their versatility and ease of use, as they allow for customization and flexibility. Modular fittings provide a standardized, interchangeable set of parts that can be used in a variety of configurations to meet different needs. Examples of modular fittings may include, but are not limited to, friction fit, male female fit, or screw fit. Other types of modular fittings configured to allow the attachment 106 to attach to modular cardiopulmonary devices may be included and are within the spirit and scope of the present invention. The modular fittings allow the user of the system to remove or attach different cardiopulmonary devices so that the user can clean and disinfect the devices between each patient.

A capsule 108 is in fluid communication with the tubular chamber and is configured for carrying the medication. In some embodiments, the capsule may include a sensor (156 in FIG. 2) for detecting the amount of medication within the capsule. An atomizer 110 is disposed at least proximate to the capsule and in fluid communication with the tubular chamber. The atomizer is configured to atomize the medication that is disposed within the capsule. The atomizer is configured to produce particles having a particle diameter ranging from about 1.5 micrometers (μm, or microns) to about 6 micrometers. The atomizer includes a vibrating mesh membrane. As the medication passes through the vibrating mesh membrane, the membrane nebulizes the medication to create a nebulized medication that includes a plurality of particles. The vibrating mesh membrane produces nebulized medication by vibrating at high frequency to trigger particle, or droplet, formation from the medication solution against an inner surface of the membrane on an outer surface of the membrane. The vibrating mesh membrane is a metal piece or plate having a plurality of openings extending through the piece, such that the metal piece, when electrically stimulated to undergo piezoelectric vibration, oscillates against the medication in the capsule 108, causing some of the medication to move through the openings and form small particles on or above the outer surface of the active mesh. The vibrating mesh membrane vibrates at between about 150 kHz and about 300 kHz upon electrical stimulation by an AC|DC current directed to the vibrating mesh membrane. However, other frequencies may be used and are within the spirit and scope of the present invention. The vibrating mesh membrane includes material such as pure titanium, platinum, or palladium, or alloys thereof or the like, or laminated layers of titanium, platinum, or palladium or the like, to produce a piezoelectric effect that results in mesh vibration and particle formation over the outer surface of the mesh in the mouthpiece interior volume. Piezoelectricity is the ability of a material to develop electric charge in response to applied mechanical stress.

The atomizer produces particles that are atomized droplets of the medication. Particles that are larger than 5 micrometers are unable to penetrate into the alveoli of the lungs and are thus of reduced efficiency in being rapidly absorbed by the circulatory system and/or body tissues. The ability of particles to penetrate into the lungs and be absorbed by the depends on the size of the particles. Inhalable particles, ranging in size from 1.5 micrometers to about 6 micrometers, penetrate into the lungs as far as the bronchi because the cilia of the lungs filter the inhalable particles from further travel into the lung volume. Particles ranging in size from 1.5 micrometers to about 5 micrometers are able to penetrate into the alveoli in the lungs and are readily absorbed through the alveoli into the circulatory system and body tissues.

The medication in the capsule is a fluid solution configured to treat patients for different situations. The solution includes an aqueous solution that includes an active ingredient and sodium chloride. When atomized by the atomizer in the capsule, the atomized medication is configured to break a patient's blood brain barrier. The active ingredient includes at least one of nicotine, caffeine, a plurality of vitamins, kratom, Vitamin B12, cotinine, adalimumab, cannabidiol ("CBD"), tetrahydrocannabinol ("THC"), psilocybin, *Cannabis*, ketamine and any combination thereof. The active ingredient may also include exosomes, analgesics, antifungals, Benzodiazepines, Antiarrhythmic agents, anti-aging agents, rapamycin, metformin, calcium channel blockers, antibiotics, anti-inflammatory, anti-gout, alpha-beta-adrenergic agonists, Nitroglycerin, adrenergic bronchodilators, cardiovascular agents, central nervous system stimulants and/or depressants, diabetic agents, diuretics, immunologic agents, gastrointestinal agents, common biologics like Humira, Lantus, Remicade, Enbrel, vaccines, psychotherapeutic agents, opiate partial antagonists, opioids, pulmonary agents, hormonal agents, weight loss agents, vitamins/minerals/supplements, Antihyperlipidemics, proprotein convertase subtilisin/kexin type 9 (PCSK9) Inhibitors, Evolocumab, Alirocumab, Inclisiran, Diuretics, Furosemide, Bumetanide, Torsemide, Beta-2 Adrenergic Agonists, Salmeterol, Long-Acting Beta Agonist, Vilanterol, Formoterol, Anticholinergics, Umeclidinium, Glycopyrrolate, Corticosteroid: Budesonide, Fluticasone, Bronchodilators, Tiotropium, Over-active Bladder Medications, Anticholinergics, Ditropan (oxybutynin), Tolterodine, Darifenacin, Muscarinic Antagonists, narcotic antagonists, Trospium, Fesoterodine, Migraine Therapies, Calcitonin gene-related peptide (CGRP) Receptor Blockers (gepants and monoclonal antibodies ((mAb)), Ubrelvy, Triptans, Ergots, Antiemetics, antagonists of the serotonin, histamine, muscarinic and neurokinin systems, Selective Serotonin 5-hydroxy tryptamine 3 (HT3) Antagonists, Zofran (ondansetron), Diabetic and Weight loss agents, Glucagon-like peptide 1 (GLP-1), Semaglutide, Gastric inhibitory polypeptide (GIP)+GLP-1, Mounjaro™ (Tirzepatide), Anticonvulsants, Pulmonary medications, Hormones, Biologics, Regenerative Drugs, all essential drugs and medicine as defined by World Health Organization, vitamins, caffeine and energy medications, all emergency medicine medications, integrative therapeutics, peptides, ozone, o2, white curcumin, exosomes, gene therapy vectors, erectile dysfunction medications, such as sildenafil citrate, tadalafil, Cialis®, Viagra®, future classes of therapeutics, Yohimbine, and Haloperidol. The active ingredient may also include preservatives, such as Sodium benzoate, and/or anti-yeast agents, such as potassium sorbate. Other preservatives for medication may be used and are within the spirit and scope of the present invention.

The solution further includes a buffer and/or stabilizer. The buffer helps stabilize and maintain the pH level of the solution. The active ingredient includes approximately up to 10% of the solution. Sodium chloride includes approximately between 10% to 90% of the solution. The buffer includes approximately between 1% to 5% of the total solution. The solution has a pH of approximately between 4 pH and 7.5 pH. The pH range is critical to decrease the effects that the active ingredient may have on the body when inhaled, e.g., an increased amount of acute toxicity which may be present in unprotonated active ingredients above a certain pH.

In a first example solution, the solution is for at least decreasing withdrawal symptoms of a person addicted to nicotine. Said solution includes cotinine being the active ingredient in the solution including approximately between 0.5% and 8% of the solution and a sugar alcohol including approximately between 0.5% to 3% of the solution. The solution further includes a buffer including ethyl alcohol and citric acid. The ethyl alcohol includes approximately between 0.1% to 3% of the solution, and the citric acid comprising approximately between 0.1% to 3% of the solution. Cotinine helps reduce symptoms of nicotine withdrawal. The sugar alcohol and citric acid act as sweeteners to counter the bitterness of cotinine when inhaled. In another embodiment, the solution of the first embodiment may be mixed with a small dose of nicotine.

In a second example solution, the solution is a pulmonary irrigation solution. The solution includes adalimumab being the active ingredient including approximately between 1% to 10% of the solution and a sugar alcohol including approximately between 0.1% to 1% of the solution. Adalimumab helps treat a variety of diseases by fighting infections or bacteria within the lungs. The solution further includes a stabilizer including polyol including approximately between 0.1% to 5% of the solution and surfactant comprising approximately between 0.1% to 5% of the solution. The solution may also include at least one of preservative (at 0.1% of the solution) and anti-mold and anti-yeast agent at (0.1% of the solution), The polyol is at least one of sucrose, histidine, and succinate. The surfactant is polyetherimide. At least one of the buffer and the stabilizer includes at least one buffer selected from the group consisting of histidine, succinate, phosphate, citrate, acetate, sodium bicarbonate, maleate, and tartrate buffers. The buffer does not include a combination of a citrate buffer and a phosphate buffer. This solution is intended for use in the induction of sputum production where sputum production is indicated, such as with Rheumatoid Arthritis, Ankylosing Spondylitis, ulcerative Colitis, Psoriasis, Psoriatic Arthritis, Cystic Fibrosis patients and Bronchoalveolar lavage procedures.

In a third example solution, the active ingredient is naloxone, also known as NARCAN®. Naloxone rapidly counters and/or reverses the effects of opioids. Naloxone is the standard treatment to counter opioid overdoses. Inhalation of naloxone through a portable AVI could quickly save the life of opioid users who overdose.

In a fourth example solution, the active ingredient is colloidal silver. Colloidal silver is a liquid solution including a plurality of silver particles. Colloidal silver treatment can heal a variety of infections, such as the common cold or respiratory infections.

In a fifth example solution, the active ingredient is glucagon. Glucagon is a hormone that raises blood glucose levels and the concentration of fatty acids in the bloodstream. Glucagon treatment helps people who suffer from hypoglycemia. Hypoglycemia occurs when the blood glucose levels are lower than the standard range.

An air inlet 112 and a first one-way valve 114 is in fluid communication with the resilient air bladder configured to allow fresh air to enter the resilient air bladder. The air inlet includes an opening on which first one-way valve 114 is mounted. An air outlet 116 and a second one-way value 118 is in fluid communication the resilient air bladder and the tubular chamber. The first one-way valve 114 allows fresh air outside the bladder to move into the air bladder through that valve and prevents air from moving out of the first one-way valve 114 when the first one-way valve moves between the deflated state to the fully inflated state.

Fresh air is forced in direction A1 through the second one-way valve and to the tubular chamber when the resilient air bladder deflates. The second one-way valve may be a check valve. The air bladder deflates when opposing forces in directions H1 and I1 are applied via squeezing the air bladder. When the resilient air bladder deflates, fresh air is expelled out of the air outlet 116 in direction A1, and the first one-way valve 114 prevents air from being pushed out from the resilient air bladder through the air inlet. Because the resilient air bladder must return to its original shape, the air bladder automatically inflates in directions H2 and I2 when the forces stop squeezing it. Shown in FIG. 1, when the resilient air bladder inflates, fresh air enters through the air inlet 112 in direction A2 and is drawn into the resilient air bladder, and the second one-way valve 118 prevents air from within the tubular chamber from entering the resilient air bladder thereby not causing air to be potentially sucked from a patient.

In one embodiment, the medical device is equipped with at least one sensor 172 (also shown in FIG. 34A) for monitoring fluid parameters various components of the device, thereby allowing for precise control and delivery of atomized medication. These sensors may be strategically placed in areas such as within tubular chambers, the mask attachment, or the capsule itself to gauge the various fluid parameters. The at least one sensor is configured to monitor and/or measure fluid parameters including but not limited to viscosity, density, pH, conductivity, turbidity, salinity, dissolved oxygen or nitrogen levels, particle size, temperature, and pressure within the device's system. For example, the at least one sensor may include sensors such as viscosity sensors, density sensors, pH sensors, conductivity sensors, turbidity sensors, salinity sensors, gas sensors for monitoring dissolved oxygen or nitrogen, particle size analyzers, temperature sensors, and pressure sensors, all of which can play pivotal roles in understanding and controlling the fluid parameters within the device.

For instance, pressure sensors may be used within the chambers to ensure that the fluid, such as a medication, is at the appropriate pressure for atomization. Additionally, the device may include sensors designed to measure fluid parameters, including the oxygen (O2) and carbon dioxide (CO2) content during inhalation and exhalation. These may encompass specific gas sensors like oxygen sensors, used to measure O2 content, and nondispersive infrared (NDIR) sensors for CO2 content. Such a configuration allows the device to adapt to the patient's respiratory needs and tailor the delivery of the medication, thereby optimizing treatment efficacy and patient comfort. These enhancements in sensor technology contribute to a more personalized and efficient means of administering medication compared to conventional methods.

These sensors can measure the viscosity, indicating the flow characteristics, and density, which helps in calculating the exact concentration of medication. The pH level of the fluid can be monitored to ensure its compatibility with the patient's needs. Electrical conductivity provides insights into the fluid's composition and purity, while turbidity sensors assess the clarity and potential contamination. The salt concentration or salinity is measured for certain medication types, and dissolved gases such as oxygen or nitrogen are monitored to ensure proper formulation. The particle size and distribution within the fluid are measured for determining how the medication may be absorbed by the body. Standard measurements of temperature and pressure are also undertaken, given their direct impact on fluid behavior, and thus the delivery and effectiveness of the medication.

For example, at least one of the sensors may be used to measure O2 inhaled by the patient and the CO2 exhaled by the patient over a period of time. Additionally, the data measured may be used to establish a metabolic signature or profile of the patient over time that can be used to create a baseline metabolic profile of the patient. The metabolic signature may be used to compare a with a second metabolic signature of the patient at a second period of time for the same patient or for other patients. In certain embodiments the second metabolic profile may be taken from different patients with certain known conditions, such as COVID, influenza, tuberculosis, heart disease. However, other conditions may be used to create the second metabolic profile for which is to be compared with other metabolic signatures of the patient taken over other periods of time. The periods of time, we be longer periods so that certain patterns and anomalies may be identified.

When the device is used with a resilient air bladder 102 to manually control the inhalation and exhalation of the patient, the sensors may be used for monitoring and regulating the pressure within the air bladder, assessing the flow rate of the inhalation and exhalation, detecting any abnormalities in the respiratory pattern, and ensuring that the prescribed dosage of atomized medication is delivered in synchronization with the patient's breathing cycle. Additionally, the sensors can provide feedback on various fluid parameters such as oxygen content, carbon dioxide content, and humidity, thus enhancing the efficiency and safety of the delivery system and allowing for timely adjustments to the medication delivery or respiratory support as required by the patient's condition.

The base unit further includes a housing 120 and a first channel 122 spanning from a first side 124 of the housing to a second side 126 of the housing. The housing may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The housing may be made of other materials and is within the spirit and the disclosure. The housing may be formed from a single piece or from several individual pieces joined or coupled together. The components of the housing may be manufactured from a variety of different processes including an extrusion process, a mold, casting, welding, shearing, punching, folding, 3D printing, CNC machining, etc. However, other types of processes may also be used and are within the spirit and scope of the present invention.

The system further includes a first longitudinal axis 128 of the first channel. A first end portion 130 of the first channel is configured to receive a portion of a conduit 132 that is in fluid communication with the air outlet of the resilient air bladder, and a second end portion 134 of the first channel configured to receive a portion of the mouthpiece or the mask 142. The first end portion and second end portion include openings configured to receive the conduit and mask, respectively. The channel may have walls that have smooth surfaces so that air and medication may easily move toward the user or provide a path for air and medication to be in fluid communication with the mouthpiece of the mask. The system further includes a second channel 138 disposed on the housing configured to receive a portion of the capsule 108 and a second longitudinal axis 140 defined by the second channel. In one embodiment, the second channel may be circular in shape, however other shapes may be used and are within the spirit and scope of the present invention. The base unit includes an opening 141 of the second channel that receives a portion of the capsule. The second longitudinal axis defines at most a 90-degree angle relative to the first longitudinal axis of the first channel. In the present embodiment, the angle 143 between the second longitudinal axis and first longitudinal axis is at a 45-degree angle. However, other angles that allow the medication to easily flow into the second channel may be used and are within the spirit and scope of the present invention.

The fresh air then moves through tubular chamber in direction B while the atomized medication moves through base unit in direction C such that the fresh air and the medication atomized by the atomizer mix together within the tubular chamber to create a mixture 170. The system further includes a mask 142 defining a mask chamber 144 within the mask. The mask is configured to be positioned over the patient's mouth and nose. The mask has a rim 146 extending about a periphery of the mask for forming a seal with the patient's face and a mouthpiece defining a tubular shaped body. The mixture 170 of the fresh air and the atomized medication flows towards the mask in direction D.

The system further includes a processor 148 housed by the housing of the base unit. Two electrical contacts 152 are positioned within the second channel. The capsule also includes two electrical contacts (shown in FIG. 2) that mate with the two electrical contacts within the second channel providing electrical communication with the power source 154 of the base unit. The power source may be a battery power source. In the present embodiment, the battery power source may be a battery power source, such as a standard dry cell battery commonly used in low-drain portable electronic devices (i.e., AAA batteries, AA batteries, etc.). Other types of batteries may be used including rechargeable batteries, aluminum air batteries, lithium batteries, paper batteries, lithium-ion polymer batteries, lithium iron phosphate batteries, magnesium iron batteries etc. Additionally, other types of battery applications may be used and are within the spirit and scope of the present invention. For example, a battery stripper pack may also be used. Additionally, other types of power sources may also be used and are within the spirit and scope of the present invention. In other embodiments, the power source may be an external power source. For example, the system may include a power cable that can connect to an electrical wall outlet. Other types of external power sources may be used and are within the spirit and scope of the present invention.

The base unit may also include a sensor 156 that detects whether a capsule is inserted into the second channel or not. The housing also houses a user interface 150. The user interface is configured to be acted on by a rescuer to start the atomizer to atomize the medication. The user interface may include controls to set or adjust the rate of medication to administer, to start or stop the atomizer, and/or to gain authorization to the base unit. The user interface may also include a graphical display configured to receive gestures such as touches, swipes, etc. to control the device. The user interface may also be controlled by receiving sound commands that are received by an audio sensor and then processed by the processor. The processor is configured for receiving a signal to start the atomizer to atomize the medication, sending a second signal to the atomizer to cause the atomizer to atomize the medication within the capsule and convey the atomized medication into the second channel, receiving a third signal from the sensor when the sensor detects that the medication within the capsule is less than a minimum threshold, and sending a fourth signal to turn off the atomizer after the third signal is received. For example, the minimum threshold may be an amount of fluid that is left in the container is less than 1/12 the total of medication in the capsule. For example, the sensor may detect that minimum threshold amount of medication is within the capsule, send the signal to the processer, then the processer may send a signal to stop the atomizer.

In some embodiments, the system may include a storage case such as, but not limited to, a briefcase. The storage may be able to hold multiple attachments 106, that can be charged by a power source within the storage case. The briefcase may require security measures to be unlocked. For example, unique codes or a fingerprint scanner may be used as a security measure. The storage case may include slots to hold a capsule that may be prefilled or non-prefilled with medication. The storage case would be very useful in medical emergencies.

Referring now to FIG. 2, a side view of a system 200 for administering medication to a patient is shown, according to a second embodiment. Instead of the mask in the first embodiment, the second embodiment of the system for administering medication to a patient includes a mouthpiece 205. In one embodiment, the mouthpiece may be a tubular shaped body that is shaped to be inserted into a patient's mouth so that the user may inhale atomized medication into the patient's mouth.

The system 200 also includes electrical contacts 152 exposed on the inner surface of the second channel 138 that pair with electrical contacts 215 exposed on the outer surface of the capsule. When electrical contacts 152 and 215 are touching each other, the sensor 156 sends a signal to the processor 148, which sends a signal to turn on the power source 154. The power source then provides electrical power to the capsule 108 such that the atomizer begins atomizing the medication if there is electrical communication between contacts 152 and 215. The main difference between the first embodiment and the second embodiment is that they have different medical components (mask vs. mouthpiece) in attachment with the receiving sections 107 and 109 of the base unit. The system also includes an interface 150 on the second side of the base unit and is configured to allow the user to send signals to the processor to control the atomizer. The second embodiment allows a rescuer, medical professional, or in certain cases the patient to use the system on a patient that is positioned upright and is conscious, unlike the first embodiment, wherein the patient is laying down and may be unconscious. Upright means that the patient's body is substantially vertical so the patient's head 160 is substantially vertical.

Figure 11B:
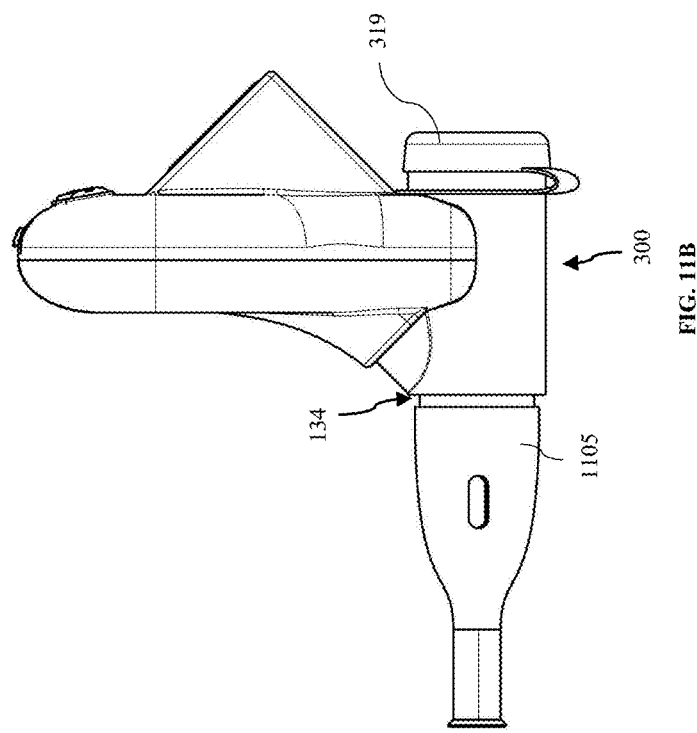
FIG. 11B is a side view of a system for administering medication to a patient, according to the third embodiment.
Figure 11A:
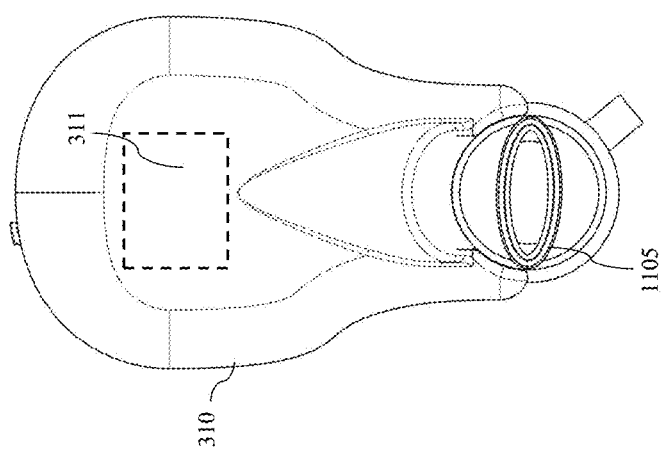
FIG. 11A is a front view of a system for administering medication to a patient, according to the third embodiment.

Referring now to FIGS. 3A through 3D, 11A, 11B, and 12, various views of a third embodiment of the system for administering medication to a patient are shown. FIG. 3A is a diagram of side view of the base unit 300 of the system for administering medication to a patient, according to the third embodiment. FIG. 3B is a diagram of a side view of the base unit 300 of the system for administering medication to a patient, according to the third embodiment. FIG. 3C is a diagram 301 illustrating the main electrical components of the system for administering medication to a patient, according to the third embodiment. FIG. 3D is a diagram 301 illustrating the main electrical components of the system for administering medication to a patient, according to the third embodiment. Additionally, FIGS. 11A through 12 also depict views of other examples of the third embodiment of the system for administering medication to a patient. FIG. 11A and FIG. 11B are various views of the system having a mouthpiece 1105 in attachment with the base unit 300, according to the third embodiment. FIG. 11A may include a graphical display 311 that is configured to provide visual instructions, warnings, maintenance items to the patient, such as when to start inhaling, when to stop inhaling, battery life of the device etc. when the device is in operation. The system may also include an audio component such as a speaker 314 to provide audio instructions (that are similar to the instructions provided by graphical display 311).

Figure 4:
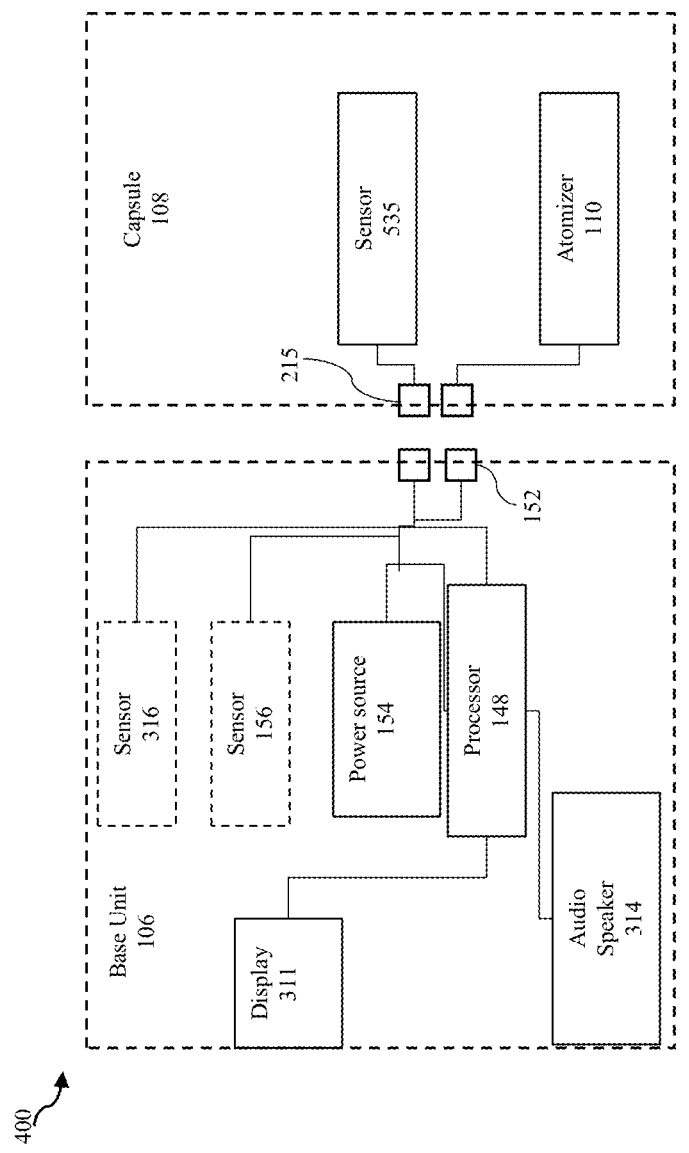
FIG. 4 is a diagram illustrating the main electrical components of a system for administering medication to a patient, according to an example embodiment.

As shown in FIG. 4, the system may also include a sensor 316 for receiving audio commands from a user, such as when to start or stop the atomizer; however, other type of audio commands may be used and are within the spirit and scope of the present invention. The attachment may also include a cap 319 or cover that covers the opening of the receiving section. The cap may be configured to cover the opening so that when no bag is attached to the receiving section, the device may still be used as an atomizer for atomizing medication.

It is understood that the device may include at least one sensor, or a plurality of sensors, consistent with this disclosure. These sensors may be implemented in various locations and configurations within the device to monitor and measure vital parameters, fluid dynamics, and operational states, thereby contributing to the precise control and safety of the medication administration. While specific examples of sensor types and their applications have been described, these are not meant to be limiting. The incorporation of sensors within the device can be adapted to suit various needs and may extend beyond the examples provided herein. Such variations and adaptations are contemplated to be within the spirit and scope of the present invention, highlighting the flexibility and comprehensiveness of the system's design in catering to a wide range of requirements and scenarios in administering medication to patients.

Referring back to FIGS. 3A and 3B, the housing includes biasing elements 305 that are positioned between the housing 120 and an engaging element 310 that receives the capsule. In one embodiment, the biasing elements may be compressing springs. However, other biasing elements may be used and are within the spirit and scope of the present invention. The engaging element is a component that a user of the system interacts with to start the atomization of the medication. The engaging element is in attachment with the housing 120 of the base unit. The engaging element is similar to a button such that the user pushes down on the engaging element, which then interacts with the housing of the base unit. The engaging element may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The engaging element may be made of other materials and is within the spirit and the disclosure. The engaging element may be formed from a single piece or from several individual pieces joined or coupled together. The components of the engaging element may be manufactured from a variety of different processes including an extrusion process, a mold, casting, welding, shearing, punching, folding, 3D printing, CNC machining, etc. However, other types of processes may also be used and are within the spirit and scope of the present invention. The engaging element is shaped such that a user of the system can use one hand to push down on the engaging element. The third embodiment is convenient because it allows the user to self-administer medication.

A patient can push down or apply a force on the engaging element in direction E such that the engaging element moves towards the housing. When force in of line E is applied to overcome the expansion force of the spring, the engaging element 310 moves toward the housing to a certain extent so that the electrical contacts 312 of the housing and the electrical contacts 315 of the capsule contact each other to provide electrical communication between the power source and the atomizer in the capsule. The patient must provide enough force downward to hold down to allow the electrical contacts to remain in contact such that the atomizer continues to atomize the medication in the capsule. This causes the medication to be dispensed into the tubular chamber 104 for as long as electrical contacts of the housing are in contact with the electrical contacts of the capsule. The atomized medication then moves in direction B towards the end portion 320 of the base unit where a mouthpiece or mask may be attached to. The end portion 320 is similar to the first end portion 130 and the second end portion 134 such that it includes a receiving section with modular fittings. Referring back to FIG. 11B, the user may view the graphical display 311, which may provide instructions as to how long to apply force to cause the medication to be atomized by the device. Shown in FIGS. 11A and 11B, a mouthpiece 1105 is in attachment with the end portion 320.

Figure 12:
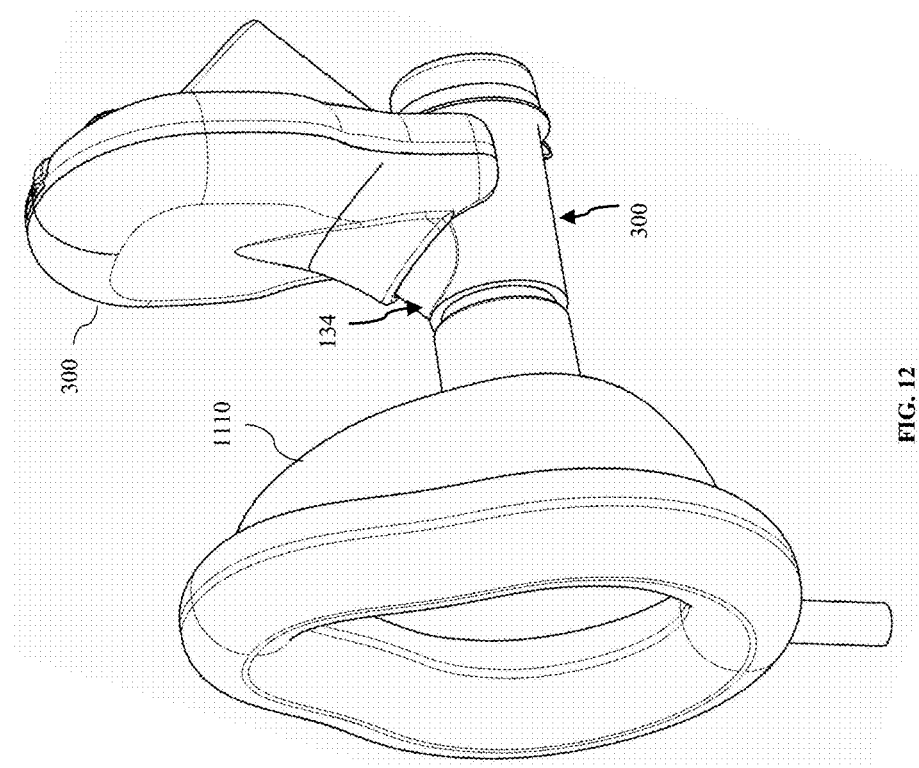
FIG. 12 is a perspective view of a system for administering medication to a patient, according to the third embodiment.
Figure 13:
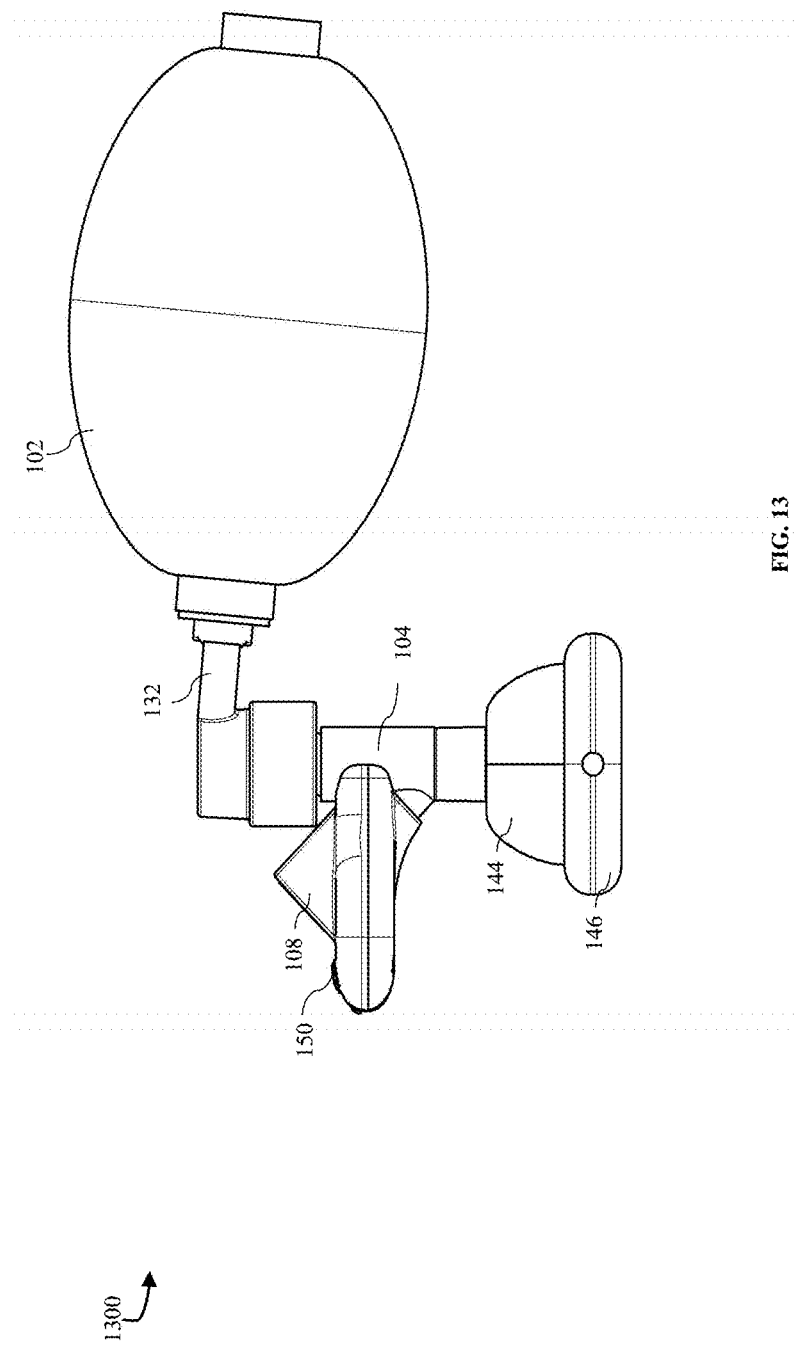
FIG. 13 is a side view of a system for administering medication to a patient, according to the first embodiment.
Figure 15A:
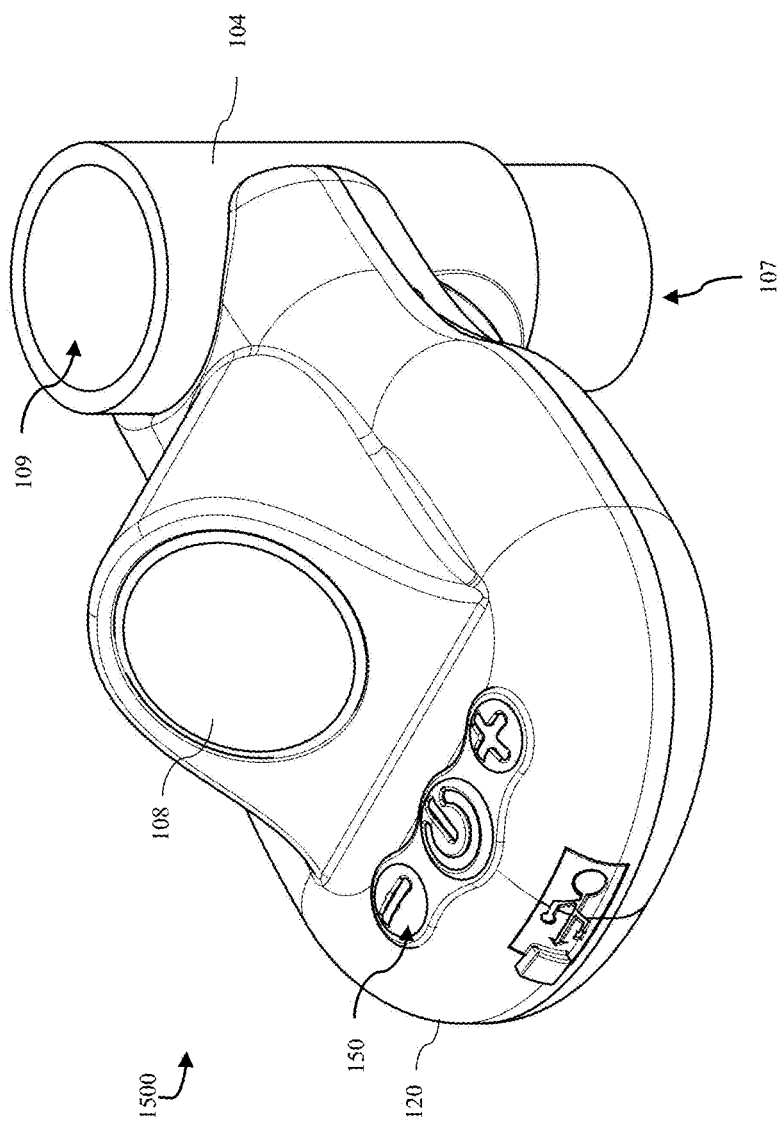
FIG. 15A is a perspective view of an attachment for administering medication to a patient, according to the first embodiment.
Figure 15B:
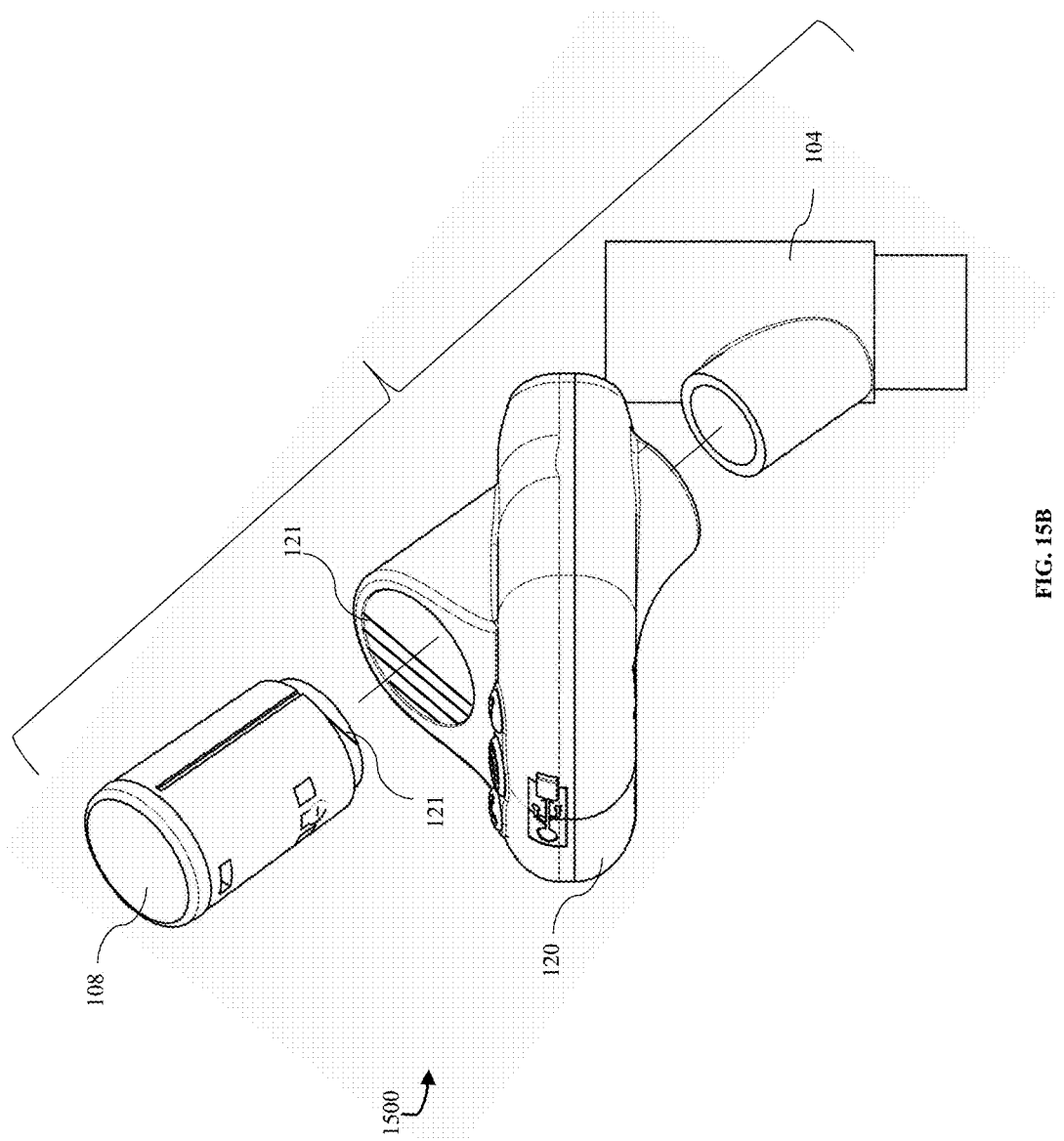
FIG. 15B is an exploded perspective view of an attachment for administering medication to a patient, according to the first embodiment.

Referring to FIG. 12, a perspective view of system having a mask 1110 in attachment with the base unit 300, according to a third example embodiment is shown. In FIG. 12, a mask is in attachment with the end portion 320. The third embodiment can be easily used by one person as opposed to the first embodiment and second embodiment because only one hand is needed. A conscious patient can perform treatment on themselves when using the third embodiment. The capsule may also include a sensor 535, also shown in FIG. 5, that detects the amount of medication remaining in the capsule.

Figure 16B:
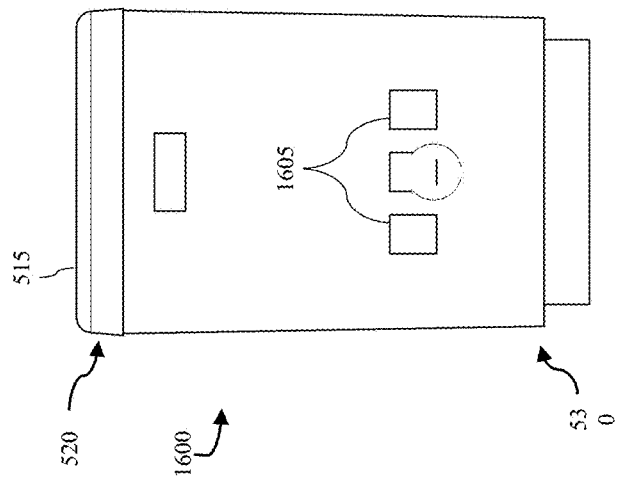
FIG. 16B is a front view of the capsule, according to a second example embodiment.
Figure 16A:
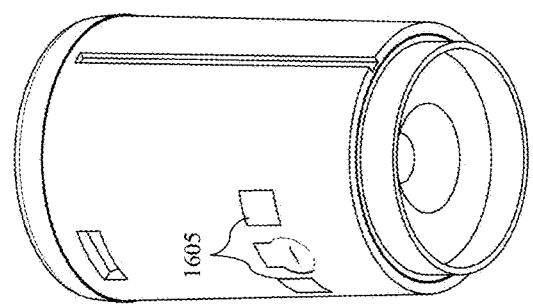
FIG. 16A is a bottom perspective view of the capsule, according to a second example embodiment.
Figure 18B:
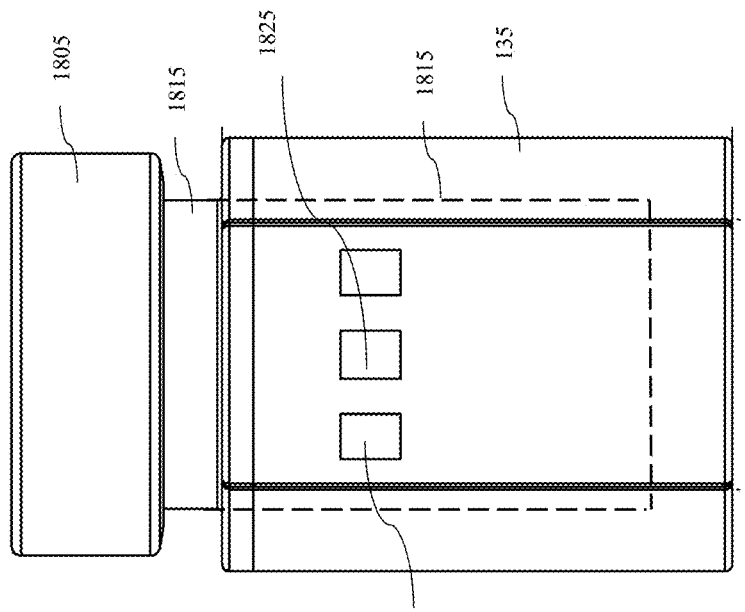
FIG. 18B is a side view of the capsule, according to the third example embodiment.
Figure 18A:
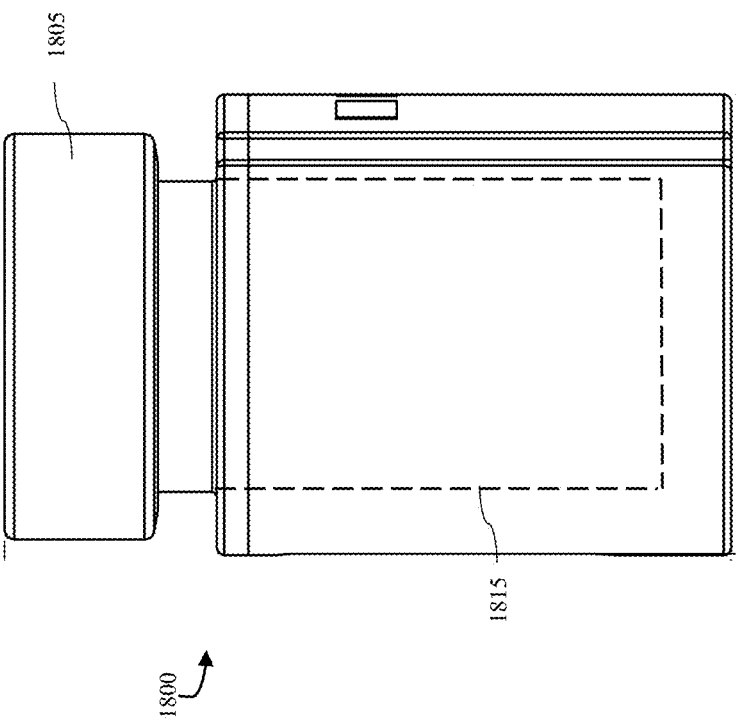
FIG. 18A is a side view of the capsule, according to a third example embodiment.
Figure 18C:
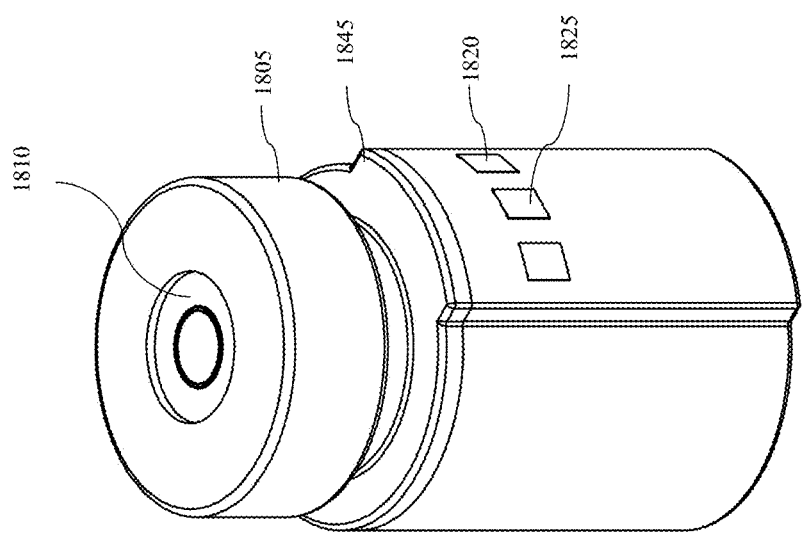
FIG. 18C is a perspective view of the capsule, according to the third example embodiment.

Referring now to FIG. 5, FIGS. 16A and 16B, and FIGS. 18A through 18D, a single chamber capsule is shown, according to various example embodiments. FIG. 5 shows a front view of a capsule 500, according to first example embodiment. FIGS. 16A and 16B illustrate various views of a capsule 1600 according to a second example embodiment. Additionally, FIGS. 18A through 18D illustrates various views of capsule 1800, according to a third example embodiment. The capsule 1600 includes a different design of capsule 500. Capsule 1800 is a single chamber capsule having a refillable rubberized section and/or stopper and/or seal to receive at least one medication. Moreover, FIGS. 17A and 17B illustrate a fourth embodiment of a capsule having more than one chamber, namely, a first chamber for holding medication and a second chamber for atomizing the medication once the capsule is engaged and/or activated. Said chambers are initially separate until the capsule is engaged as to breach a divider or seal between the chambers enabling the first and second chamber to be in fluid communication with one another. This embodiment is further detailed below.

Figure 6B:
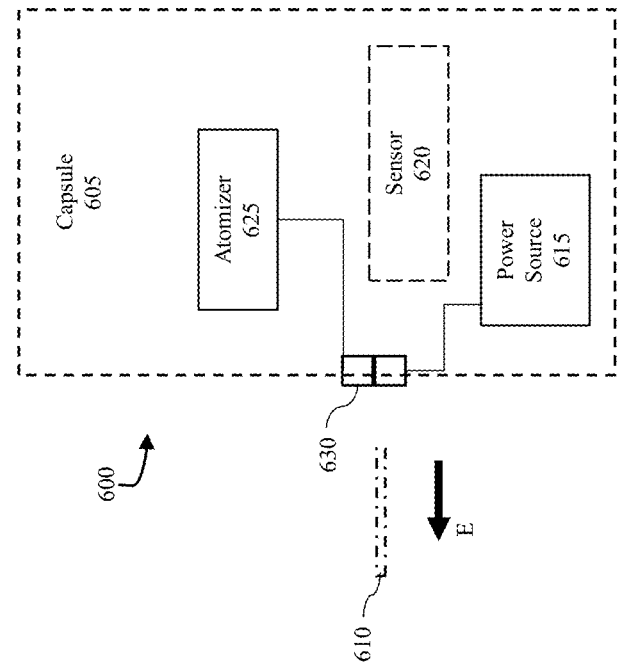
FIG. 6B is a diagram illustrating the main electrical components of the capsule, wherein an electrical insulator in form of a tab is removed from between two contacts, according to an example embodiment.
Figure 6A:
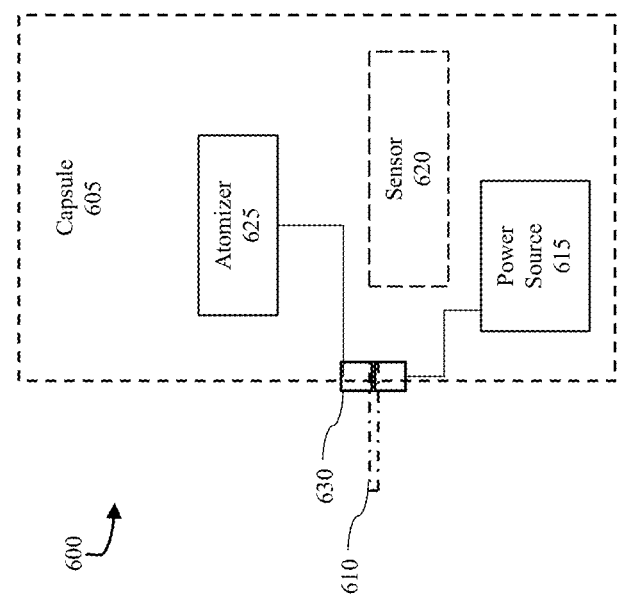
FIG. 6A is a diagram illustrating the main electrical components of the capsule, wherein an electrical insulator in form of a tab is positioned between two contacts, according to an example embodiment.

The capsule includes a capsule chamber 505 for housing the medication 510 and a rubber section 515 covering an open side 520 of the capsule. In the present embodiment, the capsule chamber can hold up to 20 milliliters of fluid. In other embodiments, the capsule chamber may hold other volumes of fluid, which are within the spirit and scope of the present invention. The rubber section allows for medication to be inserted into the capsule. A user of the capsule may add medication by inserting a syringe through the rubber section and using the syringe to dispense the medication into the capsule chamber 505. The capsule further includes the atomizer 525 proximate to a second side 530 of the capsule and a sensor 535 for detecting the amount of the medication in the capsule. In operation, the capsule chamber is above the atomizer and abuts the atomizer such sensor 620, and the atomizer 625 in electrical communication. The power source 615 is the same as the power source 545 described with reference to FIG. 5. The capsule also includes at least two contacts 630 that can provide electrical communication between the power source and the atomizer. In FIG. 6A, the electrical contacts are separated by a tab that blocks the electrical communication between the power source and the atomizer. The tab may be comprised of material including rubber, synthetic rubber, like latex or silicone, and plastics such as polyvinyl chloride, Teflon (PTFE—Polytetrafluoroethylene), and Polyethylene. However, other materials configured to insulate electricity may be used and are within the spirit and scope of the present invention. They offer excellent resistance to electricity, and their physical properties can be adjusted to suit specific applications.

When a user of the capsule pulls the tab out from between the electrical contacts, the electrical contacts can contact each other and provide electrical communication between the power source and the atomizer. In this embodiment, the amount of energy within the power source is configured to run out after all of the medication within the capsule is atomized. This is useful for medical emergencies because the rescuer can quickly pull out the tab and quickly insert the capsule into the base unit.

Figure 7:
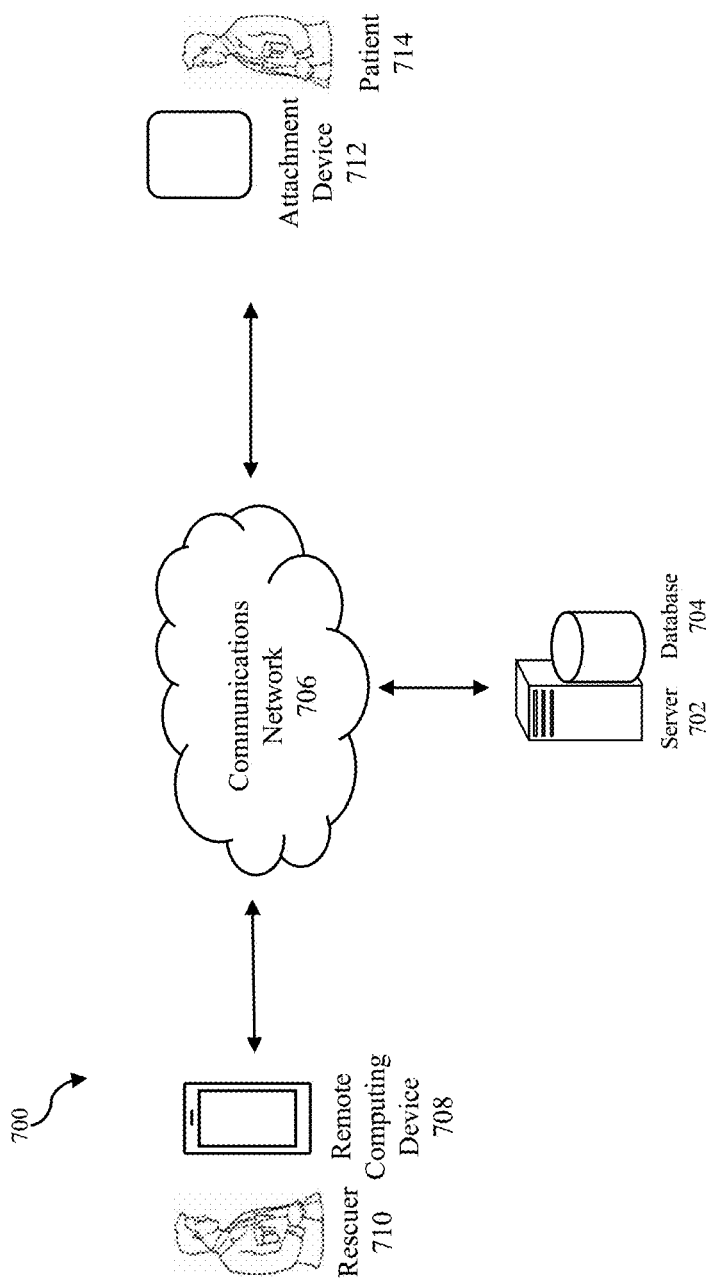
FIG. 7 is a diagram of an operating environment that supports a system of administering medication to a patient, according to an example embodiment.

Referring now to FIG. 7. is a diagram of an operating environment 700 that supports a system of administering medication to a patient is shown, according to an example embodiment. FIG. 7 is a diagram of an operating environment that supports a system of administering medication to a patient, according to an example embodiment. The most prominent element of FIG. 7 is the server 702 associated with repository or database 704 and further coupled with the communications network 706, which can be a circuit switched network, such as the Public Service Telephone Network (PSTN), or a packet switched network, such as the Internet or the World Wide Web, the global telephone network, a cellular network, a mobile communications network, or a Personal Area Network (PAN), such as Bluetooth® or any combination of the above. In one embodiment, network 706 is a secure network wherein communications between endpoints are encrypted so as to ensure the security of the data being transmitted. Server 702 is a central controller or operator for the functionality that executes on at least a remote computing device 708 and an attachment device 712, via various methods.

Figure 1:
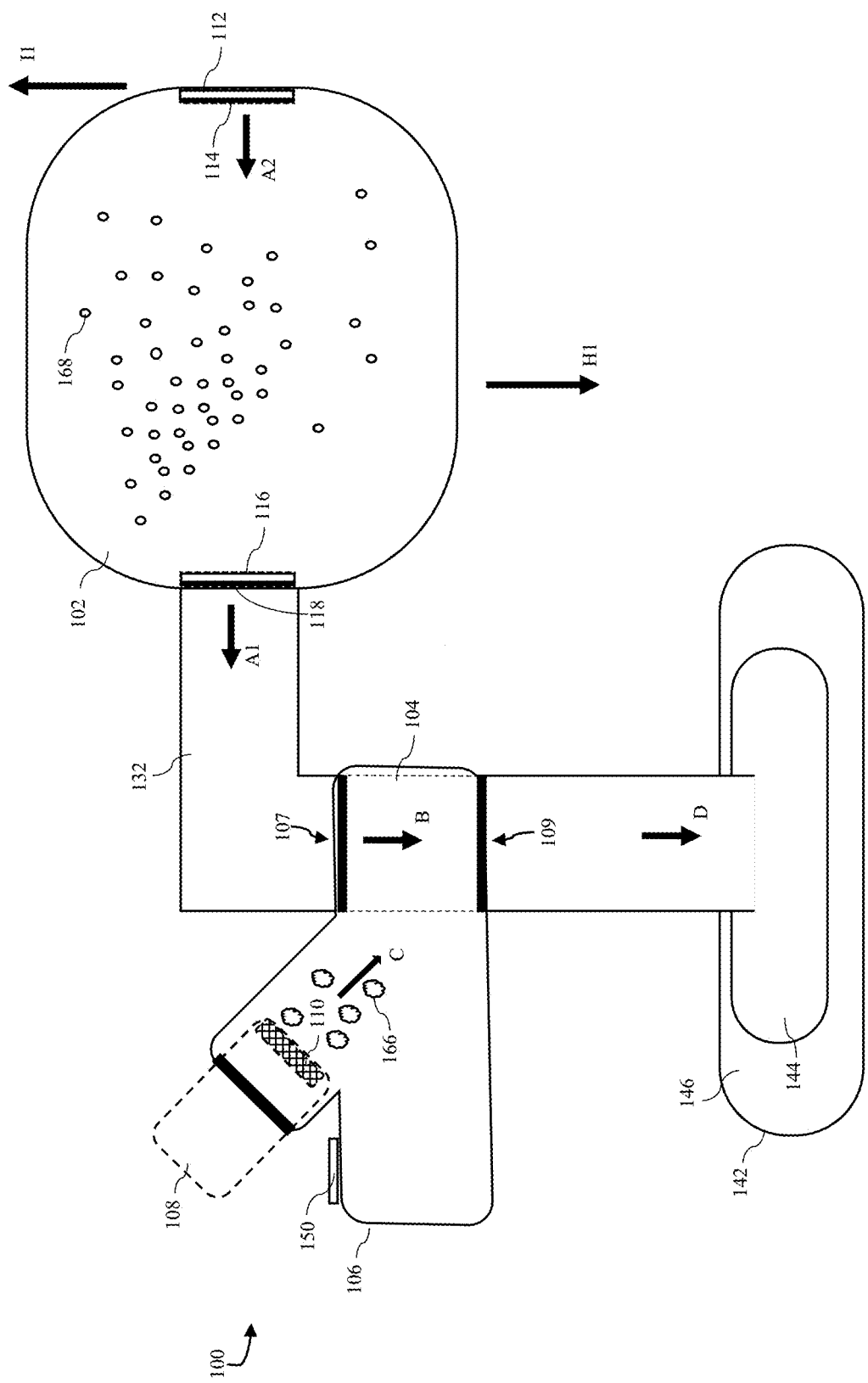
FIG. 1 is a diagram of a side view of a system for administering medication to a patient, according to a first embodiment.

FIG. 7 further includes the remote computing device 708 and the attachment device 712, which are computing devices that each may be smart phones, mobile phones, tablet computers, handheld computers, laptops, or the like. The remote computing device corresponds to a rescuer 710, and the attachment device 712 corresponds to the attachment 106, or base unit (in FIG. 1), that is associated with the cardiopulmonary device positioned on the face of the patient 714. The remote computing device and attachment device may include transceivers for communicating over the network 706. In some embodiments, the capsule may also include a transponder such that a user can link the capsule to the attachment device. Each of the computing devices includes a user interface and/or graphical user interface. In certain embodiments, the system may communicate between the remote computing device and the attachment device, over the communications network, where the rescuer is a person who is providing aid to a patient, and the patient is a person needing medical attention. The users of the system input selections via a user interface on the remote computing device to be sent through the communications network via a data packet and to the attachment device.

FIG. 7 further shows that server 702 includes a repository or database 704, which may be one or more of a relational database comprising a Structured Query Language (SQL) database stored in a SQL server, a columnar database, a document database and a graph database. Computing devices 708 and 712 may also each include their own database. The repository or database 704 serves data from a database, which is a repository for data used by server 702 and the remote computing device during the course of operation of the invention. The repository or database 704 may be distributed over one or more nodes or locations that are connected via network 706.

FIG. 7 shows an embodiment wherein networked computing devices 708 and 712 may interact with server 702 and repository or database 704 over the network 706. Server 702 includes a software engine that delivers applications, data, program code and other information to networked computing devices 708 and 712. The software engine of server 702 may perform other processes such as audio and/or video streaming or other standards for transferring multimedia data in a stream of packets that are interpreted and rendered by a software application as the packets arrive. It should be noted that although FIG. 7 shows only two networked mobile computing devices 708 and 712, the system of the present invention supports any number of networked mobile computing devices connected via network 706, having at least the remote computing device 708 and the attachment device 712.

Server 702 also includes program logic comprising computer source code, scripting language code or interpreted language code that is compiled to produce executable file or computer instructions that perform various functions of the present invention. In another embodiment, the program logic may be distributed among more than one server 702, computing devices 708 and 712, or any combination of the above.

Note that although server 702 is shown as a single and independent entity, in one embodiment of the present invention, the functions of server 702 may be integrated with another entity, such as each of computing devices 708 and 712. Further, server 702 and its functionality, according to a preferred embodiment of the present invention, can be realized in a centralized fashion in one computer system or in a distributed fashion wherein different elements are spread across several interconnected computer systems.

Figure 1A:
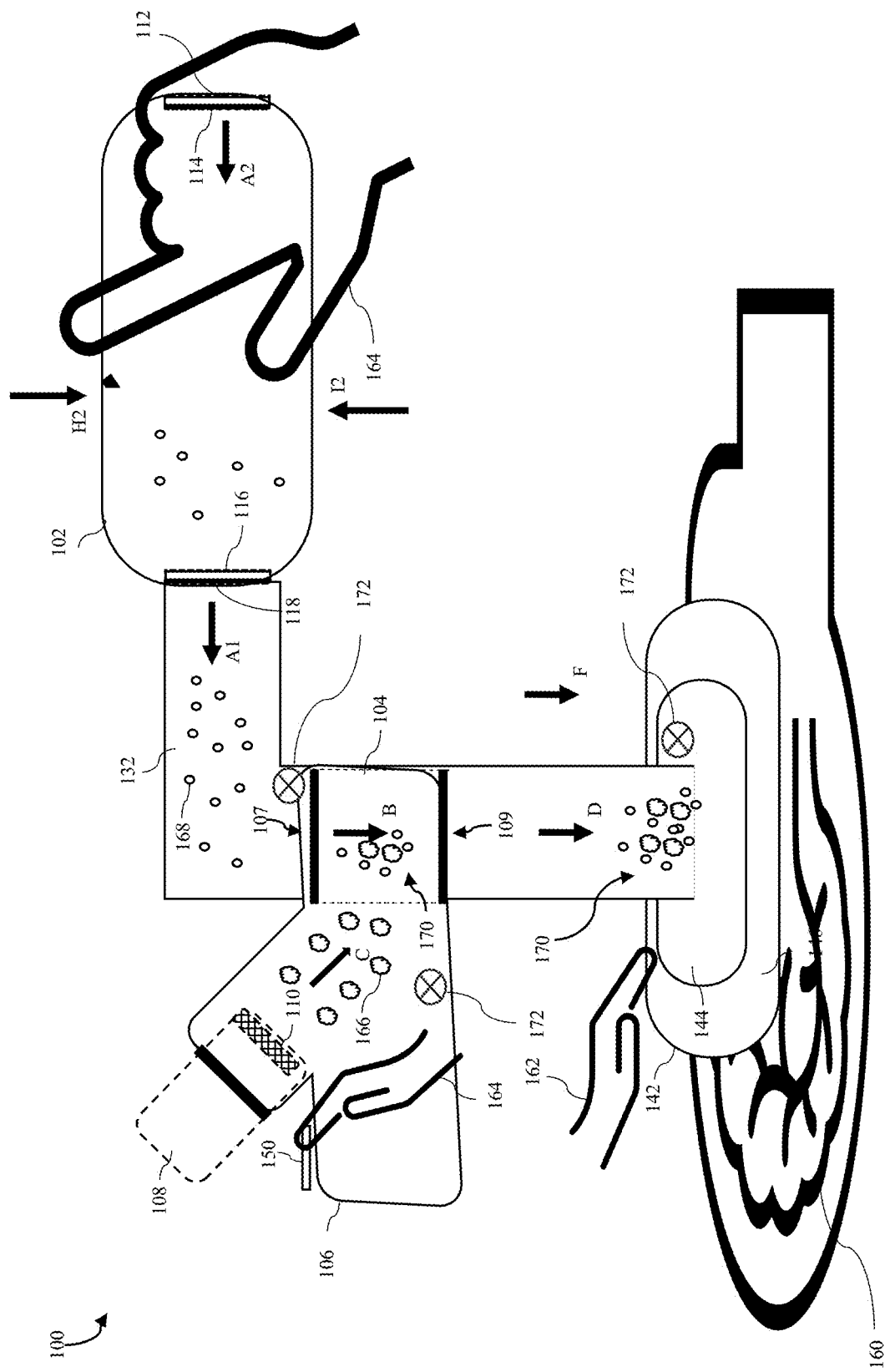
FIG. 1A is a diagram of a side view of a system for administering medication to a patient, wherein the resilient air bladder is deflated by the force of a rescuer, according to a first embodiment.
Figure 1B:
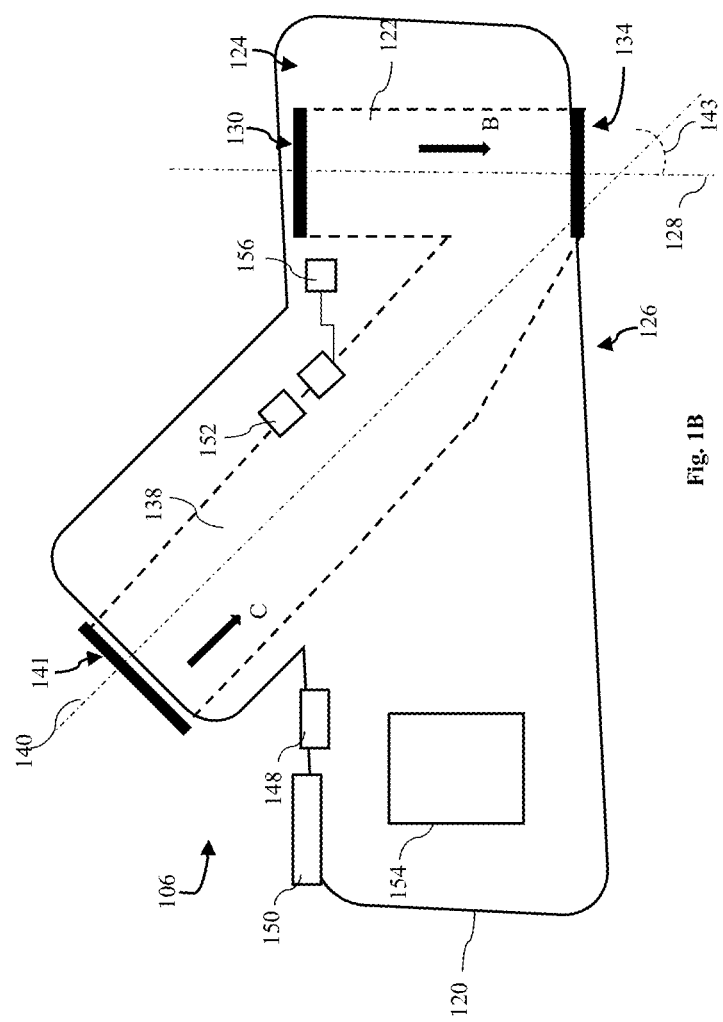
FIG. 1B is a diagram of a side view of an attachment for administering medication to a patient, according to a first embodiment.
Figure 8:
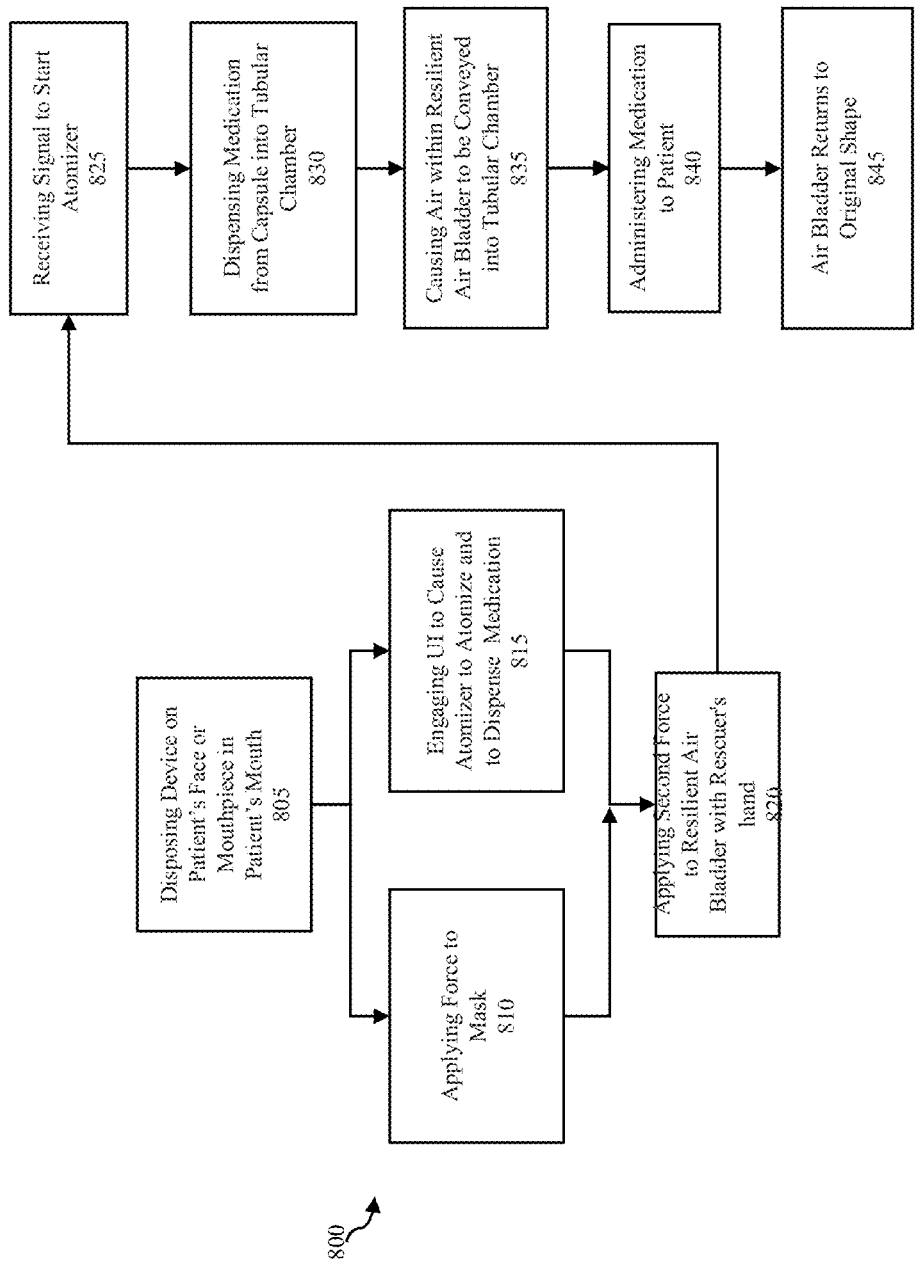
FIG. 8 is a flowchart diagram illustrating steps for a method of administering medication to a patient, according to an example embodiment.

The process of administering medication to the patient will now be described with reference to FIG. 8 and FIG. 1A. FIG. 8 is a flowchart diagram illustrating steps for a method 800 of administering medication to a patient, according to an example embodiment. FIG. 1A is a diagram of the system 100 showing the patient's head 160 and the hands of the rescuer. In step 805, prior to dispensing the medication from the capsule, the rescuer disposes the mask of the device over the patient's mouth and nose and/or a mouthpiece to be inserted into the patient's mouth. In step 810, the rescuer uses a hand to apply a force to the mask to obtain a substantially air-tight seal against the patient's face. The substantially air-tight seal is created because the rim 146 surrounds the nose and mouth of the patient and is pressed against the patient's face. Shown in FIG. 1A, the rescuer, uses a hand 162 to apply a force in direction F to hold the mask 142 over the patient's face. The force in the direction of F causes the substantially airtight seal. It is understood that the substantially airtight seal needs to allow most of the medication to be administered to a patient's face. In step

815, while applying the force with the hand to the mask, the rescuer engages, with a second hand (164 in FIG. 1A) of the rescuer, the user interface 150 on the device to cause the atomizer to atomize the medication (510 in FIG. 5) and to dispense the atomized medication 166 from the capsule. In step 820, while applying the force to the mask with the hand of the rescuer and either during or after engaging the user interface to cause the dispensing of the medication from the capsule, the rescuer applies a second force with the second hand 164 of the rescuer, to the resilient air bladder 102 so that the fresh air 168 within the resilient air bladder is conveyed via the conduit 132 from the resilient air bladder 102 and into the tubular chamber 104 such that the air conveyed from the resilient air bladder and the medication dispensed from the capsule is administered to the patient. In step 825, prior to dispensing the medication from the capsule, the system receives, with a processor, a signal to start the atomizer 110 to atomize the medication. In step 830, the system dispenses, using the atomizer, the medication from the capsule in fluid communication with the tubular chamber, into the tubular chamber. As mentioned above, the maximum amount of medication or amount of time the medication is atomized may be adjusted based on a variety of factors. The angle between the longitudinal axis of the second channel and the longitudinal axis of the first channel may be approximately 45 degrees so that the atomized medication can easily move and combine with air within the first channel.

In step 835, the system causes fresh air 168 within a resilient air bladder in fluid communication with the tubular chamber to be conveyed from the resilient air bladder 102 through the conduit 132. The fresh air then flows into the tubular chamber to mix with the atomized medication. In step 840, the air conveyed from the resilient air bladder and the medication dispensed from the capsule is administered to the patient. In step 845, the resilient air bladder 102 returns to its original shape such that the rescuer may squeeze it again to supply more fresh air into the system.

It is understood that this method is a continuous cycle and that each step of method 800 may operate concurrently with another step of method 800 to provide efficient administration of medication within the system. In other embodiments, the method may further include additional steps to promote efficient administration of medication consistent with the systems disclosed herein.

Figure 9:
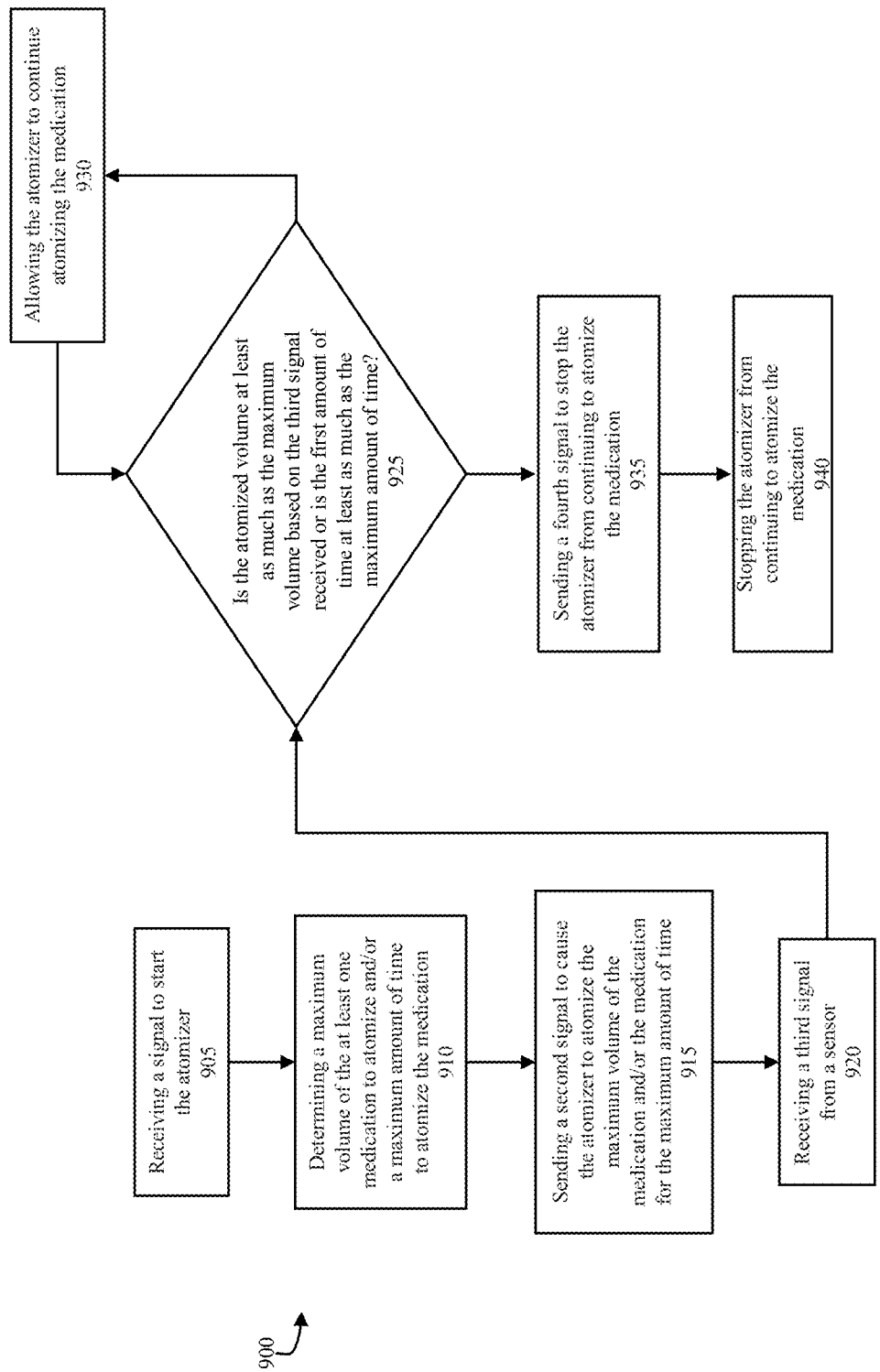
FIG. 9 is a flowchart diagram illustrating steps for a method of atomizing medication, according to an example embodiment.

With reference to FIG. 7 and FIG. 9, the process of atomizing the medication will be described. FIG. 9 is a flowchart diagram illustrating steps for a method 900 of atomizing medication, according to an example embodiment. The method 900 is performed by the processor of the attachment device. In step 905, the attachment device 712 receives a signal to start the atomizer to atomize the medication. The signal is received from the remote computing device. The signal may include data that allows the processor within the attachment device to determine that the atomizer should start to atomize medication within the capsule. Additionally, the data may include information to set the atomizer to atomize for a certain amount of time (for example a minimum or maximum) or certain amount of fluid (for example a minimum or maximum). This allows the rescuer or medical professional to control the dosage of the medication to the patient. The attachment device 712 may communicate with the remote computing device via Bluetooth®. The attachment device 712 may include security measures, such as requiring the rescuer to input a unique identifier, such as a security code or biometric information (such as a fingerprint) via the remote computing device to send the signal. For example, the rescuer may be a medical professional that is assigned a Personal Identification Number ("PIN") that, when entered into the remote computing device, allow the remote computing device to send the signal to start the atomizer within the capsule. Other examples of security codes may include, but are not limited to, a one-time-password, two-factor authentication codes, activation codes, or access codes. Other types of security measures configured to prevent unauthorized usage of the system may be used and are within the spirit and scope of the present invention.

In step 910, the attachment device determines, based on the signal, a maximum volume of the medication to atomize or a maximum amount of time to atomize the medication. The maximum amount of time can be set to a certain amount of time and can be adjusted during operation. For example, the maximum amount of time may be 2-10 seconds, 1 minute, etc. The maximum volume can be set to a certain volume and adjusted during operation. For example, the maximum volume may be 1, 2 or 4 milliliters. However, other embodiments may be used and are within the spirit and scope of the present invention. In step 915, the attachment device sends, to the atomizer, a second signal to cause the atomizer to atomize the maximum volume of the medication and/or the medication for the maximum amount of time. The maximum volume and the maximum amount of time depends on the signal sent by the remote computing device. In step 920, the attachment receives, from the atomizer, a third signal from the sensor that monitors an atomized volume of the medication within the capsule and/or a first amount of time the atomizer atomizes the medication. In step 925, the processor of the attachment device determines if the atomized volume is at least as much as the maximum volume based on the third signal received and/or the first amount of time is least as much as the maximum amount of time. In step 930, if the attachment device determines the atomized volume is not at least as much as the maximum volume based on the third signal received and/or the first amount of time is not at least as much as the maximum amount of time, the attachment device allows the atomizer to continue atomizing the medication. In step 935, after the attachment device determines the atomized volume is at least as much as the maximum volume based on the third signal received and/or the first amount of time is least as much as the maximum amount of time, the attachment device sends a fourth signal to stop the atomizer from continuing to atomize the medication within the capsule. In step 940, the attachment device stops the atomizer from continuing to atomize the medication within the capsule.

It is understood that this method is a continuous cycle and that each step of method 900 may operate concurrently with another step of method 900 to provide efficient atomization of medication within the system. In other embodiments, the method may further include additional steps to promote efficient atomization of medication consistent with the systems disclosed herein. In some embodiments, the steps of method 900 may be performed by a processor within the capsule.

Figure 10:
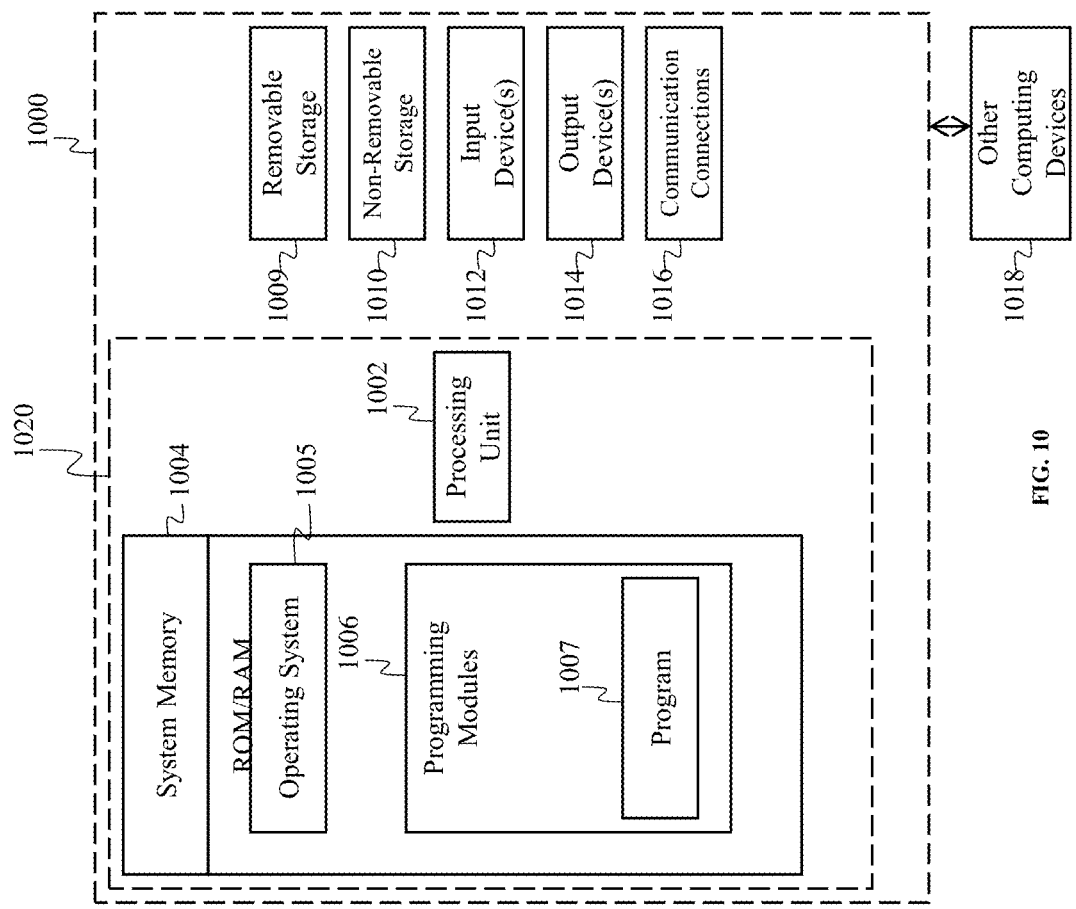
FIG. 10 is a block diagram of a system including a computing device and other computing devices, according to an exemplary embodiment of present technology.

Referring now to FIG. 10, a block diagram of a system including an example computing device 1000 and other computing devices is shown, according to an exemplary embodiment of present technology. Consistent with the embodiments described herein, the aforementioned actions performed by devices 708 and 712 may be implemented in a computing device, such as the computing device 1000 of FIG. 10. Any suitable combination of hardware, software, or firmware may be used to implement the computing device 1000. The aforementioned system, device, and processors are examples and other systems, devices, and processors may include the aforementioned computing device. Furthermore, computing device 1000 may include an operating environment for systems 100 and methods 800, 900 and others described herein. Methods 800, 900 and others described herein may operate in other environments and are not limited to computing device 1000.

With reference to FIG. 10, a system consistent with an embodiment of the invention may include a plurality of computing devices, such as computing device 1000. In a basic configuration, computing device 1000 may include at least one processing unit 1002 and a system memory 1004. Depending on the configuration and type of computing device, system memory 1004 may include, but is not limited to, volatile (e.g., random access memory (RAM)), non-volatile (e.g., read-only memory (ROM)), flash memory, or any combination or memory. System memory 1004 may include operating system 1005, and one or more programming modules 1006. Operating system 1005, for example, may be suitable for controlling computing device 1000's operation. In one embodiment, programming modules 1006 may include, for example, a program module 1007 for executing the actions of devices 708 and 712, for example. Furthermore, embodiments of the invention may be practiced in conjunction with a graphics library, other operating systems, or any other application program and is not limited to any particular application or system. This basic configuration is illustrated in FIG. 10 by those components within a dashed line 1020.

Computing device 1000 may have additional features or functionality. For example, computing device 1000 may also include additional data storage devices (removable and/or non-removable) such as, for example, magnetic disks, optical disks, or tape. Such additional storage is illustrated in FIG. 10 by a removable storage 1009 and a non-removable storage 1010. Computer storage media may include volatile and nonvolatile, removable and non-removable media implemented in any method or technology for storage of information, such as computer readable instructions, data structures, program modules, or other data. System memory 1004, removable storage 1009, and non-removable storage 1010 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 1000. Any such computer storage media may be part of device 1000. Computing device 1000 may also have input device(s) 1012 such as a keyboard, a mouse, a pen, a sound input device, a camera, a touch input device, microphone for capturing audio sound (which may include commands to operate the device). Output device(s) 1014 such as a display, speakers, a printer, etc. may also be included. The aforementioned devices are only examples, and other devices may be added or substituted.

Computing device 1000 may also contain a communication connection 1016 that may allow device 1000 to communicate with other computing devices 1018, such as over a network in a distributed computing environment, for example, an intranet or the Internet. Communication connection 1016 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 1004, including operating system 1005. While executing on processing unit 1002, programming modules 1006 (e.g., program module 1007) may perform processes including, for example, one or more of the stages of the methods 800, 900 as described above. The aforementioned processes are examples, and processing unit 1002 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. It is understood that, in certain embodiments, the functions/acts noted in the blocks may occur out of order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Referring now to FIG. 17A through FIG. 17C views of capsule 1700 are shown, according to example embodiments. FIGS. 17A and 17B are cross-sections of a side view of the capsule 1700 illustrating two distinct chambers, according to an example embodiment. The capsule 1700 includes a first chamber 1705, a second chamber 1710, and the atomizer 1715. The first chamber includes the medication in a liquid formulation, and the second chamber is below and separate from the first chamber. A membrane 1720 is disposed between the first chamber and the second chamber. The capsule 1700 further includes a stop 1725 that inhibits or prevents the first chamber from translating relative to the second chamber. The stop may include an extruding tab 1730 that allows a user of the system to pull the stop. When a force is applied in direction J onto a top portion 1732 of the first chamber 1705, the first chamber translates relative to the second chamber such that the first chamber is pushed towards the second chamber. Then, the translation of the first chamber towards the second chamber ruptures the membrane to provide fluid communication between the first chamber and the second chamber. The capsule may include a rupturing element 1735, such as a needle, which can puncture the membrane between the first chamber and the second chamber.

When the membrane is ruptured, the gravity causes the liquid formulation to flow from the first chamber into the second chamber. An atomizer is disposed proximate to a portion 1740 or lower end of the second chamber that is distal to the first chamber. The second chamber abuts the atomizer such that gravity causes the medication in the second chamber to abut the atomizer. Gravity pushes the medication through the atomizer.

The use of a two-chamber capsule provides distinct advantages for shipping and transport of medications by enabling a controlled release mechanism. The first chamber serves as a storage compartment where the medication is securely held until activated, while the second chamber allows fluid communication with the medication after activation.

During shipping and transport, the medication remains confined within the first chamber of the two-chamber capsule, providing a stable and secure environment. This configuration prevents unintended exposure or premature mixing of the medication with any accompanying fluids or substances, ensuring the integrity and potency of the medication during transit. Upon activation, typically through a user-initiated action, the capsule's design allows for controlled fluid communication between the first and second chambers. This enables the release of the medication into the second chamber, where it becomes available for administration or further processing.

By separating the storage and activation stages, the two-chamber capsule minimizes the risk of premature degradation or alteration of the medication during shipping. This feature enhances the stability and shelf life of the medication, preserving its efficacy and therapeutic properties until it is ready for use. Moreover, the controlled release mechanism provided by the two-chamber design allows for precise dosing and administration. Activation at the desired time ensures that the medication is mixed with the accompanying fluid or solvent in the second chamber when it is most appropriate for administration. This feature is particularly beneficial for medications requiring reconstitution or those with specific timing requirements for optimal effectiveness. Overall, the two-chamber capsule's ability to store the medication separately from the accompanying fluid or solvent during shipping and transport provides advantages in terms of stability, potency, and controlled release. This design ensures that the medication remains protected until activation, allowing for safe and effective administration while maintaining the desired therapeutic outcomes.

FIG. 17C is a side view of the capsule 1701 having a pull clip 1745, according to an example embodiment. The pull clip is in attachment with the stop 1725 and allows a user to pull the stop out in direction G. The first chamber 1705 is a removable vial that may be stored separately. A removable vial would help improve the shelf life of the medication and keep the medication secure during transport. The second chamber 1710 includes a tapered wall sections 1750, in which the cross-sectional diameter of the lower end of the second chamber is less than the cross-sectional diameter of the atomizer 1715. The tapered section acts as a ramp for the medication to direct the medication into the atomizer. The rupturing element 1755 is a sharp edge that punctures the membrane when the first chamber is pushed down. The sharp edge spans within the perimeter of the membrane. The user can push on the top portion 1732 of the first chamber in the direction of J, which causes the sharp blade to break the membrane 1720.

Referring now to FIGS. 18A through 18B, the capsule 1800 is shown, according to an example embodiment. FIG. 18A is a side view of the capsule 1800, according to an example embodiment. FIG. 18B is a side view of the capsule 1800, according to an example embodiment. FIG. 18C is a perspective view of the capsule 1800, according to an example embodiment. FIG. 18D is an exploded perspective view of the capsule 1800, according to an example embodiment. Capsule 1800 may be used in the first embodiment, second embodiment, and third embodiment of the system for administering medication to a patient. Capsule 1800 may also be used in the inhaler embodiment shown in FIGS. 23 through 25 and in the wand, embodiment shown in FIGS. 26 through 27. The capsule 1800 is an advanced drug delivery system that incorporates innovative features to ensure precise administration and monitoring of medication and fluid levels. Capsule 1800 includes substantially similar components to the capsule 500 described above with reference to FIG. 5. As shown, capsule 1800 includes a crimp 1805, a rubberized seal 1810 to receive medication, at least one chamber 1815, electrical contacts 1820, at least one sensor 1825 for monitoring a level of medication and/or fluid, a mesh 1830, and a housing 1835. The crimp is a structural securing element used to hold the rubberized seal to the chamber. The crimp provides structural integrity and ensures the stability of the capsule's internal elements, contributing to the overall functionality and reliability of the device.

Rubberized seal 1810 is specifically designed to receive medication within capsule 1800. Composed of elastomeric materials, such as natural or synthetic rubber, this seal creates an airtight and secure enclosure for the medication, preventing leakage or contamination. The rubberized seal's resilience and deformable properties enable it to adapt to the medication's shape and size, ensuring a snug fit. The rubberized seal is an elastomeric component designed to facilitate the secure and airtight reception of medication boluses acting as a refillable container within the capsule. The seal exhibits resilient and deformable characteristics, allowing it to effectively enclose and retain the boluses while ensuring the integrity of the container's contents. The rubberized seal comprises a resilient material, typically composed of natural or synthetic rubber, or other suitable elastomers. This material possesses desirable properties such as flexibility, elasticity, and compression resistance, rendering it able to be pierced by a needle to inject medication within the seal and/or container. In its preferred embodiment, the rubberized seal is integrated into a refillable container, forming a tight and hermetic seal when engaged. The capsule may feature an opening or orifice in the crimp specially designed to receive the medication boluses or provide access to the rubberized seal to allow a user to inject medication into the rubberized seal by way of manual insertion or automated dispensing.

Capsule 1800 incorporates at least one chamber 1815 to hold the medication securely. These chambers are designed to accommodate the desired amount and formulation of medication, ensuring proper storage and controlled release. The number of chambers may vary based on the specific application and intended use of the capsule, such as FIG. 17A and FIG. 17B which employ a two-chamber capsule as described above. Electrical contacts 1820 are integrated into capsule 1800 to facilitate communication and power transfer between the device and the capsule. These contacts enable data exchange, power supply, or control signals, supporting functions such as monitoring, data recording, or activating specific features of the device. Capsule 1800 incorporates at least one sensor 1825 to monitor the level of medication and/or fluid within the capsule. These sensors may employ various technologies such as pressure sensors, level sensors, or other suitable sensing mechanisms. By accurately detecting and relaying this information, the sensor(s) enable precise medication dosage and monitoring.

Mesh 1830 is specifically designed to facilitate the atomization or aerosolization of the medication contained within the capsule. The atomizing mesh is composed of a fine material with micro-sized openings that allow for the breakup of the liquid medication into tiny droplets or particles, creating an inhalable or respirable mist. During the activation process, when the medication is intended for administration, the liquid medication is transferred or directed towards the atomizing mesh. As the medication flows through the mesh, it encounters the fine openings, which disrupt the liquid into a spray or mist-like form. The atomized medication, consisting of smaller droplets or particles, becomes suitable for inhalation or respiratory delivery. This mechanism allows for efficient and targeted delivery of the medication to the desired site within the respiratory system, maximizing its effectiveness and bioavailability.

Housing 1835 forms the outer structure of capsule 1800, providing a protective enclosure for the internal components. The housing may be composed of various materials, such as plastic, metal, or composite materials, offering durability and shielding the internal elements from external influences or damage. The housing may include a plurality of cutouts for the electrical components, namely, the sensor and the electrical contacts. Additionally, the housing may include a cutout which may be an opening 1840 allowing the user to see or visualize the level of medication within the at least one chamber 1815. The at least one chamber may be transparent and/or have a transparent section that corresponds to the opening 1840 and/or may include alphanumeric fluid level indicators.

In certain embodiments, as shown in FIG. 18C, the housing of the capsule exhibits an asymmetrical shape 1845 in the form of a protruding wedge or dovetail. This distinctive design feature serves a specific purpose within the invention, allowing for precise orientation and proper alignment of the capsule within the device. The protruding wedge or dovetail shape of the housing functions as a guiding mechanism for the capsule. It enables the user to align and insert the capsule into the device in a predetermined orientation, ensuring that the components and interfaces of the capsule correspond correctly with those of the device. The asymmetrical nature of the protrusion restricts the capsule from being inserted in any other position, ensuring that it is securely and accurately positioned within the device. This design consideration promotes reliable functionality and prevents potential errors or malfunctions that may arise from incorrect alignment.

Additionally, the protruding wedge or dovetail shape contributes to the overall stability and secure engagement of the capsule within the device. By creating a locking or interlocking mechanism between the capsule and the device, the asymmetrical shape enhances the overall robustness and reliability of the system. The incorporation of a protruding wedge or dovetail as an asymmetrical shape within the housing of the capsule represents an innovative aspect of the invention. It allows for intuitive and foolproof orientation and alignment, ensuring seamless operation and optimal performance of the device.

The inclusion of a refillable capsule in the disclosed invention represents a significant advancement over the prior art, offering a range of advantages and improvements. The refillable capsule introduces enhanced convenience, cost savings, and environmental benefits to the field of medication administration. By enabling multiple uses, the refillable capsule eliminates the need for single-use disposable capsules, leading to substantial cost savings for users. This economic advantage is further complemented by the reduction of waste, promoting sustainability and environmental stewardship. Moreover, the refillable nature of the capsule allows for personalized medication administration, as users can easily refill it with the specific medication and dosage required for their individual needs. This flexibility not only optimizes therapeutic outcomes but also simplifies medication management by eliminating the need for multiple specialized devices or capsules. Additionally, the user-friendly design facilitates a straightforward refilling process, ensuring ease of use and minimizing the likelihood of errors or confusion. Overall, the inclusion of a refillable capsule in the invention provides users with improved convenience, cost savings, and a more sustainable approach to medication administration.

Referring now to FIG. 19, a side view of a diagram 1900 of the device in operation for a patient in an intubated state, wherein the device 1902 is in attachment with an endotracheal tube 1905 and a conduit of a ventilator 1910, according to an example embodiment. The device includes a tubular chamber that is a removable modular tubular extension, according to the second embodiment or third embodiment shown in FIGS. 21 and 22, respectively. The removable modular tubular extension includes a first extension tubular chamber 1920, which includes a first extension receiving section 1925 and a second extension chamber receiving section 1930. The first extension tubular chamber defines the first channel 1935. The removable modular tubular extension further includes a second extension tubular chamber 1940 substantially in fluid communication with the first extension tubular chamber. The second extension tubular chamber is configured to be received by a device receiving section 1942 such that the second extension tubular chamber is in fluid communication with the second channel 1944 of the device, which also receives the capsule 1946. Therefore, when inserted into the second channel of the device, the second extension tubular chamber defines a portion 1945 of the second channel. The atomized medication forms a stable and uniform aerosol, or generally homogeneous aerosol, when combined with the air in the first channel. An endotracheal tube is in attachment with the first extension receiving section 1925 so that endotracheal tube is in fluid communication with the tubular chamber and the conduit. The conduit 1950 is received by the second extension receiving section 1930 and is in fluid communication with an air outlet of a respiratory support device, such as the a ventilator 1910.

In some cases, the weight of the attachment device may be an issue when the user must put down the attachment device during usage. Therefore, in some embodiments, the capsule may be configured to be received directly by the modular tubular extension. The capsule and the attachment device may include a Universal Serial Bus ("USB") port such that a USB cord can provide electrical communication between the attachment device and the capsule. This allows the capsule and the modular tubular extension to rest on the patient without the weight of the device, which can be placed elsewhere.

Referring now to FIGS. 23 through 25 and FIGS. 34A through 34D, an inhaler embodiment of the device 2300 for administering medication to a patient is shown. The device 2300 includes an electrical insulator 2305 in the form of a tab that can be pulled by the user of the device. The electrical insulator prevents electrical communication between a replaceable power source 2310 and the capsule 2315. Once the electrical insulator is pulled, the replaceable power source can provide electrical power to the capsule such that the atomizer 2320 is powered by the power source. As described above with reference to FIGS. 17A and 17B, the user of the device must press on the capsule to allow the fluid medication to flow towards the atomizer. The atomized medication flows through the second channel 2325 towards the first channel 2330 leading to an outlet 2335 on which the patient can position their mouth. Device 2300 allows the patient to inhale the atomized medication from the second channel without the help of a medical professional or any other user. Device 2300 may also include an outlet covering or cap 2340 to cover the outlet of the device when stored. In the present embodiment, device 2300 does not include a resilient air bladder. However, in some embodiments, it may be configured to receive a resilient air bladder on an end 2345 that is distal to the outlet 2335.

In one example embodiment, as shown in FIGS. 34A through 34D, the device may include a button 3450. The button functions as a small control mechanism that serves various critical purposes. In one embodiment, the button may be designed to engage or disengage the device, activate the atomization process, or lock, unlock, or eject a capsule that contains the medication. The button may be mechanically or electronically linked to different components such as the atomizer, the capsule housing, or locking mechanisms. Pressing the button may initiate the flow of medication from the capsule to the atomizer, lock the capsule in place for use, unlock it for removal or replacement, or activate ejection mechanisms to release a spent capsule. The materials for the button could be chosen from durable plastics, metals, or other suitable materials that are both ergonomic and hygienic. The inclusion of a multifunction button represents an enhancement over previous designs by consolidating various control functions into a single, user-friendly interface. This consolidation enhances the usability of the inhaler, provides more precise control, and allows for more efficient handling. Moreover, it could be particularly beneficial for users with limited dexterity or those requiring quick and easy access to their medication, contributing to a more compact and streamlined design.

In certain embodiments, each press of the button may release a predetermined bolus of atomized medication. This function ensures exact control, allowing for the administration of a specific dose of atomized medication into the patient's respiratory system. The button may be intricately connected to the medication chamber, atomizer, and other system components, coordinating to atomize and meter the correct volume of medication for each press.

Referring to FIGS. 25A through 25H, various embodiments of the device or formulation delivery system 2500 are disclosed. FIG. 25A shows a fully assembled electronic formulation delivery system 2500, showing various sections, such as a first section 2502, a second section 2504, and a third section 2506 come together to form a cohesive and functional unit. In the disclosed embodiment, the device is segmented into three detachable sections, 2502, 2504, and 2506, each designed to be interchangeable and replaceable, providing a high degree of modularity to its overall design. This feature allows users to customize or upgrade individual sections according to their preferences or wear-and-tear requirements. For example, a user could replace a spent cartridge or update to a newer version without having to discard the entire device, significantly extending its lifespan. Additionally, the ability to interchange parts can accommodate a variety of functionalities or aesthetics, such as varying reservoir sizes, battery capacities, or exterior designs. It is noted that other embodiments having the second and third sections integrated to form a single component as a removable cartridge is also covered within the scope of the invention. FIG. 25A provides a comprehensive view of the device in its operational state. FIG. 25B illustrates a schematic view of a first side of the device or the formulation delivery system 2500. It is noted that formulation delivery system and device may be used interchangeably throughout the document for some embodiments, as the formulation delivery system refers to the device of the embodiments as shown in FIGS. 25A through 25H. The term "user" comprises, but is not limited to, a human being, an animal, or a patient, among other possible entities.

In the embodiment, formulation may be a liquid form of a substance including one of pharmaceutical, therapeutic, or cosmetic substances, to address specific conditions or enhance skin health. For example, pharmaceutical substances may include a medication, such as antibiotics or antifungal solutions designed to treat infections. In some embodiments, the medication may also include therapeutic substances including a regenerative medication targeting treatment of tissue repair and regeneration in the user. Regenerative medications include bioactive agents or biological agents capable of stimulating cellular growth, differentiation, and repair. The medication may comprise a combination of growth factors, cytokines, stem cells, or other agents known to facilitate tissue regeneration and repair. In another embodiment, the medication comprises one of peptides, proteins, growth factors, cytokines, exosomes, and extracellular vesicles derived from human mesenchymal stem cells suspended and/or dissolved in an aqueous medium. In another embodiment, the medication is an aqueous suspension and solution comprising cells, cellular byproducts, and cell-derived products. The cells, the cellular byproducts, and cell-derived products are stem cells. It is noted that bioactive agent and biological agent may be used interchangeably throughout the document, as the biological agent may have a bioactive effect in some embodiments. Cosmetic substances may include hyaluronic acid or vitamin C serums for skin rejuvenation. The device atomizes and delivers these substances in a fine mist form to achieve targeted treatment or skincare benefits.

In the fully assembled configuration, the first section 2502, which includes a mouthpiece having a first attaching structure at one end, attaches to the second section 2504 including the removable cartridge. The removable cartridge includes a second attaching structure the end that couples with the first section. The connection between these two sections is designed to be secure and leak-proof, ensuring efficient transfer of medication to the atomizer. For the mouthpiece, the first attaching structure may be a set of grooves or rails that align with corresponding features on the cartridge. The first attaching structure may also include a magnetic coupling system that uses magnets embedded within the mouthpiece to attract metallic components on the cartridge, facilitating an easy snap-on attachment. On the removable cartridge, the second attaching structure may include protrusions or tabs that are shaped to slide into the mouthpiece grooves, locking the cartridge in place. Alternatively, a twist-and-lock mechanism may be used, where the cartridge features a threaded neck that screws into a mating threaded socket on the mouthpiece or metal connectors that couple with the magnets on the mouthpiece. These designs allow for a robust connection that can withstand the motion and force of daily use while still being straightforward for the user to replace or interchange the cartridge when needed.

The third section 2506, housing the electronics including a power source or battery, a Printed Circuit Board (PCB) that connects to the second section 2504. The second section includes an electrical contact, such as contacts 2520 and 2521 of FIG. 25C, and the third section includes connectors 2523, 2530 on one end of the third section. During coupling of the second section and the third section, the electrical contacts 2520 and 2521 of the second section mate with connectors 2523, 2530 of the third section to establish electrical communication. The alignment of the electrical contacts and the connectors facilitates the transfer of power and communication signals necessary for the device's operation. In one embodiment the third section may comprise a processor. The design ensures that the electronic components in the third section effectively controls the atomization process in the second section. In another embodiment, the third section may house a display to provide relevant information to the user through the display 2510, as shown in FIG. 25B. The relevant information may include amount of dosage, remaining battery life, alerts and notifications for cartridge replacement, maintenance requirements, or error messages if the device is malfunctioning. Additionally, the relevant information may include usage statistics, such as frequency of use or average session length, which assists users in monitoring their consumption habits, and current power setting or temperature at which the device is operating.

The mouthpiece is specifically designed for the user to receive the formulation in a mist form. This mouthpiece features an opening, numbered 2501, that is comfortably inserted into the user's mouth, allowing for the direct inhalation of the liquid formulation once it is atomized. The design and functionality of the mouthpiece is selected such that the mist is delivered efficiently and comfortably to the user. Various types of mouthpieces can be employed depending on the specific medical needs or preferences of the user. These may vary in shape, size, or material, each designed to optimize the delivery of the mist while providing comfort and ease of use. For size variations, the mouthpiece can range from slim, discreet tips designed for portability and ease of storage, to larger, ergonomically shaped options that provide a more comfortable user experience during extended sessions. As for material choices, durable plastics are commonly used for their heat-resistant properties and comfortable feel. Alternatively, metal mouthpieces, made from stainless steel or aluminum, offer a premium touch and the added benefit of being easy to clean. In various examples, glass or ceramic can be used due to their inert properties and ability to preserve the purity of flavor. Silicone is another option, known for its softness and flexibility, which can contribute to a more comfortable and adaptable user experience. Each material and size offers a different aesthetic and tactile sensation, providing the user with a range of options to personalize the device.

The fully assembled device forms an elongated cylindrical body, resembling a cigar in shape and size, as shown in FIGS. 25A and 25B. The body is characterized by its cylindrical form, meaning its cross-sectional profile is circular and consistent throughout its length. The term 'elongated' refers to the body's length being significantly greater than its diameter, giving the device a stretched, slender appearance. This uniform cylindrical shape is chosen for its structural integrity, providing robustness and durability essential for a handheld electronic device. Additionally, the elongated aspect of the cylinder makes the device easy and comfortable to hold, aligning with ergonomic principles for handheld devices. The design's slim profile also contributes to its portability, allowing for easy storage and discreet use in various settings. In various embodiments, the device may depart from the conventional cylindrical design to incorporate alternative shapes that cater to different aesthetic preferences or ergonomic considerations. For instance, the device could adopt a rectangular or box-like shape, providing a flat base for stability when set down and a larger internal volume for components or a higher capacity battery. Some designs might feature an oval or elliptical cross-section, which can offer a more natural and comfortable grip. Ergonomic shapes, such as those with contoured profiles, can be molded to fit snugly in the user's hand, enhancing the tactile experience and ease of use. Sleeker, pen-style designs may also be used for their discreetness and portability. These varied shapes can also serve functional purposes, such as improving device stability, portability, or user experience.

As noted above, the system is inherently modular, allowing for the interchangeability of parts in its fully assembled configuration. This modularity is a key aspect of the device's design, enhancing its versatility and adaptability to different user needs. The system's modularity primarily revolves around the second section, the removable cartridge, which contains the formulations or medicated fluid. Users have the flexibility to choose from multiple second sections, each potentially containing different medications or combinations thereof. This feature is particularly beneficial for users who require a regimen involving multiple medications, as it allows for the convenient and efficient switching of cartridges without the need for multiple separate devices. The system ensures that these removable cartridges can be easily attached and detached from the first section, which includes the mouthpiece. The receiving section in the first section is tailored to accommodate various cartridges, facilitating a secure and leak-proof connection regardless of the cartridge chosen. This interchangeability is achieved without compromising the functionality or efficiency of the medication delivery process.

Furthermore, the third section, housing the electronic components and power source, is designed to seamlessly integrate with any of the interchangeable second sections. This ensures that the device's electronic controls and power supply remain consistent and reliable, irrespective of the cartridge in use. The electrical contacts and communication interfaces are standardized across different cartridges, allowing for a uniform operation. Additionally, the overall design of the device is portable and resembles the shape of a cigar, enhancing its ease of use, especially in terms of handling and carrying. This compact, cigar-shaped design allows users to hold and operate the device naturally, similar to using a traditional inhaler or similar handheld medical devices. The device is easy to use and facilitates the positioning and stabilization of the mouthpiece when administering the mist. The portability and ergonomic design are particularly advantageous for users who require regular medication administration, offering them the convenience of therapy on the go without drawing undue attention.

Figure 25A:
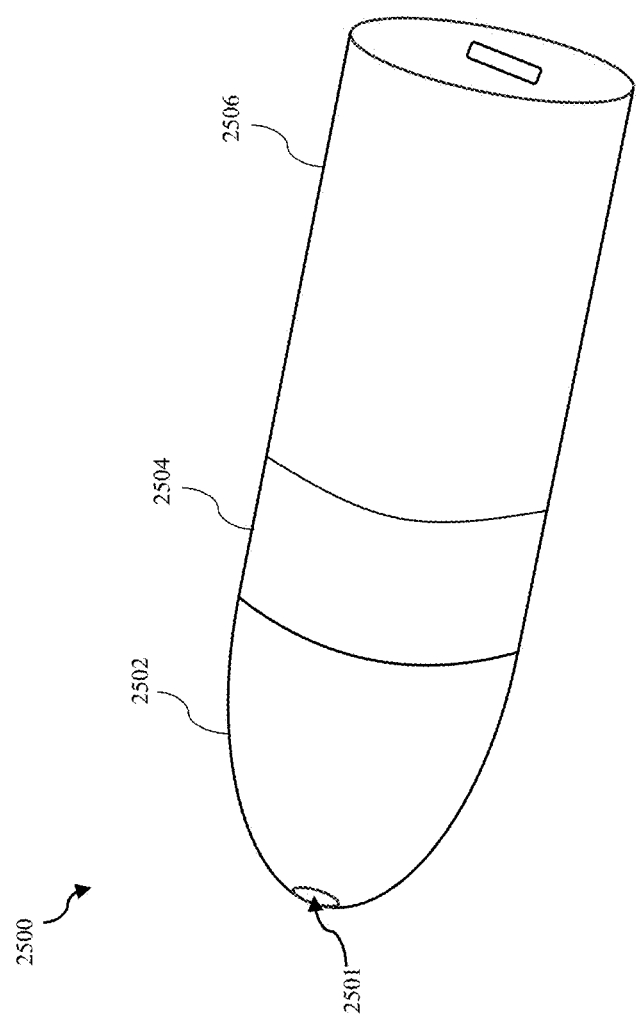
FIG. 25A illustrates a device for administering at least one formulation to a user, according to an embodiment.
Figure 25B:
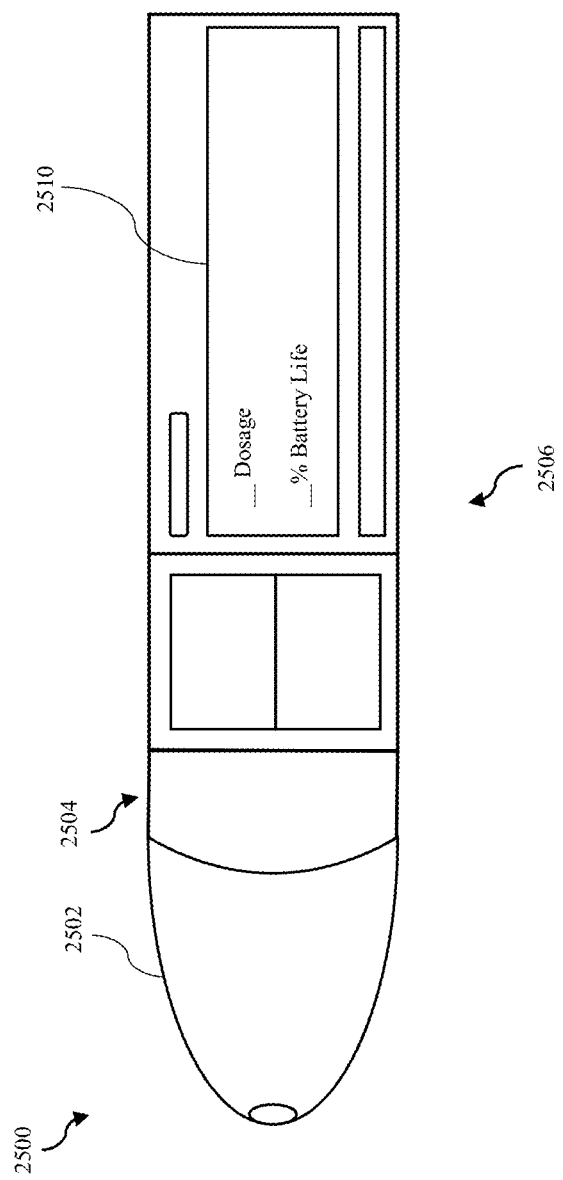
FIG. 25B illustrates a side schematic view of a device for administering at least one formulation to a user, according to another embodiment.
Figure 25C:
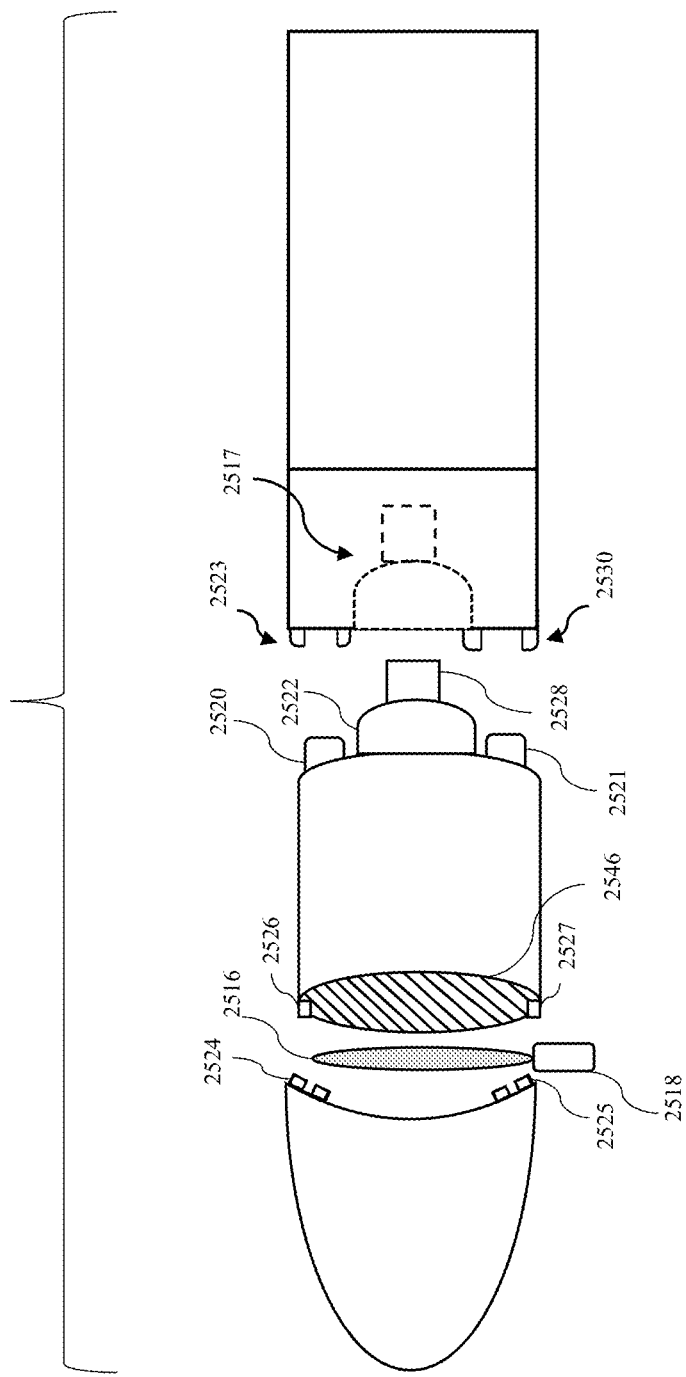
FIG. 25C illustrates an exploded view of a device for administering at least one formulation to a user, according to an embodiment.

FIG. 25C illustrates an exploded perspective view of the device with various interconnected sections of the device. FIG. 25C illustrates the mouthpiece component that includes the first attaching structures having attachment portions 2524, 2525 designed for secure coupling with corresponding parts of the second section during assembly. Additionally, a covering member 2516 is shown having a pull tab 2518. This covering member serves as a protective layer for the atomizer designed to protect the atomizer when not in use. The covering member can be engaged and removed by a user through the pull tab for operational or maintenance purposes. Incorporating the covering member to shield the atomizer when not in use presents significant advantages, especially in terms of hygiene and longevity of the device. This protective measure guards the atomizer against dust, debris, and accidental spills, which can compromise the atomizer's functionality or lead to contamination of the substance being vaporized. In an example embodiment, the pull tab extends out from an open portion of the mouthpiece such as the portion that is not inserted into the user's mouth or into any other component of the device. This strategic placement ensures that the mouthpiece can remain comfortably in place during use, without interfering with the user's comfort. The user can activate the pull tab to remove the protective covering over the atomizer without needing to remove the mouthpiece from their mouth or detach it from the device. This seamless integration allows for a quick transition from a protected state to active use, enhancing the device's usability and effectiveness during operation. In one embodiment, the covering member is retractable and directly coupled to the atomizer, enabling the user to expose the atomizer by pulling a tab during use. This pull tab can be hooked to an external tab disposed on the outer wall of the removable cartridge to keep the atomizer accessible while in use. After use, the covering member automatically retracts to its original position, ensuring the atomizer is covered and protected without requiring additional user intervention. This feature not only enhances the usability of the device by making the operation smoother and more convenient but also prevents contamination, thus extending the overall lifespan of the device and maintaining optimal performance over time.

FIG. 25C further depicts the second section of the device, identifiable as the removable cartridge, which is fitted with two attachments 2526 and 2527, at its first end. These attachments are specifically configured to connect to the attachment portions 2524 and 2525 of the mouthpiece. The opposite end of this section features electrical contacts 2520 and 2521, positioned at the end distal to an atomizer 2546. These contacts are purposed for establishing an electrical connection necessary for the device's operation. As shown, the section has the atomizer 2546 placed on an opposite side of the electrical contacts. Positioning the atomizer opposite to the electrical contacts in the removable cartridge section offers several distinct advantages. Primarily, this configuration minimizes the risk of electrical interference or heat damage to the sensitive electronic components. By keeping the atomizer that generates the most heat away from the electrical contacts, it helps preserve the integrity and lifespan of the circuitry. Furthermore, this arrangement enhances safety by reducing the likelihood of electrical shorts that could occur if liquid from the atomizer were to come into contact with the electrical contacts. Additionally, placing the atomizer at one end and the contacts at the other can optimizes the internal layout of the cartridge, allowing for a more efficient use of space within the device. This spatial efficiency can lead to a more compact design, making the device easier to handle and more aesthetically pleasing while maintaining functional robustness.

The atomizer 2546 is an essential component for converting the formulation including a medicated fluid into a fine aerosol. Generally, atomizers in drug delivery systems are components for creating fine particles suitable for inhalation. In one example embodiment, the atomizer is characterized by a vibrating mesh. Unlike traditional atomizers that often use heat or pressure, the vibrating mesh atomizer consists of a fine mesh with numerous small holes that vibrate at high frequencies. This vibration turns the liquid medication into a fine mist, creating an aerosol that is easy to inhale. This method of atomization is particularly effective in producing a consistent particle size, ensuring that the medication is optimally absorbed by the lungs. This precise control over the aerosolization process is crucial for treatments requiring accurate dosing. Additionally, the atomizer may be configured to provide a consistent particle size for the aerosol, ensuring that the medication is effectively absorbed by the user's lungs. This precise control over particle size is critical for ensuring the efficacy of the medication, particularly for treatments where dosage accuracy is paramount.

The third section of the device is equipped with connectors 2523, 2530. These connectors are designed to align and mate with the electrical contacts 2520 and 2521 of the second section, enabling electrical communication. The design of the removable cartridge and the third section of the device can incorporate various types of electrical contacts and connectors to ensure reliable and efficient electrical connectivity. For instance, the removable cartridge may feature spring-loaded pogo pins that provide a consistent connection even with movement or wear, which are matched by corresponding recessed contacts on the third section. Alternatively, flat, pad-type contacts could be used for a slim profile, requiring precise alignment with similar flat connectors in the third section. Magnetic connectors are another option, offering the benefits of easy alignment and attachment while also naturally repelling dust and debris. Additionally, blade or leaf-style contacts, known for their durability and strong electrical connection, could be employed, interfacing with slotted connectors on the third section. Each type of contact and connector is selected based on the specific requirements for electrical performance, mechanical robustness, and ease of use, providing flexibility in the device's design to cater to various operational environments and user preferences. The body of this third section includes a slot 2517 or a receiving portion, intended to accommodate the cap 2522 and handle 2528 of the cartridge in an assembled configuration. The handle 2528 provides a means for the user to manipulate the cartridge, facilitating insertion or removal from the second section of the device. Incorporating a handle to manipulate the wick assembly significantly enhances the usability and maintenance of the device, particularly concerning the removal and attachment of the wick assembly to the removable cartridge. This feature allows users to easily and safely adjust, replace, or clean the wick assembly without directly touching potentially delicate parts or contaminated areas, thereby reducing the risk of damage to the device or exposure to residual substances. A handle provides a firm grip and precise control over the assembly process, ensuring that the wick is properly aligned and securely fastened within the cartridge. This not only simplifies the assembly and disassembly processes, making them more user-friendly and less time-consuming, but also helps maintain the optimal performance of the device by ensuring that the wick is always correctly positioned for efficient vaporization.

Figure 25E:
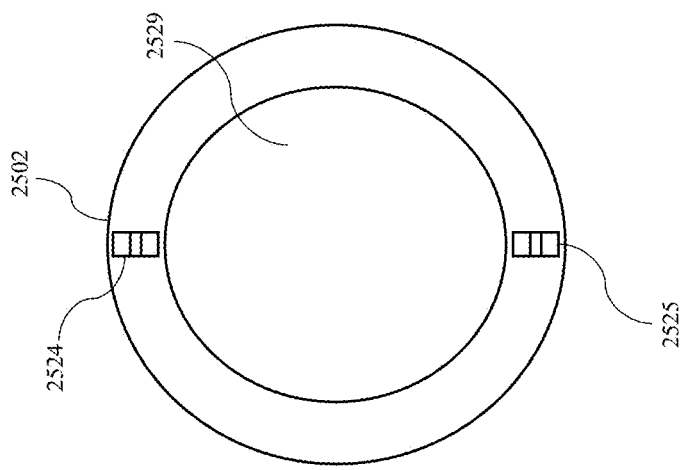
FIGS. 25D and 25E illustrate various views of a mouthpiece of a device for administering at least one formulation to a user, according to an embodiment.
Figure 25D:
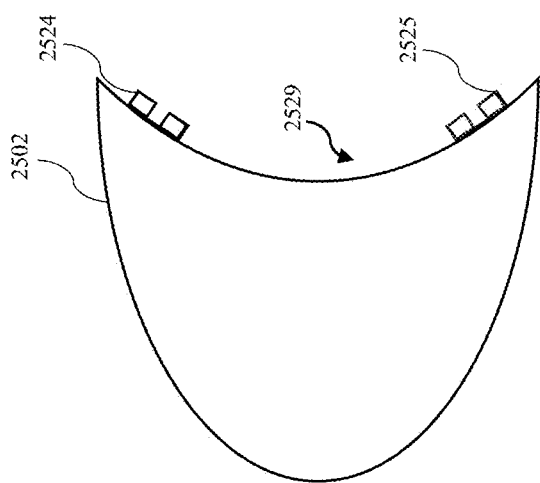

Referring now to FIGS. 25D and 25E that illustrate the first section 2502 of the electronic medication delivery system, according to an example embodiment. The first section 2502, which is the mouthpiece, serves as the primary interface for the user's interaction with the device and is essential in the delivery of the medicated aerosol. FIG. 25D is a side schematic view of the first section 2502 of the electronic medication delivery system, and FIG. 25E is the front schematic view of the electronic medication delivery system. As shown in FIGS. 25D and 25E, the first section 2502 comprises the mouthpiece that the user places in their mouth to inhale the medication.

The first section features the mouthpiece, which is designed for user comfort and the effective administration of medicated aerosol into the respiratory system of the user. Typically, this is where the user inhales the medication. The ergonomic design of the mouthpiece ensures a comfortable fit against the user's lips and mouth, facilitating easy use and efficient medication delivery. Both the shape and the materials of the mouthpiece are selected to enhance comfort during use, while also ensuring durability and maintaining hygiene.

The first section also includes a receiving section 2529. This part of the device is designed to interface with a portion of the second section of the system, which contains the wick assembly. The receiving section 2529 is a connection point in the first section for attaching to the second section of the system. The receiving section of the device is designed to ensure a secure and seamless connection with the removable cartridge from the second section, facilitating a harmonious integration between the two components. This feature, essential for the device's functionality, consists of an opening tailored to receive a specific portion of the cartridge, enabling it to be inserted into the mouthpiece's body. The design of this receiving section allows for a snug fit that not only secures the cartridge firmly in place but also ensures that the integrity of the aerosol pathway is maintained for optimal medication delivery. The design of the connection takes into consideration the physical fit including the dimension and the ease with which users can replace or interchange cartridges, aiming for a balance between secure engagement and user-friendly interaction. The first attaching structure including attachment points, 2524 and 2525, are crafted to engage with the second attaching structure including tabs on the second section. These connections are made through a snap-fit mechanism, a common type of attachment that allows for easy assembly and disassembly. These snap-fit attachments utilize mating components that click together, often with one part featuring a protruding tab that snaps into a recess or slot in the mating component. Other types of attachments that could be used in such devices include threaded fasteners, such as screws or bolts, bayonet mounts (which require a push and twist action), magnetic attachments, and sliding locks. The choice of attachment type depends on factors such as the required strength of the connection, the need for ease of disassembly, and the desired durability of the mechanism.

The receiving section is engineered to provide a secure and leak-proof connection with the cartridge. To achieve this, it incorporates a mating mechanism. This mechanism is designed to be intuitive and user-friendly, allowing for easy attachment and detachment of the cartridge. It may involve a specific geometrical design, such as a grooved or contoured interface, which aligns precisely with corresponding features on the cartridge. This ensures a snug fit and maintains the alignment of the two sections, critical for proper operation of the device. In one example embodiment, the mating mechanism may incorporate magnetic elements. These magnets are strategically placed on adjacent surfaces of corresponding sections to facilitate alignment and attachment, providing a user-friendly experience. For example, when the cartridge is brought close to the receiving section, the magnetic attraction helps guide it into the correct position, ensuring a proper and effortless connection.

In addition to magnetic alignment, the receiving section may feature a twist-and-lock mechanism. This may involve a simple rotational motion by the user to engage and secure the cartridge. The twist-and-lock system is particularly effective in providing a firm and stable connection, which is crucial for the consistent functioning of the device.

Furthermore, the receiving section may integrate a rubberized gasket. This gasket is situated at the interface between the receiving section and the cartridge, creating a tight seal upon connection. The rubberized material is chosen for its flexibility and durability, ensuring an airtight seal that prevents leakage of the medicated fluid. This seal is vital for maintaining the integrity of the medication delivery process.

In addition to its physical design, the receiving section may also include materials or coatings that enhance the connection's durability and performance. For instance, the use of a high-grade, medical-safe material ensures both biocompatibility and longevity. The choice of material plays a significant role in maintaining the integrity of the fluid pathway, preventing contamination, and ensuring the device's overall reliability. Additionally, the material selection for the mouthpiece is critical. It must be durable enough to withstand repeated use and potential exposure to medication, yet soft enough to provide comfort during inhalation. The materials are chosen to be non-reactive with the medication, ensuring that the medication's efficacy is not compromised. The removable cartridge, which is cylindrical in this depiction, may alternatively be designed in various shapes such as rectangular, oval, or customized forms to fit specific devices or user preferences. The shape of the cartridge is often dictated by ergonomic considerations, the volume of medication it needs to hold, and how it will interface with the device. For instance, a flat, disc-shaped cartridge might be employed to create a more compact device, while a larger cylindrical shape might be used to contain a greater volume of medication for devices intended for multiple doses or extended use.

Figure 25F:
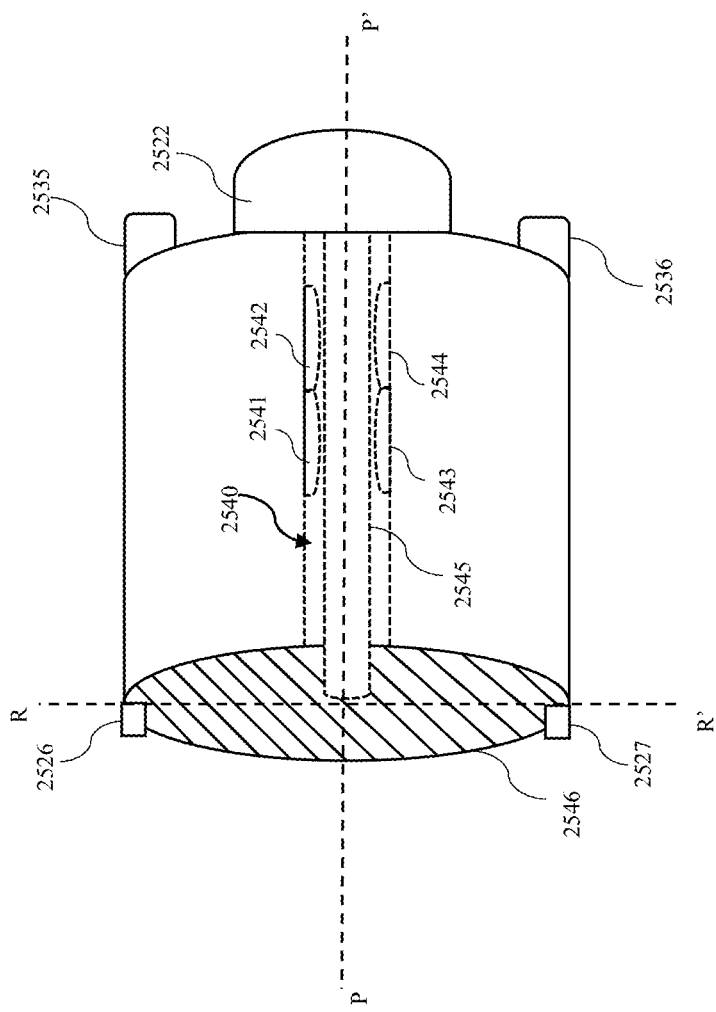
FIG. 25F illustrates a removable cartridge of a device for administering at least one formulation to a user, according to an embodiment.
Figure 25G:
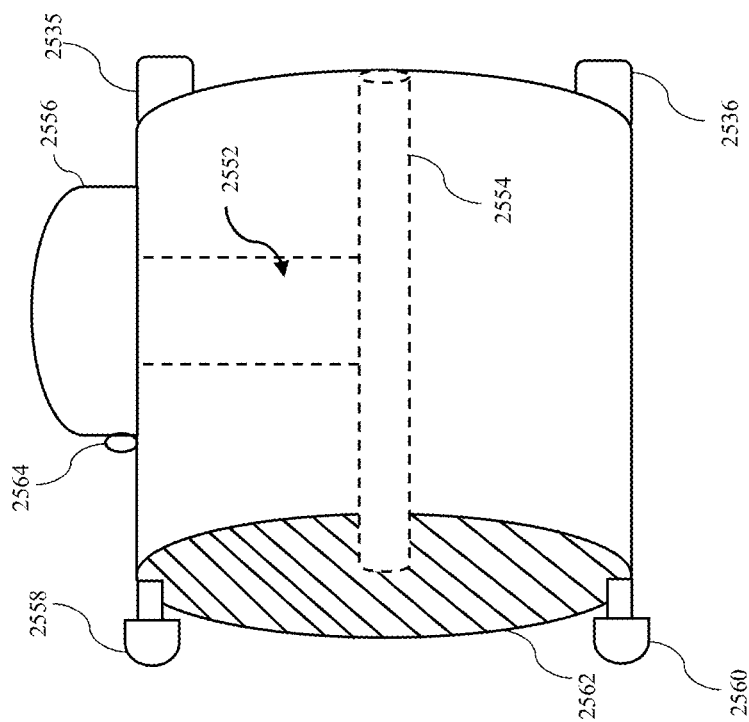
FIGS. 25G and 25H illustrates another removable cartridge of a device for administering at least one formulation to a user, according to an embodiment.
Figure 25H:
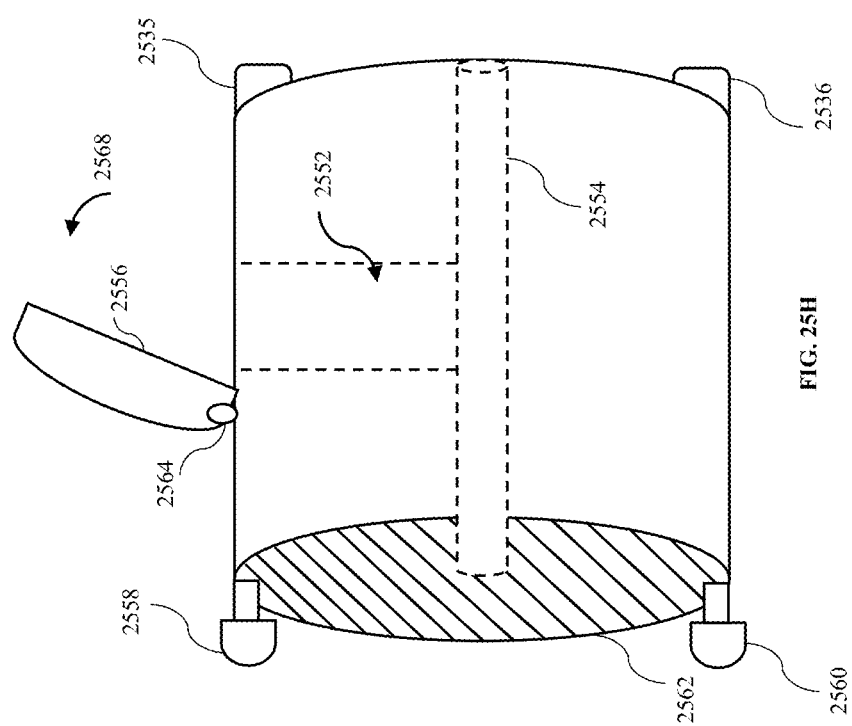

FIG. 25F illustrates the removable cartridge designed for use in a formulation delivery device. This figure showcases the removable cartridge, which includes an elongated channel 2540, an atomizer 2546, a wick assembly with a cap 2522 and a wick 2545, and various internal guides 2541, 2542, 2543, 2544. In the context of a medication device, the removable cartridge serves as the reservoir for the medicated formulation. The interchangeable nature of the cartridge allows for ease of refilling or replacing the medication, thus offering flexibility and convenience to the user. This feature is particularly beneficial for patients requiring multiple medications or dosages, as it simplifies the process of switching between different medication types without the need for multiple devices. The removable cartridge, which is cylindrical in this depiction, could alternatively be designed in various shapes such as rectangular, oval, or customized forms to fit specific devices or user preferences. The shape of the cartridge is often dictated by ergonomic considerations, the volume of medication it needs to hold, and how it will interface with the device. For instance, a flat, disc-shaped cartridge might be employed to create a more compact device, while a larger cylindrical shape might be used to contain a greater volume of medication for devices intended for multiple doses or extended use.

Within the cartridge, the channel 2540 runs the length of the cartridge from the first end to the second end. This channel is sized to accommodate the dimensions of the wick, ensuring that the wick can be saturated with medication while maintaining the necessary capillary action to draw the medication towards the atomizer. The wick assembly, integral to the function of the device, features the removable cap 2522, and the wick 2545, which are designed as a singular unit. The design is such that removing the cap from the cartridge also withdraws the wick from the channel, and reinserting the cap positions the wick back into the channel. This setup is strategically devised so that the cap remains external to the channel while the wick resides within, fully inside the channel. In various embodiment, the channel may contain the formulation and the wick may be immersed in the formulation. Other embodiments, where the channel does not contain the formulation and houses the wick is also covered within the scope of the invention. The wick within a medication device is a crucial component that absorbs the medication and, upon activation, directs it toward the atomizer for nebulization. The wick's material is selected based on its absorbency and compatibility with the formulation, often being made from cotton, synthetic fibers, or ceramic materials. Its utility lies in its ability to provide a consistent and controlled delivery of medication, which is particularly important for ensuring accurate dosages and effective treatment.

Guides, also referred to as alignment ribs, numbered 2541, 2542, 2543, and 2544, are affixed to the interior wall of the channel to ensure the correct placement and stabilization of the wick within the cartridge. In the embodiment, the wick is affixed within the removable cartridge. These alignment ribs can vary in shape, such as straight, curved, or angular and can be made from a range of materials that are chosen for their durability and compatibility with the medication. For instance, plastic ribs might be used for their resilience and moldability, while metal ribs could be selected for their strength and rigidity. The size of these ribs is also variable, designed proportionally to fit the internal dimensions of the channel and the size of the wick. The atomizer is strategically located at one end of the cartridge, opposite the end where the removable cap is placed. In this configuration, the wick is oriented transversely or substantially perpendicular to a plane of the atomizer, allowing for an effective transfer of medication. The perpendicular or transverse arrangement of the wick's longitudinal axis, PP, to the atomizer's longitudinal axis, RR", ensures an efficient pathway for the formulation to reach the atomizer. This orientation enables one end of the wick to maintain direct contact with the atomizer, allowing the formulation to be conveyed efficiently for nebulization. The relative position of the wick being substantially perpendicular to the atomizer allows the entire cross-sectional surface of the wick to abut directly against the atomizer. This specific configuration ensures that the maximum surface area of the wick is in contact with the atomizer, facilitating a complete and consistent transfer of the liquid formulation from the wick's reservoir to the atomizer. Further, the channel extends from a portion of an outer wall of the removable cartridge to the wick and the capsule is disposed within the channel such that the capsule is arranged transversely to a longitudinal axis of the wick. Additionally, the cartridge is equipped with electrical contacts, 2535 and 2536, at the end opposite the atomizer, enabling it to interface with the power source of the medication delivery device, ensuring that the atomizer receives the necessary energy to aerosolize the medication for inhalation. This design provides precision in medical device manufacturing, where every component must work synergistically to deliver safe and effective treatment to patients.

The electrical contacts are designed to interface with corresponding contacts on a subsequent section. Regarding the first section, it integrates with the second section and the second section further integrates with the third section. These contacts are strategically placed to ensure a reliable electrical connection upon the assembly of the two sections. The primary function of these contacts is to facilitate the transfer of power and control signals between the sections. For instance, when the cartridge, containing the medicated fluid, is attached to the first section, the electrical contacts activate the atomizer within the first section, initiating the process of converting the fluid into an aerosol.

The electrical contacts in the receiving section may include an electrical mating portion. This mating portion is designed to ensure a consistent and uninterrupted electrical connection between the receiving section and the interchangeable cartridge, even when the atomizer is in operation and vibrating. The vibration of the atomizer, necessary for converting the medicated fluid into an aerosol, presents a potential challenge for maintaining a stable electrical connection. To address this, the electrical mating portion is engineered to accommodate movement without losing contact. This could be achieved through the use of spring-loaded contacts, flexible conductive materials, or a design that allows for a certain degree of movement while still maintaining an electrical connection.

The electrical mating portion is designed to be robust and to provide a secure connection that can withstand the mechanical stress caused by the atomizer's vibration. This design ensures that there is no disruption in the power supply or control signals between the sections of the device. It is essential for the reliable function of the atomizer and, consequently, for the effective delivery of the medication. Additionally, the electrical mating portion may be integrated in a way that aligns effortlessly with the corresponding contacts on the cartridge. This ease of alignment is important for ensuring that the device is user-friendly and that the process of changing cartridges is straightforward and error-proof.

Each section may feature electrical contacts designed for connection with another section. These contacts are crucial for the transmission of power and communication signals between the sections. The electrical contacts are strategically positioned to align with corresponding contacts in an adjacent section. This alignment ensures a secure and efficient electrical connection when the sections are assembled. The contacts are typically made of conductive materials known for their durability and resistance to corrosion, such as gold or silver alloys, to ensure a reliable connection over the lifespan of the device. The design of these contacts takes into account the need for a stable connection that can withstand regular use. This includes considerations for easy alignment and connection, ensuring that when the second and third sections are joined, the electrical contacts meet with minimal effort from the user. This user-friendly design is essential for the regular replacement or refilling of the cartridge in the second section.

In some embodiments, the electrical contacts may include features such as spring-loaded pins or pressure contacts. These features ensure a consistent electrical connection even when there is slight movement or misalignment between the sections. They provide the necessary flexibility while maintaining a strong electrical contact, crucial for the uninterrupted operation of the atomizer and other electronic components in the device.

Figure 26:
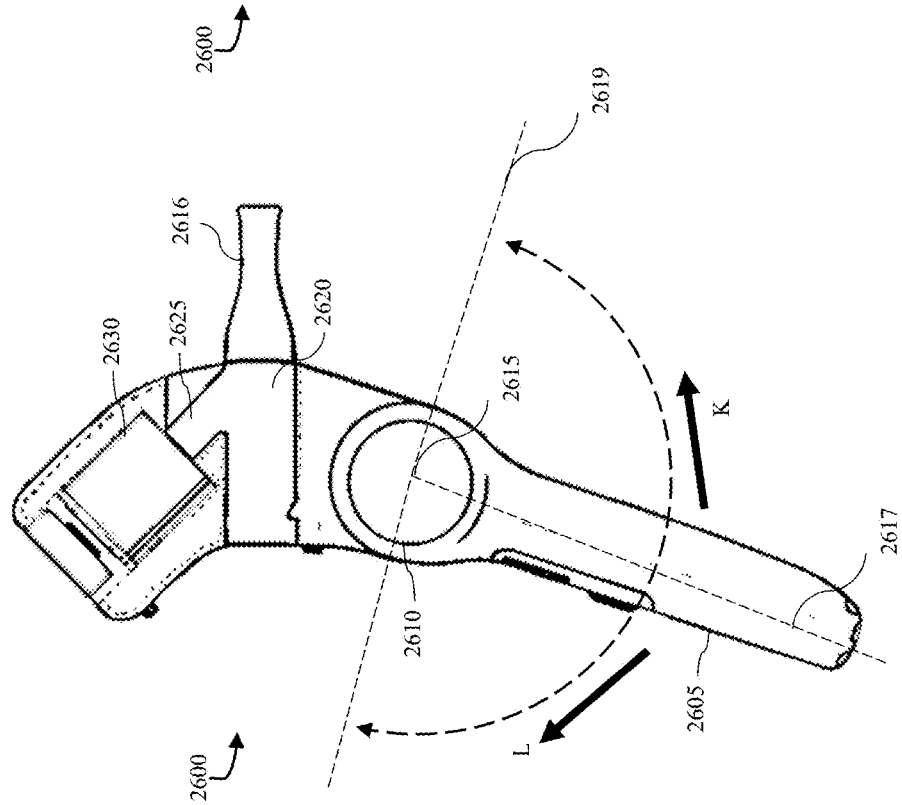
FIG. 26 illustrates the device for administering at least one medication to a patient in an unconscious state to a conscious state, according to a wand embodiment.

Furthermore, the electrical contacts are designed to facilitate not just power transmission from the third section's power source to the atomizer in the first section via the second section but also to allow communication signals to be sent and received. This includes signals related to the control of the atomization process, feedback from sensors in the second section, and information display on the user interface.

FIG. 25G illustrates the removable cartridge having a distinct variation from the embodiment outlined in FIG. 25F. The embodiment of FIG. 25G has the positioning of the removable cap 2556, which is situated on the side of the atomizer of the removable cartridge, rather than on an opposite end of the atomizer. The removable cartridge contains a channel 2552, which is an elongated passage extending from a section of the cartridge's outer wall near the cap to the wick 2554. This channel is critical as it forms the path through which the medication travels from its storage area within the cartridge to the wick, ready for atomization. In this embodiment, the channel 2552 is substantially perpendicular or transversely to a plane of the wick 2554, a design that suggests intentionality in how the medicated formulation is delivered to the wick. The wick is securely attached within the body of the cartridge, fixed at one inner wall and reaching out to the atomizer at the opposite end. This attachment can be achieved through a variety of methods. For example, the wick may be embedded into the cartridge during the manufacturing process, mechanically fastened with small clips or tabs, or held in place with non-reactive, medical-grade adhesives. The chosen method typically balances the need for a firm hold to prevent movement during use and the convenience of replacement if necessary.

The perpendicular orientation of the wick to the atomizer plays a pivotal role in the uniform distribution of the medicated formulation. When the wick is attached centrally to the atomizer, it allows for an even spread of the liquid across the atomizing component, contributing to a consistent aerosol output. The advantages of this design include more efficient medication delivery, leading to potentially better therapeutic outcomes, minimized wastage of medication due to uneven spreading, and the prevention of hotspots that could lead to inconsistent atomization. The cap's attachment mechanism is represented in the drawing by a hinged connection, which allows the cap to swing open, presumably illustrated in FIG. 25H. The hinge 2564, enables a controlled opening of the cap, allowing the user to refill the channel 2552 with medication as needed. The figure indicates the cap's pivotal movement along the direction marked as 2568. This hinge system ensures that when the cap is in the closed position, the channel 2552 is fully covered, maintaining the sterility of the wick and the medication. In an open position, the cap exposes the channel, providing access for medication refills for absorption by the wick. Other methods of cap attachment might include a slide-and-lock mechanism, where the cap slides into place before locking, or a magnetic system that allows for a secure closure without physical clips or latches.

In this embodiment, the insert tabs, such as 2558 and 2560, are positioned on one end of the cartridge. These tabs, with their rounded edges, are designed for effortless insertion into the corresponding part of the mouthpiece. Pushing the cartridge into the mouthpiece until the tabs click into place ensures the cartridge is securely attached, providing the user with a clear indication that the device is ready for use. The design of these tabs is critical not only for a secure fit but also for ensuring ease of cartridge replacement by the user, contributing to the overall practicality and maintenance of the medication delivery device.

In the disclosed embodiments, the formulation is not directly contained in the removable cartridge but instead the wick is pre-absorbed with the formulation is used. This design significantly reduces the likelihood of leaks and spills, as the liquid is securely held within the wick's fibers, which can enhance the device's reliability and user confidence during transport and use. The pre-absorption method ensures that the formulation is evenly distributed across the wick, promoting consistent vapor production and efficient utilization of the substance without the need for frequent refills. This setup also simplifies the cartridge replacement process, as users can swap out the wick assembly without handling the liquid directly, making the process cleaner and more convenient. Additionally, this approach can improve the longevity of the device by minimizing the exposure of liquid to sensitive components such as the atomizer and electrical contacts, thereby preserving their function and reducing maintenance needs. Overall, the use of a pre-absorbed wick in a removable cartridge enhances the practicality, efficiency, and user-friendliness of the device.

Referring now to FIGS. 26, 27, 36A through 36C, views of a wand embodiment of the device 2600 for administering medication to a patient are shown. FIG. 26 is a partial cross-sectional side view of the wand embodiment. FIG. 27 is a perspective view of the wand embodiment. FIGS. 36A through 36C show additional embodiments of the wand. The device 2600 includes a handle 2605 configured to be held a user to administer medication to a patient. The device 2600 includes a pivoting and/or rotating element 2610 configured to alter the angle between the handle and a mouthpiece. The rotating element may be a button to engage a locking mechanism to allow the handle 2605 to change position or relative angle. The rotating element allows the device to rotate and/or pivot about origin 2615. The handle may have at least 180 degrees of rotation—or at least 90 degrees or rotation from the position shown in FIG. 26 where the device is centered about axis 2617 and may rotate in any such direction toward axis 2619. This may allow the user to better visualize the display on the device.

Figure 27:
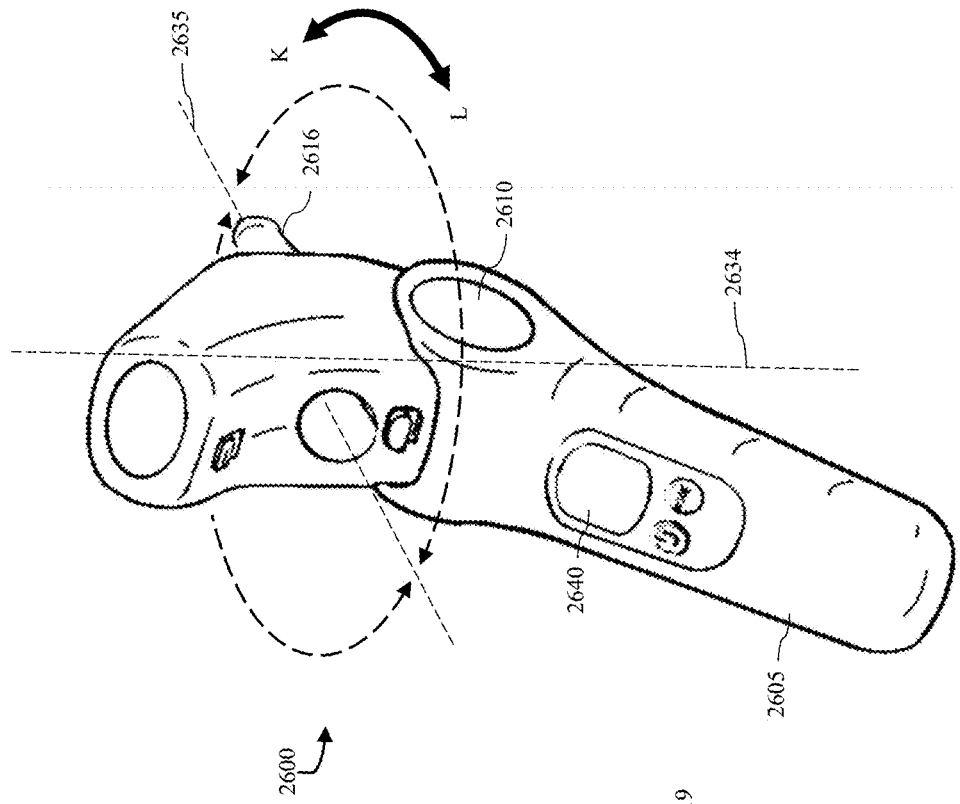
FIG. 27 illustrates the device for administering at least one medication to a patient in an unconscious state to a conscious state, according to an wand embodiment.

The mouthpiece 2616 is in fluid communication with the first channel 2620 and second channel 2625 that are configured to guide the flow of atomized medication from the capsule 2630. In some embodiments, as shown in FIG. 27, the device 2600 may be able to rotate about axis 2634 to reorient the mouthpiece direction relative to axis 2635. In one embodiment, the upper portion of the device may rotate, whereas in another embodiment, the lower portion of the device, namely, the handle, may rotate in the manner indicated by the arrows in FIG. 27. The rotation about axis 2634 may best be described as a twist or rotational motion. The rotation motion allows the administrator of the medication to view the display on the device and/or have access to the controls. For example, if the user is self-administering the atomized medication, the user may want visualization of the screen while they are using the mouthpiece, as shown in FIG. 36C. Similarly, if a third party is administering the device to another, maybe a child or unconscious person for example, then the administrator would want to visualize the screen or display 2640 on the device such that it opposed and/or faced away from the position of the mouthpiece and/or mask. It is understood that the device may have at least 180 degrees of rotation to allow the orientation of the display to align on the same side as the mouthpiece and or oppose the mouthpiece, as necessary. It is understood that FIG. 26 illustrates a first type of rotation, namely, rotating about an origin or pivoting, and FIG. 27 illustrates a second type of rotation, namely, rotating about an axis.

Figure 19:
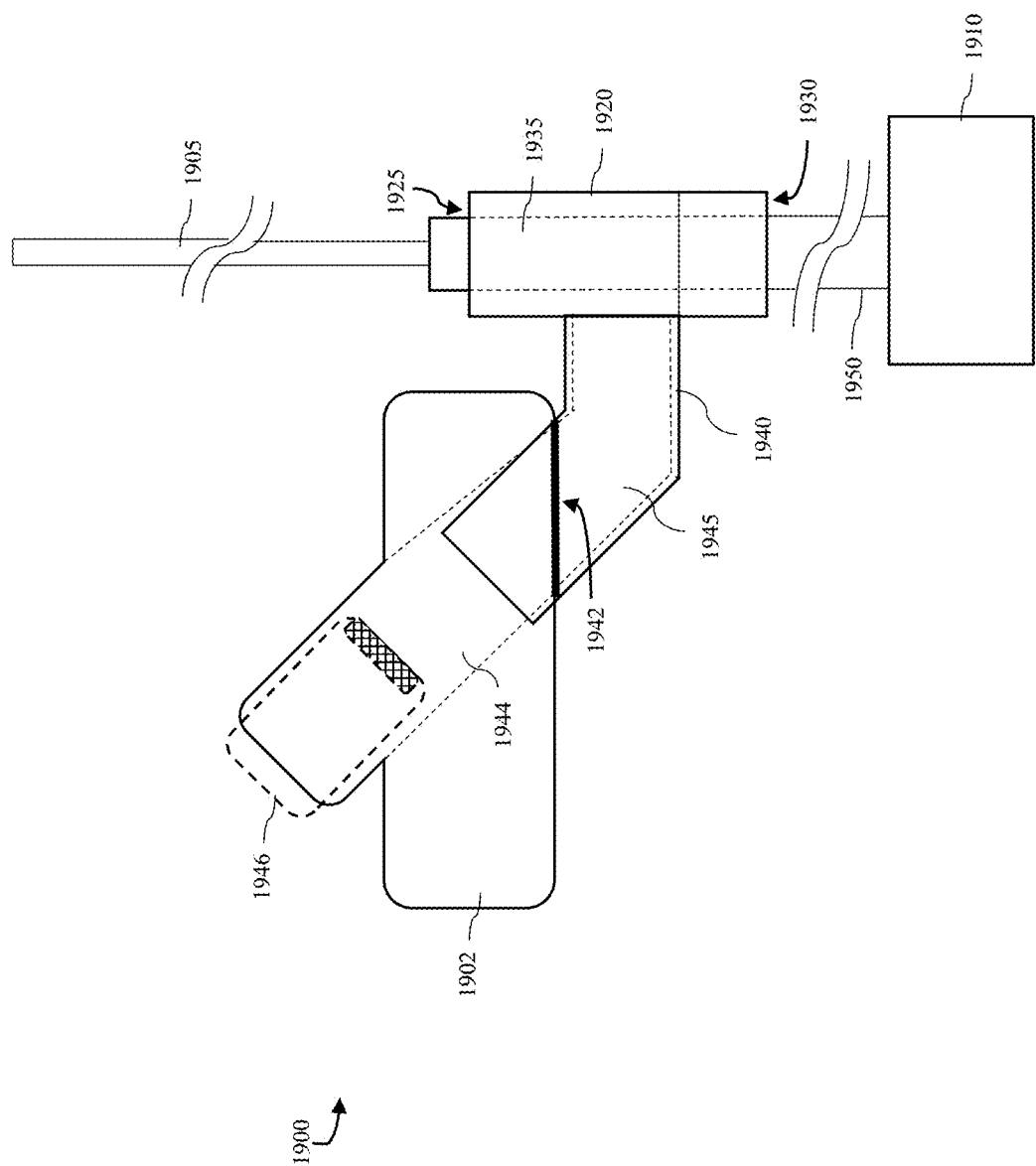
FIG. 19 illustrates a diagram of the device in operation for a patient in an intubated state, wherein the device is in attachment with an endotracheal tube and a ventilator, according to an example embodiment.

In some embodiments, the mouthpiece 2616 may be flexible and configured to be attached to the modular tubular extension. This allows device 2600 to be used as the attachment device shown in FIG. 19. Additionally, the handle 2605 may include arms or a cradle to maintain the device 2600 in an upright position when resting on a patient's chest.

Figure 28:
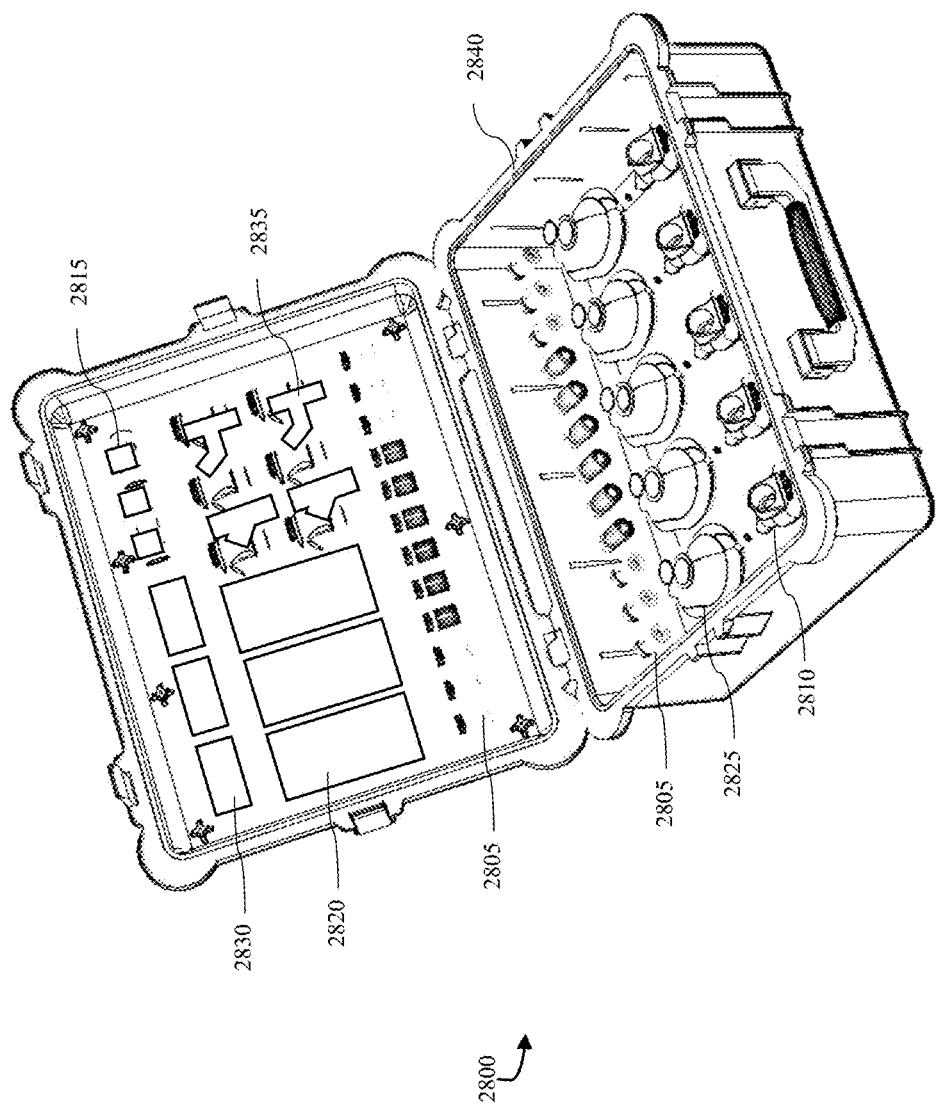
FIG. 28 illustrates a kit for converting a device for administering at least one medication to a patient in an unconscious state to a conscious state, according to an example embodiment.

Referring now to FIG. 28, a kit 2800 for converting a device for administering at least one medication to a patient in an unconscious state to a conscious state is shown, according to an example embodiment. The kit includes at least the components described in method 2900 below. The kit includes capsules 2805, the medical devices 2810 or base units, and removable caps 2815 to cover at least one receiving section of the medical device. The kit may further include resilient air bladders 2820 for removably attaching to receiving sections of the medical device, and mouthpieces and masks 2825 for removably attaching to a receiving section. The kit may further include power sources 2830 and modular tubular extensions 2835 for removably attaching to a receiving section. The kit also includes a case 2840 for enclosing the capsules, the medical devices, the caps, the resilient air bladders, the mouthpieces, the masks, the power sources, and the modular tubular extensions. The kit is configured to provide necessary components for various medical situations in which medication must be administered. The case may also include receiving sections or slots configured to securely hold each of the aforementioned components within the case.

The case may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The case may be made of other materials and is within the spirit and the disclosure. The case may be formed from a single piece or from several individual pieces joined or coupled together. The components of the case may be manufactured from a variety of different processes including an extrusion process, a mold, casting, welding, shearing, punching, folding, 3D printing, CNC machining, etc. However, other types of processes may also be used and are within the spirit and scope of the present invention.

Figure 29A:
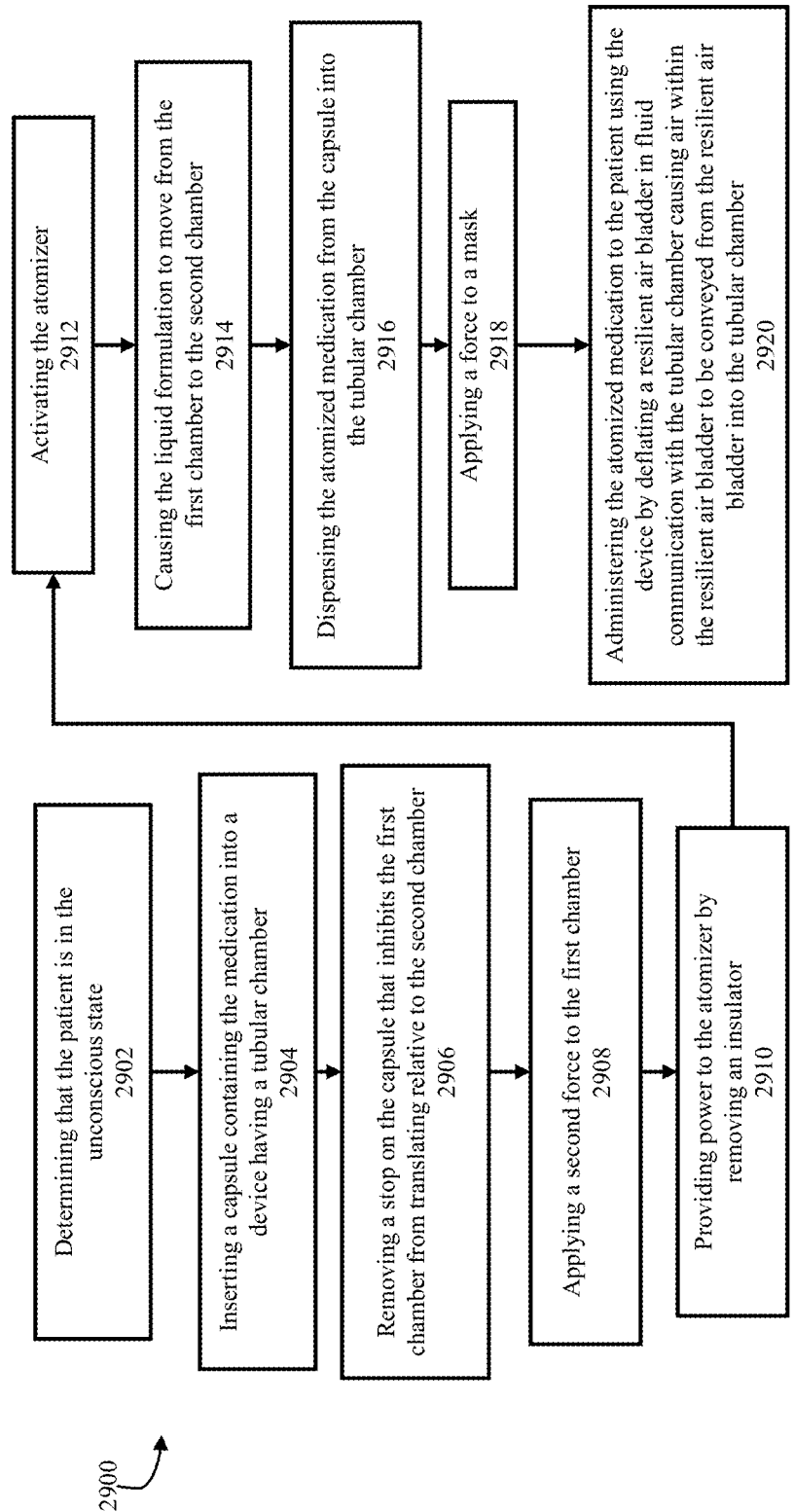
FIG. 29A is a flowchart diagram illustrating steps for a method for converting a device for administering at least one medication to a patient in an unconscious state to a conscious state, according to an example embodiment.
Figure 29B:
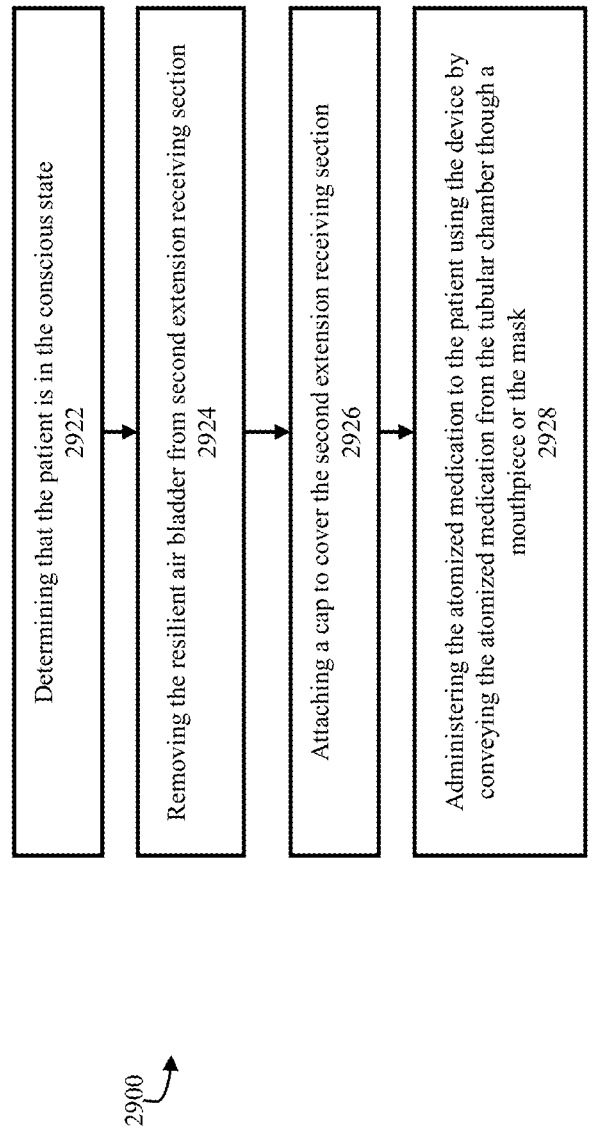
FIG. 29B is a flowchart diagram illustrating steps for a method for converting a device for administering at least one medication to a patient in an unconscious state to a conscious state, according to an example embodiment.
Figure 29C:
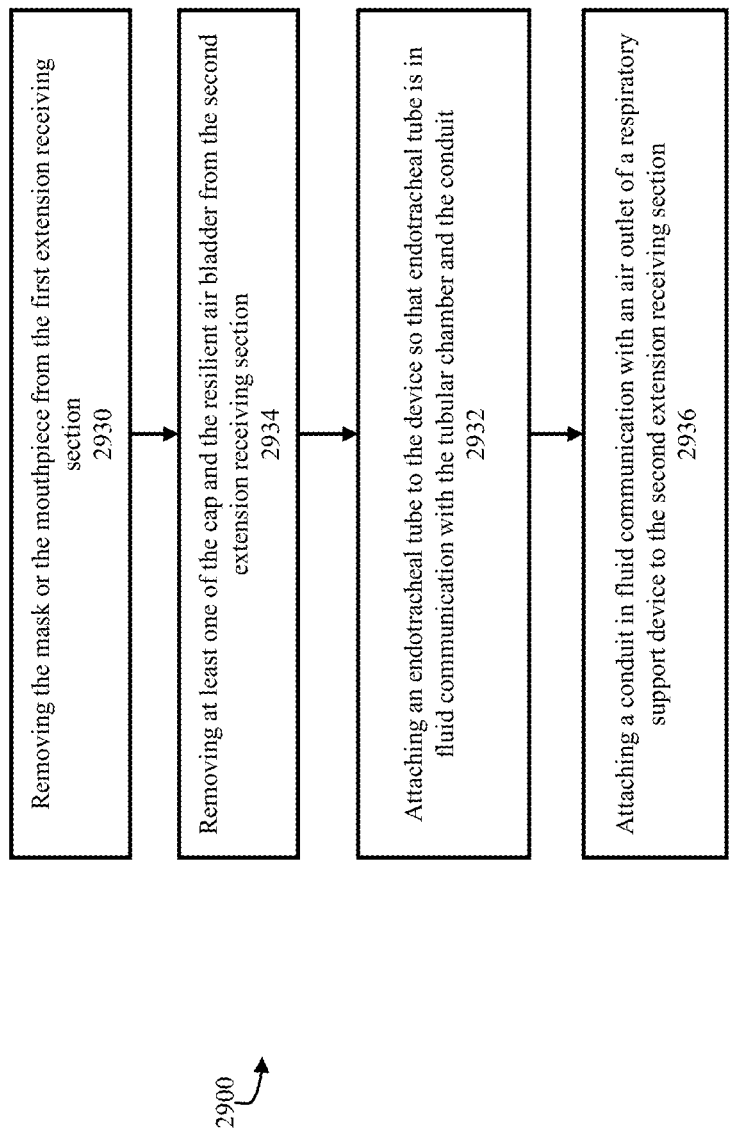
FIG. 29C is a flowchart diagram illustrating steps for a method for converting a device for administering at least one medication to a patient in an unconscious state to a conscious state, according to an example embodiment.

Referring specifically to FIGS. 29A through 29C, with intermittent reference to FIGS. 1 through 28 as indicated below, a flowchart diagram of a method 2900 for administering at least one medication to a patient when the patient is unconscious and when the patient is consciousness and for converting a device for administering at least one medication to a patient in an unconscious state to a conscious state is shown, according to an example embodiment. Unless otherwise stated, generally, the method described herein is not limited to the particular order of the disclosed steps. While the disclosed order provides certain improvements over the prior art, it should be understood that the method steps can be rearranged, modified, or performed in alternative sequences without departing from the scope of the disclosure. In certain embodiments, the method steps may occur concurrently, simultaneously, independently, dependently, or in any other suitable manner, as determined by the specific implementation and requirements. The flexibility of the method allows for adaptability and optimization based on various factors, such as system resources, data availability, and user preferences. Therefore, the specific arrangement and order of the method steps should be interpreted as illustrative rather than limiting, and the disclosure encompasses all variations, modifications, and alternatives falling within the scope of the appended claims.

Method 2900 begins with step 2902, wherein a user determines that the patient is in the unconscious state. Method 2900 includes removing and inserting the second extension tubular chamber of the removable modular tubular extension into a device receiving section depending on the state of the patient. For example, in most unconscious states or conscious states, the device will be in attachment with the first embodiment of the removable modular tubular extension 2000 shown in FIG. 20. The system 100 in FIG. 1A may incorporate this removable modular tubular extension. In an intubated state, the device will be in attachment with the second embodiment, or third embodiment of the removable modular tubular extension shown in FIGS. 21 and 22. Shown in FIGS. 20 through 22, the removable modular tubular extensions 2000, 2100, and 2200 include a first extension tubular chamber 2005 and a second extension tubular chamber 2010. The first extension tubular chamber includes a first extension receiving section 2015 and a second extension receiving section 2020. The first extension tubular chamber defines the first channel 2025 that provides fluid communication between the second channel, the attachments, such as the endotracheal tube and the conduit of the ventilator, received by the first extension receiving section and the second extension receiving section. When inserted into the device, the second extension tubular chamber defines a portion 2030 of the second channel on the device.

Figure 29D:
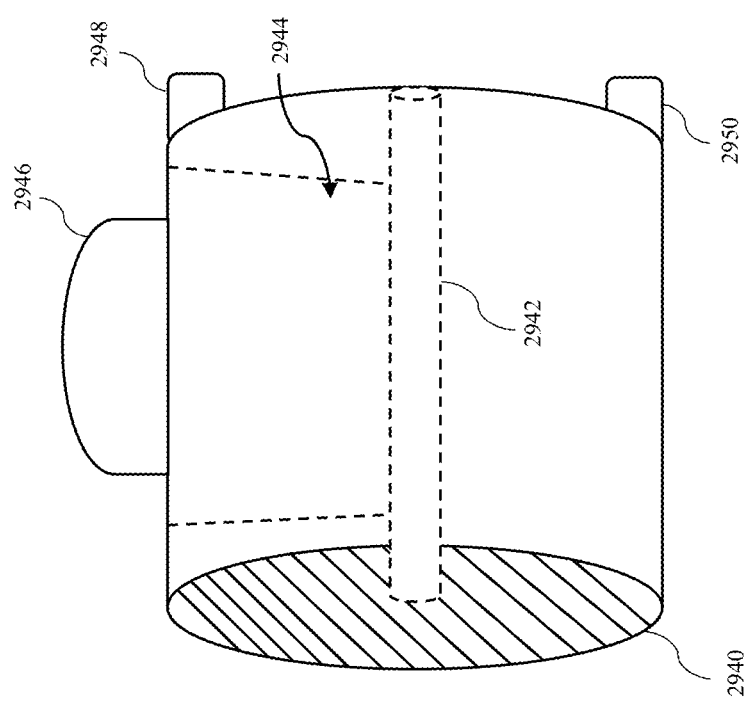
FIG. 29D illustrates a removable cartridge of a device for administering at least one formulation to a user, according to an example embodiment.

FIG. 29D depicts a schematic of the formulation delivery device's cartridge and associated components. The formulation delivery system has the removable cap 2946, the reservoir 2944, the wick 2942, the atomizer 2940, and the electrical contacts 2948 and 2950. FIG. 29D has the reservoir 2944 within the body of the removable cartridge. This design represents a departure from other designs where the reservoir may be external or differently positioned. The reservoir 2944 is specifically crafted to hold the medicated formulation within the confines of the cartridge's body. Its position allows for convenient filling and refilling processes by the user. By allowing the medication to be poured directly into the reservoir, this design simplifies the process of medication management and helps to minimize waste. At the bottom portion of the reservoir, the wick 2942 is disposed such that the wick 2942 can readily access the formulation, facilitating efficient absorption and subsequent delivery to the atomizer. The wick 2942, which draws the formulation from the reservoir, is critical for the function of the device. It acts as a conduit, transferring the medication to the atomizer 2940, where it is then converted into an aerosol for inhalation. The material of the wick is selected for its capillary action and compatibility with the medication, ensuring it can transport the medication effectively and withstand the chemical properties of the formulation over time.

In this design, the atomizer 2940 is strategically located to receive the medication-laden wick. The positioning is likely to be in alignment with the design objectives, aiming to create a fine mist for inhalation while maximizing the medication's efficacy. The electrical contacts 2948 and 2950, situated for optimal energy transfer, power the atomizer, enabling it to nebulize the medication efficiently. This is essential for ensuring the device functions reliably with each use. The removable cap 2946, while not explicitly shown in the figure provided, can be assumed to be an important feature for maintaining the sterility of the reservoir and the integrity of the medication within. By securely sealing the reservoir, the cap protects the medication from environmental contaminants and prevents leakage. It may feature a design that complements the ease of use, such as a screw-on mechanism, a snap-fit seal, or perhaps a hinged flip-top for quick access. The provision of such a cap provides both usability and hygiene, in the design of personal medical devices.

The cap of the medication cartridge can be designed with various mechanisms for attachment and detachment to enhance user convenience and ensure the secure containment of the medication. A screw-top design is common, where the cap threads onto the cartridge, providing a tight seal that is both secure and easy to manipulate. A snap-fit cap features protrusions that click into corresponding recesses on the cartridge's surface, offering a simple push-pull method for removal and replacement. Magnetic caps leverage the attraction between embedded magnets for a seamless and effortless attachment that requires minimal effort to open and close. Hinged caps are yet another option, connected to the cartridge by a small, durable hinge that allows the cap to flip open and close with ease, often seen in flip-top bottles and containers. Bayonet fittings, similar to the mechanism used in camera lenses, involve aligning the cap at a specific position and then twisting it to lock or unlock. Finally, sliding caps, which glide along a set track to open or close, can be an ergonomic choice, allowing for a smooth and controlled operation. Each of these options aims to provide a reliable seal and easy access while considering the specific usability and safety requirements of the medication delivery device.

FIG. 29E depicts an embodiment wherein the cartridge 2972 is configured to integrate with a base unit 2960. The base unit is constructed with a receiving chamber containing a channel 2970, deliberately designed to receive the cartridge. A precise snap-fitting mechanism is embodied by connectors or insert tab 2976 on the cartridge that snugly fits into space 2962 of attachment 2964, and insert tab 2974 that fits into space 2968 of attachment 2966 in the base unit, ensuring a secured connection. In an embodiment, as illustrated in FIGS. 29E and 29F, the atomizer 2971 is designed with a single hole 2963 for nebulization at the center instead of a mesh across the entire surface. Additionally, the atomizer features a flat area around the hole where the connectors or insert tabs 2974 and 2976 are located. The atomizer 2971, located at one end of the cartridge 2972, is a focal component of the device, facilitating its primary function. The cartridge 2972 and base unit 2960 are constructed from a high-grade polymer, selected for its durability, chemical resistance, and suitability for precision molding. The material ensures the integrity of the device even after repeated use and exposure to the substances to be atomized. Both components are manufactured using an injection molding technique, which allows for the production of parts with complex geometries and tight tolerances, essential for the snap-fit functionality and proper alignment of the atomizer. It is noted that the disclosed embodiment illustrates an atomizer with a single hole at the center, however, other types of atomizers, which features a mesh across the entire surface as shown in other embodiments, and atomizer having multiple holes are also covered within the spirit and scope of the invention.

The primary attachment mechanism of the invention is characterized by a snap-fit design, allowing for a secure yet user-friendly interface between the cartridge 2972 and base unit 2960. Specifically, the insert tab 2976 on the cartridge is engineered to slide into and lock within the space 2962, and a similar interaction occurs as the insert tab 2974 engages with space 2968. While this embodiment showcases a mechanical snap-fit approach, alternative embodiments may incorporate different attachment strategies such as magnetic coupling, where magnets embedded in the components create a reversible and clean connection. Other possible attachment means include twist-and-lock mechanisms, where components are joined by aligning and twisting into a locked position, latch-based systems, which employ a movable latch or catch to secure components together, and protrusion tabs. These varied attachment options provide flexibility in design and user interaction, catering to different applications and preferences. The operation of the atomizer 2971 employs a piezoelectric element that vibrates at ultrasonic frequencies when energized, creating a fine mist from the liquid contained within the cartridge. This efficient atomization process is optimized for minimal waste and maximum dispersion of the atomized product. The operation and activation of the atomizer in the described device are managed by electronics housed within the removable cartridge, ensuring a streamlined and efficient user experience. This electronic assembly includes a printed circuit board (PCB) and a battery, which together form the control center for the atomizer. The PCB is programmed to regulate power delivery from the battery to the atomizer based on user inputs and pre-set conditions. This setup allows for precise control over the atomization process, enabling features such as adjustable vapor output and temperature settings, which can be tailored to individual preferences for an optimal vaping experience. The inclusion of the battery within the cartridge not only centralizes the power source but also simplifies the design, allowing for compactness and portability. By integrating these components, the cartridge becomes a self-contained module that can be easily replaced or upgraded, enhancing the device's convenience and functionality. This system not only increases the ease of maintenance and the reliability of the device but also provides users with a high degree of control over their vaping experience.

The base unit displayed in the illustration is equipped with multiple openings, each serving as a potential point of attachment for various additional parts, augmenting the device's functionality. One of these openings is designed to accommodate attachments such as a mask or a mouthpiece 2965, which directs medicated aerosol to the patient's nose and mouth. Additionally, a resilient bladder or an ambu bag 2973 can be attached to other openings as shown in FIG. 29E. This setup may serve either as a manual means for generating aerosol or as a reservoir for storing medication. These components can be designed for a snap-fit, twist-lock, or magnetic attachment, ensuring a secure and user-friendly interface. The configuration described is particularly useful in clinical settings such as hospitals. It facilitates the direct administration of medicated aerosols to patients, either through manual operation or automated delivery systems. The versatility of the base unit's design allows it to be customized according to the user's needs, facilitating a range of functions from direct inhalation therapy to assisted delivery mechanisms, thereby enhancing the device's applicability for various respiratory treatments.

Figure 29F:
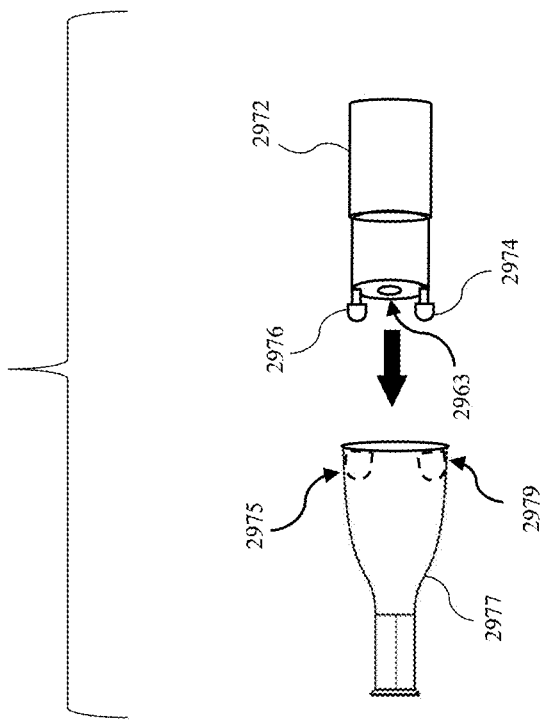
FIG. 29F depicts a removable cartridge and a mouthpiece for administering at least one formulation to a user, according to an example embodiment.
Figure 29E:
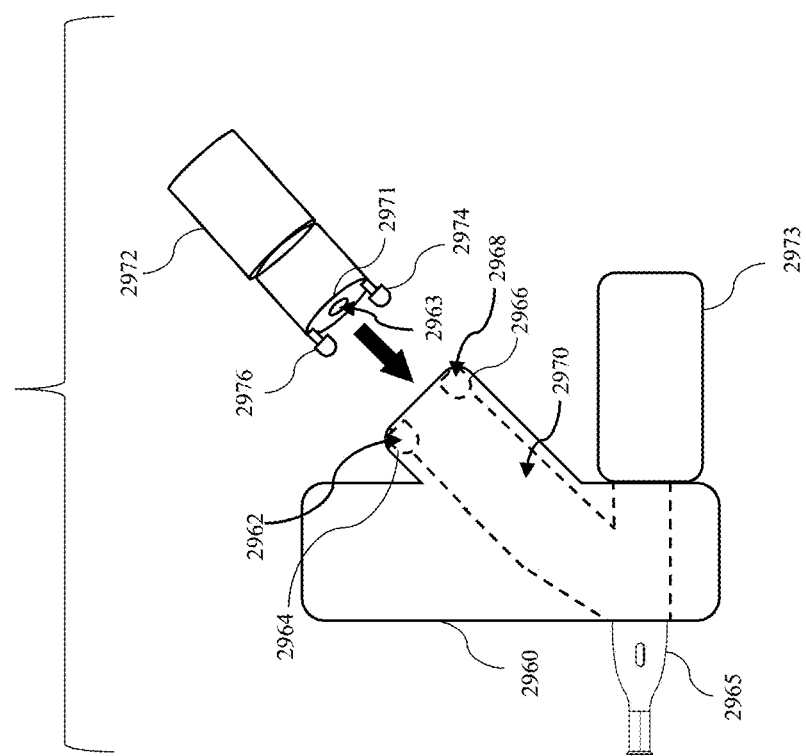
FIG. 29E illustrates a removable cartridge and a base unit of a device.

FIGS. 29E and 29F depict the removable cartridge being interchangeable with the base unit 2960 and a mouthpiece 2977. In FIG. 29E, the removable cartridge attaches to the base unit, and in FIG. 29F, the removable cartridge connects to the mouthpiece 2977 using the same insert tabs 2974 and 2976. These tabs are inserted into corresponding gaps of the attachments 2975 and 2979 on the inner wall of the mouthpiece. The insert tab 2976 fits snugly into the gap provided by attachment 2975 of the mouthpiece, and the insert tab 2974 fits into a gap provided by attachment 2979 of the mouthpiece. Both attachments, 2975 and 2979, are strategically positioned on the inner wall of the mouthpiece to ensure a secure coupling. This design facilitates a robust connection and allows for easy assembly and disassembly. The utilization of same tabs for modular attachment to various components, such as the base unit and the mouthpiece offers significant advantages in terms of device modularity. This uniformity allows the removable cartridge to be used across different applications and requirements, enhancing the versatility of the device. For instance, as depicted in FIG. 29F, this modularity contributes to a compact structure that is easily portable, enabling users to carry the device discreetly in their pockets and transport it to different locations without hassle. Such a design not only meets diverse user needs but also maximizes the functional adaptability of the device, catering to various usage scenarios with ease. The embodiment shown in FIG. 29F features a specific design of the mouthpiece, it is noted that the scope of the invention includes various other shapes and designs of the mouthpiece as detailed in other embodiments. This inclusivity ensures that the invention can be adapted to different use cases and preferences, making the device applicable in various settings.

Figure 29G:
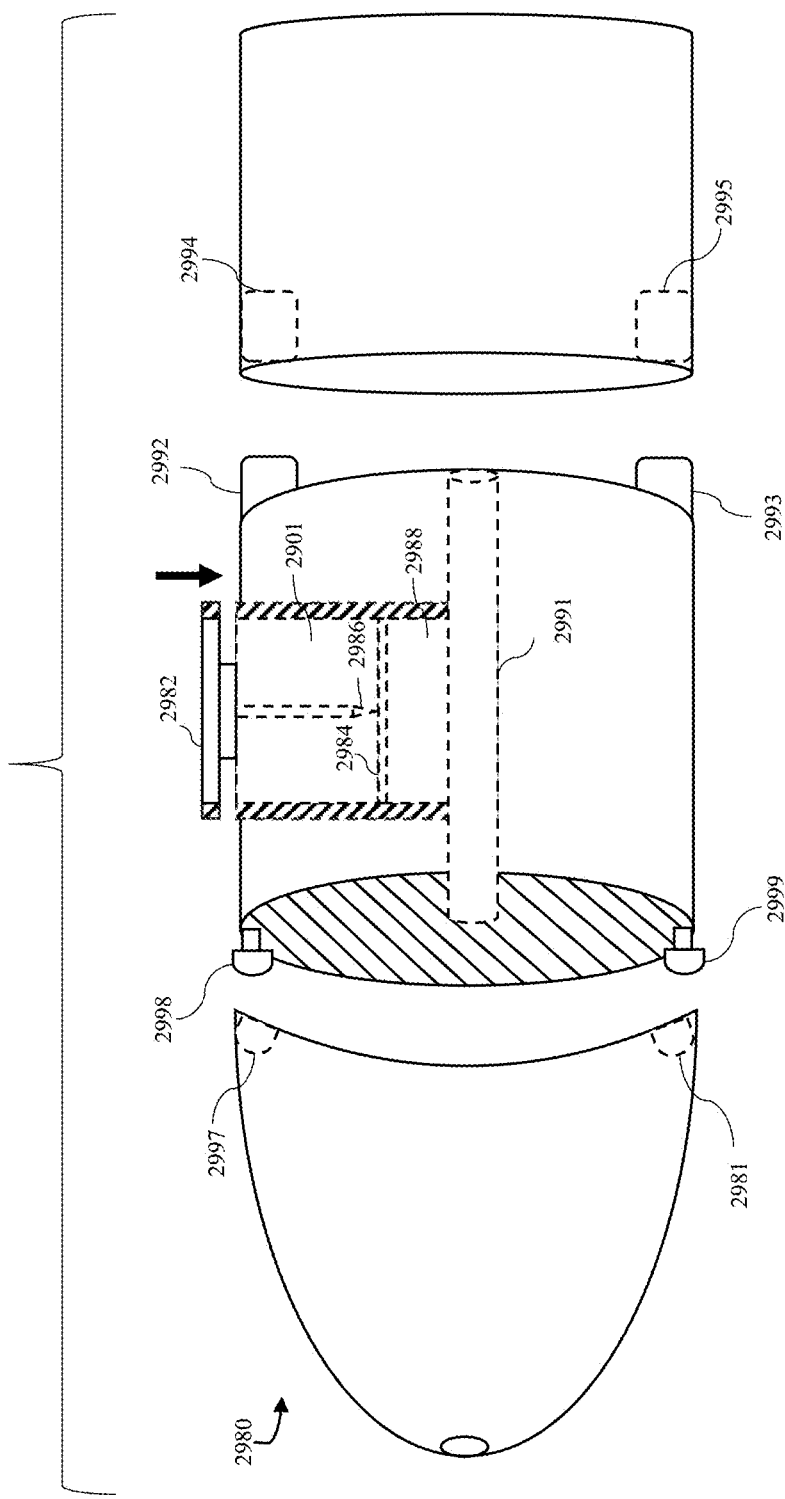
FIG. 29G illustrates a modular device for administering at least one formulation to a user, according to an example embodiment.

FIG. 29G illustrates another embodiment of the device 2980 having the removable cartridge. The removable cartridge has a capsule defining more than one chamber, namely, a first chamber 2901 for holding the formulation therein and a second chamber 2988 that is in direct contact with a portion of the wick 2991 for absorbing the formulation by the wick once the capsule is engaged and/or activated. Said chambers are initially separate until the capsule is engaged as to breach a divider or a sealing member 2984 between the chambers enabling the first and second chamber to be in fluid communication with one another. This embodiment is further detailed below. The removable cartridge has insert tabs 2998, 2999 on one end, and electrical contacts 2992 and 2993 on opposite end.

Figure 29I:
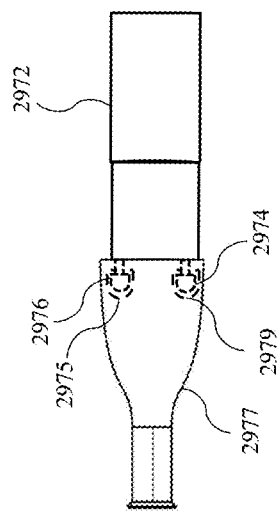
FIGS. 29H and 29I illustrate fully assembled configurations of a cartridge with a base unit and a mouthpiece, according to an example embodiment.
Figure 29H:
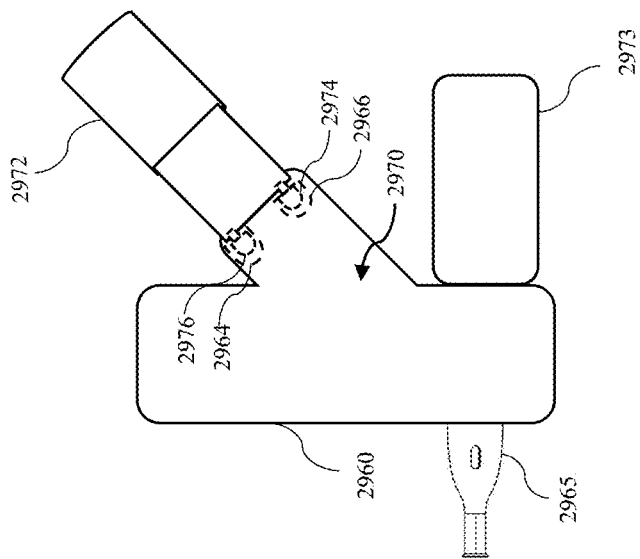

FIGS. 29H and 29I illustrate fully assembled configurations of the cartridge with the base unit and the mouthpiece. FIG. 29H illustrates the assembly where the cartridge 2972 of FIG. 29E, is inserted within the base unit 2960. This assembly is characterized by the precise positioning of the connector or insert tab 2976 into the attachment 2964 of the base unit. Concurrently, the complementary connector or insert tab 2974 is engaged within another attachment point, 2966 of the base unit. This dual-connection configuration ensures a secure and stable integration of the cartridge with the base unit, forming a unified and operational assembly.

FIG. 29I presents the cartridge integrated within the mouthpiece 2977. In this arrangement, the same insert tab 2976 is fitted within the attachment 2975 of the mouthpiece, establishing a firm and precise coupling. The same insert tab 2974 is positioned within the attachment 2979, which is located within an inner surface of the mouthpiece. This insertion and coupling process results in a seamless interface between the cartridge and the mouthpiece, for ease of use and functionality. The cartridge 2972 provides interchangeability and compatibility with different components. It is noted within the scope of the invention that the connectors located on the cartridge may be positioned on any part of the cartridge's outer surface that engages with another component, such as the base unit or the mouthpiece. Correspondingly, the attachment points within the receiving component are designed to be positioned in alignment with the connectors of the cartridge. This flexibility in the configuration of the connectors and attachments facilitates ease of assembly and enhances the modularity of the system.

Figure 32:
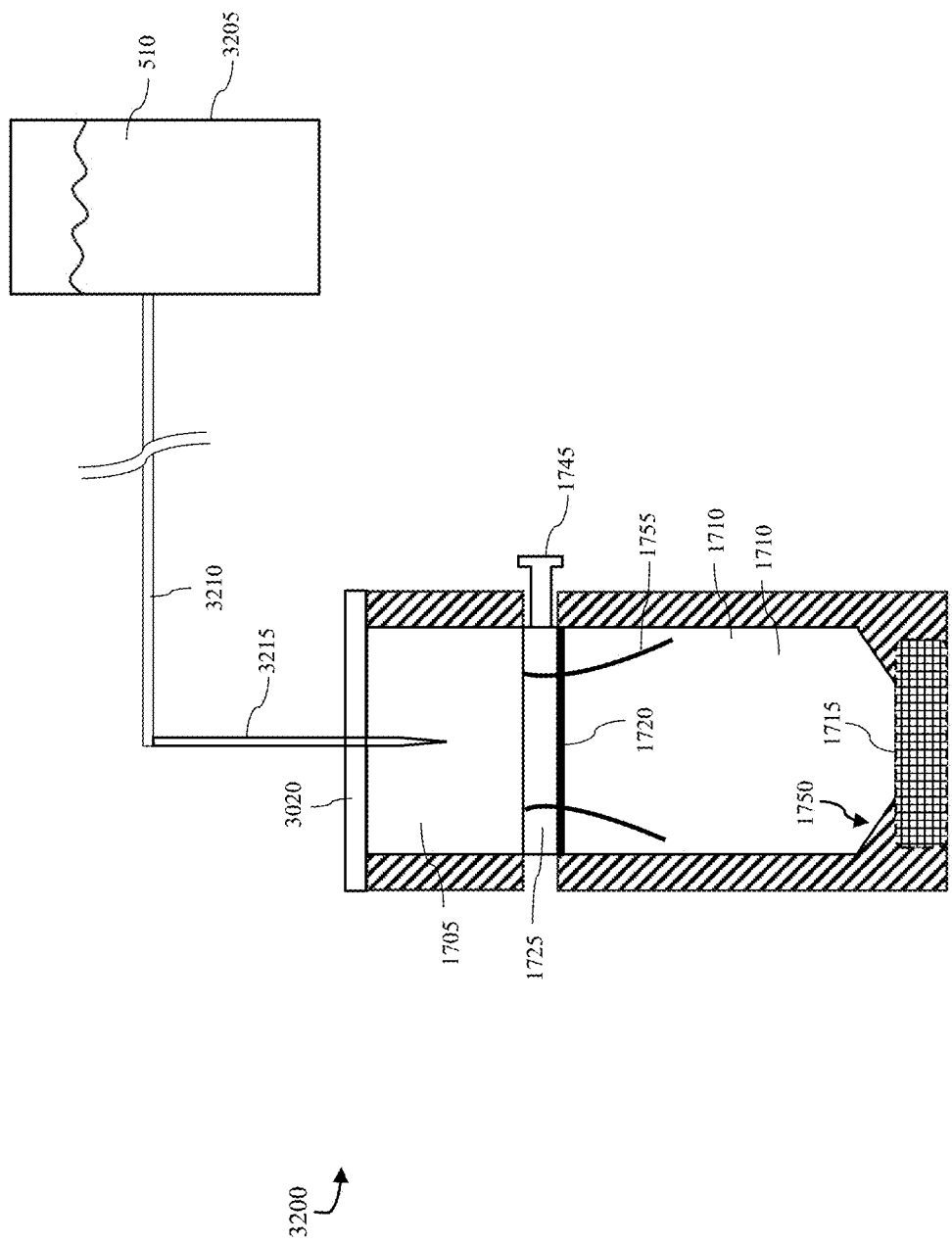
FIG. 32 is a cross-section of a side view of the capsule system, wherein an external container is in fluid communication with the capsule system, according to an example embodiment.
Figure 32B:
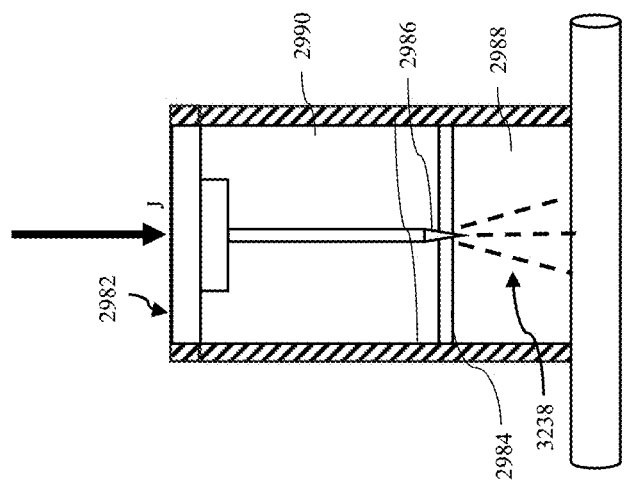
FIGS. 32A and 32B illustrate operation of a removable cartridge of a device for administering at least one formulation to a user, according to an example embodiment.
Figure 32A:
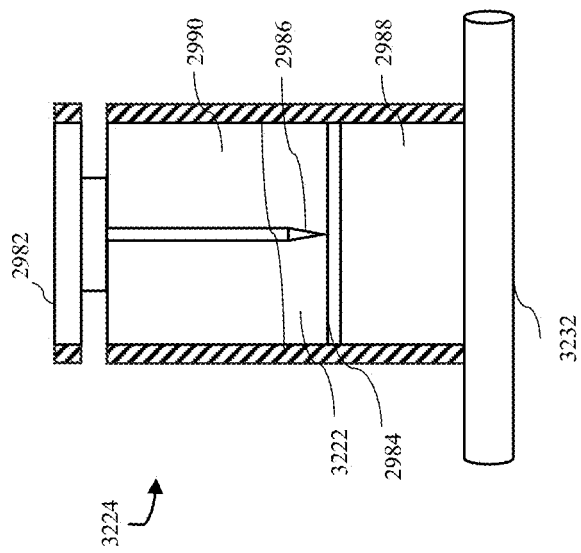

FIGS. 32A and 32B illustrate the activation of the capsule 3224 of the device shown in embodiment of FIG. 29G. In reference to FIGS. 32A and 32B, the first chamber 2901 includes the formulation in a liquid form, and the second chamber 2988 is below and separate from the first chamber. The sealing membrane 2984 is disposed between the first chamber and the second chamber. In various embodiments, the capsule 3224 may include a stop that inhibits the first chamber from translating relative to the second chamber. The stop may include an extruding tab that allows a user of the system to pull the stop.

In an example, when a force is applied in direction J onto a top portion 2982 of the first chamber 2990, the first chamber translates relative to the second chamber such that the first chamber is pushed towards the second chamber. Then, the translation of the first chamber towards the second chamber ruptures the membrane to provide fluid communication between the first chamber and the second chamber. The capsule may include a rupturing element 2986, such as a needle, which can puncture the sealing membrane 2984 between the first chamber and the second chamber.

When the membrane separating two chambers is ruptured, gravitational forces facilitate the transfer of the liquid formulation as droplets 3238 from the upper chamber (first chamber) to the lower chamber (second chamber). Positioned near the lowermost segment of the second chamber, or the lower end, the wick 3232 is strategically placed. This positioning of the wick is crucial as it is the farthest point from the first chamber within the second chamber. The configuration is such that the second chamber directly adjoins the wick. This proximity allows gravity to efficiently channel the formulation onto the wick for absorption and conveying the formulation to the atomizer, as one of the wick abuts the atomizer as shown in FIG. 29G. In the present embodiment, the first chamber can hold up to 20 milliliters of fluid. In other embodiments, the capsule chamber may hold other volumes of fluid, which are within the spirit and scope of the present invention.

The design ensures that the formulation saturates the wick thoroughly, which then channels it efficiently to the atomizer. This system is particularly advantageous for ensuring a consistent and controlled delivery of medication. The positioning of the wick relative to the chambers maximizes the capillary action needed to draw the liquid through the wick fibers towards the atomizer, enhancing the device's efficiency in vaporizing the medication for inhalation. This configuration not only simplifies the design but also improves the reliability and effectiveness of the medication delivery system, offering significant improvements over prior art by eliminating the need for mechanical pumps or other complex mechanisms.

The first chamber functions primarily as a secure storage compartment, effectively isolating the medication until it is needed. This isolation is crucial for maintaining the stability and integrity of sensitive compounds, particularly those susceptible to environmental variables such as temperature and humidity. Upon activation, which can be triggered by external pressure, a twist mechanism, or a chemical reaction, the barrier between the two chambers is breached, enabling the previously isolated medication to move into the second chamber. The second chamber facilitates fluid communication with the medication, allowing it to mix with other components necessary for the delivery or activation of the drug. This could include solvents to dissolve the medication or other substances designed to modify the medication's delivery profile, such as buffers or stabilizers. The design of the second chamber often includes features to promote effective mixing and ensure complete dissolution or combination of the components involved.

This dual-chamber configuration not only enhances the safety and effectiveness of the medication by separating reactive components until the point of use but also simplifies the administration process for end-users. It ensures that the medication can be stored and transported in a more stable and inert form, reducing the risk of premature activation or degradation during transit. Furthermore, this system can be tailored to specific medical needs, allowing for immediate or delayed activation based on treatment requirements, thereby providing significant improvements over traditional single-chamber systems in terms of both safety and efficacy.

During shipping and transport, the formulation remains confined within the first chamber of the two-chamber capsule, providing a stable and secure environment. This configuration prevents unintended exposure or premature mixing of the medication with any accompanying fluids or substances, ensuring the integrity and potency of the medication during transit. Upon activation, typically through a user-initiated action, the capsule's design allows for controlled fluid communication between the first and second chambers. This enables the release of the medication into the second chamber, where it becomes available for administration or further processing.

By separating the storage and activation stages, the two-chamber capsule minimizes the risk of premature degradation or alteration of the medication during shipping. This feature enhances the stability and shelf life of the medication, preserving its efficacy and therapeutic properties until it is ready for use. Moreover, the controlled release mechanism provided by the two-chamber design allows for precise dosing and administration. Activation at the desired time ensures that the medication is mixed with the accompanying fluid or solvent in the second chamber when it is most appropriate for administration. This feature is particularly beneficial for medications requiring reconstitution or those with specific timing requirements for optimal effectiveness. Overall, the two-chamber capsule's ability to store the medication separately from the accompanying fluid or solvent during shipping and transport provides advantages in terms of stability, potency, and controlled release. This design ensures that the medication remains protected until activation, allowing for safe and effective administration while maintaining the desired therapeutic outcomes. It is noted that medication and formulation may be used interchangeably in some embodiments, as they refer to the substance contained in the capsule for nebulization and delivery to the user.

FIGS. 32C and 32D illustrate an embodiment where the capsule has a rubber section as a covering member 3244 covering an open portion on a top side 3250 of the capsule. The capsule includes a chamber 3246 for receiving the formulation 3222 and a rubber section as the seal or covering member 3244 covering the open portion of the chamber of the capsule. The rubber section allows for formulation to be inserted into the capsule. The capsule further includes the wick 3248 proximate to a second or bottom side of the capsule. The wick, as shown in FIG. 29G abuts the atomizer. In operation, a user of the capsule may add formulation by inserting a syringe through the rubber section and using the syringe to dispense the formulation into the capsule chamber 3246. As shown in FIGS. 32C and 32D, the syringe 3240 having a plunger 3254, and a needle 3242 contains the formulation 3252 and the syringe is inserted through the covering member 3244 into the chamber 3246. The syringe is inserted along a direction P such that a portion of the needle 3242 is positioned inside the chamber 3246, shown in FIG. 32D. Once inserted, the plunger 3254 of the syringe is drawn with a downward force applied in the direction Q, as shown in FIG. 32D. The formulation is released by the needle in form of droplets 3256 and received by the portion of the wick 3248. The formulation is absorbed by the wick and conveyed to the atomizer. The capsule chamber is above the wick 3248 and abuts the wick 3248 such that gravity allows the formulation to be received and absorbed by the wick. Gravity forces the formulation down such that the formulation presses down against the wick. In an embodiment, there may be a sensor implemented in the capsule. For example, the sensor may be a float sensor that measures the level of liquid in the capsule chamber. The float sensor is a continuous level sensor featuring a magnetic float that rises and falls as liquid levels change. The movement of the magnetic float creates a magnetic field that actuates a hermetically sealed reed switch located in the stem of the level sensor, triggering the switch to open or close. Other types of sensors configured to detect the amount of liquid in the capsule chamber may be used and are within the spirit and scope of the present invention. Additionally, the maximum amount of formulation or time may be adjusted depending on the patient, medication and variety of other factors.

In an embodiment, the covering member 3244 is a removeable covering, such as, but not limited to, a cap or seal, in attachment with the top side 3250 of the capsule to preserve the formulation and/or prevent the formulation from leaking. The removeable covering allows users of the system to store capsules for emergency use or long-term use, depending on the type of removeable covering. In some embodiments, the capsule may be color-coded for emergency medication or may include labels that identify the medication within the capsule. The capsule may also include a locking element that prevents the capsule from atomizing the medication unless an access code is provided.

In the embodiments described, a variety of liquid formulations can be utilized depending on the specific medical or therapeutic application intended. These formulations may include, but are not limited to, solutions, suspensions, and emulsions. Solutions are homogeneous mixtures where the medication is completely dissolved in a solvent, typically water or an organic solvent like ethanol, which ensures rapid and uniform delivery upon administration. Suspensions are heterogeneous mixtures where the medication particles are dispersed throughout the solvent but are not dissolved; this form is useful for substances that are insoluble or unstable in a solvent, providing a controlled release as the particles slowly dissolve over time. Emulsions, which are mixtures of two immiscible liquids where one is dispersed in the other as fine droplets, often include an oil phase and a water phase, and are particularly beneficial for drugs that require a buffered release or enhanced absorption. Each of these formulations can be tailored with additives such as stabilizers, buffers, and preservatives to enhance the stability, efficacy, and shelf life of the medication, thereby providing significant improvements over prior art by optimizing drug delivery and patient compliance.

Figure 32E:
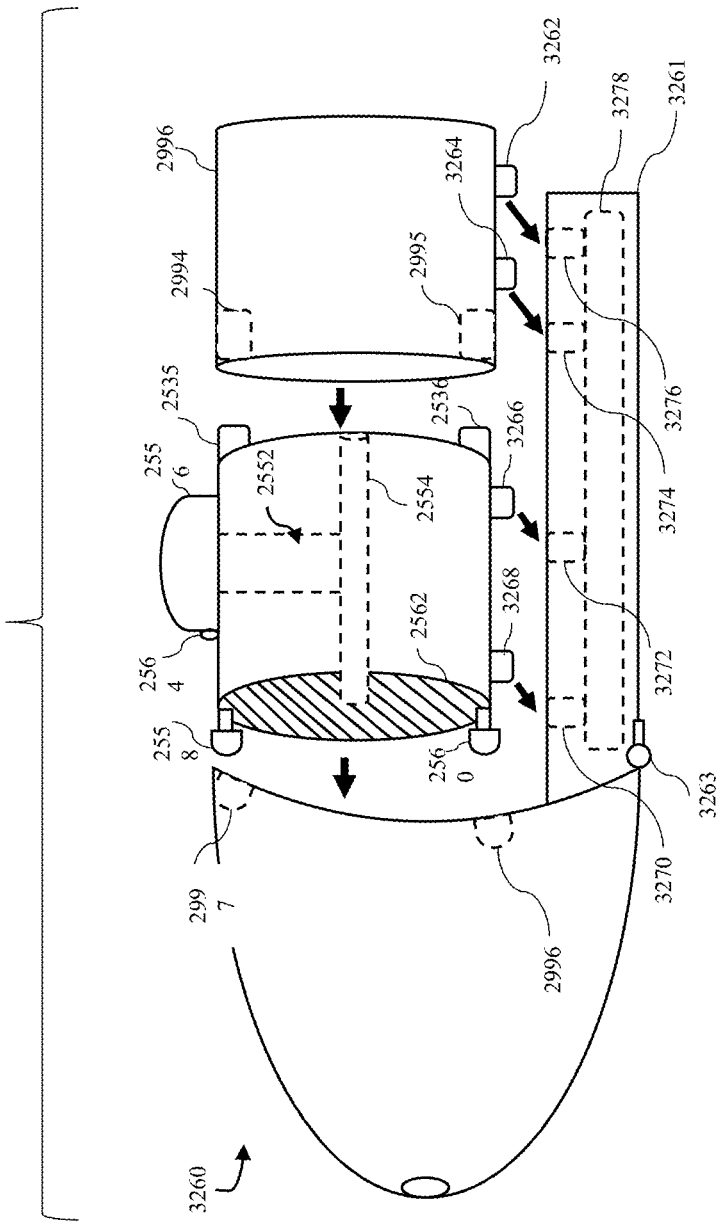
FIG. 32E is a diagram of a device for administering at least one formulation to a user, according to an example embodiment.

FIG. 32E illustrates an embodiment of a vaping device, specifically showing the structural and functional integration of its electrical components. The device 3260 features a circuit board 3261, which is coupled to the bottom portion of the mouthpiece. Although the figures depicts the circuit board 3261 attached to the bottom side, other embodiments disclosing the circuit board to be attached on the top side are also covered within the scope of the invention. Within the body of circuit board 3261 lies the main Printed Circuit Board (PCB) 3278, forming the central hub for the device's electrical operations. The circuit board 3261 is securely affixed to the mouthpiece by a locking element 3263, ensuring a stable and durable connection that withstands usage forces. Alternative methods for affixing the circuit board could include snap-fit mechanisms, adhesive bonding, ultrasonic welding, or the use of magnets for a tool-free assembly and easier maintenance. These alternatives could offer varying degrees of permanence and ease of disassembly, catering to different design priorities such as repairability or manufacturing efficiency.

Moving to the removable cartridge of the device, it is equipped with a channel 2552 that allows for the transport of the liquid from the cartridge to the wick 2554. The design ensures that the wick remains in direct contact with the atomizer 2562, which is crucial for the efficient vaporization of the liquid. The removable cartridge is designed for easy attachment to the mouthpiece, facilitated by two insert tabs 2558 and 2560 that slide into cavities 2997 and 2981. This method of attachment not only provides a secure fit but also allows for quick replacement of the cartridge.

The external surface of the removable cartridge is provided with a cap 2556, which features a hinge 2564, providing a protective cover for the cartridge and potentially preventing leakage or contamination of the contents. The hinged design of the cap offers convenience for the user, allowing easy access for refilling the cartridge without complete detachment from the device.

The removable cartridge housing electrical contacts 3268 and 3266 are designed to fit snugly within the connectors 3270 and 3272 of the mouthpiece. The removable cartridge features electrical contacts 2535 and 2536, which correspond to connectors 2994 and 2995 of the removable battery 2996. The removable battery has contacts 3262 and 3264 for engaging with connectors 3272 and 3274. When the cartridge is engaged with the mouthpiece, a complete electrical circuit is formed as the contacts 3268 and 3266 mate with connectors 3270 and 3272. Simultaneously, the battery contacts are aligned and inserted within board connectors 3274 and 3276. This configuration establishes the necessary electrical communication between the atomizer, the battery, and the circuit board, enabling the device to function as designed, converting the liquid formulation into an inhalable vapor efficiently.

The embodiment described, featuring a circuit board attached to the bottom of the mouthpiece and a top-loading mechanism for the removable cartridge and battery or other electronics, presents advantages for both functionality and user experience. By positioning the circuit board at the bottom, the design utilizes the typically unused space within the mouthpiece's lower region, thus facilitating a more compact and streamlined device profile. This spatial arrangement allows for a reduction in the overall length and diameter of the device, contributing to a sleek and portable design. Additionally, centralizing the weight at the bottom of the device can contribute to a more balanced and comfortable hold for the user. The bottom placement of the circuit board also provides a natural separation from the heating elements and liquid reservoir, reducing the risk of heat damage or liquid intrusion to the sensitive electronic components, which enhances the durability and reliability of the device.

Furthermore, the top-loading configuration for the cartridge and battery offers considerable advantages in terms of maintenance and usability. This design simplifies the process of replacing or refilling the cartridge and swapping the battery without the need to disassemble the entire device or disturb the circuit board, which can be a delicate operation. It also provides a quick and intuitive method for users to interact with the device, facilitating better access and visibility to the components that require more frequent handling. The design minimizes the complexity of assembly and can result in a more cost-effective production process. For the user, it translates into a more user-friendly product that requires less effort to maintain. The modular nature of this design means that the device can be easily customized or upgraded, allowing for a range of cartridges or batteries to be interchangeably used, thus offering flexibility and extending the product's market appeal. Overall, this architecture not only maximizes the internal space but also aligns with the modern demand for compact, efficient, and user-centric electronic devices.

Figure 32F:
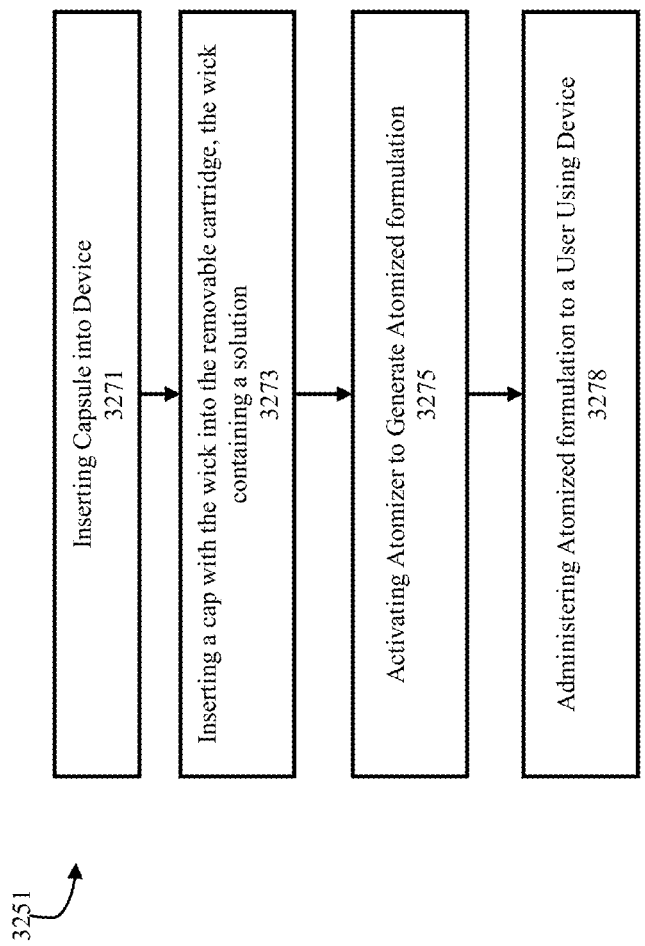
FIG. 32F is a flowchart diagram illustrating steps for a method for assembling a device for administering at least one formulation to a user, according to an example embodiment.

FIG. 32F is a method 3251 for atomizing formulation, according to an example embodiment. In step 3271 of the method, the user begins by inserting the capsule into the device. For example, the capsule comprising the wick assembly, as shown in FIGS. 25F through 25H, and 29D is inserted into the removable cartridge. This step is critical as it involves the precise placement of the capsule within the housing to ensure proper alignment with the internal mechanisms of the device. In some embodiments, the wick is placed into a channel having guides 2541 through 2544 to enable smooth and unhindered placement of the wick, as shown in FIG. 25F. The design of the capsule and the device is such that it can only be inserted in the correct orientation, thus preventing any operational errors. This insertion may involve a click-fit mechanism, magnetic alignment, or a screw-in motion that secures the capsule in place. Once inserted, the device is primed and ready for the subsequent steps in the medication delivery process. Moving on to step 3273, a cap with an attached wick is inserted into the removable cartridge. This wick has already been saturated with the solution, which contains the medication intended for delivery. The cap plays a dual role by securing the wick in place and also ensures the solution is contained within the cartridge to prevent leakage. The design allows for the cap to be securely fastened to the cartridge, often with a locking mechanism that also maintains the optimal position of the wick for the atomization process.

In step 3275, the atomizer is activated, initiating the process of generating atomized medication. This is where the device transforms the formulation from the wick into a fine mist that can be inhaled by the user. The activation of the atomizer is typically controlled by a button or a sensor that detects inhalation. Following the activation, in step 3278 the user administers the atomized formulation via the device. The design of the mouthpiece ensures that the medication is delivered efficiently and comfortably to the user, allowing for optimal absorption and therapeutic effect. The precise control over the atomization process allows the user to receive the correct dosage as prescribed, providing both efficacy and safety in the treatment regimen.

Referring to FIGS. 35A through 35C, the removable modular tubular extension 2000 is shown according to additional example embodiments. The y-shaped extension includes a receiving section 3505 in fluid communication with the second extension tubular chamber 2010. The receiving section 3505 is configured for receiving a capsule 3508. Capsule 3508 is understood to represent any embodiment of a capsule consistent with the present disclosure. It is further understood, that capsule 3508 may represent and/or include, in certain embodiments, a medicine vial. A standard medicine vial, a prevalent form in which medications are often stored, typically consists of a cylindrical container made of glass or plastic with a sealed cap. These vials are designed to hold liquid or powdered medications and are available in standard volumes. Common volumes for standard medicine vials range from smaller 1-milliliter units to larger sizes, such as 10, 20, 30, or even 50 milliliters, allowing for the containment of various quantities of medication. This adaptability of the device and/or capsule 3508 to receive a standard medicine vial or other described capsules enhances the flexibility of the system, ensuring that it can be tailored to specific needs and applications in administering medication.

In certain embodiments, the receiving section may further include a cross section corresponding to the cross-sectional shape of the capsule to facilitate the insertion of the capsule into the device. In certain embodiments, the receiving section may also include electrical contacts on the interior surface of the receiving section to align with the electrical contacts on the capsule. Extension 2000 may further include a button 3450 being the button disclosed in the embodiment of FIGS. 34A through 34D and as described herein. Moreover, the device may include a pull tab electrical insulator 2305 as shown and described herein in reference to FIGS. 23 through 25.

The removable modular tubular extension may be comprised of metallic material such as carbon steel, stainless steel, aluminum, Titanium, other metals or alloys, composites, ceramics, polymeric materials such as polycarbonates, such as Acrylonitrile butadiene styrene (ABS plastic), Lexan™, and Makrolon™. other materials having waterproof type properties. The removable modular tubular extension may be made of other materials and is within the spirit and the disclosure. The removable modular tubular extension may be formed from a single piece or from several individual pieces joined or coupled together. The components of the removable modular tubular extension may be manufactured from a variety of different processes including an extrusion process, a mold, casting, welding, shearing, punching, folding, 3D printing, CNC machining, etc. However, other types of processes may also be used and are within the spirit and scope of the present invention. The modular tubular extension, as an integral component of the medical device, can also be constructed from a variety of materials that conform to the stringent requirements of medical device applications. Examples of suitable materials include medical-grade plastics such as polyethylene (PE), polypropylene (PP), polyvinyl chloride (PVC), and thermoplastic elastomers (TPE). These plastics offer a combination of biocompatibility, flexibility, and ease of manufacturing, making them well-suited for medical device tubing. Silicone, known for its excellent biocompatibility, high-temperature resistance, and flexibility, is commonly utilized in medical tubing and catheters. For applications requiring strength and durability, stainless steel may be employed due to its corrosion resistance. Titanium and titanium alloys, renowned for their strength, low density, and biocompatibility, find utility in medical implants. Nitinol, a shape memory alloy, is employed in devices necessitating dynamic shape changes. Biodegradable polymers like polylactic acid (PLA) and polyglycolic acid (PGA) are used for temporary medical devices that degrade over time. The choice of material for the modular tubular extension depends on factors such as the intended use, desired properties, biocompatibility, sterilization compatibility, and regulatory compliance, all of which ensure patient safety and device performance within the confines of medical device regulations.

It should be noted that the device may be comprised of the same materials as the modular tubular extension. The utilization of the same materials for both the modular tubular extension and the medical device holds significant importance within the present invention. Consistency in material composition ensures compatibility and minimizes the risk of material interactions or incompatibilities that could compromise device performance or patient safety. This approach assures biocompatibility throughout the device, reducing the likelihood of adverse reactions or complications. Moreover, employing identical materials simplifies manufacturing and processing, eliminating the need for additional material compatibility testing and streamlining production processes. From a regulatory perspective, employing consistent materials facilitates the submission and approval process, as it provides a clear and well-documented rationale for material selection and ensures compliance with relevant standards. By maintaining material consistency, the device's structural integrity, durability, and performance characteristics remain consistent, fostering reliability and enhancing the overall quality of the medical device.

In the second embodiment of removable modular tubular extension 2100, the second extension tubular chamber includes a first section 2105 and a second section 2110. The first section is configured to be received by the device and has an angle 2115 relative to the second section. Angle 2115 is approximately 135 degrees. The second section 2110 is perpendicular to the first extension tubular chamber such that the angle between the second section and the first extension tubular chamber is at angle 2120, which is approximately 45 degrees. This allows the atomized medication to travel through the second channel into the first channel such that the flow of fresh air can push the atomized medication upwards in the first channel. Shown in FIG. 22, the third embodiment of the removable modular tubular extension is similar to the second embodiment. However, the third embodiment includes a rotating element 2205 that alters angle 2115 between the first section and the second section. The rotating element allows the device and the tubular chamber to be positioned at an angle that is optimal for various positions of the patient.

In one embodiment, the second extension tubular chamber may include a variable angle and/or partial composition from a flexible material, thereby enabling a variable angle within the conduit. By incorporating a variable angle within the conduit, the invention provides increased flexibility and adaptability in fluid communication with the first extension tubular chamber. The conduit can be adjusted to different angles or orientations, accommodating diverse system configurations or specific requirements. This adjustability allows for precise routing of fluids, optimizing flow dynamics and enhancing the overall performance of the system. Furthermore, the conduit's composition may be comprised of a flexible material in at least a portion of the conduit, namely the portion requiring the variable bend and/or angle, which contributes to the variable angle capability. The flexible nature of the material enables the conduit to bend or flex at the desired angle, facilitating seamless fluid communication with the first channel. This flexibility allows for smooth and uninterrupted flow, minimizing pressure losses or restrictions within the system. The incorporation of a conduit with a variable angle and flexibility within the invention presents numerous advantages. It enables the adaptation of fluid routing to specific needs, optimizing system performance and efficiency. The variable angle capability ensures accurate and targeted fluid delivery, promoting precise control and distribution within the system. Additionally, the flexibility of the conduit material enhances durability and resilience, mitigating the risk of damage or failure during operation.

Next, in step 2904, the user. inserts the capsule containing the medication into the device, or base unit, having the tubular chamber. In step 2906, the user removes the stop on the capsule that inhibits the first chamber from translating relative to the second chamber. In step 2908, the user applies a second force to the first chamber causing the first chamber to translate relative to the second chamber rupturing a membrane disposed between the first chamber and the second chamber thus providing fluid communication between the first chamber and the second chamber. In step 2910, the user provides power to the atomizer by removing an insulator that prevents electrical communication between the atomizer and a power source. In step 2912, the processor activates the atomizer to atomize the medication to generate at least one atomized medication comprising a plurality of particles. Each particle of said plurality of particles is at most four microns in diameter. In step 2914, gravity causes the liquid formulation to move from the first chamber to the second chamber. In step 2916, the device dispenses the atomized medication from the capsule into the tubular chamber. In step 2918, the user applies a force to a mask that is positioned over the patient's nose and the patient's mouth and in fluid communication with the tubular chamber. In step 2920, the user administers the atomized medication to the patient using the device by at least partially deflating a resilient air bladder in fluid communication with the tubular chamber causing air within the resilient air bladder to be conveyed from the resilient air bladder into the tubular chamber.

With reference to FIG. 29B, in step 2922, the user determines that the patient is in the conscious state. Therefore, the user must convert the device such that the patient can inhale the atomized medication by themselves. Next, in step 2924, the user removes the resilient air bladder from the second extension receiving section. In step 2926, the user attaches a cap to cover the second extension receiving section. Steps 2922 through 2926 convert the device into the device illustrated in FIGS. 11A through 12, in which a cap is covering the first receiving section and a mouthpiece or mask is in attachment with the second receiving section. In step 2928, the user administers the atomized medication to the patient using the device by conveying the at least one atomized medication from the tubular chamber though the mouthpiece that is in fluid communication with the tubular chamber or the mask that is positioned over the patient's nose and the patient's mouth and in fluid communication with the tubular chamber.

With reference to FIG. 29C, in step 2930, the user removes the mask or the mouthpiece from the first extension receiving section. In step 2932, the user removes the cap or the resilient air bladder from the second extension receiving section. In one embodiment, it is understood that instead of removing the resilient air bladder, mouthpiece, cap, and/or mask, the method 2900 may include removing the removable modular tubular extension from the device and inserting a second removable modular tubular extension. Then, the user inserts the second modular tubular extension into a device receiving section such that the second extension tubular chamber is in fluid communication with the second channel of the device and such that the second extension tubular chamber defines a portion of the second channel. The second removable modular tubular extension may be those of embodiments shown in FIGS. 21 and 22. If the third embodiment of the removable modular tubular extension is inserted, then the user adjusts the angle (2115 in FIG. 22) between the first extension tubular chamber and the second extension tubular chamber of the second extension tubular chamber to a predetermined angle. Additionally, the user locks the angle between the first section and the second section at the predetermined angle. In step 2934, the user attaches an endotracheal tube to the device so that endotracheal tube is in fluid communication with the tubular chamber and the conduit. In step 2936, the user attaches a conduit in fluid communication with an air outlet of a respiratory support device to the second extension receiving section. Steps 2930 through 2936 convert the device to the example embodiment shown in FIG. 19. These steps allow the device to be used when the patient is in an intubated state.

Referring now to FIGS. 30A and 30B, views of a capsule system 3000 for use with a medical device for administering at least one atomized medication to a patient are shown, according to an example embodiment. The capsule system includes at least one chamber, the medication 510 disposed within the chambers, and an atomizer 1715 at a lower end portion 3010 of the capsule system. The atomizer converts liquid into a fine spray or mist. The chambers include a first chamber 1705 disposed above a second chamber 1710. The first chamber includes the medication, and the second chamber includes the tapered wall sections 1750. The atomizer is disposed proximate to a bottom portion 3015 of the second chamber. The configuration of having the first chamber containing the medication situated above the second chamber with the atomizer ensures that the medication flows or is directed from the first chamber into the second chamber by the force of gravity. The materials for the chambers may include, but are not limited to, biocompatible materials that are suitable for storing medication and for constructing an atomizer, such as medical-grade plastics, stainless steel, ceramics, or other non-reactive materials. Two separate chambers facilitate ease of cleaning or replacing parts, reduce the risk of contamination, and contribute to a more compact and streamlined design of the capsule system.

The second chamber includes tapered wall sections 1750 to direct the at least one medication toward the mesh of the atomizer. The tapered wall sections refer to a compartment or space featuring a sloping or gradually narrowing wall within its structure. This specific design is implemented to guide or direct the medication toward the atomizer. The tapered wall section serves to concentrate the medication flow towards the atomizer, thus enhancing the atomization process and ensuring that the medication is uniformly spread. This optimizes the flow path of the medication, thus potentially improving the consistency and efficiency of the atomization process, and thereby enhancing the overall effectiveness of the medication delivery.

The capsule system further includes a stopper 3020 in fluid communication with the second chamber. The stopper is a self-sealing rubber stopper that covers the open side of the first chamber. The materials for this self-sealing stopper may include, but are not limited to, elastomers, silicone rubber, or other flexible and resilient materials that provide a tight seal while allowing temporary access when needed. In a medical context, a self-sealing rubber stopper is used to seal containers like vials or chambers, and it can be punctured by a syringe or other device to access the contents without permanently compromising the seal. The stopper is self-sealing, meaning that it automatically returns to a closed or sealed position after being accessed or penetrated, such as during a refilling process. This ensures that the integrity of the chamber's contents is maintained without requiring manual resealing. The materials for this self-sealing stopper may include, but are not limited to, elastomers, silicone or butyl rubber, or other flexible and resilient materials that that have been carefully formulated to offer the right balance of elasticity, resilience, and chemical resistance. These materials provide a tight seal while allowing temporary access when needed. The material must be compliant with pharmaceutical or medical standards. The rubber stopper enhances the usability of the device, particularly in scenarios where repeated access to the chamber is required, such as for refilling. It ensures a consistent and secure seal, thereby maintaining sterility and preventing leaks, and it simplifies the handling of the device, reducing the potential for user error.

The capsule system also includes a housing 3025 that substantially encloses the chambers. The housing is a protective case or enclosure designed to contain and protect internal components. This provides a controlled environment for the medication contained within the chamber. The composition of the capsule and the chamber may include, but are not limited to, materials suitable for medical applications, such as medical-grade plastics or bio-compatible metals, ensuring safe and effective operation within the medical device environment.

The capsule includes a capsule width 3030 and the chambers includes a chamber width 3035 such that the chamber width substantially spans the capsule width. In some embodiments, the chamber width may span at least 50 percent of the capsule width. In other embodiments, the chamber width may span at least 50 percent of the capsule width. In this embodiment, the walls of the chambers are designed to abut the walls of the housing, thereby forming a connection that often provides stability, containment, and precise alignment within the system. This alignment may facilitate the controlled flow of medication, prevent leakage, and contribute to the correct orientation and functioning of other components, such as sensors, atomizers, or electrical contacts. The chambers substantially occupy a cavity with the capsule without any voids between a chamber wall of the chamber and a housing wall of a housing of the capsule. This means that the size of the chamber, as determined by its transverse dimension or diameter, is almost as large as that of the capsule system itself. Therefore, the chamber effectively maximizes the available internal space of the capsule, minimizing any wasted or unused space within the capsule system. This arrangement of the chamber width substantially spanning the capsule width represents an improvement over prior art in the field of medical devices. It allows for efficient use of space within the capsule system, potentially accommodating larger medication volumes or multiple functionalities within the same capsule size. This leads to increased utility of the medical device without necessitating a proportional increase in its physical size, thus improving the overall efficiency and user experience.

A membrane 1720 preventing fluid communication is disposed between the first chamber from the second chamber. The membrane is a thin, flexible layer or barrier that prevents the passage of liquid. The membrane may include, but is not limited to, a range of impermeable materials that are compatible with the medication and the atomizer, such as certain plastics, elastomers, or composite materials that are engineered to provide a secure yet breakable or penetrable barrier. The membrane allows precise control over the release and flow of medication into the atomizer. This can lead to reduced risk of contamination or spillage and the possibility of more sophisticated release mechanisms that can be tailored to specific medical needs or patient preferences.

At least one rupturing element 1755 is in attachment with the first chamber 1705 or the second chamber 1710 such that the at least one rupturing element configured to engage the membrane 1720 when a first force is applied to translate the first chamber relative to the second chamber 1710. This rupturing element is configured to engage with a membrane that separates two chambers. Engagement occurs when a predetermined force, termed a first force, is applied, translating the first chamber relative to the second. This relative movement prompts the rupturing element to come into contact with the membrane, puncturing or tearing it to allow fluid communication between the chambers. Such a mechanism can enable the flow of medication or another substance from one chamber to the other or activate specific functionalities within the medical device. Compared to previous designs, the careful configuration of the rupturing element for engagement with the membrane in response to a specific force represents a controlled, precise mechanism for regulating fluid communication within the system. It allows for more control over medication dosage, timing, or mixing of components and enhances safety by ensuring that the membrane is ruptured under controlled conditions.

When the first chamber is pushed towards the second chamber, the rupturing elements pierce and break the membrane such that the membrane becomes a ruptured membrane 3040 to allow the medication to flow out of the first chamber and into the second chamber. A stop 1725 is disposed between the first chamber and the second chamber inhibiting the first chamber from translating relative to the second chamber.

The rupturing element may be composed of materials that provide the necessary strength, sharpness, and resilience for the intended function. Materials such as stainless steel, hard plastics, or other biocompatible materials may be used to provide the necessary strength, sharpness, and resilience to ensure that the rupturing element performs effectively without compromising the integrity or sterility of the contents.

The capsule further includes a plug 3045 disposed at the lower end portion 3010 of the capsule system. The plug includes a plug receiver 3046 and a plug cap 3048. The plug's primary function is to provide a seal or barrier at the lower end portion. The plug cap includes a protruding section 3050 configured to be received by a dimple 3055 of the plug receiver. The diameter of the dimple is slightly smaller than the diameter of the protruding section 3050 such that the protruding section is tightly received by the plug dimple 3055. This provides a tight seal that prevents leakage of liquid solution. By being strategically positioned, the plug prevents the atomizer from leaking medication and contamination from external sources. Its role in the capsule system ensures that the contents of the chamber(s) are managed according to the device's operational requirements. The plug offers a targeted solution to potential issues related to leakage, flow control, and hygiene. Its presence thus contributes to the overall efficiency and effectiveness of the capsule system, marking an improvement over previous designs in the field. The plug may be constructed from, but is not limited to, various materials, such as rubber, silicone, or other elastomers, which offer properties like flexibility, resilience, and resistance to chemical interaction with the medication. The selection of materials would depend on the specific demands of the capsule system and its intended medical application.

Figure 31A:
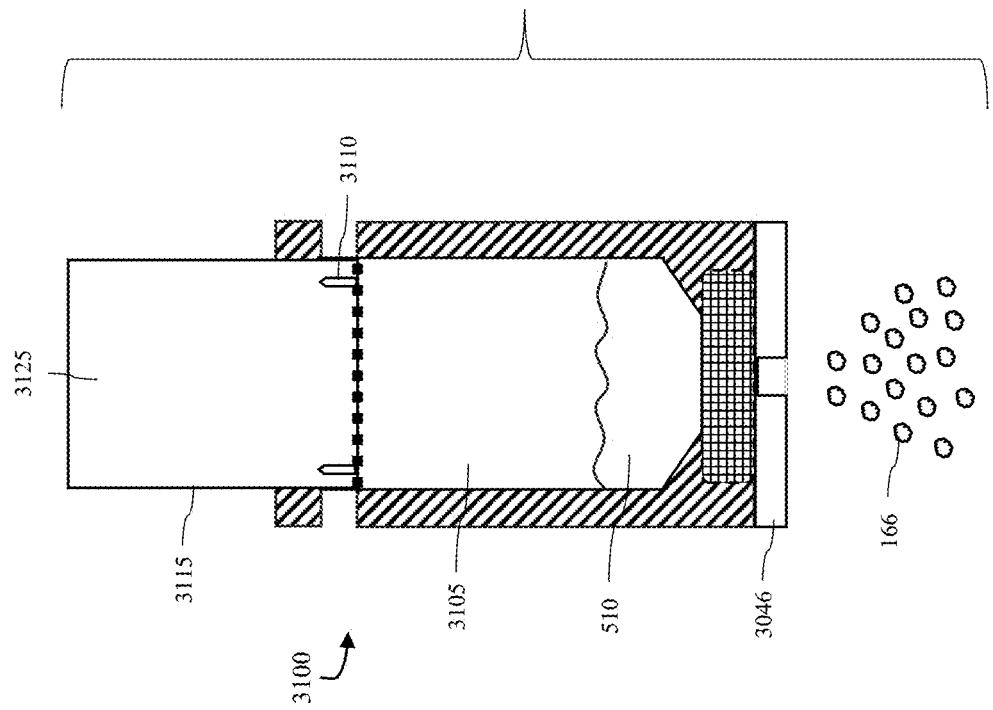
FIG. 31A is a cross-section of a side view of a capsule system including the removable container, according to an example embodiment.
Figure 31B:
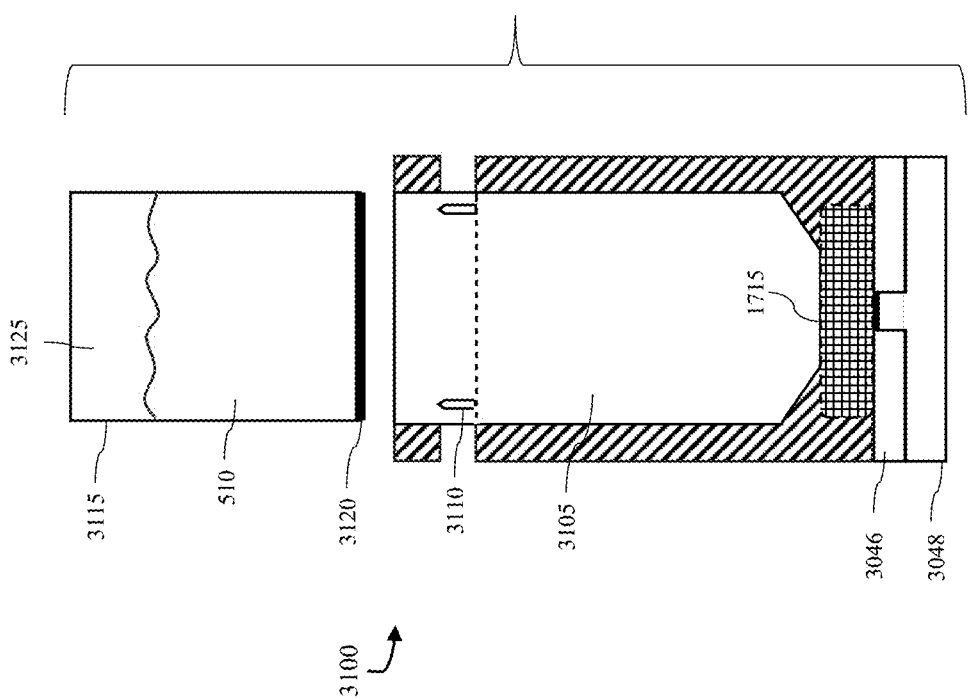
FIG. 31B is a cross-section of a side view of the capsule system, wherein the removable container is inserted, according to an example embodiment.

Referring now to FIGS. 31A through 31D, views of the capsule system 3100, 3101 for use with a medical device for administering at least one atomized medication to a patient are shown, according to an example embodiment. FIG. 31A is a cross-section of a side view of a capsule system 3100, according to an example embodiment. FIG. 31B is a cross-section of a side view of the capsule system 3100, wherein the removable container is inserted, according to an example embodiment. Capsule system 3100 includes a first chamber 3105 having an open top side and a first chamber width that substantially spans a capsule width. A rupturing element 3110 is disposed at least proximate to the first chamber. An atomizer 1715 is disposed at a lower end portion of the capsule system.

The capsule system 3100 also includes a removable container 3115 including a removable container width. The removable container is a vial having a fluid volume of 10 milliliters. Other fluid volumes may be used and are within the spirit and scope of the present invention. A seal 3120 is on the removable container. A second chamber 3125 is positioned within the removable container. The medication 510 is disposed within the second chamber. The removable container is disposed within the first chamber 3105 through the open top side of the first chamber. The container width spans substantially the first chamber width. When a force is applied on the removable container towards the first chamber, the rupturing element penetrates the seal to provide fluid communication between the first chamber and the second chamber.

The removable container functions as a specialized chamber within the capsule system, allowing for specific medications or substances to be enclosed and protected. Its removable nature offers flexibility in handling, refilling, or changing the contents without altering other parts of the system. Users of the capsule may have multiple removable containers, each labeled and containing different medications similar to commonly used medical vials. Therefore, the removable containers allow for efficient replacement or replenishment of medication for the capsule. When inserted, it integrates seamlessly with other elements such as the rupturing element and first chamber, providing a cohesive function within the overall medical device. The removable container presents a significant advancement in managing and delivering medication in medical devices. By facilitating easy insertion and removal, the container enables efficient handling, customization, and maintenance of the system. The feature of being removable allows for easier cleaning, sterilization, or replacement, thereby enhancing usability and hygiene. Its precise construction to fit within the existing chambers ensures that the functionality and integration within the device remain consistent, thus overcoming limitations found in previous designs. The removable container may be comprised of materials suitable for medical applications, ensuring biocompatibility, strength, and resistance to contamination. This could include medical-grade plastics, glass, or other sterilizable materials that comply with relevant regulatory standards. However, other materials may be used and are within the spirit and scope of the present invention.

FIG. 31C is a side perspective view of the capsule system 3101, according to an example embodiment. FIG. 31D is an exploded perspective view of the capsule system 3101, according to an example embodiment. The housing 1835 includes an asymmetrical transverse cross-sectional shape. The shape of the housing of the capsule system, when cut or viewed in a plane perpendicular to its length 3135, is not symmetrical about its center. This unique configuration ensures a specific orientation when the capsule is inserted into a medical device, allowing for accurate alignment and connection with other components within the system. The housing may be constructed from, but is not limited to, materials suitable for medical applications, such as medical-grade plastics, stainless steel, or other materials that meet necessary biocompatibility and sterility requirements. The distinct asymmetrical design of the housing provides improvements over prior art by ensuring precise alignment and engagement with corresponding components, thereby reducing the risk of improper installation or handling, and enhancing the overall functionality and reliability of the capsule system. The portion of the housing that creates the asymmetrical shape may harbor the main electrical components of the capsule system, such as the sensors, electrical contacts, and/or processor.

The capsule system 3101 further includes at least one electrical contact 1820 and at least one sensor. The sensor is a fluid sensor that can detect various properties related to the fluid, such as its level, flow rate, or presence. The fluid sensor is configured to detect and monitor the level or presence of medication within the first chamber and/or second chamber of the capsule system. The fluid sensor operates in coordination with other components to ensure proper dispensing of medication. By continually monitoring the fluid level, it provides real-time feedback, enabling precise control over the dosage and alerting the system if the medication reaches a critical level. The fluid sensor adds an additional layer of control and safety in the medication administration process, reducing the risk of administering incorrect dosages, and enhancing the ability to provide tailored treatment regimens. The capsule system 3101 may include a fluid sensor for the removable container 3115 and a second fluid sensor for the first chamber 3105. The electrical contacts are in electrical communication with a power source. The electrical contacts refer to the conductive interface designed to establish a connection within an electronic circuit. The electrical contacts may be composed of, but are not limited to, conductive materials such as copper, gold, or alloys, providing efficient energy transmission without significant loss. This provision for electrical communication with a power source offers improvements over prior art by allowing for consistent and controlled operations of the capsule system, enhancing both reliability and performance, particularly in comparison with manually operated or less sophisticated electronically controlled systems.

With reference to FIG. 32, a cross-section of a side view of the capsule system 3200, wherein an external container 3205 is in fluid communication with the capsule system, is shown, according to an example embodiment. The first chamber 1705 is in fluid communication with an external container via an elongated tube 3210. The external container has the medication 510. In some embodiments, the external container is an intravenous line ("IV") solution bag that holds the medication solution. The external container is an intravenous bag or infusion bag being a sterile, flexible container holding fluids, medications, and/or other solutions. The external container may be made of medical-grade plastic materials that are compatible with the solutions they contain. The external container and tube enable the controlled transfer of medication or other substances. This connection allows the capsule system to draw the medication from an external source, either continuously or in measured quantities, depending on the requirements of the medical device and treatment protocol. The elongated tube serves as the conduit for this transfer, maintaining a controlled and sterile pathway between the components.

The most common IV bags are typically made of polyvinyl chloride (PVC) or polyolefin, which are flexible, transparent, and resistant to chemical interactions with the fluids and medications inside. The elongated tube and connecting elements that facilitate this fluid communication may be constructed of biocompatible and inert materials, such as medical-grade silicone, polyurethane, or other suitable polymers. These materials ensure that the integrity and purity of the medication are maintained during transfer.

The elongated tube provides fluid communication between the first chamber and the external container. The fluid and/or the medication from the bag flows through tubing connected to the IV catheter. The elongated tube is in attachment with the first chamber of the capsule. In one embodiment, a medical needle 3215 is attached to the distal end of the elongated tube, and the needle is inserted into the self-sealing rubber stopper of the capsule and partially into the first chamber. The medication will continuously drip, at an adjustable flow rate, into the at least one chamber of the capsule.

The external container and elongated tube permit the medical device to access larger volumes of medication or other fluids stored externally, thus enabling longer or more complex treatment regimens without the need to refill the internal chamber frequently. The ability to connect with external containers also allows for versatility in medication types and concentrations, providing customization to individual patient needs. By maintaining a secure and sterile pathway for fluid transfer, this embodiment ensures safety and efficiency in delivering medication.

Figure 33:
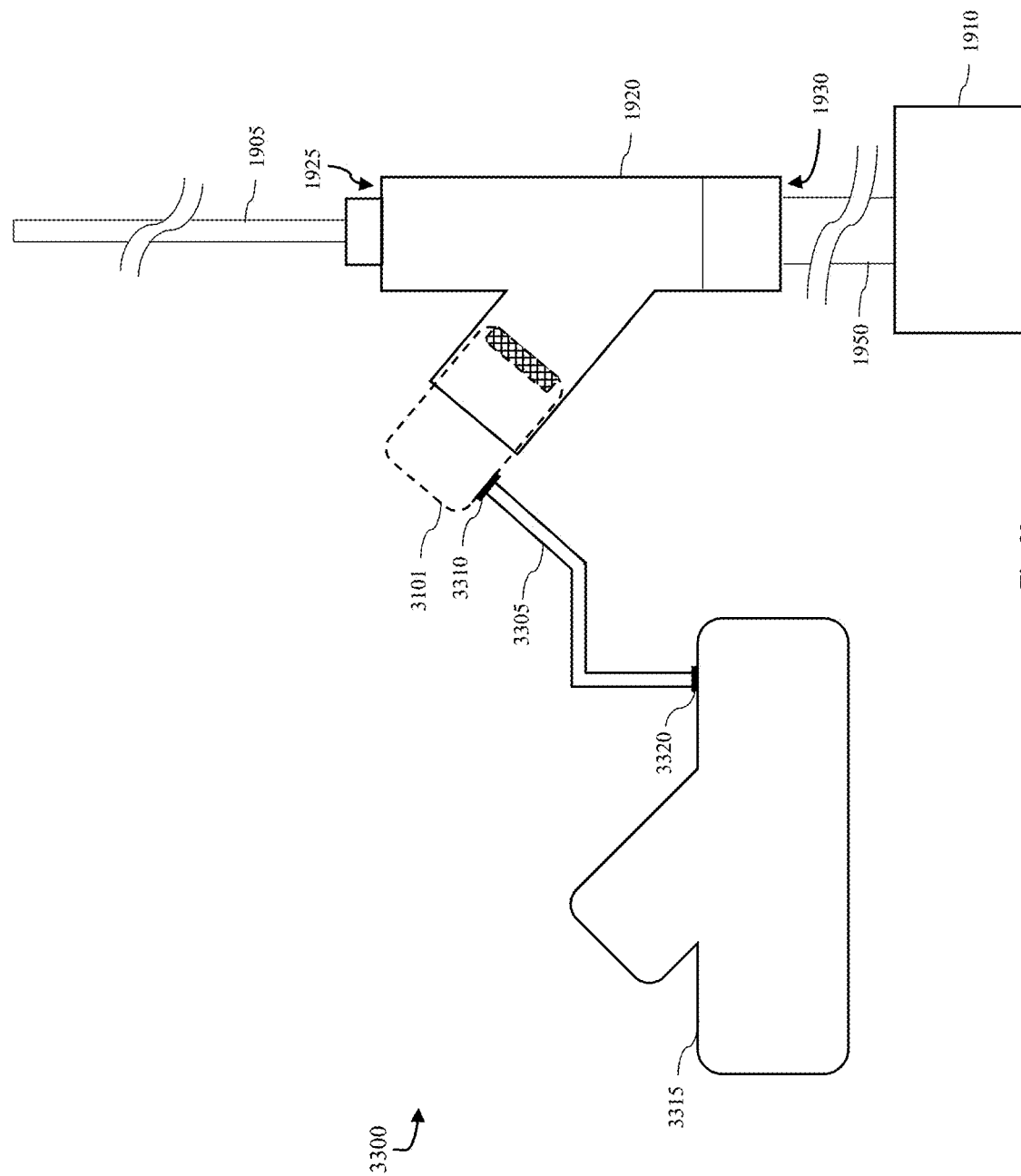
FIG. 33 is a diagram of the capsule system for use with a medical device for administering at least one atomized medication to a patient, according to an example embodiment.
Figure 34B:
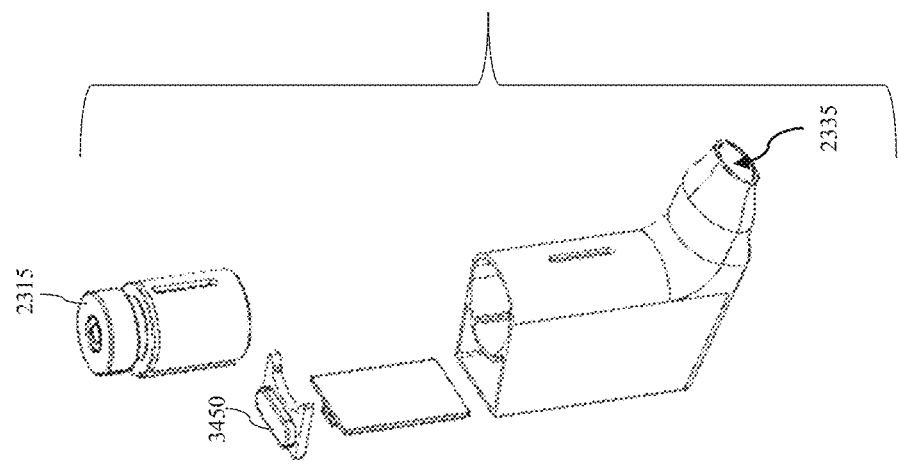
FIG. 34B is an exploded perspective view of the medical device, according to an example embodiment.
Figure 34A:
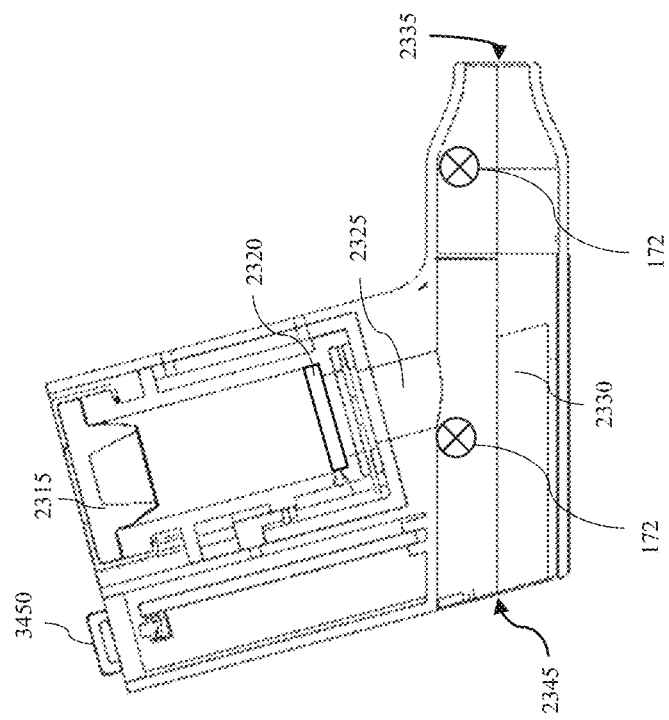
FIG. 34A is a cross-section of a side view of the medical device, according to an example embodiment.
Figure 34D:
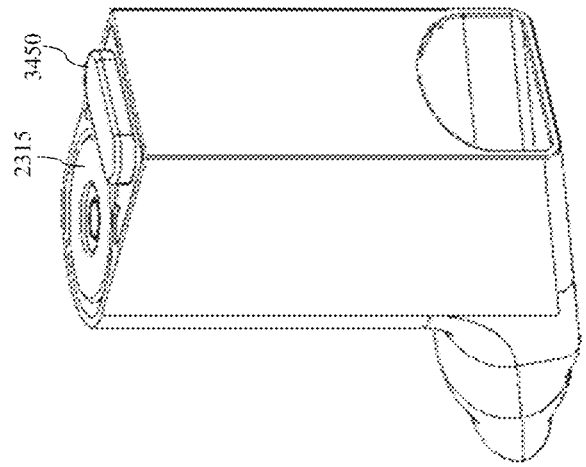
FIG. 34D is a perspective back view of the medical device, according to an example embodiment.
Figure 34C:
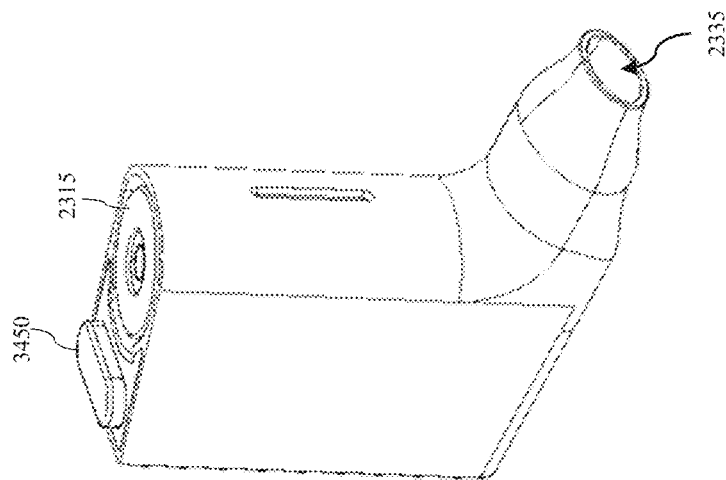
FIG. 34C is a perspective front view of the medical device, according to an example embodiment.
Figure 35B:
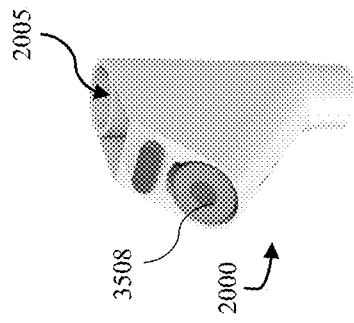
FIG. 35B is a perspective view of the medical device, according to an example embodiment.
Figure 35C:
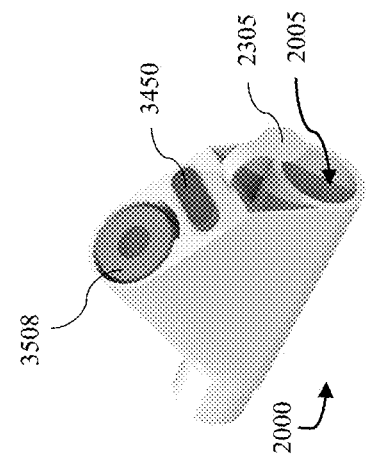
FIG. 35C is a perspective view of the medical device, according to an example embodiment.
Figure 35A:
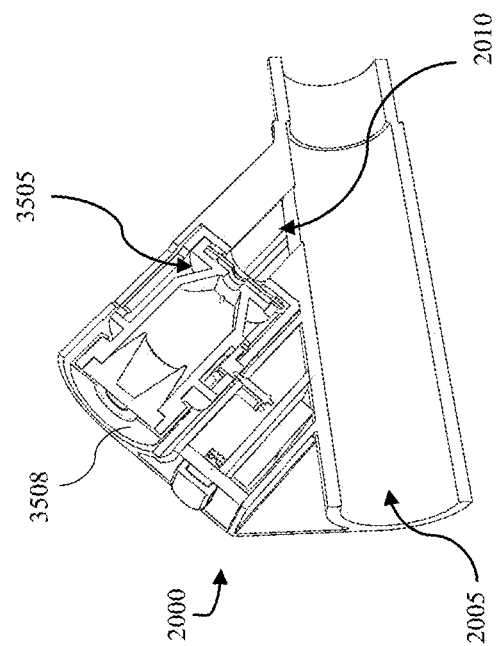
FIG. 35A is a cross-section of a perspective side view of the medical device, according to an example embodiment.

With reference to FIG. 33, a diagram of the capsule system 3300 for use with a medical device for administering atomized medication to a patient is shown, according to an example embodiment. The capsule system further includes an electrical conductor 3305 connecting the capsule to a remote-control device 3315 such that the capsule includes a port 3310. The remote-control device 3315 may be the medical device or base unit that includes a display, a processor, and a power source. In certain embodiments, the medical device may have a port 3320. The display allows for visual feedback and interaction, the processor controls the operations and data processing, and the power source provides energy for the system. The conductor enables data and control signals to be sent between the capsule and the remote-control device, ensuring synchronized operation and real-time control of the medication administering process. In certain embodiments, the remote-control device is separate from the device which receives the capsule. A remote-control device typically refers to an electronic device used to operate another device from a distance, typically wirelessly. Within the capsule system, the remote-control device interacts with the capsule through an electrical conductor connecting to a port. It may comprise elements such as a display, a processor, and a power source. This integration allows healthcare providers or patients to monitor, adjust, and control the capsule system's operation, facilitating tailored treatment regimens and responsive care.

An electrical conductor is any material or substance through which electric current can pass easily. It includes not only wires and cables but also components like metal bars, plates, or even certain liquids and gases. Conductors are characterized by their ability to carry electrical charges with minimal resistance. The capsule may include more than one conductor as well. The electrical conductor may be an electrical lead. An electrical lead is a conductor or wire that is used to connect an electrical device to a power source, such as a charger connecting a device to an outlet—or in the context of this invention, connect the capsule to the medical device. The electrical conductor may be made from, but are not limited to, materials such as copper, silver, or gold, known for their high electrical conductivity and reliability. The insulation surrounding the conductor would typically be made of materials resistant to medical environments, such as Teflon or other medical-grade polymers.

The port is a specific interface or receptacle on an electronic device or apparatus that facilitates the transfer of data, electrical signals, power, or other information between the device and external components, such as cables, connectors, or peripherals. The port typically comprises a well-defined physical and electrical structure designed to accommodate compatible connectors, ensuring secure and reliable connections. The structure of the port may correspond to the electrical lead such that the port is configured with a compatible shape, size, and electrical layout that matches the design of the electrical lead. The port typically includes male or female terminals, pins, or contacts, strategically positioned within the receptacle to match the corresponding connectors or plugs on the electrical lead. The electrical lead, in turn, features complementary male or female connectors designed to fit precisely into the corresponding terminals of the port. The port's structural design may also incorporate additional features such as locking mechanisms, shielding, or protective covers to enhance durability, prevent accidental disconnections, and safeguard against potential hazards. It is understood that the term "port" should be construed to encompass a broad range of configurations, including but not limited to, input/output (I/O) ports, charging ports, data transfer ports, audio ports, video ports, or any other interface specifically engineered to enable communication, interaction, or power exchange between the capsule and external entities or devices.

The electrical conductor and ports enhance the functionality, flexibility, and user experience of the medical device.

Unlike previous designs that may rely solely on manual control or limited interface, this configuration allows for precise control, monitoring, and customization of the treatment. The integration with a remote-control device equipped with a display, processor, and power source enables a more sophisticated and tailored approach to medication administration, potentially improving treatment outcomes, patient compliance, and healthcare professionals' efficiency. This represents a significant advancement over prior art, adding value to the medical field by increasing the utility and effectiveness of the capsule system. For example, this embodiment allows the capsule and the modular tubular extension to rest on the patient without the weight of the remote-control device, which can be placed elsewhere.

Figure 37:
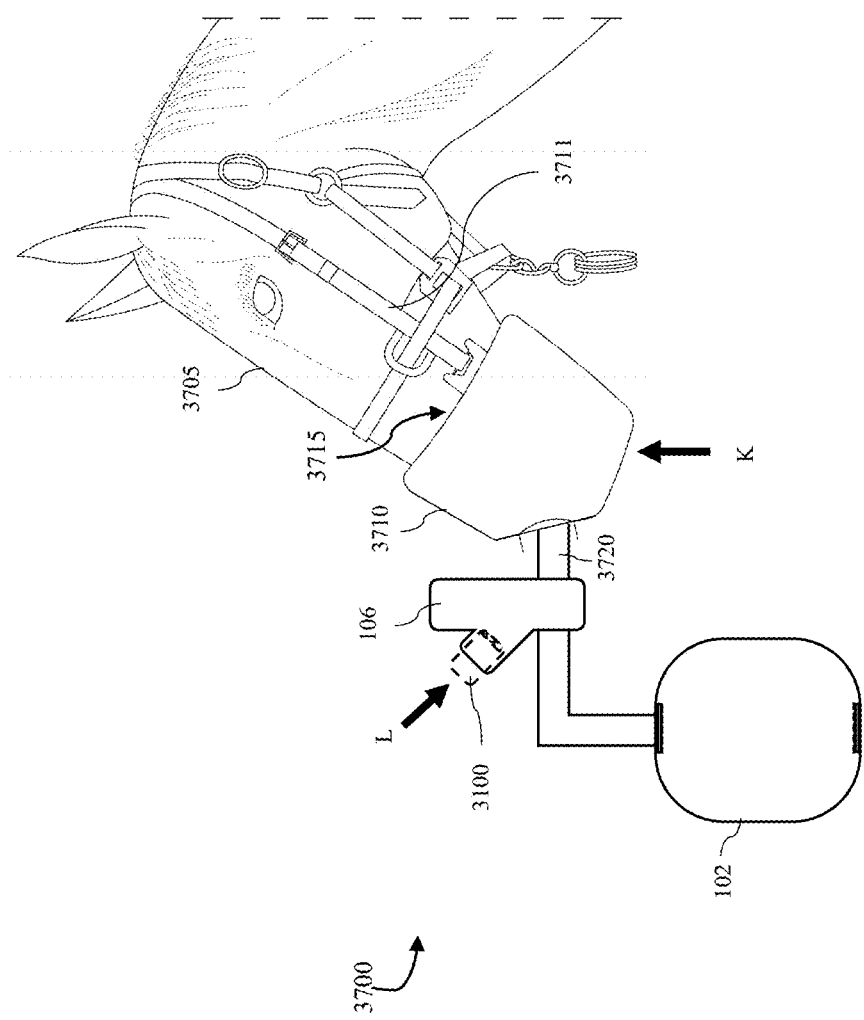
FIG. 37 is a diagram of a system for veterinary administration of at least one medication to an animal, according to an example embodiment.

Referring now to FIG. 37, a diagram of a system 3700 for veterinary administration of at least one medication to an animal is shown, according to an example embodiment. The animal is a mammal. More specifically, the animal may be cattle. In the present embodiment, the animal is a horse 3705. In other embodiments, other animals may be treated using system 3700. System 3700 includes the attachment 106 in fluid communication with the mask 3710 and the resilient air bladder 102. In some embodiments, instead of the resilient air bladder, the system may be in attachment with a respiratory support device configured to provide airflow to the system. The mask 3710 is a standard medical mask that is commonly used in the veterinary field. The mask 3710 is configured to cover the muzzle 3715 of the horse. The muzzle, or snout, of an animal is the projecting jaws and nose of the animal. Other types of medical masks may be used depending on the animal being treated.

The medication may be an aqueous suspension or a solution including at least one of cells, cellular byproducts, and cell-derived products. The aqueous suspension refer to a liquid medium, primarily water-based, in which the cells or cell-derived materials are suspended or dissolved. Cells may include, but are not limited to, various types of biological cells, such as somatic cells, stem cells, or even specialized cells like nerve or muscle cells. Cells refer to living cells, such as stem cells, which can be used for regenerative therapies. Cellular byproducts may include, but are not limited to, elements like enzymes, waste products, or signaling molecules produced by cells. Cell-derived products may include molecules synthesized by cells, such as proteins, lipids, or nucleic acids. The cells can be of any type suitable for veterinary applications, with properties that are deemed therapeutic. Cell byproducts are substances produced naturally by cells and may have therapeutic effects. Examples could include enzymes or antibodies that can have a direct therapeutic action or facilitate other biological processes beneficial to the animal's health. Cell-derived products are materials produced from cells but may not be naturally occurring. For example, proteins engineered for specific therapeutic actions would fall under this category. The use of an aqueous suspension as the medium for these cellular components offers significant advantages over prior art, such as improved bioavailability and rapid onset of therapeutic effects. The method of administration, via atomization and inhalation, represents a significant technological advancement, optimizing the delivery and efficacy of the medication. The components of the system, such as the tubular chamber and atomizer, may be composed of materials that are biologically inert, such as medical-grade plastics or metals, to maintain the medication's integrity throughout the administration process. The inclusion of cells, cellular byproducts, and cell-derived products as the constituents of the medication underscores the present invention's utility in cutting-edge veterinary treatments, such as regenerative medicine.

In some embodiments, the cells, the cellular byproducts, and cell-derived products are stem cells. Generally, stem cells are unspecialized cells with the unique capacity to differentiate into various cell types and possess self-renewal capabilities. Specifically, these stem cells can be adult stem cells, embryonic stem cells, or induced pluripotent stem cells, among other types. The stem cells serve as the active agent in the aqueous suspension and are intended for therapeutic applications in veterinary medicine. The inclusion of stem cells as the active ingredient offers significant improvements over the prior art, notably in the areas of tissue regeneration and healing. Due to their unique properties of differentiation and self-renewal, stem cells provide a highly efficacious treatment option for various degenerative and acute conditions in animals. The aqueous suspension containing stem cells can be specifically formulated to be compatible with the device's materials, which may include biocompatible plastics or metals. This ensures the integrity and efficacy of the stem cells from the point of encapsulation to the point of administration. In a veterinary context, this could mean regenerating tissues damaged by injury, disease, or age.

In some embodiments, the cell-derived products are exosomes. Exosomes are nanoscale, membrane-bound vesicles that are secreted by most cell types, including stem cells. They are a subset of extracellular vesicles that typically range in size from about 30 to 150 nanometers. Exosomes contain various bioactive molecules such as proteins, lipids, and nucleic acids (like RNA). They play a key role in cell-to-cell communication and have been found to be involved in a variety of physiological and pathological processes. Exosomes are natural carriers of biological information, functioning almost like tiny 'message parcels' between cells. They can modulate immune responses, facilitate tissue repair, and even transfer genetic material. The use of exosomes in the aqueous solution offers improvements over prior art by facilitating targeted delivery of bioactive molecules to specific cells or tissues. This enhances the treatment's efficacy and potentially reduces side effects. The exosome-containing solution is designed to be compatible with the materials of the device, which may include medical-grade plastics or metals, thereby preserving the integrity and activity of the exosomes throughout the administration process.

In some embodiments, the medication includes at least one of peptides, proteins, growth factors, cytokines, exosomes, and extracellular vesicles derived from human mesenchymal stem cells ("hMSCs") suspended and/or dissolved in an aqueous medium. These bioactive agents derived from hMSCs are either suspended or dissolved in the aqueous medium. The hMSCs exhibit a multipotent differentiation potential, which means they can differentiate into various cell lineages, specifically those of mesenchymal origin. This includes, but is not limited to, osteocytes (bone cells), chondrocytes (cartilage cells), and adipocytes (fat cells).

Peptides and proteins may include amino acid sequences involved in cellular signaling or structural functions. Growth factors are proteins that regulate cell growth and division, while cytokines are small proteins involved in cell signaling. Exosomes and extracellular vesicles are membrane-bound carriers of bioactive molecules. This form of medication offers improvements over the prior art by providing a targeted and efficient method of delivering a complex mixture of bioactive molecules. These molecules interact synergistically to promote tissue repair, modulate immune responses, and carry out other therapeutic functions, thereby enhancing the overall efficacy of the treatment. The aqueous medium and the bioactive molecules are specifically formulated to be compatible with the materials of the device, which may be composed of medical-grade plastics or metals, ensuring that the integrity and bioactivity of the medication are maintained throughout the administration process.

In some embodiments, the medication includes no preservatives. Preservatives are substances added to medications to prolong shelf life by inhibiting microbial growth or chemical degradation. The absence of preservatives offers several advantages over the prior art, one of which is the potential for reduced risk of allergic reactions or sensitivities in the animal receiving treatment. Additionally, a preservative-free formulation can be advantageous in maintaining the biological activity and integrity of sensitive bioactive agents like peptides, proteins, or cellular components. The medication and the device are engineered to be compatible, often using medical-grade plastics or metals to ensure that the integrity of the preservative-free medication is maintained throughout the administration process.

In some embodiments, the medication includes bioactive molecules including proteins, lipids, and ribonucleic acid (RNA). Bioactive molecules are substances that exert a biological effect on living tissues. In this particular formulation, proteins may act as enzymes, signal molecules, or structural components; lipids could serve as signaling molecules or membrane components; and RNA may act as a template for protein synthesis or have other regulatory functions. The inclusion of these bioactive molecules offers several advantages over prior art, such as the potential for multi-target therapeutic effects, given the diverse functional roles of proteins, lipids, and RNA. Additionally, this formulation may provide more natural or physiologically compatible treatment options, reducing the likelihood of adverse reactions. The materials constituting the device through which this medication passes are carefully selected, typically involving medical-grade plastics or metals, to ensure that the bioactive molecules maintain their integrity and activity throughout the administration process.

The medication is a regenerative medication targeting treatment of tissue repair and regeneration in the animal. Regenerative medications include bioactive agents capable of stimulating cellular growth, differentiation, and repair. The medication may include a combination of growth factors, cytokines, stem cells, or other agents known to facilitate tissue regeneration and repair. Compared to prior art, this specific type of medication provides several advantages, such as a targeted and potentially more effective approach to tissue repair and regeneration. This innovation minimizes the need for surgical intervention or long recovery periods, thereby offering a more convenient and less invasive treatment option. The regenerative medication and the materials of the device, which may include medical-grade plastics or metals, are formulated to be compatible, thus maintaining the medication's bioactivity and efficacy throughout the administration process.

Aerosol administration of the abovementioned medication embodiments allow for direct deposition into the respiratory tract, facilitating rapid absorption into the bloodstream. This ensures immediate bioavailability, which can be crucial for timely therapeutic effects. Aerosol administration avoids the need for injections or surgical interventions, reducing the risk of complications such as infections or tissue damage. This non-invasive method is also more patient-friendly and can be more easily accepted by animals, especially when considering veterinary applications. For conditions affecting the respiratory system, aerosol administration can provide a localized delivery, ensuring a high concentration of therapeutic entities at the target site. This is especially beneficial for treating lung diseases or injuries. By delivering these entities directly to the target site, systemic exposure can be reduced, potentially minimizing side effects or adverse reactions in other parts of the body. The nano-size of exosomes and some vesicles allows for efficient penetration into deeper lung tissues, ensuring a wide distribution and reaching cells that might be inaccessible with larger particles. Aerosolizing these entities in an appropriate medium can help in preserving their structural and functional integrity, ensuring that they retain their therapeutic potential upon administration. The present disclosure can be calibrated to deliver precise doses, ensuring consistent and controlled administration of these therapeutic entities. Aerosol administration can be more convenient than repeated injections or infusions, leading to better compliance, especially in chronic conditions.

Referring now to FIG. 38A, a flowchart diagram illustrating steps for a method 3800 for veterinary administration of at least one medication to an animal is shown, according to an example embodiment. In this embodiment, method 3800 begins with step 3802, in which the user inserts the capsule into the device. The capsule may be any one of the previously mentioned capsules, such as capsules 500, 1600, 1700, 1701, 1800, capsule system 3000, capsule system 3100, capsule system 3101, and 3200. The device may be the base unit/attachment, also referred to as medical device, such as attachment 106, base unit 300, attachment 1500, and remote-control device 3315. Depending on the situation, different modular tubular extensions may be in attachment with the device. For example, the animal may be unconscious and lying on the ground. Therefore, the device and modular tubular extension must be configured to treat an animal laying on the ground. Then, in step 3804, the user activates the atomizer within the capsule to generate atomized medication, which travels to the tubular chamber. In step 3806, the user partially deflates the resilient air bladder to provide airflow and convey fresh air towards the tubular chamber. This causes the fresh air to mix with the atomized medication in the tubular chamber. Deflating the resilient air bladder also conveys the mixture of fresh air and atomized medication toward the mask. In some embodiments, airflow can be provided using other means, such as the respiratory support device previously described. Then, in step 3808, the user administers the atomized medication to the animal using the device.

Referring now to FIG. 38B, a flowchart diagram illustrating steps for a method 3801 for veterinary administration of at least one medication to an animal is shown, according to an example embodiment. FIG. 37 will also be reference relative to method 3800. Method 3801 begins with step 3810, in which the user inserts a capsule containing the medication into a device in fluid communication with a tubular chamber. The capsule may be any one of the previously mentioned capsules, such as capsules 500, 1600, 1700, 1701, 1800, capsule system 3000, capsule system 3100, capsule system 3101, and 3200. The device may be the base unit/attachment, also referred to as medical device, such as attachment 106, base unit 300, attachment 1500, and remote-control device 3315. Next, in step 3812, prior to activating the atomizer, the user provides power to the atomizer by removing an insulator that prevents electrical communication between the atomizer and a power source. The insulator may be the insulator 2305 shown in FIG. 23.

Then, in step 3814, the user activates the atomizer to atomize the medication to generate atomized medication.

In step 3816, prior to administering the atomized medication to the animal using the device, the user applies force K to the mask 3710, positioned over an animal's muzzle and in fluid communication with the tubular chamber. This mask is tailored to fit securely over the facial structure or "muzzle" of an animal, which is the projecting part of the face that includes the nose and mouth. Applying a force could be manual, such as pressing or adjusting the mask onto the animal's muzzle, or it could be mechanized, involving components like straps, clamps, or inflatable sections. For example, in one embodiment a strap 3711 or plurality of straps may be used to attach the mask to the animal. This applied force ensures that the mask remains in place, offering a consistent and effective seal during the procedure so that a minimum amount of medication is dispersed outside of the mask. By applying force to the mask, unintentional loss of medication is minimized, and the desired concentration of the medication can be maintained within the mask, ensuring effective delivery.

In step 3818, prior to causing the liquid formulation to move from the first chamber to the second chamber, the user removes a stop on the capsule that inhibits the first chamber from translating relative to the second chamber. Removing a stop entails physically disengaging, dislodging, or eliminating the device or mechanism that imposes the aforementioned restriction. By doing so, the first chamber is now allowed to move or adjust its position relative to the second chamber. Such movement could be in the form of sliding, rotating, tilting, or any other type of translational motion, depending on the design of the capsule. However, other forms of disengagement of the stop may be used and are within the spirit and scope of the present disclosure. For example, in another embodiment, the stop may be the stop 1725 shown in FIGS. 17A-17C.

In step 3820, after removing the stop of the capsule, the user applies a second force L to the first chamber causing the first chamber to translate relative to the second chamber rupturing the membrane disposed between the first chamber and the second chamber thus providing fluid communication between the first chamber and the second chamber. Causing the first chamber to translate in relation to the second chamber denotes a controlled movement or repositioning of the first chamber with respect to the second chamber. Translation may include sliding, shifting, or any relative motion that brings two chambers closer together or further apart. Once the membrane is ruptured, the previously isolated chambers are now connected, establishing "fluid communication" between them. This means that substances, such as liquids or gases, can now flow or transfer freely from one chamber to the other. This provides precise control over the timing and conditions of interaction between the chamber contents, enhancing the system's adaptability and functionality. This modular approach ensures that interactions or mixings between the chambers occur only when desired, maximizing the capsule's efficiency and potential applications, and distinguishing it from less flexible systems. Then, in step 3822, because rupturing the membrane provides fluid communication between the first chamber and second chamber, the liquid formulation moves from the first chamber to the second chamber.

In step 3824, the user at least partially deflates the resilient air bladder in fluid communication with the tubular chamber causing air within the resilient air bladder to be conveyed from the resilient air bladder into the tubular chamber. Deflating the resilient air bladder causes fresh air contained within it to be pushed or conveyed out. The released air flows directly into the tubular chamber within the attachment 106. The tubular chamber, being a conduit or passage, receives this air and may be used to aid in the process of conveying atomized medication and fresh air.

In step 3826, deflating the resilient air bladder further conveys the atomized medication through the second tubular chamber 3720. The second tubular chamber is disposed between the animal's muzzle and the tubular chamber. Conveying fresh air towards the second tubular chamber causes the atomized medication to form a substantially stable and uniform aerosol with the fresh air. Then, in step 3828, the user administers the atomized medication to the animal using the device.

It is understood that this method is a continuous cycle and that each step of method 3800 may operate concurrently with another step of method 3800 to provide efficient administration of medication to an animal within the system. In other embodiments, the method may further include additional steps to promote efficient administration of medication consistent with the systems disclosed herein.

The embodiments described in the context of the disclosed invention serve as examples and are non-limiting. While specific configurations, functionalities, and arrangements of elements like the button, atomizer, chambers, and sensors have been detailed, these descriptions are illustrative and not intended to restrict or confine the invention to these exact embodiments. The invention's underlying principles and concepts allow for various modifications, adaptations, and variations. Different designs and arrangements can be developed to meet particular needs or applications without departing from the scope and spirit of the invention. This flexibility ensures that the invention can be tailored to a broad array of medical devices, enhancing the application in diverse scenarios and providing improvements over the existing art in multiple contexts.

Referring now to the Figures, FIG. 39 is a side view of an active vibrating instrument ("AVI") 3900, according to an example embodiment. The AVI includes a reservoir 3905 the contains a liquid solution 3910. The reservoir is in attachment with an inner surface of a vibrating mesh membrane 3915. The solution is provided in a sterile, sealed syringe 3935. A channel 3920 is in attachment with an outer surface of the vibrating mesh membrane 3915. The AVI is configured to produce particles 3925 having a particle diameter ranging from about 1.5 micrometers (μm, or microns) to about 6 micrometers. As the solution passes through the vibrating mesh membrane, the vibrating mesh membrane 3915 nebulizes the solution to create a nebulized solution that includes the particles 3925. The vibrating mesh membrane 3915 produces nebulized solution by vibrating at high frequency to trigger particle, or droplet, formation from the solution 3910 against an inner surface of the membrane on an outer surface of the membrane. The inner surface of the membrane faces the reservoir, and the outer surface of the membrane faces a channel 3920. The vibrating mesh membrane is a metal piece or plate having a plurality of openings extending through the piece, such that the metal piece, when electrically stimulated to undergo piezoelectric vibration, oscillates against the solution 3910 in the reservoir 3905, causing some of the solution to move through the openings and form small particles on or above the outer surface of the vibrating mesh membrane 3915. The vibrating mesh membrane 3915 vibrates at between about 150 kHz and about 300 kHz upon electrical stimulation by an AC|DC current directed to the vibrating mesh membrane. The vibrating mesh membrane includes material such as pure titanium, platinum, or palladium, or alloys thereof or the like, or laminated layers of titanium, platinum, or palladium or the like, to produce a piezoelectric effect that results in mesh vibration and particle formation over the outer surface of the mesh in the mouthpiece interior volume. Piezoelectricity is the ability of a material to develop electric charge in response to applied mechanical stress.

The particles are atomized droplets of the solution 3910. Particles that are larger than 5 micrometers are unable to penetrate into the alveoli of the lungs and are thus of reduced efficiency in being rapidly absorbed by the circulatory system and/or body tissues. The ability of particles to penetrate into the lungs and be absorbed by the depends on the size of the particles. Inhalable particles, ranging in size from 1.5 micrometers to about 6 micrometers, penetrate into the lungs as far as the bronchi because the cilia of the lungs filter the inhalable particles from further travel into the lung volume. Particles ranging in size from 1.5 micrometers to about 5 micrometers are able to penetrate into the alveoli in the lungs and are readily absorbed through the alveoli into the circulatory system and body tissues. The AVI 3900 further includes a channel 3920 that encloses the particles 3925 of the nebulized solution created by the AVI. The atomized droplets flow in the direction A towards a user of the AVI. The opening 3930 in the channel 3920 may be attached to a mouthpiece and/or nosepiece configured to be positioned on the user's face. In some embodiments, the AVI may be used within a disposable pen-type vaporizer. The pen-type vaporizer would provide more portability than a standard nebulizer and thus would be more convenient.

Referring now to FIG. 40, a block diagram 4000 of a solution 4005 for use with the AVI is shown, according to an example embodiment. The solution includes an aqueous solution 4005 that includes an active ingredient 4010 and sodium chloride 4015. The active ingredient includes at least one of nicotine 4310 of FIG. 43C, caffeine 4315 of FIG. 43D, a plurality of vitamins, kratom 4320 of FIG. 43E, Vitamin B12 4325 of FIG. 43F, cotinine 4300 of FIG. 43G, adalimumab 4305 of FIG. 43B, cannabidiol ("CBD") 4330, tetrahydrocannabinol ("THC") 4335 of FIG. 43H, psilocybin 4340 of FIG. 43I, *Cannabis* 4335, ketamine 4345 of FIG. 43J and any combination thereof. The active ingredient may also include analgesics, antifungals, antibiotics, anti-inflammatory, anti-gout, cardiovascular agents, central nervous system stimulants and/or depressants, diabetic agents, diuretics, immunologic agents, gastrointestinal agents, common biologics like Humira, Lantus, Remicade, Enbrel, vaccines, psychotherapeutic agents, opiate partial antagonists, pulmonary agents, hormonal agents, weight loss agents, and vitamins/minerals/supplements.

The solution further includes a buffer and/or stabilizer 4020. The buffer helps stabilize and maintain the pH level of the solution. The active ingredient includes approximately up to 10% of the solution. Sodium chloride includes approximately between 10% to 90% of the solution. The buffer includes approximately between 1% to 5% of the total solution.

The solution is sterile, non-pyrogenic, additive and preservative free, and provided in sterile unit-of-use, blow-fill-seal cartridges/capsules. The solution being mixed into an aqueous solution allows for its long-term storage. The capsules are configured to conveniently fill up the reservoir of the AVI. For smaller, portable AVI, cartridges may be used such that the solution is quickly replaced when a cartridge is emptied. The cartridges are conveniently detachable from the AVI.

Referring to FIG. 41, the solution has a pH 4105 of approximately between 4 pH and 7.5 pH, as shown in the pH scale 4100. The pH range is critical to decrease the effects that the active ingredient may have on the body when inhaled, e.g., an increased amount of acute toxicity which may be present in unprotonated active ingredients above a certain pH.

Referring now to FIG. 42, a flow diagram of a method 4200 of administering the solution for use with the AVI, according to an example embodiment. Method 4200 begins with step 4201 which includes mixing the solution. In step 4205, mixing the solution includes combining the active ingredient and the sodium chloride into an aqueous solution. Then, step 4210 includes combining buffer and/or stabilizers with the aqueous solution created in step 4205. In step 4215, mixing the step 4201 further includes adding sugar alcohol and water to the aqueous solution. The sugar alcohol may include erythritol, mannitol, sorbitol, xylitol, lactitol, isomalt, maltitol, and hydrogenated starch hydrolysates. Other sugar alcohols may be used and are within the spirit and scope of the present invention. The solution created by steps 4205, 4210, and 4215. Method 4200 then includes providing the solution in a sterile, sealed syringe in step 4220. In step 4225, the method includes filling the reservoir of the AVI with the solution using the syringe. Next, in step 4230, the method includes nebulizing the solution across the vibrating mesh membrane. Nebulizing the solution generates the nebulized solution in step 4235. Finally, in step 4240, the method includes administering the nebulized solution to the user. It is understood that this method is a continuous cycle and that each step of method 4200 may operate concurrently with another step of method 4200 to administer medication through an AVI within the system. In other embodiments, the method may further include additional steps to administer medication through an AVI consistent with the systems disclosed herein.

With reference now to FIGS. 43A through 45, several embodiments of the solution for use with the AVI will be described. In a first embodiment, the solution is for at least deceasing a plurality of withdrawal symptoms of a person addicted to nicotine. Said solution includes cotinine being the active ingredient in the solution including approximately between 0.5% and 8% of the solution and a sugar alcohol 4500 of FIG. 45 including approximately between 0.5% to 3% of the solution. The solution further includes a buffer including ethyl alcohol 4400 of FIG. 44A and citric acid 4405 of FIG. 44B. The ethyl alcohol includes approximately between 0.1% to 3% of the solution, and the citric acid comprising approximately between 0.1% to 3% of the solution. Cotinine helps reduce symptoms of nicotine withdrawal. The sugar alcohol and citric acid act as sweetener to counter the bitterness of cotinine when inhaled. In another embodiment, the solution of the first embodiment may be mixed with a small dose of nicotine.

In a second embodiment, the solution is a pulmonary irrigation solution. The solution includes adalimumab being the active ingredient including approximately between 1% to 10% of the solution and a sugar alcohol 4500 including approximately between 0.1% to 1% of the solution. The solution further includes a stabilizer including polyol including approximately between 0.1% to 5% of the solution and surfactant comprising approximately between 0.1% to 5% of the solution. The polyol is at least one of sucrose 4410 of FIG. 44C, histidine 4415 of FIG. 44D, and succinate 4420 of FIG. 44E. The surfactant is polyetherimide 4440 of FIG. 44I. At least one of the buffer and the stabilizer includes at least one buffer selected from the group consisting of histidine, succinate, phosphate 4430 of FIG. 44G, citrate 4435 of FIG. 44H, acetate 4425 of FIG. 44F, sodium bicarbonate 4445 of FIG. 44J, maleate 4450 of FIG. 44K, and tartrate 4455 buffers of FIG. 44L. The buffer does not include a combination of a citrate buffer and a phosphate buffer. Adalimumab is a therapeutic biologic used in the treatment of various autoimmune and inflammatory conditions. As a monoclonal antibody, it specifically targets and neutralizes tumor necrosis factor alpha (TNF-α), a substance in the body that contributes to inflammation and immune system activity. Adalimumab is widely used in the management of rheumatoid arthritis, a condition characterized by chronic joint inflammation. Its efficacy extends to other autoimmune disorders such as psoriatic arthritis, which affects the skin and joints, and ankylosing spondylitis, a type of spinal arthritis. Additionally, Adalimumab has shown effectiveness in treating inflammatory bowel diseases, including Crohn's disease and ulcerative colitis, where it helps in reducing inflammation of the gastrointestinal tract. It is also used in certain dermatological conditions like plaque psoriasis, providing relief from skin symptoms. The broad application of Adalimumab in these conditions underscores its role as a critical therapeutic agent in the management of various chronic inflammatory and autoimmune disorders.

In a third embodiment, the active ingredient is naloxone 4350. Naloxone rapidly counters and/or reverses the effects of opioids. Naloxone is the standard treatment to counter opioid overdoses. Inhalation of naloxone through a portable AVI could quickly save the life of opioid users who overdose.

In a fourth embodiment, the active ingredient is colloidal silver 4600 in FIG. 46. Colloidal silver is a liquid solution 4605 including a plurality of silver particles 4610. Colloidal silver treatment can heal a variety of infections, such as the common cold or respiratory infections.

In a fifth embodiment, the active ingredient is glucagon 4355 of FIG. 43L. Glucagon is a hormone that raises blood glucose levels and the concentration of fatty acids in the bloodstream. Glucagon treatment helps people who suffer from hypoglycemia. Hypoglycemia occurs when the blood glucose levels are lower than the standard range.

Referring now to FIGS. 43K and 47 through 50, multiple pharmaceutical compositions are illustrated. In the disclosed embodiments, various pharmaceutical solutions are presented for use with a vibrating mesh nebulizer, each tailored for specific therapeutic purposes. These solutions are meticulously formulated with precise concentrations of active ingredients and are designed to operate within a defined pH range, ensuring both efficacy and stability for nebulization.

Generally, the pH of these pharmaceutical compositions is between 3 pH to 7.5 pH. In other embodiments, the pH may be more ideally maintained between 4 pH and 7.5 pH. This precise pH control is critical for several reasons integral to the efficacy, stability, and safety of the compositions. Firstly, the stability of active ingredients such as naloxone, yohimbine, albuterol, and tolazoline is highly pH-dependent. Deviations from the optimal pH range can lead to the degradation or alteration of these compounds, thereby compromising the therapeutic effectiveness and shelf-life of the pharmaceutical product. Secondly, the solubility of the active ingredients is influenced by pH, where maintaining the pH within this defined range ensures consistent dissolution, crucial for effective delivery, particularly in nebulizer applications.

Furthermore, aligning the pH range with physiological levels minimizes potential irritation or discomfort upon administration, especially pertinent for mucosal or inhaled routes. This consideration is vital for patient compliance and comfort. Additionally, the prescribed pH range facilitates appropriate chemical interactions within the composition, preventing undesirable reactions between the active ingredients, excipients, and stabilizers, thus preserving the intended pharmacological action. Moreover, certain pH levels play a pivotal role in inhibiting microbial growth, thus contributing to the preservative efficacy of the formulation. This aspect is especially critical in ensuring the safety and longevity of the pharmaceutical composition.

The disclosed pharmaceutical composition are designed for treating conditions such as opioid overdose and opioid dependency. This composition is characterized by its versatility and precision in formulation, catering to varying therapeutic needs. At its core, the composition includes an aqueous solution of sodium chloride, providing a stable and biocompatible medium. Incorporated within this solution is at least one active ingredient, chosen from a group comprising naloxone, yohimbine, and albuterol. The concentration of this active ingredient is carefully calibrated to be between 0.025% and 25% of the aqueous solution, ensuring optimal therapeutic efficacy. Critical to the composition's stability and compatibility with human physiology is the maintenance of a pH range approximately between 3 and 7.5. This pH range is chosen to maximize the stability of the active ingredients, ensure patient comfort upon administration, and maintain the chemical integrity of the composition.

In embodiments where naloxone is the active ingredient, its concentration is finely tuned to approximately 4% to 6% of the aqueous solution, aligning with its optimal therapeutic window for treating opioid overdose. For compositions containing yohimbine, the concentration is adjusted to approximately 2.5% to 6%, catering to its pharmacological role in opioid dependency management. In the case of albuterol, its concentration is maintained at a precise range of approximately 0.025% to 0.075%, leveraging its therapeutic benefits while ensuring safety and efficacy. Additionally, some embodiments may include tolazoline, constituting approximately 50% to 75% of the aqueous solution, broadening the composition's therapeutic spectrum.

The disclosed dosages are calibrated based on a standard human adult weight of 150 pounds. For administering these compositions, specific dosing guidelines are established: for example, a dose of 0.1 ml is nebulized and delivered in 3 breaths, while a larger dose of 0.3 ml is nebulized across 9 breaths. The achievement of the total intended dose is reached upon the nebulization and administration of 0.3 ml of the pharmaceutical composition. When these pharmaceutical compositions are prepared and stored in capsules, they are formulated in quantities sufficient to allow for a number of breaths, providing flexibility in dosing. This approach is particularly advantageous as it negates the need to alter the pharmaceutical composition itself to accommodate variations in patients' body weights. For example, the capsule may contain 3 mL of the pharmaceutical composition, a volume that accommodates multiple dosing regimens for flexible treatment. This capacity is particularly beneficial for varying patient needs, allowing for adjustable dosing, such as 0.1 ml in 3 breaths or 0.3 ml in 9 breaths, without the need for frequent refills. This design ensures efficient and consistent delivery of medication, crucial in treatments like opioid overdose and dependency. Depending on the patient's specifications, the dosage can be effectively adjusted by modifying the number of breaths through which the composition is administered. This method ensures that each patient receives a tailored dose proportional to their body weight, enhancing the precision and efficacy of the treatment.

To further streamline this process, the nebulizing device can be equipped with a functionality that requires the input of the patient's body weight. Upon receiving this input, the device is programmed to automatically administer the correct number of breaths corresponding to the appropriate dose. This feature adds a layer of convenience and accuracy, reducing the potential for manual errors in dosage calculation. It ensures that patients receive the optimal amount of medication based on their individual needs, aligning with the overarching goal of personalized medical care. This integration of patient-specific dosing with intuitive device functionality represents a significant advancement in the field of pharmaceutical delivery, particularly for treatments involving complex dosing regimens like those for opioid overdose and dependency.

In variations of the pharmaceutical composition, the active ingredient(s) may be dissolved in a diluent selected from a group consisting of sterile water, normal saline, and sodium chloride. It is noted that normal saline has a specific concentration (usually 0.9% sodium chloride in water), which is physiologically compatible with the body's fluids. This selection offers flexibility in formulation, accommodating different administration routes and patient tolerances. Furthermore, the composition may be enhanced with a buffer chosen from a group comprising histidine, succinate, phosphate, citrate, acetate, sodium bicarbonate, maleate, and tartrate buffers. These buffers aid in maintaining the desired pH range, contributing to the stability and efficacy of the composition.

In an ideal embodiment of the pharmaceutical composition for use with a vibrating mesh nebulizer, buffers may be excluded to accommodate patients who may experience adverse reactions, such as vasoconstriction, from these additives. Eliminating buffers is particularly critical for sensitive patients or those with specific health conditions where additional compounds might complicate treatment.

To ensure the sterility and purity of the composition in the absence of buffers, the capsules are meticulously hermetically sealed. This sealing is crucial for maintaining a bacteria-free environment, thus preserving the medication's sterility from manufacture to administration. This sealing plays a crucial role in ensuring the sterility of the pharmaceutical composition from the point of manufacture through to administration. By creating an airtight and bacteria-free environment within each capsule, the risk of contamination is significantly minimized. This approach not only maintains the purity and efficacy of the medication but also reduces the likelihood of introducing external pathogens that could be detrimental to patient health.

Below are various example embodiments of the pharmaceutical compositions contemplated by this disclosure.

Regarding a first pharmaceutical composition, or first solution being a naloxone-based pharmaceutical composition; this pharmaceutical composition comprises naloxone 4350 as the active ingredient, dissolved in an aqueous solution of sodium chloride, where the sodium chloride concentration is maintained between 0.6% and 3%. Naloxone constitutes approximately 4% to 6% of the total composition. In certain embodiments, the composition may solely consist of these elements, while in other embodiments, it may include additional components such as buffers for pH stability, stabilizers to enhance shelf-life, or other active ingredients that synergize with naloxone, all falling within the scope of this disclosure.

Regarding a second pharmaceutical composition, or second solution being a naloxone and yohimbine 4700 based pharmaceutical composition; this composition features a combination of naloxone and yohimbine in an aqueous sodium chloride solution. The sodium chloride concentration ranges from 0.6% to 3%, with naloxone present at 4% to 6%, and yohimbine at 2.5% to 6%. While certain embodiments focus solely on these components, others might include additional elements such as buffers for pH stability, stabilizers, or other active ingredients compatible with naloxone and yohimbine, adhering to the intended therapeutic application of the composition.

Regarding a third pharmaceutical composition, or third solution being a naloxone, yohimbine, and albuterol 4800 based pharmaceutical composition; this comprehensive pharmaceutical composition integrates naloxone 4350, yohimbine 4700, and albuterol 4800 in an aqueous sodium chloride base. The sodium chloride concentration is from 0.6% to 3%, with naloxone at 4% to 6%, yohimbine at 2.5% to 6%, and albuterol between 0.025% to 0.075%. Some embodiments of this composition may be limited to these ingredients, while others could incorporate additional components like buffers, stabilizers, or other active ingredients that complement the primary agents without departing from the intended scope of the composition.

Regarding a fourth pharmaceutical composition, or fourth solution being a naloxone 4350 and tolazoline 4900 based pharmaceutical composition; this composition pairs naloxone with tolazoline in an aqueous sodium chloride solution, where the sodium chloride concentration ranges from 0.6% to 3%. Here, naloxone comprises approximately 4% to 6% of the composition, while tolazoline is included at a concentration of about 50% to 75%. Alternative embodiments may include buffers for pH adjustment, stabilizers, or other active ingredients that fit within the therapeutic objectives of the solution.

Regarding a fifth pharmaceutical composition, or fifth solution being a yohimbine, based pharmaceutical composition; this solution contains yohimbine 4700 as the sole active ingredient in an aqueous sodium chloride base, where the sodium chloride concentration is between 0.6% and 3%. Yohimbine constitutes approximately 2.5% to 6% of the composition. Some embodiments might be exclusively yohimbine-based, whereas others could include additional components like buffers, stabilizers, or other active ingredients that are consistent with yohimbine's pharmacological profile and therapeutic goals.

Regarding a sixth pharmaceutical composition, or sixth solution being a naloxone and albuterol based pharmaceutical composition; in this pharmaceutical composition, naloxone 4350 and albuterol 4800 are combined in an aqueous sodium chloride solution, with the sodium chloride concentration ranging from 0.6% to 3%. Naloxone is formulated at approximately 4% to 6% of the composition, while albuterol is between 0.025% to 0.075%. While certain embodiments concentrate solely on these two active ingredients, others might encompass additional components like buffers, stabilizers, or other active ingredients that are compatible and supportive of the therapeutic objectives.

Regarding a seventh pharmaceutical composition, or seventh solution being a yohimbine and albuterol based pharmaceutical composition; this pharmaceutical composition combines yohimbine and albuterol in an aqueous sodium chloride base. The sodium chloride concentration ranges from 0.6% to 3%, with yohimbine between 2.5% to 6%, and albuterol between 0.025% to 0.075%. While the basic composition includes just these components, alternative embodiments could incorporate additional elements such as buffers, stabilizers, or other active ingredients, as long as they align with the intended therapeutic use and overall.

Regarding an eighth pharmaceutical compound, a pharmaceutical composition specifically formulated to address opioid dependency is disclosed. This composition combines the active ingredient naloxone, a potent opioid antagonist, with buprenorphine 5000, a partial opioid agonist. The buprenorphine component plays a critical role in this formulation by adhering to the mu-opioid receptors, thereby facilitating the targeted delivery of naloxone to these receptors. Notably, naloxone is typically unable to effectively reach the mu-opioid receptors without the presence of buprenorphine. This synergistic relationship between buprenorphine and naloxone is central to the efficacy of the medication, known commercially as Suboxone® and Zubsolv®. This embodiment leverages the unique pharmacological properties of both naloxone and buprenorphine, offering an effective treatment modality for patients grappling with opioid dependency, and aligns with current therapeutic protocols in addiction medicine. Various pharmaceutical compositions comprising buprenorphine and/or naloxone are contemplated and disclosed herein. In the disclosed embodiments below, a series of pharmaceutical compositions are designed for use with a vibrating mesh nebulizer, focusing on the administration of buprenorphine, both alone and in combination with naloxone, for the treatment of pain and opioid use disorder. These formulations consider the pharmacokinetics of buprenorphine, including its half-life and morphine equivalent dosing, and are pioneering in exploring the potential of inhaled buprenorphine.

First, said composition includes buprenorphine 5000 as the active ingredient, dissolved in sterile water with a sodium chloride content ranging from 0% to 3%. The buprenorphine concentration is approximately 0.02% to 0.045% (0.2 mg/ml to 0.45 mg/ml). The solution's pH, adjusted using hydrochloric acid, is maintained between 3.5 and 7.8. Such a formulation may be applicable for administering said medication in situations that require immediate acute pain relief, such as in the field of military and first responder application. In certain embodiments, this composition may further includes a cytochrome P450 3A inhibitor at a predetermined strength, alongside buprenorphine. The inhibitor's inclusion aims to decrease the clearance of buprenorphine, potentially extending its half-life. Such a formulation may be used for treating chronic pain relief and also for naloxone sensitive opioid dependency.

Second, in this formulation, buprenorphine 5000 is combined with naloxone. Both active ingredients are dissolved in sterile water, maintaining sodium chloride ranging from 0% to 3%. The buprenorphine concentration varies between 0.01% and 0.4% (0.1 mg/ml to 4 mg/ml), and naloxone between 0.025% and 0.2% (0.25 mg/ml to 2 mg/ml). The pH is similarly adjusted to fall between 3.5 and 7.8. Such a formulation may be applicable for treating opioid dependency. In certain embodiments, this solution may combine buprenorphine and naloxone with a cytochrome P450 3A inhibitor. The inclusion of the inhibitor is intended to enhance the pharmacological effectiveness of buprenorphine.

These pharmaceutical compositions including a cytochrome P450 3A inhibitor improve over the prior art by extending the half-life of buprenorphine, particularly in its hydrochloride form, where the half-life is notably shortened. This reduction in half-life can impede the effectiveness of buprenorphine in achieving the desired goals of decreasing tolerance at the cellular level, which is crucial for chronic pain relief and managing opioid dependence. To address this challenge, the composition includes the addition of a Cytochrome P450 3A inhibitor, such as a specified amount of citalopram. The incorporation of this inhibitor is a deliberate strategy to prolong the half-life of buprenorphine. By doing so, the composition effectively reinstates the original objective of diminishing opioid receptor activity and reducing tolerance. This enhancement is particularly significant in Formula 2, designed for opioid dependence treatment, where maintaining the therapeutic effectiveness of buprenorphine over a prolonged period is crucial for successful patient outcomes. The addition of the P450 3A inhibitor thus represents a critical improvement in the formulation, optimizing its efficacy for both chronic pain management and opioid dependency treatments.

Overall, these formulations are directed towards the administration of buprenorphine 5000 and its combinations, utilizing nebulizer technology for potentially more effective and controlled delivery. The versatility in concentration ranges and the addition of a metabolic inhibitor demonstrate an innovative step in optimizing drug delivery for pain management and opioid use disorder treatment. The active ingredients, naloxone and/or buprenorphine, may be combined in an aqueous solution of sodium chloride, providing a stable and biocompatible medium. The concentration of this active ingredient is carefully calibrated to be between 0.025% and 25% of the aqueous solution, ensuring optimal therapeutic efficacy. Critical to the composition's stability and compatibility with human physiology is the maintenance of a pH range approximately between 3 and 7.5. This formulation provides a means of atomized administration of the medication for treatment of opioid exposure and/or dependency.

In the context of the aforementioned pharmaceutical compositions, specifically designed for the treatment of opioid overdose and dependency and xylazine exposure, said pharmaceutical compositions are meticulously prepared and stored within capsules for atomized administration to patients. The process begins with the precise selection and measurement of active ingredients, such as naloxone, yohimbine, albuterol, tolazoline, and buprenorphine. These ingredients are quantified to achieve the desired concentrations, ranging from 0.025% to 25% of the total composition. Concurrently, an aqueous solution of sodium chloride, or alternative diluents such as sterile water or normal saline, is prepared, ensuring a sodium chloride concentration between 0.6% and 3%.

Subsequently, the active ingredients are dissolved in this aqueous medium, ensuring complete dissolution and uniform distribution. Critical to the stability and patient compatibility of the composition is the adjustment of pH, typically maintained within the range of 3 to 7.5. This is achieved through the judicious use of buffers, including but not limited to histidine, succinate, phosphate, citrate, acetate, sodium bicarbonate, maleate, or tartrate. Upon formulation, the composition undergoes rigorous quality control testing to confirm the accuracy of active ingredient concentrations, appropriate pH levels, and overall stability.

Once the pharmaceutical composition meets all specified criteria, it is carefully filled into specially designed capsules. These capsules are tailored for compatibility with vibrating mesh nebulizers and are fabricated from materials that are inert to the composition. Ensuring the integrity of the composition, the capsules are hermetically sealed, safeguarding against environmental factors such as moisture, light, and air, which could otherwise compromise the active ingredients.

The storage of these capsules is managed under controlled conditions, typically at temperatures conducive to maintaining the stability of the pharmaceutical composition. This aspect of the invention is crucial for preserving the therapeutic efficacy of the composition until the point of administration.

For patient administration, a capsule is loaded into a vibrating mesh nebulizer. The capsule is inserted into a device equipped with a device chamber. This device includes a receiving section with an opening, which is covered by a removable cap to define what is termed as a capped chamber. Upon activation, the device induces the capsule's contents, the pharmaceutical composition, to atomize into a fine mist by dispensing the pharmaceutical composition from the capsule, which is in fluid communication with this capped chamber, into the capped chamber itself. The resulting aerosolized medication is administered to the patient by being conveyed from this capped chamber, then inhaled by the patient, facilitating rapid, targeted, controlled, and effective delivery of the active ingredients directly to the respiratory tract.

In certain embodiments, the medical situation of the respective patient, or multiple patients, may involve removing the removable cap from the receiving section of the device. The initial act of removing the cap serves a dual purpose: it not only prepares the device for the impending atomization process but also establishes an open interface for the subsequent attachment of the air bladder. This opening is essential for facilitating the fluid communication requisite for effective atomization.

Subsequently, the resilient air bladder is attached to the receiving section of the device. Upon the attachment of the resilient air bladder, a seamless fluidic pathway is established between the bladder and the chamber of the device. This air bladder is designed to be in fluid communication with the chamber via the opening, facilitating an enhanced mechanism for conveying the atomized pharmaceutical composition to the patient. This addition of the air bladder aids in the efficient and effective delivery of the medication, ensuring that the therapeutic agents are administered in an optimized manner suitable for the treatment of opioid-related conditions.

With reference to FIGS. 30A through 31D, the specific configuration for administering a pharmaceutical composition with yohimbine as the active ingredient is of notable interest, particularly given yohimbine's known instability in liquid form. This capsule system, designed for atomized administration, solves this challenge through its dual-reservoir structure.

The capsule comprises a first reservoir, which is dedicated to containing the active ingredient, yohimbine hydrochloride. The concentration of yohimbine hydrochloride is meticulously calibrated within the range of 0.05 to 0.25 mg per kg of a patient's body weight. Considering yohimbine's inherent instability when dissolved, it is crucially stored in a powdered or solid form in this first reservoir. This approach is essential to maintain the integrity and efficacy of yohimbine until the moment of administration, circumventing the stability issues associated with liquid formulations. In certain embodiments, the amount of dry weight yohimbine may be suitable such that, when mixed with the diluent, the amount of yohimbine comprises approximately between 2.5% and 6% of the aqueous solution.

Adjacent to this is the second reservoir, which is distinctively formulated to include a diluent, chosen from options such as sterile water, normal saline, and sodium chloride, and may also contain a buffer selected from a group including histidine, succinate, phosphate, citrate, acetate, sodium bicarbonate, maleate, and tartrate buffers. The presence of these buffers aids in maintaining the desired pH level, crucial for the stability and effectiveness of the yohimbine once it is in solution.

The method, as outlined above, includes the critical step of moving the yohimbine from the first reservoir to the second reservoir to combine the yohimbine with the diluent to formulate the pharmaceutical composition. In one embodiment, this transfer is facilitated by rupturing a membrane that separates these two compartments, thereby allowing fluid communication between them. The membrane's rupture, triggered at the time of administration, ensures that yohimbine is mixed with the diluent and/or buffer only immediately prior to administration, thus effectively addressing the stability concerns.

In certain embodiments, the capsule system may be configured for administering light-sensitive pharmaceuticals. Accordingly, said capsule, and/or the respective reservoirs or chambers, may be darkly tinted or non-transparent. This is crucial for protecting active ingredients, like yohimbine, from light-induced degradation. The dark tint or non-transparency effectively blocks harmful light, particularly UV and visible light, maintaining the integrity and efficacy of the medication. The materials used are selected for their light-blocking properties and compatibility with pharmaceutical standards, ensuring the safety and stability of the contents. This approach simplifies storage and handling, allowing for safer and more convenient use in various settings. Thus, the design of darkly tinted or non-transparent capsules or vials is a key feature in preserving the potency and effectiveness of light-sensitive medications.

A further aspect of the method of administering the pharmaceutical composition involves the removal of a stop that initially inhibits the movement of the first reservoir relative to the second reservoir. This stop's removal is a key activation step, enabling the translation of the first reservoir towards the second and the subsequent engagement of the rupturing mechanism. This design ensures that the mixing of yohimbine with the diluent and/or buffer is a controlled and deliberate process, occurring only when the pharmaceutical composition is intended to be administered.

By causing the first chamber or first reservoir to be in fluid communication with the second chamber or second reservoir, the active ingredient is then mixed with the diluent and/or buffer within the capsule chamber, which is typically the second chamber/reservoir. This chamber contains the diluent and/or buffer, while the active ingredient, like yohimbine, is initially segregated in a separate reservoir. The mixing process is activated by a user or an automated mechanism, leading to the rupture of a membrane barrier that separates the active ingredient from the diluent and buffer. This rupture, facilitated by a built-in rupturing element, enables the active ingredient in its powdered or solid form to merge with the diluent, such as sterile water, normal saline, or sodium chloride. If included, the buffer—which could be histidine, succinate, phosphate, citrate, acetate, sodium bicarbonate, maleate, or tartrate—assists in maintaining an optimal pH level, crucial for the stability and efficacy of the resultant solution.

Upon the mixing of these components, a homogeneous pharmaceutical composition is formed within the capsule chamber. This composition is then ready for the final stage of atomized administration. The capsule system, typically equipped with a vibrating mesh atomizer proximate to the capsule chamber, transforms the liquid composition into a fine aerosol. This aerosolized form is ideal for inhalation, ensuring efficient and effective delivery of the medication to the patient. In certain embodiments of this pharmaceutical system, the system is configured to cater to specific medical emergencies, ensuring the precise and controlled mixing of the active ingredients with the diluent and buffer for effective administration. In one embodiment, the system includes the administration of naloxone, an active ingredient renowned for its efficacy in reversing opioid overdose. However, it is noteworthy that naloxone alone generally does not address opioid dependency, a condition that may be more effectively managed by a combination of buprenorphine and naloxone. This embodiment, therefore, may encompass a formulation specifically targeting opioid overdose scenarios. In another embodiment, the system is adapted for the administration of yohimbine. Unlike naloxone, yohimbine does not counteract opioid overdose but is effective in reversing the effects of xylazine, an emerging concern in public health. This embodiment ensures that yohimbine is delivered in a controlled manner, suitable for addressing complications arising from xylazine exposure.

Each embodiment of this system reflects a dedicated focus on addressing the distinct requirements of different medical emergencies, be it opioid overdose or xylazine-related complications. This versatility in design underscores the commitment to advancing pharmaceutical administration's efficiency and efficacy, particularly in critical care settings where precise and targeted treatment is paramount.

In summary, this capsule system represents a sophisticated and highly effective solution for administering yohimbine, particularly given its instability in liquid form. The dual-reservoir design, coupled with a precise rupturing mechanism and the careful separation of yohimbine from the diluent until the point of use, ensures the stability, potency, and efficacy of the medication, thereby addressing a significant challenge in the pharmaceutical administration of yohimbine.

The two-reservoir capsule design, exemplified by the innovative system described herein, offers a versatile and efficient solution for isolating various active ingredients prior to administration. It is understood that this capsule system can be adapted for a wide range of pharmaceutical compositions, including those requiring multiple active ingredients. In such scenarios, the capsule may be configured to include one or more first reservoirs or chambers, each initially housing a distinct active ingredient. These first chambers are effectively isolated from a second reservoir, typically containing a diluent or buffer, by one or more membranes. The membranes serve as a barrier, maintaining separation of the active ingredients from the diluent or buffer until the point of administration. This separation is crucial for preserving the stability and efficacy of the active ingredients, especially those sensitive to premature mixing or environmental factors. When required, the membranes can be ruptured or otherwise breached, allowing for the controlled release of each active ingredient into the second reservoir. This results in a combined pharmaceutical composition that is ready for atomized delivery. The adaptability of this at least two-reservoir system to accommodate multiple active ingredients in separate chambers underscores its potential in providing tailored and sophisticated medication delivery solutions, particularly in treatments requiring complex pharmaceutical regimens.

The pharmaceutical composition comprising yohimbine hydrochloride, formulated for treating opioid overdose and dependency, is adaptable for various methods of administration, each tailored to optimize efficacy and patient convenience. The pharmaceutical composition includes the active ingredient, yohimbine hydrochloride, and a diluent selected from the group consisting of sterile water, normal saline, and sodium chloride.

When combined with sterile water as a diluent, the pharmaceutical composition is suitable for intramuscular injection. This method involves injecting the yohimbine hydrochloride solution, with a concentration ranging from 0.05 to 0.25 mg per kg of the patient's body weight, directly into the muscle tissue. Intramuscular injection offers a relatively quick onset of action, as the drug is absorbed into the bloodstream through the muscle fibers. This route is particularly useful in emergency scenarios where swift response is crucial and when intravenous access is not readily available.

Alternatively, when the composition uses normal saline as the diluent, the pharmaceutical composition is configured for intravenous administration. This method involves delivering the yohimbine hydrochloride solution directly into the bloodstream through a vein. Intravenous administration ensures rapid distribution of the medication throughout the body, offering immediate therapeutic effects, which is essential in acute care situations like opioid overdose.

In cases where sodium chloride is used as the diluent, the composition is prepared for atomized aerosol delivery as describe above. Each of these administration methods offers distinct benefits. Intramuscular and intravenous injections provide rapid drug delivery in emergency situations, while atomized aerosol delivery offers a non-invasive alternative with direct respiratory system delivery. The flexibility in the choice of diluent and the inclusion of suitable buffers ensure that the pharmaceutical composition remains stable and effective, regardless of the chosen method of administration. This adaptability underscores the composition's versatility in addressing the varied needs of patients suffering from opioid overdose or dependency.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A formulation delivery system, comprising:
- a mouthpiece having a first attaching structure at one end;
- a removable cartridge having a second attaching structure, wherein the second attaching structure is removably attached to the first attaching structure of the mouthpiece, the removable cartridge comprising:
  - an atomizer disposed at a first end portion of the removable cartridge;
  - a wick assembly comprising:
    - a removable cap; and
    - a wick comprising an absorbent material for absorbing a fluid, wherein a first end of the wick is attached to the removable cap, and a second end of the wick abuts the atomizer such that the wick is configured to transport the fluid to the atomizer; and
  - a channel defined by the removable cartridge, the channel extending to the first end portion of the removable cartridge, wherein the wick is removably disposed within the channel, and the removable cap is disposed externally to the channel; and electronics, in removable electrical communication with the removable cartridge.

2. The formulation delivery system of claim 1 further comprising a covering member disposed at the first end portion of the removable cartridge to cover the atomizer.

3. The formulation delivery system of claim 2 wherein the covering member comprises a pull tab to allow pulling of the covering member before using the mouthpiece.

4. The formulation delivery system of claim 1, wherein the removable cartridge has an electrical contact and the electronics has a connector to engage the electrical contact and activate the atomizer.

5. The formulation delivery system of claim 1, wherein the wick abuts the atomizer such that the wick is arranged transversely to a plane of the atomizer.

6. A formulation delivery system, comprising:
a base unit defining a receiving chamber; and
a removable cartridge, wherein a portion of the removable cartridge is disposed within the receiving chamber of the base unit, the removable cartridge comprising:
  an atomizer disposed at a first end portion of the removable cartridge, the first end portion being removably disposed within the receiving chamber of the base unit;
  a wick assembly comprising:
    a removable cap; and
    a wick comprising an absorbent material for absorbing a fluid, wherein a first end of the wick is attached to the removable cap, and a second end of the wick abuts the atomizer such that the wick is configured to transport the fluid to the atomizer;
  a channel defined by the removable cartridge, the channel extending to the first end portion of the removable cartridge, wherein the wick is removably disposed within the channel, and the removable cap is disposed externally to the channel; and
  electronics, in removable electrical communication with the removable cartridge.

7. The formulation delivery system of claim 6, wherein the base unit defines a mixing chamber and a plurality of openings.

8. The formulation delivery system of claim 7, wherein the receiving chamber is in fluid communication with the mixing chamber, and the plurality of openings receive at least one of a portion of a conduit of a resilient air bladder, is configured to a mouthpiece and a mask.

9. The formulation delivery system of claim 6, wherein the removable cartridge has an electrical contact and the electronics has a connector to engage the electrical contact and activate the atomizer.

* * * * *